US012180464B2

(12) United States Patent
Embree et al.

(10) Patent No.: US 12,180,464 B2
(45) Date of Patent: Dec. 31, 2024

(54) MICROBIAL COMPOSITIONS AND METHODS OF USE FOR CANINE ENTEROPATHY AND DYSBIOSIS

(71) Applicant: Native Microbials, Inc., San Diego, CA (US)

(72) Inventors: Mallory Embree, San Diego, CA (US); Grant Gogul, Cardiff, CA (US); Fan Yang, San Diego, CA (US)

(73) Assignee: Native Microbials, Inc., San Diego, CA (US)

( * ) Notice: Subject to any disclaimer, the term of this patent is extended or adjusted under 35 U.S.C. 154(b) by 0 days.

(21) Appl. No.: 17/818,834

(22) Filed: Aug. 10, 2022

(65) Prior Publication Data

US 2022/0386647 A1 Dec. 8, 2022

Related U.S. Application Data

(63) Continuation of application No. PCT/US2021/017487, filed on Feb. 10, 2021.

(60) Provisional application No. 63/083,178, filed on Sep. 25, 2020, provisional application No. 62/972,337, filed on Feb. 10, 2020.

(51) Int. Cl.

*C12N 1/20* (2006.01)
*A23K 10/18* (2016.01)
*A23K 20/163* (2016.01)
*A23K 20/174* (2016.01)
*A23K 40/30* (2016.01)
*A23K 50/42* (2016.01)
*A23K 50/48* (2016.01)
*A61P 1/12* (2006.01)

(52) U.S. Cl.

CPC .............. *C12N 1/205* (2021.05); *A23K 10/18* (2016.05); *A23K 20/163* (2016.05); *A23K 20/174* (2016.05); *A23K 40/30* (2016.05); *A23K 50/42* (2016.05); *A23K 50/48* (2016.05); *A61P 1/12* (2018.01); *C12N 1/20* (2013.01)

(58) Field of Classification Search

CPC ................................ C12N 1/205; A23K 10/18
USPC .......................................................... 435/243
See application file for complete search history.

(56) References Cited

U.S. PATENT DOCUMENTS 4,647,536 A 3/1987 Mosbach et al.
5,104,662 A 4/1992 Kalsta et al.
5,290,765 A 3/1994 Wettlaufer et al.
5,605,793 A 2/1997 Stemmer
5,733,568 A 3/1998 Ford
5,837,458 A 11/1998 Minshull et al.
6,210,891 B1 4/2001 Nyren et al.
6,258,568 B1 7/2001 Nyren
6,274,320 B1 8/2001 Rothberg et al.
7,427,408 B2 9/2008 Merritt et al.
7,488,503 B1 2/2009 Porzio et al.
7,998,502 B2 8/2011 Harel
8,097,245 B2 1/2012 Harel et al.
8,101,170 B2 1/2012 Plail et al.
8,345,010 B2 1/2013 Fitzgibbon et al.
8,460,726 B2 6/2013 Harel et al.
9,469,835 B2 10/2016 Bronshtein
9,540,676 B1 1/2017 Zengler et al.
11,207,374 B2 12/2021 Pamer et al.
2010/0316769 A1* 12/2010 Czarnecki-Maulden .................... G09B 19/0092 426/62
2011/0280840 A1 11/2011 Blaser et al.
2011/0280847 A1 11/2011 Sorg et al.
2015/0173397 A1 6/2015 Martinez Villagran et al.
2015/0190435 A1 7/2015 Henn et al.
2015/0267163 A1 9/2015 Liao et al.
2016/0326574 A1 11/2016 Gordon et al.
2017/0087196 A1 3/2017 Pamer et al.
2018/0369296 A1 12/2018 Ganz et al.
2020/0078418 A1 3/2020 Wagner et al.
2020/0093886 A1 3/2020 Pamer et al.
2022/0104517 A1 4/2022 Perea et al.
2022/0370547 A1 11/2022 Pamer et al.

FOREIGN PATENT DOCUMENTS

WO WO-2008076975 A1 6/2008
WO WO-2010111347 A2 9/2010
WO WO-2010111565 A2 9/2010
WO WO-2010138522 A2 12/2010

(Continued)

OTHER PUBLICATIONS

Benyacoub et al., "Supplementation of Food with Enterococcus faecium (SF68) Stimulates Immune Functions in Young Dogs", Nutritional Immunology, vol. 133(4), pp. 1158-1162. (Year: 2003).*

(Continued)

*Primary Examiner* — Michelle F. Paguio Frising
*Assistant Examiner* — Grant C Currens
(74) *Attorney, Agent, or Firm* — COOLEY LLP

(57) ABSTRACT

The disclosure relates to isolated microorganisms—including novel strains of the microorganisms—microbial ensembles, and compositions comprising the same. Furthermore, the disclosure teaches methods of utilizing the described microorganisms, microbial compositions, and compositions comprising the same, in methods for treating or preventing gastrointestinal enteropathy or dysbiosis in canines. In particular aspects, the disclosure provides methods of treating or preventing morbidity and mortality caused by GI pathogenesis or autoimmunity.

18 Claims, 14 Drawing Sheets

Specification includes a Sequence Listing.

(56) References Cited

FOREIGN PATENT DOCUMENTS

| | | | | |
|---|---|---|---|---|
| WO | WO-2011094469 A2 | 8/2011 | | |
| WO | WO-2014082050 A1 | 5/2014 | | |
| WO | WO-2014121298 A2 * | 8/2014 | ............. | A61K 35/37 |
| WO | WO-2014121301 A1 | 8/2014 | | |
| WO | WO-2014121302 A2 | 8/2014 | | |
| WO | WO-2014121304 A1 | 8/2014 | | |
| WO | WO-2014145958 A2 | 9/2014 | | |
| WO | WO-2015077794 A1 | 5/2015 | | |
| WO | WO-2015179437 A1 | 11/2015 | | |
| WO | WO-2017160711 A1 | 9/2017 | | |
| WO | WO-2018064165 A2 | 4/2018 | | |
| WO | WO-2018112553 A1 | 6/2018 | | |
| WO | WO-2018187272 A1 | 10/2018 | | |
| WO | WO-2018195467 A1 | 10/2018 | | |
| WO | WO-2018218211 A1 | 11/2018 | | |
| WO | WO-2019032573 A1 | 2/2019 | | |
| WO | WO-2019071516 A1 | 4/2019 | | |
| WO | WO-2019227085 A1 | 11/2019 | | |
| WO | WO-2019227418 A1 | 12/2019 | | |
| WO | WO-2020118054 A1 | 6/2020 | | |
| WO | WO-2020150712 A1 | 7/2020 | | |
| WO | WO-2020150717 A1 | 7/2020 | | |
| WO | WO-2020154523 A2 | 7/2020 | | |
| WO | WO-2021108728 A1 | 6/2021 | | |
| WO | WO-2021146639 A1 | 7/2021 | | |

OTHER PUBLICATIONS

Alshawaqfeh et al., "A dysbiosis index to assess microbial changes in fecal samples of dogs with chronic inflammatory enteropathy", FEMS Microbiology Ecology, vol. 93, pp. 1-8. (Year: 2017).*

Maldonado-Contreras et al., "Dysbiosis in a canine model of human fistulizing Crohn's disease", bioRxiv, article 815589, pp. 1-27. (Year: 2019).*

Barko et al., "The Gastrointestinal Microbiome: a Review," J Vet Intern Med. (2018) 32:9-25.

Bennett, et al., "Toward the $1000 human genome," Pharmacogenomics (2005); 6(4):373-382.

Bentley, et al., "Accurate whole human genome sequencing using reversible terminator chemistry." Nature (2008); 456(7218): 53-59.

Blondel et al., "Fast unfolding of communities in large networks," Journal of Statistical Mechanics: Theory and Experiment, vol. 2008, Oct. 2008.

Burgain, et al, "Encapsulation of probiotic living cells: From laboratory scale to industrial applications." Journal of Food Engineering (2011); 104 (4): 467-483.

Caporaso et al., "Ultra-high-throughput microbial community analysis on the Illumina HiSeq and MiSeq platforms," The ISME Journal (2012); 6: 1621-1624.

Coelho et al., "Similarity of the dog and human gut microbiomes in gene content and response to diet," BMC Microbiome, (2018) 6:72.

Colby, et al., "Calculating synergistic and antagonistic responses of herbicide combinations." Weeds (1967); 15 (1): 20-22.

Crameri et al., "DNA shuffling of a family of genes from diverse species accelerates directed evolution." Nature (1998); 391(6664): 288-291.

Crameri et al., "Molecular evolution of an arsenate detoxification pathway by DNA shuffling." Nature Biotechnology (1997); 15(5): 436-438.

De Almeida et al., "Transgenic expression of two marker genes under the control of an *Arabidopsis* rbcS promoter: Sequences encoding the Rubisco transit peptide increase expression levels." Molecular and General Genetics MGG (1989); 218(1): 78-86.

Fadrosh et al., "An improved dual-indexing approach for multiplexed 16S rRNA gene sequencing on the Illumina MiSeq platform," Microbiome (2014); 2:6, 7 pages.

GenBank Accession No. HQ792533, Uncultured organism clone ELU0127-T314-S-NI_000216 small subunit ribosomal RNA gene, partial sequence, Jul. 30, 2012 [online]. [Retrieved on Jun. 2, 2021]. Retrieved from the internet: Entire document.

Heinken et al., "Systematic assessment of secondary bile acid metabolism in gut microbes reveals distinct metabolic capabilities in inflammatory bowel disease," Microbiome (2019) 7:75, 18 pages.

Hooda et al., "Current state of knowledge: the canine gastrointestinal microbiome," Animal Health Research Reviews. (2012) 13(1):78-88.

International Preliminary Examination Report for Application No. PCTUS2021017487, mailed Aug. 25, 2022, 15 pages.

International Search Report and Written Opinion for International Application No. PCT/US2021/017487 dated Jun. 23, 2021, 19 pages.

Jones et al., "High level expression of introduced chimaeric genes in regenerated transformed plants." The EMBO Journal (Oct. 4, 1985); 4(10): 2411-2418.

Kõljalg et al., "UNITE: a database providing web-based methods for the molecular identification of ectomycorrhizal fungi," New Phytologist (2005); 166(3): 1063-1068.

Lan et al., "Using the RDP classifier to predict taxonomic novelty and reduce the search space for finding novel organisms," PLoS One (2012); 7(3): e32491, 15 pages.

Lange et al., "Cost-efficient high-throughput HLA typing by MiSeq amplicon sequencing," BMC Genomics (2014); 15:63, 11 pages.

Lee et al., "Nonradioactive Method to Study Genetic Profiles of Natural Bacterial Communities by PCR-Single-Strand-Conformation Polymorphism," Applied and Environmental Microbiology (1996); 62 (9): 3112-3120.

Mardis, Elaine R., "Next Generation DNA Sequencing Methods," Annu. Rev. Genomics Hum. Genet. (2008); 9: 387-402.

Margulies M., et al., "Genome Sequencing In Microfabricated High-density Picolitre Reactors," Nature, Sep. 15, 2005, Published Online: Jul. 31, 2005, vol. 437 (7057), pp. 376-380.

Mitra et al., "Analysis of the intestinal microbiota using Solid 16S rRNA gene sequencing and SOLiD shotgun sequencing," BMC Genomics (2013); 14(Suppl 5):S16, 11 pages.

Moore et al. "Strategies for the in vitro evolution of protein function: enzyme evolution by random recombination of improved sequences," Journal of Molecular Biology (1997); 272: 336-347.

Peckham et al., "SOLiD Sequencing and 2-Base Encoding," San Diego, CA: American Society of Human Genetics, Poster No. 2624 (2007), 1 page.

Pool-Zobel et al., "Overview of Experimental Data on Reduction of Colorectal Cancer Risk by Inulin-Type Fructans," J. Nutr. (2007); 137: 2580S-2584S.

Ramirez- Farias et al., "Effect of inulin on the human gut microbiota: stimulation of Bifidobacterium adolescentis and Faecalibacterium prausnitzii," Br J Nutr (2009); 101(4): 541-550.

Ranjard et al., "Sampling strategy in molecular microbial ecology: influence of soil sample size on DNA fingerprinting analysis of fungal and bacterial communities," Environmental Microbiology 5(11); 1111-1120 (2003).

Sanger et al., "DNA Sequencing with Chain-Terminating Inhibitors," Proceedings of the National Academy of Sciences of the United States of America, Dec. 1977, vol. 74 (12), pp. 5463-5467.

Scheinert et al., "Molecular differentiation of bacteria by PCR amplification of the 16-23S rRNA spacer," J Microbiol Meth (1996); 26: 103-117.

Schloss et al., "Assessing and improving methods used in operational taxonomic unit-based approaches for 16S rRNA gene sequence analysis." Applied and Environmental Microbiology (2011); 77.10: 3219-3226.

Schwieger et al.,"A New Approach to Utilize PCR-Single-Strand-Conformation Polymorphism for the 16S rRNA Gene-Based Microbial Community Analysis," Applied and Environmental Microbiology (1998); 64(12): 4870-4876.

Shabat, et al., "Specific microbiome-dependent mechanisms underlie the energy harvest efficiency of ruminants." The ISME Journal (2016); 10 (12): 2958-2972.

Sindern et al., "Prevalence of Clostridium perfringens netE and netF toxin genes in the feces of dogs with acute hemorrhagic diarrhea syndrome," J Vet Intern Med. (2019) 33:100-105.

(56) References Cited

OTHER PUBLICATIONS

Stemmer, Willem P.C., "DNA shuffling by random fragmentation and reassembly: in vitro recombination for molecular evolution." Proceedings of the National Academy of Sciences (1994); 91(22): 10747-10751.
Stemmer Willem P.C., "Rapid Evolution of a Protein in Vitro by DNA Shuffling," Nature, Aug. 4, 1994, vol. 370, No. 6488, pp. 389-391.
Vandamme et al., "Polyphasic taxonomy, a consensus approach to bacterial systematics." Microbiological Reviews (1996); 60.2: 407-438.
Yarza et al., "Uniting the classification of cultured and uncultured bacteria and archaea using 16S rRNA gene sequences." Nature Reviews Microbiology (2014); 12.9: 635-645.
Zhang et al., "Directed evolution of a fucosidase from a galactosidase by DNA shuffling and screening." Proc Natl Acad Sci USA. (1997); 94 (9): 4504-4509.
Ziese et al., "Effect of probiotic treatment on the clinical course, intestinal microbiome, and toxigenic Clostridium perfringens in dogs with acute hemorrhagic diarrhea," PLoS ONE (2018) 13(9): e0204691, 16 pages.
Gloor et al., "Microbiome Datasets Are Compositional: and This Is Not Optional," Front. Microbiol. (2017) 8:2224, 6 pages.
Hawinkel et al., "A broken promise: microbiome differential abundance methods do not control the false discovery rate," Briefings in Bioinformatics, 2017, 1-12, doi: 10.1093/bib/bbx104.
Mandal et al., "Analysis of composition of microbiomes: a novel method for studying microbial composition," Microbial Ecology in Health & Disease 2015, 26: 27663, 7 pages.
Database EMBL, Database accession No. MH099652, "Uncultured bacterium clone 16S(V3+V4)-3596 16S ribosomal RNA gene, partial sequence." Mar. 28, 2018, 2 pages.
Extended European Search Report for European Application No. 21754431.1 dated May 29, 2024, 17 pages.
Partial Supplementary European Search Report for European Application No. 21754431.1 dated Mar. 4, 2024, 19 pages.

* cited by examiner

*E. coli* control

Ascusk9_546A

Ascusk9_17A

MICROBIAL COMPOSITIONS AND METHODS OF USE FOR CANINE ENTEROPATHY AND DYSBIOSIS

CROSS-REFERENCE TO RELATED APPLICATIONS

This application is a continuation of International Application No. PCT/US2021/017487, filed Feb. 10, 2021, which claims the benefit of priority to U.S. Provisional Application No. 62/972,337 filed on Feb. 10, 2020 and U.S. Provisional Application No. 63/083,178, filed on Sep. 25, 2020; each of which are herein incorporated by reference in their entireties.

TECHNICAL FIELD

The present disclosure relates to isolated and biologically pure microorganisms that have applications, inter alia, in the prevention and treatment of enteropathy or dysbiosis in canines. The disclosed microorganisms can be utilized in their isolated and biologically pure states, as well as being formulated into compositions. The disclosure provides a microbial ensemble, containing at least two members of the disclosed microorganisms, as well as methods of utilizing said microbial ensemble. Furthermore, the disclosure provides for methods of modulating the canine gastrointestinal microbiome.

STATEMENT REGARDING SEQUENCE LISTING

The sequence listing associated with this application is provided in XML format and is hereby incorporated by reference into the specification. The name of the XML file containing the Sequence Listing is ASBI_018_03US_SeqList_ST26. The XML file is 350,346 bytes, was created on Aug. 3, 2022 and is being submitted electronically via USPTO Patent Center.

BACKGROUND

Canines are colonized by microbes in the gastrointestinal (GI) tract, on the skin, and in other epithelial and tissue niches such as the oral cavity, eye surface and vagina. The GI tract harbors an abundant and diverse microbial community. It is a complex system, providing an environment or niche for a community of many different species or organisms, including diverse strains of bacteria. Hundreds of different species may form a commensal community in the GI tract in a healthy animal, and this complement of organisms evolves from the time of birth to ultimately form a functionally mature microbial population. Interactions between microbial strains in these populations and between microbes and the host, e.g. the host immune system, shape the community structure, with availability of and competition for resources affecting the distribution of microbes. Such resources may be food, location and the availability of space to grow or a physical structure to which the microbe may attach. For example, host diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In dysbiosis or general enteropathy, the composition and functions of the microbial flora can be lost or significantly altered, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections of the gut. For instance, canines become more susceptible to pathogenic infections when the normal intestinal microbiota has been disturbed due to use of broad-spectrum antibiotics. Many of these diseases and disorders are chronic conditions that significantly decrease an animal's quality of life and can be fatal.

Thus far, replacement or supplementation of the gut microbiome in canines has largely been limited to oral supplementation of freeze-dried microbes that are typically found in yogurts, and fecal transplantation. Both instances have potential for treating varying degrees of gut dysbiosis conditions. Oral supplementation has a greater ease of use, but selecting the right microorganisms for the greatest efficacy is difficult. Fecal transplantation is considered to be a procedure of last resort because it has the potential to transmit infectious or allergenic agents between hosts, involves the transmission of potentially hundreds of unknown strains from donor to patient, and is difficult to perform on a mass scale. Additionally, fecal transplantation is inherently non-standardized, inconsistent, and different desired and/or undesired material may be transmitted in any given donation. Thus, there is a need for defined compositions that can be utilized to treat the spectrum of diseases and conditions drawn to enteropathy by decreasing the animal's susceptibility to infection and/or facilitating the restoration of healthy gut microbiota.

Thus there is a need for an effective, defined, and reproducible treatment for enteropathies and dysbiosis disorders in canines. In order to prepare a therapeutic with commercial potential, we have designed bacterial compositions of isolated bacterial strains with a plurality of beneficial properties based on our understanding of those bacterial strains and our analysis of the properties that would enhance the utility and commercialization of a bacterial composition.

Therefore, in response to the need for durable, efficient, and effective compositions and methods for treatment of enteropathies and GI dysbioses, in particular serious pathogenic infections, as well as maintenance of general GI health, we provide compositions and methods for treating canines in response to enteropathies or on a prophylactic basis.

SUMMARY OF THE DISCLOSURE

In some embodiments, the present disclosure provides a microbial composition comprising: (a) a purified microbial population that comprises one or more bacteria with a 16S nucleic acid sequence that shares at least 97% sequence identity with a nucleic acid sequence selected from SEQ ID NOs: 1-333; and (b) one or more carriers suitable for canine administration. In some embodiments, the purified microbial population comprises a bacterium with a 16S nucleic acid sequence sharing at least 97% sequence identity with SEQ ID NO: 19. In some embodiments, the purified microbial population comprises a bacterium with a 16S nucleic acid sequence comprising SEQ ID NO: 19. In some embodiments, the purified microbial population comprises a bacterium with a 16S nucleic acid sequence sharing at least 97% sequence identity with SEQ ID NO: 172. In some embodiments, the purified microbial population comprises a bacterium with a 16S nucleic acid sequence comprising SEQ ID NO: 172. In some embodiments, the purified microbial population comprises a bacterium with a 16S nucleic acid sequence sharing at least 97% sequence identity with SEQ ID NO: 237. In some embodiments, the purified microbial population comprises a bacterium with a 16S nucleic acid sequence comprising SEQ ID NO: 237. In some embodiments, the purified microbial population comprises a bacterium with a 16S nucleic acid sequence sharing at least 97% sequence identity with SEQ ID NO: 326. In some embodiments, the purified microbial population comprises a bacterium with a 16S nucleic acid sequence comprising SEQ ID NO: 326. In some embodiments, the purified microbial population comprises a bacterium with a 16S nucleic acid sequence sharing at least 97% sequence identity with SEQ ID NO: 327. In some embodiments, the purified microbial population comprises a bacterium with a 16S nucleic acid sequence comprising SEQ ID NO: 327. In some embodiments, the purified microbial population comprises a bacterium with a 16S nucleic acid sequence sharing at least 97% sequence identity with SEQ ID NO: 328. In some embodiments, the purified microbial population comprises a bacterium with a 16S nucleic acid sequence comprising SEQ ID NO: 328. In some embodiments, the purified microbial population comprises a bacterium with a 16S nucleic acid sequence sharing at least 97% sequence identity with SEQ ID NO: 329. In some embodiments, the purified microbial population comprises a bacterium with a 16S nucleic acid sequence comprising SEQ ID NO: 329. In some embodiments, the purified microbial population comprises a bacterium with a 16S nucleic acid sequence sharing at least 97% sequence identity with SEQ ID NO: 330. In some embodiments, the purified microbial population comprises a bacterium with a 16S nucleic acid sequence comprising SEQ ID NO: 330. In some embodiments, the purified microbial population comprises a bacterium with a 16S nucleic acid sequence sharing at least 97% sequence identity with SEQ ID NO: 331. In some embodiments, the purified microbial population comprises a bacterium with a 16S nucleic acid sequence comprising SEQ ID NO: 331. In some embodiments, the one or more bacteria comprises a 16S nucleic acid sequence that shares at least 97% sequence identity with a nucleic acid sequence selected from SEQ ID NOs: 19, 172, 237, and 326-331. In some embodiments, the one or more bacteria comprises a 16S nucleic acid sequence selected from SEQ ID NOs: 19, 172, 237, and 326-331. In some embodiments, the one or more bacteria comprises a 16S nucleic acid sequence that shares at least 97% sequence identity with SEQ ID NOs: 19, 172, and 326. In some embodiments, the one or more bacteria comprises a 16S nucleic acid sequence of SEQ ID NOs: 19, 172, and 326. In some embodiments, the one or more bacteria comprises a 16S nucleic acid sequence that shares at least 97% sequence identity with SEQ ID NOs: 19, 172, 237, 326, 328, 330, and 331. In some embodiments, the one or more bacteria comprises a 16S nucleic acid sequence of SEQ ID NOs: 19, 172, 237, 326, 328, 330, and 331.

In some embodiments, the microbial composition is comprised of spores. In some embodiments, the microbial composition is embedded in a wax. In some embodiments, the microbial composition is encapsulated. In some embodiments, the encapsulated microbial composition comprises a polymer selected from the group consisting of: a saccharide polymer, an agar polymer, an agarose polymer, a protein polymer, and a lipid polymer. In some embodiments, the microbial composition is preserved in a glass matrix.

In some embodiments, the one or more carriers are selected from the group consisting of: an edible feed grade material, an aluminosilicate-containing mineral, a zeolite, calcium carbonate, a prebiotic, and a flavoring agent. In some embodiments, the prebiotic is an inulin, an oligosaccharide, and/or a vitamin. In some embodiments, the one or more carriers are inulin, calcium carbonate, activated charcoal, and/or yucca. In some embodiments, the flavoring agent is dried yeast, cheese flavoring, beef flavoring, fish flavoring, chicken flavoring, and/or pork flavoring.

In some embodiments, the one or more bacteria is present in the composition at a concentration of about $10^2$ to about $10^{15}$ cells per gram of said composition. In some embodiments, the one or more bacteria is present in the composition at a concentration of at least $10^2$ cells per gram of said composition.

In some embodiments, the microbial composition is mixed with or sprinkled on top of animal feed. In some embodiments, the microbial composition is formulated as a tablet, a pill, a capsule, a powder, a solution, a suspension, or an emulsion. In some embodiments, the microbial composition is formulated as a pill. In some embodiments, the microbial composition is formulated as a food. In some embodiments, the microbial composition is formulated as a dry food, a wet food, a kibble, or a raw food.

In some embodiments, the present disclosure provides a microbial composition comprising: (a) at least one isolated microbial strain selected from the group consisting of: (i) Ascusk9_546A deposited as NRRL Accession Deposit No. B-67972; (ii) Ascusk9_672A deposited as NRRL Accession Deposit No. B-67973; (iii) Ascusk9_210B deposited as NRRL Accession Deposit No. B-67974; (iv) Ascusk9_51G deposited as NRRL Accession Deposit No. B-67975; (v) Ascusk9_33E deposited as NRRL Accession Deposit No. B-67976; (vi) Ascusk9_0G deposited as NRRL Accession Deposit No. B-67977; (vii) Ascusk9_38A deposited as NRRL Accession Deposit No. B-67987; (viii) Ascusk9_17A deposited as NRRL Accession Deposit No. B-67986; and (ix) Ascusk 9_2A deposited as NRRL Accession Deposit No. B-67985; and (b) one or more carriers suitable for canine administration.

In some embodiments, the present disclosure provides a method of imparting at least one desirable trait in a canine, the method comprising administration of the microbial composition described herein to the canine. In some embodiments, the at least one desirable trait is selected from the group consisting of: improved fecal consistency, increased regular bowel movements, reduced incidence of diarrhea, reduced incidence of constipation, less straining during defecation, reduced side-effects from antibiotics, improved dental health, brighter eyes, increased energy, increased appetite, improved fur and coat quality, decreased incidence of infectious or non-infectious disease, increased lifespan, and/or improved performance of the canine.

In some embodiments, the present disclosure provides a method of maintaining or improving gastrointestinal health in a canine, the method comprising administration of the microbial composition described herein to the canine.

In some embodiments, the present disclosure provides a method of treating or preventing gastrointestinal dysbiosis or gastrointestinal enteropathy in a canine, the method comprising administration of the microbial composition described herein to the canine. In some embodiments, the microbial composition reduces the incidence of diarrhea, improves fecal consistency, reduces straining during defecation, reduces constipation, increases regular bowel movements, reduces dysbiosis, and/or reduces enteropathy in the canine.

In some embodiments, the present disclosure provides a method of modulating the microbiome of a canine, the method comprising administering the composition described herein to the canine. In some embodiments, the modulation of the microbiome is an increase in the proportion of the one or more bacteria of the microbiome, wherein the increase is measured relative to a canine that did not have the one or more bacteria administered. In some embodiments, the modulation of the microbiome is a decrease in the proportion of the one or more bacteria present in the microbiome prior to the administration of the composition, wherein the decrease is measured relative to the microbiome of the canine prior to the administration of the composition.

In some embodiments, the present disclosure provides a method of increasing resistance of a canine to the colonization of pathogenic microbes, the method comprising the administration of the composition described herein, wherein the pathogen's ability to colonize the gastrointestinal tract of the canine is reduced.

In some embodiments, the present disclosure provides a method of treating a canine for the presence of at least one pathogenic microbe, the method comprising administration of the composition described herein. In some embodiments, after administration of the composition the relative abundance of the at least one pathogenic microbe decreases to less than 5% relative abundance in the gastrointestinal tract. In some embodiments, the relative abundance of the at least one pathogenic microbe decreases to less than 1% relative abundance in the gastrointestinal tract. In some embodiments, the at least one pathogenic microbe is undetectable in the gastrointestinal tract.

In some embodiments, the microbial composition is administered once per day throughout the lifetime of a canine. In some embodiments, the microbial composition is administered twice per day throughout the lifetime of a canine. In some embodiments, the microbial composition is administered to the canine once per day, twice per day, three times per day, once per week, twice per week, three times per week, once every two weeks, or once per month over a one month period, two month period, three month period, six month period, or twelve month period.

In some embodiments, the present disclosure provides a canine feed supplement capable of increasing a desirable phenotypic trait in a canine, the feed supplement comprising: (a) a microbial composition described herein present at a concentration that does not occur naturally in the canine; and (b) an acceptable carrier.

In some embodiments, the present disclosure provides a canine feed supplement capable of increasing a desirable phenotypic trait in a canine, the feed supplement comprising: (a) one or more bacteria comprising a 16S nucleic acid sequence that shares at least 97% sequence identity with SEQ ID NOs: 19, 172, and 326; and (b) an acceptable carrier; wherein the one or more bacteria are present in the canine feed supplement at a concentration of at least $10^2$ cells per gram of said composition.

In some embodiments, the present disclosure provides a canine feed supplement for treating or preventing gastrointestinal dysbiosis or gastrointestinal enteropathy in a canine, the feed supplement comprising: (a) one or more bacteria comprising a 16S nucleic acid sequence that shares at least 97% sequence identity with SEQ ID NOs: 19, 172, 237, 326, 328, 330, and 331; and (b) an acceptable carrier; wherein the one or more bacteria are present in the canine feed supplement at a concentration of at least $10^2$ cells per gram of said composition.

In some embodiments, the present disclosure provides a canine feed supplement capable of increasing a desirable phenotypic trait in a canine, the feed supplement comprising a *Megamonas* sp. and an acceptable carrier; wherein the *Megamonas* sp. is present in the canine feed supplement at a concentration of at least $10^2$ cells per gram of said composition.

In some embodiments, the present disclosure provides a canine feed supplement for treating or preventing gastrointestinal dysbiosis or gastrointestinal enteropathy in a canine, the feed supplement comprising a *Megamonas* sp. and an acceptable carrier; wherein the *Megamonas* sp. is present in the canine feed supplement at a concentration of at least $10^2$ cells per gram of said composition.

In some embodiments, the present disclosure provides an isolated microbial strain selected from any one of the microbial strains in Table 1.

In some embodiments, the present disclosure provides an isolated microbial strain selected from the group consisting of: (a) Ascusk9_546A deposited as NRRL Accession Deposit No. B-67972; (b) Ascusk9_672A deposited as NRRL Accession Deposit No. B-67973; (c) Ascusk9_210B deposited as NRRL Accession Deposit No. B-67974; (d) Ascusk9_51G deposited as NRRL Accession Deposit No. B-67975; (e) Ascusk9_33E deposited as NRRL Accession Deposit No. B-67976; (f) Ascusk9_0G deposited as NRRL Accession Deposit No. B-67977; (g) Ascusk9_38A deposited as NRRL Accession Deposit No. B-67987; (h) Ascusk9_17A deposited as NRRL Accession Deposit No. B-67986; and (i) Ascusk9_2A deposited as NRRL Accession Deposit No. B-67985.

In some embodiments, the present disclosure provides an isolated microbial strain comprising a polynucleotide sequence sharing at least 90% sequence identity with any one of SEQ ID NOs: 1-333.

In some embodiments, the present disclosure provides a substantially pure culture of an isolated microbial strain described herein.

Budapest Treaty on the International Recognition of the Deposit of Microorganisms for the Purpose of Patent Procedures Some microorganisms described in this application were deposited with the United States Department of Agriculture (USDA) Agricultural Research Service (ARS) Culture Collection (NRRL®), located at 1815 N. University St., Peoria, IL 61604, USA. Some microorganisms described in this application were deposited with the Bigelow National Center for Marine Algae and Microbiota, located at 60 Bigelow Drive, East Boothbay, Maine 04544, USA. Some microorganisms described in this application were deposited with the American Type Culture Collection (ATCC), located at 10801 University Boulevard, Manassas, Virginia 20108, USA.

The deposits were made under the terms of the Budapest Treaty on the International Recognition of the Deposit of Microorganisms for the Purposes of Patent Procedure. The ATCC, NRRL, and Bigelow National Center for Marine Algae and Microbiota accession numbers and corresponding dates of deposit are provided in Table 1.

In Table 1, the closest taxonomy predicted using the BLAST algorithm of the microbes are listed in column 1. The strains designated in the below table have been deposited in the labs of Native Microbials, Inc. since at least April 2019.

TABLE 1

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Prevotella copri* | Ascusk9_16 | SEQ ID NO: 1 | 0.999122033 | |
| *Prevotella copri* | Ascusk9_16A | SEQ ID NO: 2 | 0.999122033 | |
| *Prevotella copri* | Ascusk9_16B | SEQ ID NO: 3 | 0.999122033 | |
| *Prevotella copri* | Ascusk9_16C | SEQ ID NO: 4 | 0.999122033 | |
| *Prevotella copri* | Ascusk9_16D | SEQ ID NO: 5 | 0.999122033 | |
| *Prevotella copri* | Ascusk9_16E | SEQ ID NO: 6 | 0.999122033 | |
| *Prevotella copri* | Ascusk9_16F | SEQ ID NO: 7 | 0.999122033 | Bigelow, PATENT202012110 (18 Dec. 2020) Bigelow, PATENT202012112 (18 Dec. 2020) |
| *Prevotella copri* | Ascusk9_16G | SEQ ID NO: 8 | 0.999122033 | Bigelow, PATENT202012112 (18 Dec. 2020) |
| *Prevotella copri* | Ascusk9_16H | SEQ ID NO: 9 | 0.999122033 | Bigelow, PATENT202012112 (18 Dec. 2020) |
| *Prevotella copri* | Ascusk9_16I | SEQ ID NO: 10 | 0.999122033 | |
| *Prevotella copri* | Ascusk9_16J | SEQ ID NO: 11 | 0.999122033 | |
| *Megamonas funiformis* | Ascusk9_51 | SEQ ID NO: 12 | 0.983105245 | |
| *Megamonas funiformis* | Ascusk9_51A | SEQ ID NO: 13 | 0.983105245 | Bigelow, PATENT202012110 (18 Dec. 2020) Bigelow, PATENT202012112 (18 Dec. 2020) |
| *Megamonas funiformis* | Ascusk9_51B | SEQ ID NO: 14 | 0.983105245 | |
| *Megamonas funiformis* | Ascusk9_51C | SEQ ID NO: 15 | 0.983105245 | |
| *Megamonas funiformis* | Ascusk9_51D | SEQ ID NO: 16 | 0.983105245 | Bigelow, PATENT202012110 (18 Dec. 2020) |
| *Megamonas funiformis* | Ascusk9_51E | SEQ ID NO: 17 | 0.983105245 | Bigelow, PATENT202012110 (18 Dec. 2020) Bigelow, PATENT202012112 (18 Dec. 2020) |
| *Megamonas funiformis* | Ascusk9_51F | SEQ ID NO: 18 | 0.983105245 | Bigelow, PATENT202012110 (18 Dec. 2020) Bigelow, PATENT202012112 (18 Dec. 2020) |
| *Megamonas funiformis* | Ascusk9_51G | SEQ ID NO: 19 | 0.983105245 | NRRL, B-67975 (17 Jul. 2020) Bigelow, PATENT202012110 (18 Dec. 2020) Bigelow, PATENT202012111 (18 Dec. 2020) Bigelow, PATENT202012112 (18 Dec. 2020) |
| *Megamonas funiformis* | Ascusk9_51H | SEQ ID NO: 20 | 0.983105245 | |
| *Megamonas funiformis* | Ascusk9_51I | SEQ ID NO: 21 | 0.983105245 | Bigelow, PATENT202012110 (18 Dec. 2020) |
| *Megamonas funiformis* | Ascusk9_51J | SEQ ID NO: 22 | 0.983105245 | Bigelow, PATENT202012110 (18 Dec. 2020) Bigelow, PATENT202012112 (18 Dec. 2020) |
| *Ruminococcus faecis* | Ascusk9_29 | SEQ ID NO: 23 | 0.975866219 | |
| *Eubacterium nitritogenes* | Ascusk9_672 | SEQ ID NO: 24 | 0.975866219 | |
| *Eubacterium hallii* | Ascusk9_52 | SEQ ID NO: 25 | 0.971477338 | |
| *Eubacterium hallii* | Ascusk9_52A | SEQ ID NO: 26 | 0.971477338 | Bigelow, PATENT202012110 (18 Dec. 2020) |
| *Eubacterium hallii* | Ascusk9_52B | SEQ ID NO: 27 | 0.971477338 | |
| *Eubacterium hallii* | Ascusk9_52C | SEQ ID NO: 28 | 0.971477338 | |
| *Eubacterium hallii* | Ascusk9_52D | SEQ ID NO: 29 | 0.971477338 | |
| *Eubacterium hallii* | Ascusk9_52E | SEQ ID NO: 30 | 0.971477338 | |
| *Eubacterium hallii* | Ascusk9_52F | SEQ ID NO: 31 | 0.971477338 | |
| *Prevotella bryantii* | Ascusk9_467 | SEQ ID NO: 32 | 0.968627193 | |
| *Prevotella bryantii* | Ascusk9_467A | SEQ ID NO: 33 | 0.968627193 | |
| *Prevotella bryantii* | Ascusk9_467B | SEQ ID NO: 332 | 0.968627193 | Bigelow, PATENT202012110 (18 Dec. 2020) |
| *Anaerobiospirillum succiniciproducens* | Ascusk9_32 | SEQ ID NO: 34 | 0.964238312 | |
| *Catenibacterium mitsuokai* | Ascusk9_281 | SEQ ID NO: 35 | 0.964238312 | |
| *Eubacterium infirmum* | Ascusk9_156 | SEQ ID NO: 36 | 0.959849431 | |
| *Holdemanella biformis* | Ascusk9_154 | SEQ ID NO: 37 | 0.959849431 | |
| *Clostridium hiranonis* | Ascusk9_13 | SEQ ID NO: 38 | 0.959849431 | |
| *Catenibacterium mitsuokai* | Ascusk9_760 | SEQ ID NO: 39 | 0.95546055 | |
| *Allobaculum stercoricanis* | Ascusk9_8 | SEQ ID NO: 40 | 0.95546055 | |
| *Allobaculum stercoricanis* | Ascusk9_8A | SEQ ID NO: 41 | 0.95546055 | Bigelow, PATENT202012110 (18 Dec. 2020) Bigelow, PATENT202012112 (18 Dec. 2020) |
| *Prevotella copri* | Ascusk9_148 | SEQ ID NO: 42 | 0.95546055 | |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Prevotella copri* | Ascusk9_148A | SEQ ID NO: 43 | 0.95546055 | Bigelow, PATENT202012112 (18 Dec. 2020) |
| *Prevotella copri* | Ascusk9_148J | SEQ ID NO: 44 | 0.95546055 | |
| *Prevotella copri* | Ascusk9_148B | SEQ ID NO: 45 | 0.95546055 | Bigelow, PATENT202012110 (18 Dec. 2020) |
| *Prevotella copri* | Ascusk9_148C | SEQ ID NO: 46 | 0.95546055 | |
| *Prevotella copri* | Ascusk9_148D | SEQ ID NO: 47 | 0.95546055 | |
| *Prevotella copri* | Ascusk9_148E | SEQ ID NO: 48 | 0.95546055 | Bigelow, PATENT202012110 (18 Dec. 2020) Bigelow, PATENT202012112 (18 Dec. 2020) |
| *Prevotella copri* | Ascusk9_148F | SEQ ID NO: 49 | 0.95546055 | Bigelow, PATENT202012112 (18 Dec. 2020) |
| *Prevotella copri* | Ascusk9_148G | SEQ ID NO: 50 | 0.95546055 | Bigelow, PATENT202012110 (18 Dec. 2020) |
| *Prevotella copri* | Ascusk9_148H | SEQ ID NO: 51 | 0.95546055 | Bigelow, PATENT202012110 (18 Dec. 2020) |
| *Prevotella copri* | Ascusk9_148I | SEQ ID NO: 52 | 0.95546055 | Bigelow, PATENT202012112 (18 Dec. 2020) |
| *Morganella morganii* | Ascusk9_443 | SEQ ID NO: 53 | 0.95546055 | |
| *Acidicaldus organivorans* | Ascusk9_739 | SEQ ID NO: 54 | 0.948221524 | |
| *Eubacterium hallii* | Ascusk9_486 | SEQ ID NO: 55 | 0.943832643 | |
| *Parasutterella excrementihominis* | Ascusk9_563 | SEQ ID NO: 56 | 0.943832643 | |
| *Ruminococcus torques* | Ascusk9_20 | SEQ ID NO: 57 | 0.943832643 | |
| *Ruminococcus torques* | Ascusk9_20A | SEQ ID NO: 58 | 0.943832643 | |
| *Ruminococcus torques* | Ascusk9_20B | SEQ ID NO: 59 | 0.943832643 | |
| *Ruminococcus torques* | Ascusk9_20C | SEQ ID NO: 60 | 0.943832643 | |
| *Collinsella intestinalis* | Ascusk9_761 | SEQ ID NO: 61 | 0.943832643 | |
| *Blautia wexlerae* | Ascusk9_88 | SEQ ID NO: 62 | 0.943832643 | |
| *Blautia wexlerae* | Ascusk9_88A | SEQ ID NO: 63 | 0.943832643 | |
| *Blautia wexlerae* | Ascusk9_88B | SEQ ID NO: 64 | 0.943832643 | |
| *Blautia wexlerae* | Ascusk9_88C | SEQ ID NO: 65 | 0.943832643 | Bigelow, PATENT202012111 (18 Dec. 2020) |
| *Blautia wexlerae* | Ascusk9_88D | SEQ ID NO: 66 | 0.943832643 | Bigelow, PATENT202012110 (18 Dec. 2020) Bigelow, PATENT202012111 (18 Dec. 2020) Bigelow, PATENT202012112 (18 Dec. 2020) |
| *Blautia wexlerae* | Ascusk9_88E | SEQ ID NO: 67 | 0.943832643 | |
| *Eubacterium tarantellae* | Ascusk9_89 | SEQ ID NO: 68 | 0.943832643 | |
| *Bacteroides plebeius* | Ascusk9_723 | SEQ ID NO: 69 | 0.943832643 | |
| *Prevotella oulorum* | Ascusk9_728 | SEQ ID NO: 70 | 0.940982498 | |
| *Prevotella oulorum* | Ascusk9_728A | SEQ ID NO: 71 | 0.940982498 | Bigelow, PATENT202012112 (18 Dec. 2020) |
| *Prevotella oulorum* | Ascusk9_728B | SEQ ID NO: 72 | 0.940982498 | |
| *Bacillus huizhouensis* | Ascusk9_746 | SEQ ID NO: 73 | 0.938863149 | |
| *Lactonifactor longoviformis* | Ascusk9_144 | SEQ ID NO: 74 | 0.926261167 | |
| *Lactonifactor longoviformis* | Ascusk9_144A | SEQ ID NO: 75 | 0.926261167 | |
| *Lactonifactor longoviformis* | Ascusk9_144B | SEQ ID NO: 76 | 0.926261167 | |
| *Lactonifactor longoviformis* | Ascusk9_144C | SEQ ID NO: 77 | 0.926261167 | |
| *Lactonifactor longoviformis* | Ascusk9_144D | SEQ ID NO: 78 | 0.926261167 | |
| *Lactonifactor longoviformis* | Ascusk9_144E | SEQ ID NO: 79 | 0.926261167 | Bigelow, PATENT202012110 (18 Dec. 2020) |
| *Lactonifactor longoviformis* | Ascusk9_144F | SEQ ID NO: 80 | 0.926261167 | |
| *Lactonifactor longoviformis* | Ascusk9_144G | SEQ ID NO: 81 | 0.926261167 | Bigelow, PATENT202012110 (18 Dec. 2020) Bigelow, PATENT202012112 (18 Dec. 2020) |
| *Lactonifactor longoviformis* | Ascusk9_144H | SEQ ID NO: 82 | 0.926261167 | |
| *Lactonifactor longoviformis* | Ascusk9_144I | SEQ ID NO: 83 | 0.926261167 | |
| *Lactonifactor longoviformis* | Ascusk9_144J | SEQ ID NO: 84 | 0.926261167 | |
| *Bacteroides plebeius* | Ascusk9_11 | SEQ ID NO: 85 | 0.92496571 | |
| *Bacteroides plebeius* | Ascusk9_11A | SEQ ID NO: 86 | 0.92496571 | |
| *Bacteroides plebeius* | Ascusk9_11B | SEQ ID NO: 87 | 0.92496571 | Bigelow, PATENT202012110 (18 Dec. 2020) Bigelow, PATENT202012111 (18 Dec. 2020) Bigelow, PATENT202012112 (18 Dec. 2020) |
| Bacteroides plebeius | Ascusk9_11C | SEQ ID NO: 88 | 0.92496571 | |
| *Bacteroides plebeius* | Ascusk9_11D | SEQ ID NO: 89 | 0.92496571 | |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Bacteroides plebeius* | Ascusk9_11E | SEQ ID NO: 90 | 0.92496571 | |
| *Bacteroides plebeius* | Ascusk9_11F | SEQ ID NO: 91 | 0.92496571 | |
| *Bacteroides plebeius* | Ascusk9_11G | SEQ ID NO: 92 | 0.92496571 | Bigelow, PATENT202012110 (18 Dec. 2020) Bigelow, PATENT202012111 (18 Dec. 2020) Bigelow, PATENT202012112 (18 Dec. 2020) |
| *Bacteroides plebeius* | Ascusk9_11H | SEQ ID NO: 93 | 0.92496571 | |
| *Bacteroides plebeius* | Ascusk9_11I | SEQ ID NO: 94 | 0.92496571 | Bigelow, PATENT202012110 (18 Dec. 2020) Bigelow, PATENT202012111 (18 Dec. 2020) Bigelow, PATENT202012112 (18 Dec. 2020) |
| *Bacteroides plebeius* | Ascusk9_11J | SEQ ID NO: 95 | 0.92496571 | |
| *Brevundimonas faecalis* | Ascusk9_663 | SEQ ID NO: 96 | 0.923426975 | |
| *Murimonas intestini* | Ascusk9_221 | SEQ ID NO: 97 | 0.920576829 | |
| *Dialister succinatiphilus* | Ascusk9_237 | SEQ ID NO: 98 | 0.918929045 | |
| *Actinomyces coleocanis* | Ascusk9_402 | SEQ ID NO: 99 | 0.912513911 | |
| *Coprococcus comes* | Ascusk9_429 | SEQ ID NO: 100 | 0.912294519 | |
| *Coprococcus comes* | Ascusk9_429A | SEQ ID NO: 101 | 0.912294519 | |
| *Coprococcus comes* | Ascusk9_429B | SEQ ID NO: 102 | 0.912294519 | |
| *Coprococcus comes* | Ascusk9_429C | SEQ ID NO: 103 | 0.912294519 | Bigelow, PATENT202012110 (18 Dec. 2020) |
| *Coprococcus comes* | Ascusk9_429D | SEQ ID NO: 104 | 0.912294519 | |
| *Coprococcus comes* | Ascusk9_429E | SEQ ID NO: 105 | 0.912294519 | Bigelow, PATENT202012110 (18 Dec. 2020) |
| *Coprococcus comes* | Ascusk9_429F | SEQ ID NO: 106 | 0.912294519 | |
| *Coprococcus comes* | Ascusk9_429G | SEQ ID NO: 107 | 0.912294519 | |
| *Coprococcus comes* | Ascusk9_429H | SEQ ID NO: 108 | 0.912294519 | Bigelow, PATENT202012110 (18 Dec. 2020) |
| *Ruminococcus callidus* | Ascusk9_565 | SEQ ID NO: 109 | 0.911799068 | |
| *Bacteroides dorei* | Ascusk9_566 | SEQ ID NO: 110 | 0.911799068 | |
| *Clostridium septicum* | Ascusk9_691 | SEQ ID NO: 111 | 0.911799068 | |
| *Blautia schinkii* | Ascusk9_692 | SEQ ID NO: 112 | 0.911799068 | |
| *Cellulosilyticum ruminicola* | Ascusk9_317 | SEQ ID NO: 113 | 0.910975176 | |
| *Cellulosilyticum ruminicola* | Ascusk9_317A | SEQ ID NO: 114 | 0.910975176 | |
| *Acetanaerobacterium elongatum* | Ascusk9_100 | SEQ ID NO: 115 | 0.910975176 | |
| *Faecalibacterium prausnitzii* | Ascusk9_10 | SEQ ID NO: 116 | 0.910487658 | |
| *Faecalibacterium prausnitzii* | Ascusk9_10A | SEQ ID NO: 117 | 0.910487658 | |
| *Faecalibacterium prausnitzii* | Ascusk9_10B | SEQ ID NO: 118 | 0.910487658 | Bigelow, PATENT202012110 (18 Dec. 2020) Bigelow, PATENT202012112 (18 Dec. 2020) |
| *Faecalibacterium prausnitzii* | Ascusk9_10C | SEQ ID NO: 119 | 0.910487658 | |
| *Faecalibacterium prausnitzii* | Ascusk9_10D | SEQ ID NO: 120 | 0.910487658 | |
| *Faecalibacterium prausnitzii* | Ascusk9_10E | SEQ ID NO: 121 | 0.910487658 | |
| *Faecalibacterium prausnitzii* | Ascusk9_10F | SEQ ID NO: 122 | 0.910487658 | Bigelow, PATENT202012110 (18 Dec. 2020) Bigelow, PATENT202012112 (18 Dec. 2020) |
| *Faecalibacterium prausnitzii* | Ascusk9_10G | SEQ ID NO: 123 | 0.910487658 | Bigelow, PATENT202012110 (18 Dec. 2020) Bigelow, PATENT202012112 (18 Dec. 2020) |
| *Faecalibacterium prausnitzii* | Ascusk9_10H | SEQ ID NO: 124 | 0.910487658 | |
| *Faecalibacterium prausnitzii* | Ascusk9_10I | SEQ ID NO: 125 | 0.910487658 | |
| *Faecalibacterium prausnitzii* | Ascusk9_10J | SEQ ID NO: 126 | 0.910487658 | |
| *Murimonas intestini* | Ascusk9_1 | SEQ ID NO: 127 | 0.906829574 | |
| *Clostridium nexile* | Ascusk9_403 | SEQ ID NO: 128 | 0.90667939 | |
| *Ruminococcus torques* | Ascusk9_748 | SEQ ID NO: 129 | 0.898616472 | |
| *Parabacteroides merdae* | Ascusk9_509 | SEQ ID NO: 130 | 0.896497123 | |
| *Parabacteroides merdae* | Ascusk9_509A | SEQ ID NO: 131 | 0.896497123 | |
| *Parabacteroides merdae* | Ascusk9_509B | SEQ ID NO: 132 | 0.896497123 | |
| *Parabacteroides merdae* | Ascusk9_509C | SEQ ID NO: 133 | 0.896497123 | |
| *Parabacteroides merdae* | Ascusk9_509D | SEQ ID NO: 134 | 0.896497123 | |
| *Parabacteroides merdae* | Ascusk9_509E | SEQ ID NO: 135 | 0.896497123 | |
| *Parabacteroides merdae* | Ascusk9_509F | SEQ ID NO: 136 | 0.896497123 | |
| Parabacteroides merdae | Ascusk9_509G | SEQ ID NO: 137 | 0.896497123 | |
| *Clostridium hylemonae* | Ascusk9_33 | SEQ ID NO: 138 | 0.894621053 | |
| *Clostridium hylemonae* | Ascusk9_33A | SEQ ID NO: 139 | 0.894621053 | |
| *Clostridium hylemonae* | Ascusk9_33B | SEQ ID NO: 140 | 0.894621053 | Bigelow, PATENT202012110 (18 Dec. 2020) |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Clostridium hylemonae* | Ascusk9_33C | SEQ ID NO: 141 | 0.894621053 | Bigelow, PATENT202012112 (18 Dec. 2020) |
| *Clostridium hylemonae* | Ascusk9_33D | SEQ ID NO: 142 | 0.894621053 | Bigelow, PATENT202012110 (18 Dec. 2020) |
| *Cetobacterium somerae* | Ascusk9_315 | SEQ ID NO: 143 | 0.892932135 | |
| *Clostridium spiroforme* | Ascusk9_5 | SEQ ID NO: 144 | 0.891770908 | |
| *Clostridium spiroforme* | Ascusk9_5A | SEQ ID NO: 145 | 0.891770908 | |
| *Clostridium spiroforme* | Ascusk9_5B | SEQ ID NO: 146 | 0.891770908 | |
| *Odoribacter laneus* | Ascusk9_298 | SEQ ID NO: 147 | 0.891770908 | |
| *Clostridium cocleatum* | Ascusk9_25 | SEQ ID NO: 148 | 0.891308238 | |
| *Clostridium cocleatum* | Ascusk9_25A | SEQ ID NO: 149 | 0.891308238 | |
| *Clostridium cocleatum* | Ascusk9_25B | SEQ ID NO: 150 | 0.891308238 | Bigelow, PATENT202012110 (18 Dec. 2020) |
| *Terrisporobacter glycolicus* | Ascusk9_481 | SEQ ID NO: 151 | 0.889014818 | |
| *Bacteroides eggerthii* | Ascusk9_498 | SEQ ID NO: 152 | 0.887382027 | |
| *Turicibacter sanguinis* | Ascusk9_217 | SEQ ID NO: 153 | 0.885380621 | |
| *Turicibacter sanguinis* | Ascusk9_217A | SEQ ID NO: 154 | 0.885380621 | Bigelow, PATENT202012110 (18 Dec. 2020) |
| *Eubacterium coprostanoligenes* | Ascusk9_622 | SEQ ID NO: 155 | 0.884154373 | |
| *Fusicatenibacter saccarivorans* | Ascusk9_240 | SEQ ID NO: 156 | 0.88357376 | |
| *Blautia wexlerae* | Ascusk9_7 | SEQ ID NO: 157 | 0.88357376 | |
| *Bacteroides sartorii* | Ascusk9_508 | SEQ ID NO: 158 | 0.883423576 | |
| *Clostridium bolteae* | Ascusk9_176 | SEQ ID NO: 159 | 0.883196251 | |
| *Clostridium bolteae* | Ascusk9_176A | SEQ ID NO: 160 | 0.883196251 | |
| *Clostridium bolteae* | Ascusk9_176B | SEQ ID NO: 161 | 0.883196251 | |
| *Clostridium bolteae* | Ascusk9_176C | SEQ ID NO: 162 | 0.883196251 | |
| *Clostridium bolteae* | Ascusk9_176D | SEQ ID NO: 163 | 0.883196251 | Bigelow, PATENT202012110 (18 Dec. 2020) |
| *Clostridium bolteae* | Ascusk9_176E | SEQ ID NO: 164 | 0.883196251 | |
| *Clostridium hiranonis* | Ascusk9_0 | SEQ ID NO: 165 | 0.881304228 | |
| *Clostridium hiranonis* | Ascusk9_0A | SEQ ID NO: 166 | 0.881304228 | |
| *Clostridium hiranonis* | Ascusk9_0B | SEQ ID NO: 167 | 0.881304228 | Bigelow, PATENT202012110 (18 Dec. 2020) Bigelow, PATENT202012111 (18 Dec. 2020) Bigelow, PATENT202012112 (18 Dec. 2020) |
| *Clostridium hiranonis* | Ascusk9_0C | SEQ ID NO: 168 | 0.881304228 | |
| *Clostridium hiranonis* | Ascusk9_0D | SEQ ID NO: 169 | 0.881304228 | Bigelow, PATENT202012112 (18 Dec. 2020) |
| *Clostridium hiranonis* | Ascusk9_0E | SEQ ID NO: 170 | 0.881304228 | |
| *Clostridium hiranonis* | Ascusk9_0F | SEQ ID NO: 171 | 0.881304228 | Bigelow, PATENT202012110 (18 Dec. 2020) Bigelow, PATENT202012111 (18 Dec. 2020) Bigelow, PATENT202012112 (18 Dec. 2020) |
| *Clostridium hiranonis* | Ascusk9_0G | SEQ ID NO: 172 | 0.881304228 | NRRL, B-67977 (17 Jul. 2020) Bigelow, PATENT202012110 (18 Dec. 2020) Bigelow, PATENT202012111 (18 Dec. 2020) Bigelow, PATENT202012112 (18 Dec. 2020) |
| *Clostridium hiranonis* | Ascusk9_0H | SEQ ID NO: 173 | 0.881304228 | |
| *Clostridium hiranonis* | Ascusk9_0I | SEQ ID NO: 174 | 0.881304228 | Bigelow, PATENT202012110 (18 Dec. 2020) Bigelow, PATENT202012111 (18 Dec. 2020) Bigelow, PATENT202012112 (18 Dec. 2020) |
| *Clostridium hiranonis* | Ascusk9_0J | SEQ ID NO: 175 | 0.881304228 | |
| *Megamonas funiformis* | Ascusk9_526 | SEQ ID NO: 176 | 0.880723614 | |
| *Murimonas intestini* | Ascusk9_116 | SEQ ID NO: 177 | 0.877049577 | |
| *Murimonas intestini* | Ascusk9_116A | SEQ ID NO: 178 | 0.877049577 | |
| *Murimonas intestini* | Ascusk9_116B | SEQ ID NO: 179 | 0.877049577 | |
| *Murimonas intestini* | Ascusk9_116C | SEQ ID NO: 180 | 0.877049577 | Bigelow, PATENT202012110 (18 Dec. 2020) |
| Kandleria vitulina | Ascusk9_537 | SEQ ID NO: 181 | 0.876915347 | |
| *Bacteroides coprocola* | Ascusk9_59 | SEQ ID NO: 182 | 0.867179463 | |
| *Bacteroides coprocola* | Ascusk9_59A | SEQ ID NO: 183 | 0.867179463 | Bigelow, PATENT202012110 (18 Dec. 2020) |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Bacteroides coprocola* | Ascusk9_59B | SEQ ID NO: 184 | 0.867179463 | |
| *Bacteroides coprocola* | Ascusk9_59C | SEQ ID NO: 185 | 0.867179463 | |
| *Bacteroides coprocola* | Ascusk9_59D | SEQ ID NO: 186 | 0.867179463 | |
| *Bacteroides coprocola* | Ascusk9_59E | SEQ ID NO: 187 | 0.867179463 | |
| *Bacteroides coprocola* | Ascusk9_59F | SEQ ID NO: 188 | 0.867179463 | |
| *Bacteroides coprocola* | Ascusk9_59G | SEQ ID NO: 189 | 0.867179463 | Bigelow, PATENT202012110 (18 Dec. 2020) Bigelow, PATENT202012111 (18 Dec. 2020) Bigelow, PATENT202012112 (18 Dec. 2020) |
| *Bacteroides coprocola* | Ascusk9_59H | SEQ ID NO: 190 | 0.867179463 | |
| *Bacteroides coprocola* | Ascusk9_59I | SEQ ID NO: 191 | 0.867179463 | |
| *Bacteroides coprocola* | Ascusk9_59J | SEQ ID NO: 192 | 0.867179463 | Bigelow, PATENT202012110 (18 Dec. 2020) |
| *Clostridum nexile* | Ascusk9_464 | SEQ ID NO: 193 | 0.866245562 | |
| *Sarcina Maxima* | Ascusk9_735 | SEQ ID NO: 194 | 0.865100289 | |
| *Allobaculum stercoricanis* | Ascusk9_482 | SEQ ID NO: 195 | 0.865044161 | |
| *Butyricicoccus pullicaecorum* | Ascusk9_207 | SEQ ID NO: 196 | 0.863882934 | |
| *Veillonella ratti* | Ascusk9_204 | SEQ ID NO: 197 | 0.862924812 | |
| *Acinetobacter tjernbergiae* | Ascusk9_595 | SEQ ID NO: 198 | 0.861856681 | |
| *Kandleria vitulina* | Ascusk9_30 | SEQ ID NO: 199 | 0.859587149 | |
| *Kandleria vitulina* | Ascusk9_30A | SEQ ID NO: 200 | 0.859587149 | |
| *Kandleria vitulina* | Ascusk9_30B | SEQ ID NO: 201 | 0.859587149 | |
| *Kandleria vitulina* | Ascusk9_30C | SEQ ID NO: 202 | 0.859587149 | |
| *Kandleria vitulina* | Ascusk9_30D | SEQ ID NO: 203 | 0.859587149 | Bigelow, PATENT202012110 (18 Dec. 2020) |
| *Jeotgalibaca dankookensis* | Ascusk9_623 | SEQ ID NO: 204 | 0.858629027 | |
| *Blautia glucerasea* | Ascusk9_621 | SEQ ID NO: 205 | 0.858629027 | |
| *Paraprevotella clara* | Ascusk9_160 | SEQ ID NO: 206 | 0.856737004 | |
| *Murimonas intestini* | Ascusk9_31 | SEQ ID NO: 207 | 0.856509678 | |
| *Thermaerobacter nagasakiensis* | Ascusk9_23 | SEQ ID NO: 208 | 0.856493725 | |
| *Thermaerobacter nagasakiensis* | Ascusk9_23A | SEQ ID NO: 209 | 0.856493725 | |
| *Thermaerobacter nagasakiensis* | Ascusk9_23B | SEQ ID NO: 210 | 0.856493725 | |
| *Thermaerobacter nagasakiensis* | Ascusk9_23C | SEQ ID NO: 211 | 0.856493725 | |
| *Bulleidia extructa* | Ascusk9_575 | SEQ ID NO: 212 | 0.854861894 | |
| *Bacteroides rodentium* | Ascusk9_510 | SEQ ID NO: 213 | 0.85414705 | |
| *Bacteroides rodentium* | Ascusk9_510A | SEQ ID NO: 214 | 0.85414705 | |
| *Bacteroides rodentium* | Ascusk9_510B | SEQ ID NO: 215 | 0.85414705 | |
| *Bacteroides rodentium* | Ascusk9_510C | SEQ ID NO: 216 | 0.85414705 | Bigelow, PATENT202012112 (18 Dec. 2020) |
| *Collinsella intestinalis* | Ascusk9_523 | SEQ ID NO: 217 | 0.852120797 | |
| *Aerococcus urinaehominis* | Ascusk9_698 | SEQ ID NO: 218 | 0.851733493 | |
| *Clostridium hylemonae* | Ascusk9_39 | SEQ ID NO: 219 | 0.847101333 | |
| *Clostridium hylemonae* | Ascusk9_39A | SEQ ID NO: 220 | 0.847101333 | |
| *Clostridium hylemonae* | Ascusk9_39B | SEQ ID NO: 221 | 0.847101333 | Bigelow, PATENT202012112 (18 Dec. 2020) |
| *Clostridium hylemonae* | Ascusk9_39C | SEQ ID NO: 222 | 0.847101333 | |
| *Clostridium hylemonae* | Ascusk9_39D | SEQ ID NO: 223 | 0.847101333 | Bigelow, PATENT202012112 (18 Dec. 2020) |
| *Clostridium hylemonae* | Ascusk9_39E | SEQ ID NO: 224 | 0.847101333 | |
| *Clostridium hylemonae* | Ascusk9_39F | SEQ ID NO: 225 | 0.847101333 | Bigelow, PATENT202012112 (18 Dec. 2020) |
| *Bacteroides eggerthii* | Ascusk9_114 | SEQ ID NO: 226 | 0.843233027 | |
| *Lactonifactor longoviformis* | Ascusk9_58 | SEQ ID NO: 227 | 0.843139932 | |
| *Lactonifactor longoviformis* | Ascusk9_58A | SEQ ID NO: 228 | 0.843139932 | |
| *Lactonifactor longoviformis* | Ascusk9_58B | SEQ ID NO: 229 | 0.843139932 | |
| *Lactonifactor longoviformis* | Ascusk9_58C | SEQ ID NO: 230 | 0.843139932 | |
| *Lactonifactor longoviformis* | Ascusk9_58D | SEQ ID NO: 231 | 0.843139932 | Bigelow, PATENT202012110 (18 Dec. 2020) |
| *Clostridium intestinale* | Ascusk9_421 | SEQ ID NO: 232 | 0.841207734 | |
| *Blautia wexlerae* | Ascusk9_236 | SEQ ID NO: 233 | 0.83436217 | |
| *Ruminococcus faecis* | Ascusk9_215 | SEQ ID NO: 234 | 0.833253864 | |
| *Bacteroides dorei* | Ascusk9_210 | SEQ ID NO: 235 | 0.830419672 | |
| Bacteroides dorei | Ascusk9_210A | SEQ ID NO: 236 | 0.830419672 | |

TABLE 1-continued

| Microbes of the present disclosure | | | | |
|---|---|---|---|---|
| Predicted Closest Taxa of Isolated Microbes | Strain Designation | Sequence Identifier | MIC Score | Depository, Deposit No. (Deposit Date) |
| *Bacteroides dorei* | Ascusk9_210B | SEQ ID NO: 237 | 0.830419672 | NRRL, B-67974 (17 Jul. 2020) Bigelow, PATENT202012112 (18 Dec. 2020) |
| *Robinsoniella peoriensis* | Ascusk9_589 | SEQ ID NO: 238 | 0.830386714 | |
| *Clostridium glycyrrhizinilyticum* | Ascusk9_82 | SEQ ID NO: 239 | 0.830369702 | |
| *Clostridium glycyrrhizinilyticum* | Ascusk9_82A | SEQ ID NO: 240 | 0.830369702 | |
| *Clostridium glycyrrhizinilyticum* | Ascusk9_82B | SEQ ID NO: 241 | 0.830369702 | |
| *Clostridium glycyrrhizinilyticum* | Ascusk9_82C | SEQ ID NO: 242 | 0.830369702 | Bigelow, PATENT202012110 (18 Dec. 2020) Bigelow, PATENT202012111 (18 Dec. 2020) Bigelow, PATENT202012112 (18 Dec. 2020) |
| *Clostridium glycyrrhizinilyticum* | Ascusk9_82D | SEQ ID NO: 243 | 0.830369702 | Bigelow, PATENT202012111 (18 Dec. 2020) |
| *Bacteroides thetaiotaomicron* | Ascusk9_14 | SEQ ID NO: 244 | 0.830350798 | |
| *Bacteroides thetaiotaomicron* | Ascusk9_14A | SEQ ID NO: 245 | 0.830350798 | |
| *Bacteroides thetaiotaomicron* | Ascusk9_14B | SEQ ID NO: 246 | 0.830350798 | |
| *Bacteroides thetaiotaomicron* | Ascusk9_14C | SEQ ID NO: 247 | 0.830350798 | |
| *Bacteroides thetaiotaomicron* | Ascusk9_14D | SEQ ID NO: 248 | 0.830350798 | Bigelow, PATENT202012110 (18 Dec. 2020) |
| *Bacteroides thetaiotaomicron* | Ascusk9_14E | SEQ ID NO: 249 | 0.830350798 | |
| *Bacteroides thetaiotaomicron* | Ascusk9_14F | SEQ ID NO: 250 | 0.830350798 | |
| *Bacteroides thetaiotaomicron* | Ascusk9_14G | SEQ ID NO: 251 | 0.830350798 | Bigelow, PATENT202012110 (18 Dec. 2020) |
| *Bacteroides thetaiotaomicron* | Ascusk9_14H | SEQ ID NO: 252 | 0.830350798 | Bigelow, PATENT202012110 (18 Dec. 2020) |
| *Bacteroides thetaiotaomicron* | Ascusk9_14I | SEQ ID NO: 253 | 0.830350798 | |
| *Bacteroides thetaiotaomicron* | Ascusk9_14J | SEQ ID NO: 254 | 0.830350798 | |
| *Eubacterium tortuosum* | Ascusk9_115 | SEQ ID NO: 255 | 0.830253535 | |
| *Bacteroides stercoris* | Ascusk9_288 | SEQ ID NO: 256 | 0.828999214 | |
| *Bacteroides stercoris* | Ascusk9_288A | SEQ ID NO: 257 | 0.828999214 | |
| *Bacteroides stercoris* | Ascusk9_288BC | SEQ ID NO: 258 | 0.828999214 | |
| *Bacteroides stercoris* | Ascusk9_288D | SEQ ID NO: 259 | 0.828999214 | |
| *Bacteroides stercoris* | Ascusk9_288E | SEQ ID NO: 260 | 0.828999214 | Bigelow, PATENT202012112 (18 Dec. 2020) |
| *Bacteroides stercoris* | Ascusk9_288F | SEQ ID NO: 261 | 0.828999214 | |
| *Catenibacterium mitsuokai* | Ascusk9_4 | SEQ ID NO: 262 | 0.828425557 | |
| *Catenibacterium mitsuokai* | Ascusk9_4A | SEQ ID NO: 263 | 0.828425557 | |
| *Catenibacterium mitsuokai* | Ascusk9_4B | SEQ ID NO: 264 | 0.828425557 | |
| *Catenibacterium mitsuokai* | Ascusk9_4C | SEQ ID NO: 265 | 0.828425557 | |
| *Catenibacterium mitsuokai* | Ascusk9_4D | SEQ ID NO: 266 | 0.828425557 | |
| *Catenibacterium mitsuokai* | Ascusk9_4E | SEQ ID NO: 267 | 0.828425557 | |
| *Catenibacterium mitsuokai* | Ascusk9_4F | SEQ ID NO: 268 | 0.828425557 | Bigelow, PATENT202012110 (18 Dec. 2020) |
| *Catenibacterium mitsuokai* | Ascusk9_4G | SEQ ID NO: 269 | 0.828425557 | Bigelow, PATENT202012110 (18 Dec. 2020) |
| *Catenibacterium mitsuokai* | Ascusk9_4H | SEQ ID NO: 270 | 0.828425557 | |
| *Catenibacterium mitsuokai* | Ascusk9_4I | SEQ ID NO: 271 | 0.828425557 | |
| *Catenibacterium mitsuokai* | Ascusk9_4J | SEQ ID NO: 272 | 0.828425557 | |
| *Streptosporangium album* | Ascusk9_396 | SEQ ID NO: 273 | 0.828175321 | |
| *Clostridium cocleatum* | Ascusk9_218 | SEQ ID NO: 274 | 0.818295412 | |
| *Eubacerium callanderi* | Ascusk9_618 | SEQ ID NO: 275 | 0.816656463 | |
| *Terrisporobacter glycolicus* | Ascusk9_440 | SEQ ID NO: 276 | 0.81589165 | |
| *Bifidobacterium animalis* | Ascusk9_616 | SEQ ID NO: 277 | 0.815698341 | |
| *Clostridium papyrosolvens* | Ascusk9_675 | SEQ ID NO: 278 | 0.814050557 | |
| *Glautia glucerasea* | Ascusk9_9 | SEQ ID NO: 279 | 0.796815454 | |
| *Glautia glucerasea* | Ascusk9_9A | SEQ ID NO: 280 | 0.796815454 | |
| *Glautia glucerasea* | Ascusk9_9B | SEQ ID NO: 281 | 0.796815454 | |
| *Glautia glucerasea* | Ascusk9_9C | SEQ ID NO: 282 | 0.796815454 | |
| *Glautia glucerasea* | Ascusk9_9D | SEQ ID NO: 283 | 0.796815454 | Bigelow, PATENT202012112 (18 Dec. 2020) |
| *Glautia glucerasea* | Ascusk9_9E | SEQ ID NO: 284 | 0.796815454 | Bigelow, PATENT202012111 (18 Dec. 2020) |
| *Glautia glucerasea* | Ascusk9_9F | SEQ ID NO: 285 | 0.796815454 | |
| *Holdemanella biformis* | Ascusk9_6 | SEQ ID NO: 286 | 0.791567705 | |
| *Holdemanella biformis* | Ascusk9_6A | SEQ ID NO: 333 | 0.791567705 | Bigelow, PATENT202012110 (18 Dec. 2020) |
| Prevotella saccharolytica | Ascusk9_35 | SEQ ID NO: 287 | 0.776298542 | |
| *Prevotella saccharolytica* | Ascusk9_35A | SEQ ID NO: 288 | 0.776298542 | |
| *Prevotella saccharolytica* | Ascusk9_35B | SEQ ID NO: 289 | 0.776298542 | |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Prevotella saccharolytica* | Ascusk9_35C | SEQ ID NO: 290 | 0.776298542 | |
| *Prevotella saccharolytica* | Ascusk9_35D | SEQ ID NO: 291 | 0.776298542 | Bigelow, PATENT202012110 (18 Dec. 2020) |
| *Prevotella saccharolytica* | Ascusk9_35E | SEQ ID NO: 292 | 0.776298542 | |
| *Prevotella saccharolytica* | Ascusk9_35F | SEQ ID NO: 293 | 0.776298542 | |
| *Blautia stercoris* | Ascusk9_15 | SEQ ID NO: 294 | 0.775585894 | |
| *Blautia stercoris* | Ascusk9_15A | SEQ ID NO: 295 | 0.775585894 | Bigelow, PATENT202012111 (18 Dec. 2020) |
| *Blautia stercoris* | Ascusk9_15B | SEQ ID NO: 296 | 0.775585894 | Bigelow, PATENT202012112 (18 Dec. 2020) |
| *Blautia stercoris* | Ascusk9_15C | SEQ ID NO: 297 | 0.775585894 | |
| *Blautia stercoris* | Ascusk9_15D | SEQ ID NO: 298 | 0.775585894 | |
| *Blautia stercoris* | Ascusk9_15E | SEQ ID NO: 299 | 0.775585894 | Bigelow, PATENT202012112 (18 Dec. 2020) |
| *Blautia stercoris* | Ascusk9_15F | SEQ ID NO: 300 | 0.775585894 | Bigelow, PATENT202012110 (18 Dec. 2020) Bigelow, PATENT202012111 (18 Dec. 2020) Bigelow, PATENT202012112 (18 Dec. 2020) |
| *Blautia stercoris* | Ascusk9_15G | SEQ ID NO: 301 | 0.775585894 | |
| *Blautia stercoris* | Ascusk9_15H | SEQ ID NO: 302 | 0.775585894 | |
| *Ruminococcus gnavus* | Ascusk9_12 | SEQ ID NO: 303 | 0.768320969 | |
| *Ruminococcus gnavus* | Ascusk9_12A | SEQ ID NO: 304 | 0.768320969 | Bigelow, PATENT202012110 (18 Dec. 2020) Bigelow, PATENT202012111 (18 Dec. 2020) Bigelow, PATENT202012112 (18 Dec. 2020) |
| *Ruminococcus gnavus* | Ascusk9_12B | SEQ ID NO: 305 | 0.768320969 | Bigelow, PATENT202012110 (18 Dec. 2020) Bigelow, PATENT202012111 (18 Dec. 2020) Bigelow, PATENT202012112 (18 Dec. 2020) |
| *Ruminococcus gnavus* | Ascusk9_12C | SEQ ID NO: 306 | 0.768320969 | |
| *Ruminococcus gnavus* | Ascusk9_12D | SEQ ID NO: 307 | 0.768320969 | |
| *Ruminococcus gnavus* | Ascusk9_12E | SEQ ID NO: 308 | 0.768320969 | |
| *Ruminococcus gnavus* | Ascusk9_12F | SEQ ID NO: 309 | 0.768320969 | Bigelow, PATENT202012110 (18 Dec. 2020) Bigelow, PATENT202012111 (18 Dec. 2020) Bigelow, PATENT202012112 (18 Dec. 2020) |
| *Ruminococcus gnavus* | Ascusk9_12G | SEQ ID NO: 310 | 0.768320969 | |
| *Ruminococcus gnavus* | Ascusk9_12H | SEQ ID NO: 311 | 0.768320969 | Bigelow, PATENT202012110 (18 Dec. 2020) Bigelow, PATENT202012111 (18 Dec. 2020) Bigelow, PATENT202012112 (18 Dec. 2020) |
| *Murimonas intestini* | Ascusk9_3 | SEQ ID NO: 312 | 0.745561324 | |
| *Murimonas intestini* | Ascusk9_3A | SEQ ID NO: 313 | 0.745561324 | |
| *Murimonas intestini* | Ascusk9_3B | SEQ ID NO: 314 | 0.745561324 | |
| *Murimonas intestini* | Ascusk9_3C | SEQ ID NO: 315 | 0.745561324 | |
| *Murimonas intestini* | Ascusk9_3D | SEQ ID NO: 316 | 0.745561324 | |
| *Murimonas intestini* | Ascusk9_3E | SEQ ID NO: 317 | 0.745561324 | Bigelow, PATENT202012110 (18 Dec. 2020) |
| *Murimonas intestini* | Ascusk9_3F | SEQ ID NO: 318 | 0.745561324 | Bigelow, PATENT202012110 (18 Dec. 2020) Bigelow, PATENT202012112 (18 Dec. 2020) |
| *Murimonas intestini* | Ascusk9_3G | SEQ ID NO: 319 | 0.745561324 | Bigelow, PATENT202012110 (18 Dec. 2020) Bigelow, PATENT202012111 (18 Dec. 2020) Bigelow, PATENT202012112 (18 Dec. 2020) |
| *Murimonas intestini* | Ascusk9_3H | SEQ ID NO: 320 | 0.745561324 | Bigelow, PATENT202012110 (18 Dec. 2020) |
| *Murimonas intestini* | Ascusk9_3I | SEQ ID NO: 321 | 0.745561324 | |
| *Murimonas intestini* | Ascusk9_3J | SEQ ID NO: 322 | 0.745561324 | |
| *Pediococcus acidilactici* | Ascusk9_654 | SEQ ID NO: 323 | 0.808106027 | |
| *Collinsella intestinalis* | Ascusk9_17 | SEQ ID NO: 324 | 0.756269404 | |
| Megasphaera indica | Ascusk9_238 | SEQ ID NO: 325 | 0.812385525 | |

TABLE 1-continued

Microbes of the present disclosure

| Predicted Closest Taxa of Isolated Microbes | Strain Designation | Sequence Identifier | MIC Score | Depository, Deposit No. (Deposit Date) |
|---|---|---|---|---|
| *Enterococcus* sp. | Ascusk9_546A | SEQ ID NO: 326 | 0.694417871 | NRRL, B-67972 (17 Jul. 2020) |
| *Clostridium* sp. | Ascusk9_672A | SEQ ID NO: 327 | 0.975866219 | NRRL, B-67973 (17 Jul. 2020) |
| *Bacteroides* sp. | Ascusk9_33E | SEQ ID NO: 328 | 0.894621053 | NRRL, B-67976 (17 Jul. 2020) |
| *Fusobacterium* sp. | Ascusk9_38A | SEQ ID NO: 329 | 0.939443762 | NRRL, B-67987 (18 Sept. 2020) |
| *Collinsella* sp. | Ascusk9_17A | SEQ ID NO: 330 | 0.75626944 | NRRL, B-67986 (18 Sept. 2020) |
| *Fusobacterium* sp. | Ascusk9_2A | SEQ ID NO: 331 | 0.999122 | NRRL, B-67985 (18 Sept. 2020) |

DETAILED DESCRIPTION

Definitions

Figure 1:
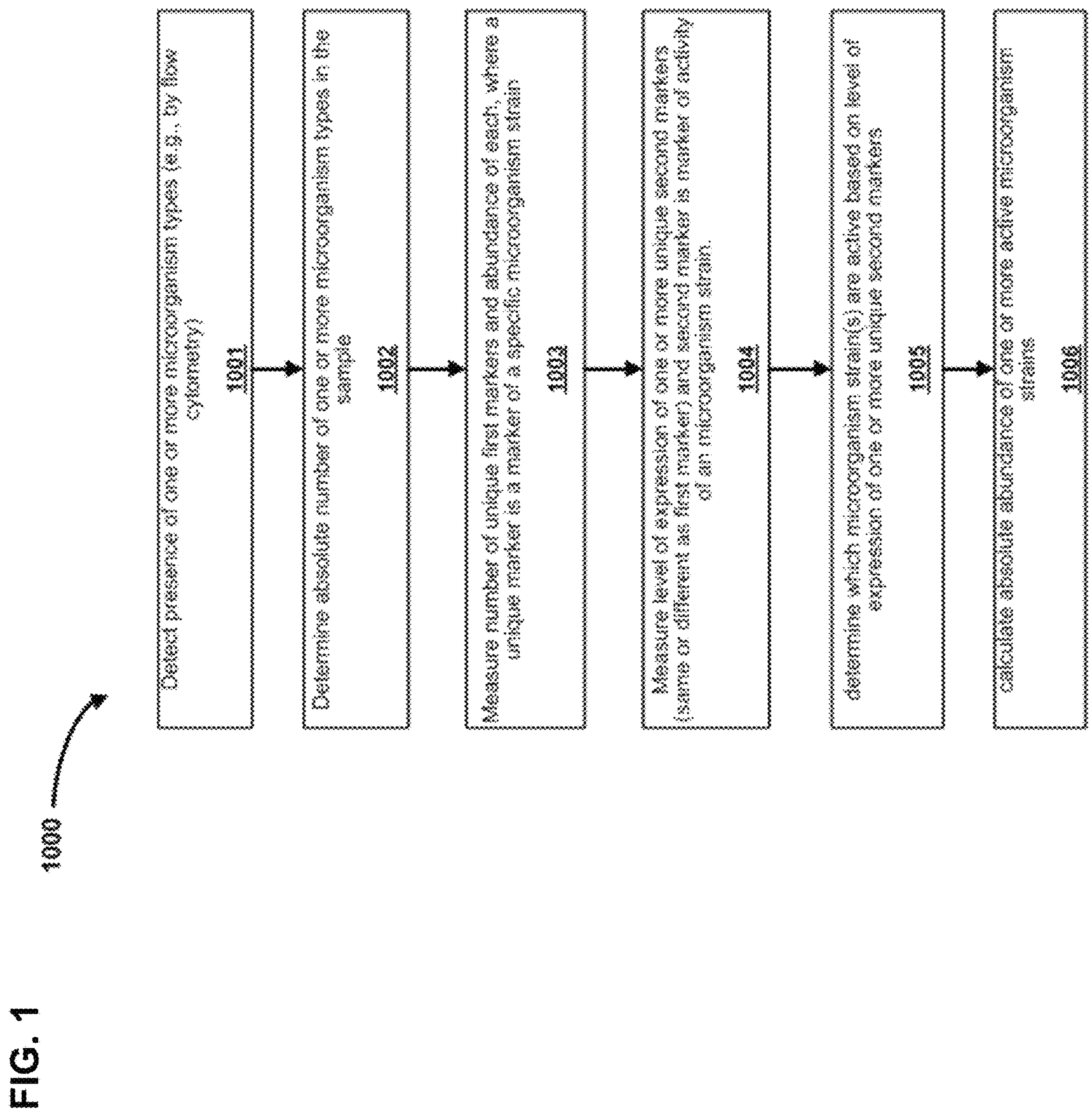
FIG. 1 shows a general workflow of one embodiment of the method for determining the absolute abundance of one or more active microorganism strains.

While the following terms are believed to be well understood by one of ordinary skill in the art, the following definitions are set forth to facilitate explanation of the presently disclosed subject matter.

The term “a” or “an” may refer to one or more of that entity, i.e. can refer to plural referents. As such, the terms “a”

or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, in particular embodiments, the terms "about" or "approximately" when preceding a numerical value indicates the value plus or minus a range of 10%.

As used herein the terms "microorganism" or "microbe" should be taken broadly. These terms are used interchangeably and include, but are not limited to, the two prokaryotic domains, Bacteria and Archaea, eukaryotic fungi and protozoa, as well as viruses. In some embodiments, the disclosure refers to the "microbes" of Table 1, or the "microbes" incorporated by reference. This characterization can refer to not only the predicted taxonomic microbial identifiers of the table, but also the identified strains of the microbes listed in the table.

The term "microbial community" means a group of microbes comprising two or more species or strains. Unlike microbial ensemble, a microbial community does not have to be carrying out a common function, or does not have to be participating in, or leading to, or correlating with, a recognizable parameter, such as a phenotypic trait of interest (e.g. decrease GI enteropathy or dysbiosis).

As used herein, "isolate," "isolated," "isolated microbe," and like terms, are intended to mean that the one or more microorganisms has been separated from at least one of the materials with which it is associated in a particular environment (for example soil, water, animal tissue).

Microbes of the present disclosure may include spores and/or vegetative cells. In some embodiments, microbes of the present disclosure include microbes in a viable but non-culturable (VBNC) state, or a quiescent state. See Liao and Zhao (US Publication US2015267163A1). In some embodiments, microbes of the present disclosure include microbes in a biofilm. See Merritt et al. (U.S. Pat. No. 7,427,408).

Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain) in association with an acceptable carrier.

As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconductive to the survival or growth of vegetative cells.

As used herein, "microbial composition" refers to a composition comprising one or more microbes of the present disclosure, wherein a microbial composition, in some embodiments, is administered to animals of the present disclosure.

As used herein, "carrier", "acceptable carrier", or "pharmaceutical carrier" refers to a diluent, adjuvant, excipient, or vehicle with which the compound is administered. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. In some embodiments, gelling agents are employed as carriers. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Hardee and Baggo (1998. Development and Formulation of Veterinary Dosage Forms. 2$^{nd}$ Ed. CRC Press. 504 pg.); E. W. Martin (1970. Remington's Pharmaceutical Sciences. 17$^{th}$ Ed. Mack Pub. Co.); and Blaser et al. (US Publication US20110280840A1).

In some aspects, carriers may be granular in structure, such as sand or sand particles. In further aspects, the carriers may be dry, as opposed to a moist or wet carrier. In some aspects, carriers can be nutritive substances and/or prebiotic substances selected from fructooligosaccharides, inulins, isomalto-oligosaccarides, lactitol, lactosucrose, lactulose, pyrodextrines, soy oligosaccharides, transgalacto-oligosaccharides, xylo-oligosaccharides, and vitamins. In some aspects, carriers can be in solid or liquid form. In some aspects, carriers can be zeolites, calcium carbonate, aluminosilicate-containing minerals, magnesium carbonate, trehalose, chitosan, shellac, albumin, starch, skim milk powder, sweet whey powder, maltodextrin, lactose, and inulin. In some aspects, a carrier is water or physiological saline.

In some aspects, one or more carrier may be zeolite. In some aspects, the zeolite is a naturally occurring zeolite or a synthetic zeolite. In some aspects, the zeolite is selected from heulandite, analcime, chabazite, clinoptilolite, natrolite, stilbite, and phillipsite.

The term "bioensemble," "microbial ensemble," or "synthetic ensemble" refers to a composition comprising one or more active microbes identified by methods, systems, and/or apparatuses of the present disclosure and that do not naturally exist in a naturally occurring environment and/or at ratios or amounts that do not exist in nature. A bioensemble is a subset of a microbial community of individual microbial species, or strains of a species, which can be described as carrying out a common function, or can be described as participating in, or leading to, or correlating with, a recognizable parameter, such as a phenotypic trait of interest (e.g. decreased incidence of GI enteropathy or dysbiosis). The bioensemble may comprise two or more species, or strains of a species, of microbes. In some instances, the microbes coexist within the community symbiotically.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. *In re Bergstrom,* 427 F. 2d 1394, (CCPA 1970)(discussing purified prostaglandins), see also, *In re Bergy,* 596 F. 2d 952 (CCPA 1979)(discussing purified microbes), see also, *Parke-Davis & Co. v. H. K. Mulford & Co.,* 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.,* 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

As used herein, "microbiome" refers to the collection of microorganisms that inhabit the digestive tract or gastrointestinal tract of an animal and the microorganism's physical environment (i.e. the microbiome has a biotic and physical component). The microbiome is fluid and may be modulated by numerous naturally occurring and artificial conditions (e.g., change in diet, disease, antimicrobial agents, influx of additional microorganisms, etc.). The modulation of the GI microbiome can be achieved via administration of one or more of the compositions of the disclosure, and can take the form of: (a) increasing or decreasing a particular Family, Genus, Species, or functional grouping of microbe (i.e. alteration of the biotic component of the GI microbiome) and/or (b) increasing or decreasing volatile fatty acids in the GI tract, increasing or decreasing pH, increasing or decreasing any other physical parameter important for gastrointestinal health (i.e. alteration of the abiotic component of the GI microbiome).

As used herein, "probiotic" refers to a substantially pure microbe (i.e., a single isolate) or a mixture of desired microbes, and may also include any additional components that can be administered to canines for restoring microbiota. Probiotics or microbial inoculant compositions of the disclosure may be administered with an agent to allow the microbes to survive the environment of the gastrointestinal tract, i.e., to resist low pH and to grow in the gastrointestinal environment. In some embodiments, the present compositions (e.g., microbial compositions) are probiotics in some aspects.

As used herein, "prebiotic" refers to an agent that increases the number and/or activity of one or more desired microbes. Non-limiting examples of prebiotics that may be useful in the methods of the present disclosure include fructooligosaccharides (e.g., oligofructose, inulin, inulin-type fructans), galactooligosaccharides, amino acids, alcohols, and mixtures thereof. See Ramirez-Farias et al. (2008. *Br. J. Nutr.* 4:1-10) and Pool-Zobel and Sauer (2007. *J. Nutr.* 137:2580-2584 and supplemental).

The term "growth medium" as used herein, is any medium which is suitable to support growth of a microbe. By way of example, the media may be natural or artificial including gastrin supplemental agar, LB media, blood serum, and tissue culture gels. It should be appreciated that the media may be used alone or in combination with one or more other media. It may also be used with or without the addition of exogenous nutrients.

The term "relative abundance" as used herein, is the number or percentage of a microbe present in the gastrointestinal tract or other organ system, relative to the number or percentage of total microbes present in said tract or organ system. The relative abundance may also be determined for particular types of microbes such as bacteria, fungi, viruses, and/or protozoa, relative to the total number or percentage of bacteria, fungi, viruses, and/or protozoa present. In one embodiment, relative abundance is determined by PCR. In another embodiment, relative abundance is determined by colony forming unit assays (cfu) or plaque forming unit assays (pfu) performed on samples from the gastrointestinal tract or other organ system of interest.

The medium may be amended or enriched with additional compounds or components, for example, a component which may assist in the interaction and/or selection of specific groups of microorganisms. For example, antibiotics (such as penicillin) or sterilants (for example, quaternary ammonium salts and oxidizing agents) could be present and/or the physical conditions (such as salinity, nutrients (for example organic and inorganic minerals (such as phosphorus, nitrogenous salts, ammonia, potassium and micronutrients such as cobalt and magnesium), pH, and/or temperature), methionine, prebiotics, ionophores, and beta glucans could be amended.

As used herein, the term "canine" includes mammals of genus *Canis, Atelocynus, Cerdocyon, Chrysocyon, Cuon, Dusicyon, Lycalopex, Lycaon, Nyctereutes, Otocyon, Speothos, Urocyon*, and *Vulpes*.

As used herein, the terms "canines" and "canids" are used synonymously to refer to mammals such as the following: domestic dog, short-eared dog, coyote, jackal, black-backed jackal, side-striped jackal, wolf, Abyssinian wolf, African golden wolf, gray wolf, dingo, crab-eating fox, maned wolf, dhole, culpeo, Darwin's fox, hoary fox, pampas fox, Sechuran fox, African hunting dog, raccoon dog, bat-eared dog, bush dog, gray fox, island gray fox, Arctic fox, Bengal fox, Blanford's fox, Cape fox, Corsac fox, fennec fox, kit fox, pale fox, red fox, silver fox, Ruppell's fox, swift fox, and Tibetan sand fox; or hybrids and/or crosses thereof.

As used herein, "improved" should be taken broadly to encompass improvement of a characteristic of interest, as compared to a control group, or as compared to a known average quantity associated with the characteristic in question. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments.

The term "marker" or "unique marker" as used herein is an indicator of unique microorganism type, microorganism strain or activity of a microorganism strain. A marker can be measured in biological samples and includes without limitation, a nucleic acid-based marker such as a ribosomal RNA gene, a peptide- or protein-based marker, and/or a metabolite or other small molecule marker.

The term "metabolite" as used herein is an intermediate or product of metabolism. A metabolite in one embodiment is a small molecule. Metabolites have various functions, including in fuel, structural, signaling, stimulatory and inhibitory effects on enzymes, as a cofactor to an enzyme, in defense, and in interactions with other organisms (such as pigments, odorants and pheromones). A primary metabolite is directly involved in normal growth, development and reproduction. A secondary metabolite is not directly involved in these processes but usually has an important ecological function. Examples of metabolites include but are not limited to antibiotics and pigments such as resins and terpenes, etc. Some antibiotics use primary metabolites as precursors, such as actinomycin which is created from the primary metabolite, tryptophan. Metabolites, as used herein, include small, hydrophilic carbohydrates; large, hydrophobic lipids and complex natural compounds.

As used herein, the term "genotype" refers to the genetic makeup of an individual cell, cell culture, tissue, organism, or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to an organism having a new genetic makeup arising as a result of a recombination event.

As used herein, the term "molecular marker" or "genetic marker" refers to an indicator that is used in methods for visualizing differences in characteristics of nucleic acid sequences.

Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions among when compared against one another. Mapping of molecular markers in the vicinity of an allele is a procedure which can be performed by the average person skilled in molecular-biological techniques.

The primary structure of major rRNA subunit 16S comprise a particular combination of conserved, variable, and hypervariable regions that evolve at different rates and enable the resolution of both very ancient lineages such as domains, and more modern lineages such as genera. The secondary structure of the 16S subunit include approximately 50 helices which result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. *Nature Rev. Micro.* 12:635-45).

A sequence identity of 94.5% or lower for two 16S rRNA genes is strong evidence for distinct genera, 86.5% or lower is strong evidence for distinct families, 82% or lower is strong evidence for distinct orders, 78.5% is strong evidence for distinct classes, and 75% or lower is strong evidence for distinct phyla. The comparative analysis of 16S rRNA gene sequences enables the establishment of taxonomic thresholds that are useful not only for the classification of cultured microorganisms but also for the classification of the many environmental sequences. Yarza et al. 2014. *Nature Rev. Micro.* 12:635-45).

As used herein, the term "trait" refers to a characteristic or phenotype. For example, in the context of some embodiments of the present disclosure; a decrease in the incidence of gastrointestinal dysbiosis, a decrease in the severity of gastrointestinal dysbiosis, a decrease in the incidence of diarrhea, a decrease in the severity of diarrhea, a decrease in the incidence of irritable bowel disease (IBD), a decrease in the severity of irritable bowel disease, a decrease in the incidence of gastrointestinal pathogen colonization, a decrease in the incidence of gastrointestinal pathogen-induced disease, a decrease in the incidence of gastrointestinal pathogen carriage, a decrease in the amount of primary bile acids present in the feces, an increase in the secondary bile acids present in the feces, an increase in fatty acid production in the GI tract, an increase in polysaccharide and lignin degradation; an increase in fat, starch, and/or protein digestion, an increase in pH balance, an increase in vitamin availability, a reduced likelihood or incidence of mortality, a reduced likelihood or incidence of morbidity, an increased production of antimicrobials, an increase in mammalian and/or microbial synthesis of vitamins; a reduction of alpha diversity of the gastrointestinal microbiome; and/or combinations thereof; and wherein said increase or decrease is determined by comparing against an animal not having been administered said composition.

The term "trait" may also be drawn to the predominance of short chain fatty acids, medium chain fatty acids, and long chain fatty acids produced or made available systemically or in the gastrointestinal tract; improved digestibility; increased degradation of cellulose, lignin, and hemicellulose; increased GI or systemic concentrations of fatty acids such as acetic acid, propionic acid, and butyric acid; etc.

A trait may be inherited in a dominant or recessive manner, or in a partial or incomplete-dominant manner. A trait may be monogenic (i.e. determined by a single locus)

or polygenic (i.e. determined by more than one locus) or may also result from the interaction of one or more genes with the environment.

In the context of this disclosure, traits may also result from the interaction of one or more canine genes and one or more microorganism genes.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "phenotype" refers to the observable characteristics of an individual cell, cell culture, organism (e.g., a canine), or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present disclosure, including but not limited to decrease in the severity of GI enteropathy and dysbiosis (e.g., decrease in diarrhea, hemorrhagic diarrhea, etc.) and the like. These results can be achieved by providing expression of heterologous products or increased expression of endogenous products in organisms using the methods and compositions of the present disclosure.

As used herein, the term "MIC" means maximal information coefficient. MIC is a type of nonparametric network analysis that identifies a score (MIC score) between active microbial strains of the present disclosure and at least one measured metadata (e.g., ability to treat/prevent GI dysbiosis or enteropathy). Further, U.S. application Ser. No. 15/217,575, filed on Jul. 22, 2016 (issued as U.S. Pat. No. 9,540,676 on Jan. 10, 2017) is hereby incorporated by reference in its entirety.

Figure 2:
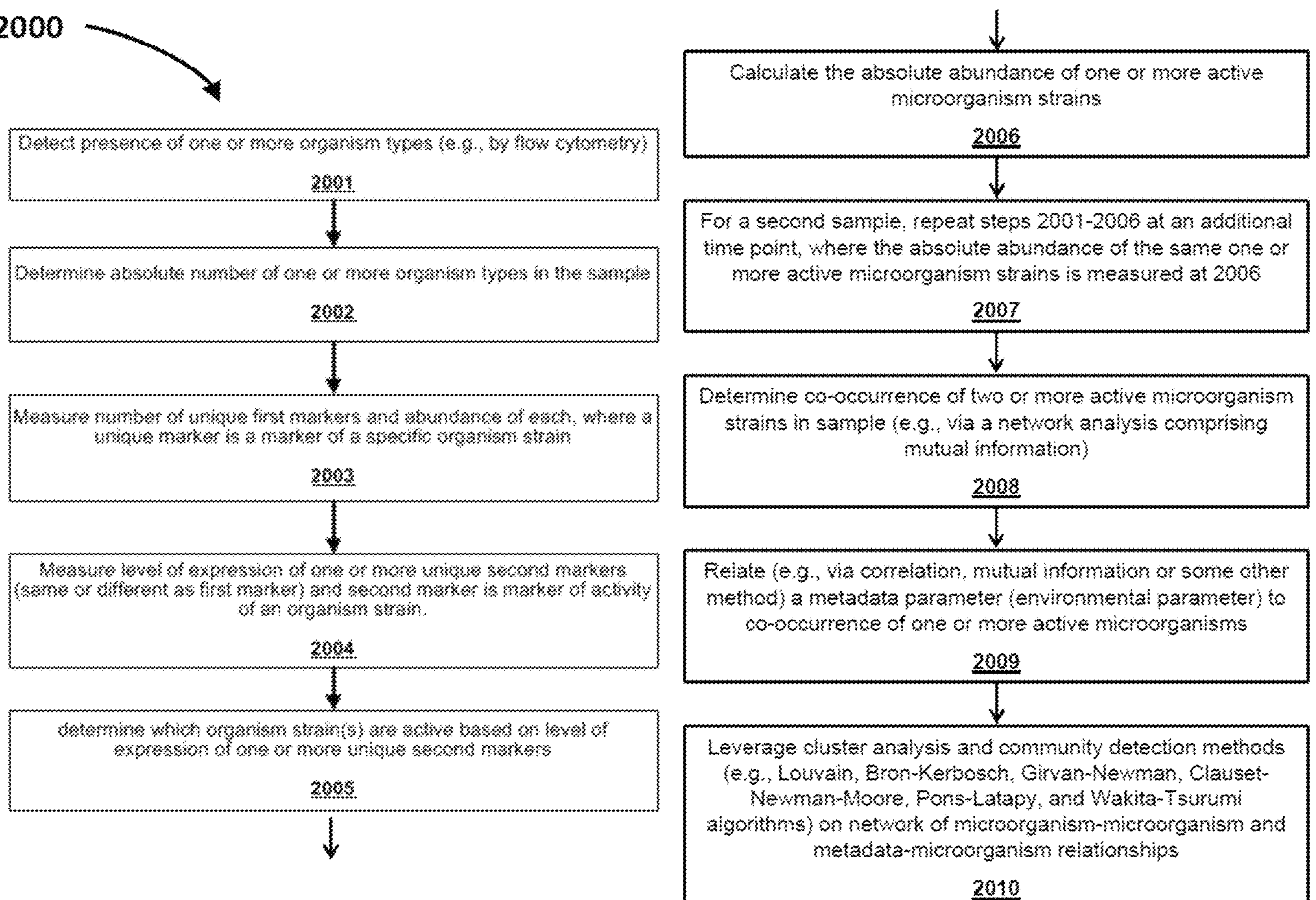
FIG. 2 shows a general workflow of one embodiment of a method for determining the co-occurrence of one or more, or two or more, active microorganism strains in a sample with one or more metadata (environmental) parameters, followed by leveraging cluster analysis and community detection methods on the network of determined relationships.
Figure 3B:
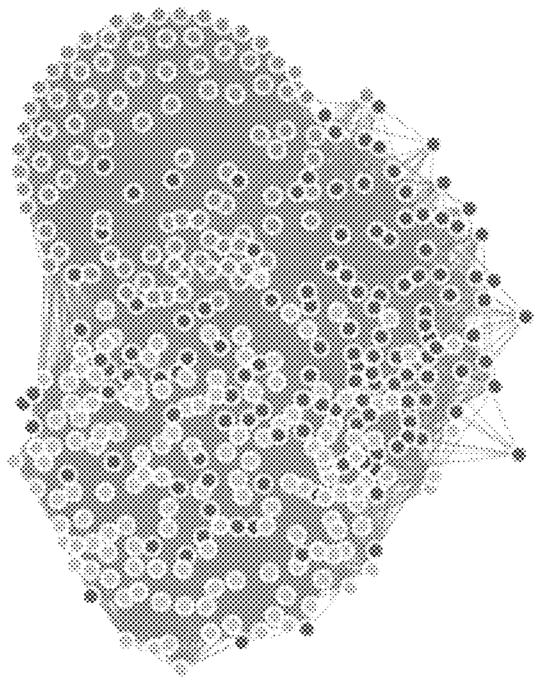
FIG. 3B further depicts the emergence of three socially distinct groups expected to be efficacious in treating and preventing IBD/diarrhea.
Figure 3A:
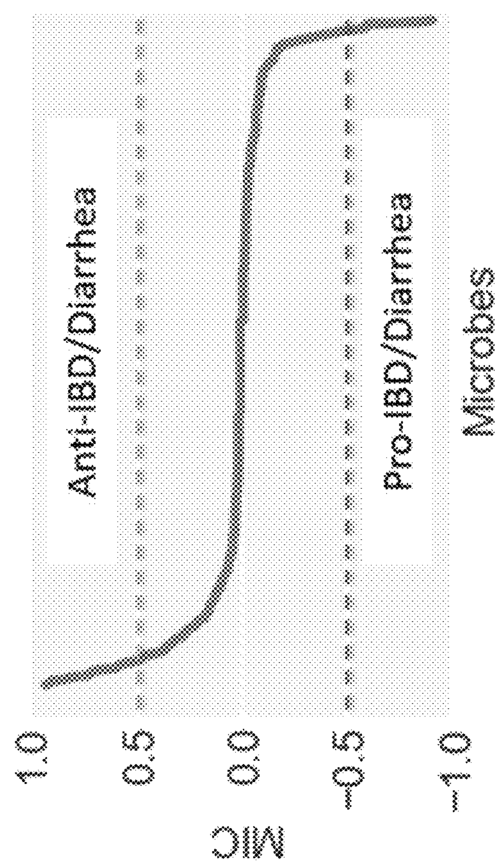
FIG. 3A depicts the cutoff list for MIC scores for target microbes for use in the present disclosure, with many of the microbes that contribute to anti-IBD/anti-diarrheal states occurring above ~0.5 MIC, and with many of the microbes that contribute to IBD/diarrheal states occurring below ~−0.5 MIC.
Figure 4B:
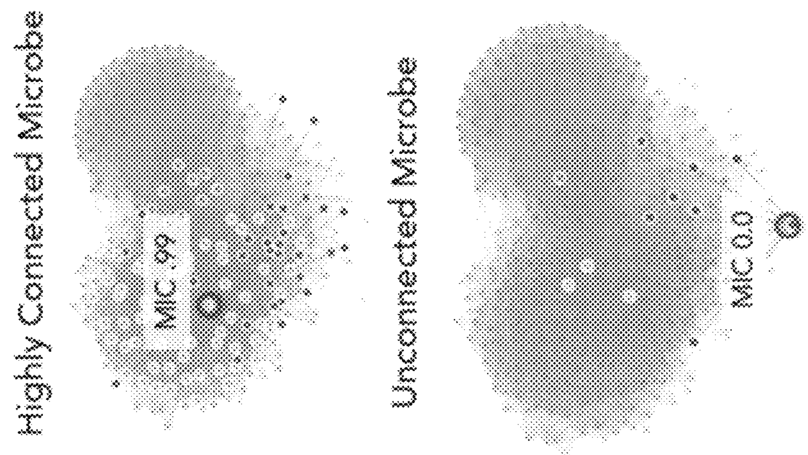
FIG. 4B depicts the IBD/diarrheal states (pro and anti) associated with highly connected microbes and unconnected microbes, with highly connected microbes exhibiting a proclivity to contributing to anti-IBD/diarrheal states (high MIC scores).
Figure 4A:
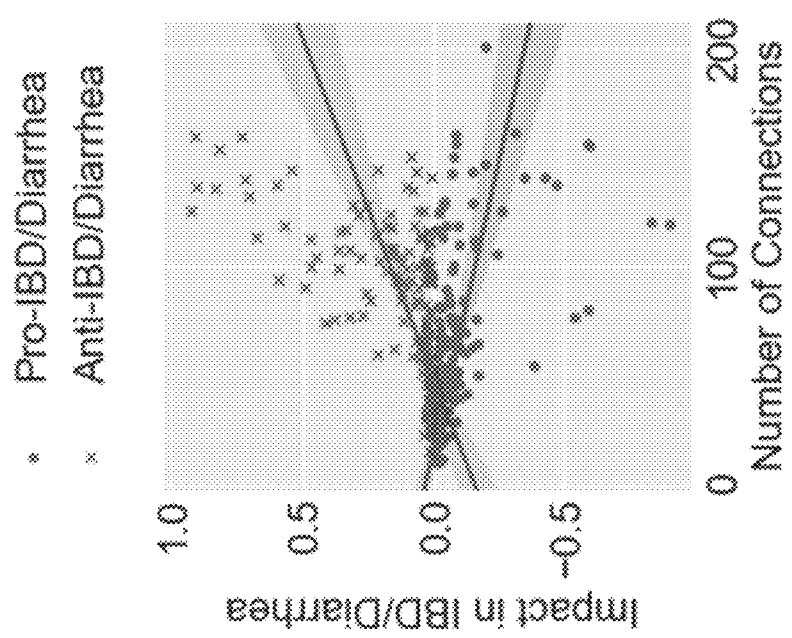
FIG. 4A depicts the impact in IBD/diarrheal states (indicated by MIC score on the Y axis) as a function of the number of network connections (X axis) shared by the microbes. Two populations emerge: microbes that contribute to IBD/diarrheal states and microbes that contribute to anti-IBD/diarrheal states.

The maximal information coefficient (MIC) is then calculated between strains and metadata 3021a, and between strains 3021b; as seen in FIG. 2. Results are pooled to create a list of all relationships and their corresponding MIC scores 3022. If the relationship scores below a given threshold 3023, the relationship is deemed/identified as irrelevant 3023b. If the relationship is above a given threshold 3023, the relationship deemed/identified as relevant 2023a, and is further subject to network analysis 3024. The following code fragment shows an exemplary methodology for such analysis, according to one embodiment:

Read total list of relationships file as links

```
threshold = 0.8
for i in range(len(links)):
  if links >= threshold
    multiplier[i] = 1
  else
    multiplier[i] = 0
end if
linkstemp = multiplier*links
final_links = links_temp[links_temp != 0]
savetxt(output_file,final_links)
output_file.close( )
```

In some embodiments, the compositions of the present disclosure comprise one or more bacteria and/or one or more fungi that have a MIC score of at least about 0.1, at least about 0.15, at least about 0.2, at least about 0.25, at least about 0.3, at least about 0.35, at least about 0.4, at least about 0.45, at least about 0.5, at least about 0.55, at least about 0.6, at least about 0.65, at least about 0.7, at least about 0.75, at least about 0.80, at least about 0.85, at least about 0.9, or at least about 0.95.

In some embodiments, the compositions of the present disclosure comprise one or more bacteria and/or one or more fungi that have a MIC score of at least 0.1, at least 0.15, at least 0.2, at least 0.25, at least 0.3, at least 0.35, at least 0.4, at least 0.45, at least 0.5, at least 0.55, at least 0.6, at least 0.65, at least 0.7, at least 0.75, at least 0.80, at least 0.85, at least 0.9, or at least 0.95.

Based on the output of the network analysis, active strains are selected 3025 for preparing products (e.g., ensembles, aggregates, and/or other synthetic groupings) containing the selected strains. The output of the network analysis can also be used to inform the selection of strains for further product composition testing.

The use of thresholds is discussed above for analyses and determinations. Thresholds can be, depending on the implementation and application: (1) empirically determined (e.g., based on distribution levels, setting a cutoff at a number that removes a specified or significant portion of low level reads); (2) any non-zero value; (3) percentage/percentile based; (4) only strains whose normalized second marker (i.e., activity) reads is greater than normalized first marker (cell count) reads; (5) log 2 fold change between activity and quantity or cell count; (6) normalized second marker (activity) reads is greater than mean second marker (activity) reads for entire sample (and/or sample set); and/or any magnitude threshold described above in addition to a statistical threshold (i.e., significance testing).

As used herein "shelf-stable" refers to a functional attribute and new utility acquired by the microbes formulated according to the disclosure, which enable said microbes to exist in a useful/active state outside of their natural environment in the gastrointestinal tract (i.e. a markedly different characteristic). Thus, shelf-stable is a functional attribute created by the formulations/compositions of the disclosure and denoting that the microbe formulated into a shelf-stable composition can exist outside the gastrointestinal tract and under ambient conditions for a period of time that can be determined depending upon the particular formulation utilized, but in general means that the microbes can be formulated to exist in a composition that is stable under ambient conditions for at least a few days and generally at least one week. Accordingly, a "shelf-stable canine supplement" is a composition comprising one or more microbes of the disclosure, said microbes formulated in a composition, such that the composition is stable under ambient conditions for at least one week, meaning that the microbes comprised in the composition (e.g. whole cell, spore, or lysed cell) are able to impart one or more beneficial phenotypic properties to a canine when administered (e.g. improved GI health, and/or modulation of the gastrointestinal microbiome).

Prior Applications

The instant subject matter is distinct over the subject matter of prior Ascus Biosciences, Inc. applications. The 16S and/or ITS sequences of the microbes of the instant disclosure are believed to be distinct over those of any prior Native Microbials, Inc. applications.

Isolated Microbes

In some aspects, the present disclosure provides isolated microbes, including novel strains of microbes presented in Table 1.

In other aspects, the present disclosure provides isolated whole microbial cultures of the microbes identified in Table 1. These cultures may comprise microbes at various concentrations.

In some aspects, the disclosure provides for utilizing one or more microbes selected from Table 1 to increase a phenotypic trait of interest in canines.

In some embodiments, the disclosure provides isolated microbial species belonging to taxonomic families of—Prevotellaceae, Veillonellaceae, Lachnospiraceae, Clostridiaceae, Succinivibrionaceae, Erysipelotrichaceae, Eubacteriaceae, Peptostreptococcaceae, Enterobacteriaceae, Acetobacteraceae, Sutterellaceae, Coriobacteriaceae, Bacteroidaceae, Bacillaceae, Caulobacteraceae, Actinomycetaceae, Ruminococcaceae, Porphyromonadaceae, Fusobacteriaceae, Moraxellaceae, Carnobacteriaceae, Clostridiales, Aerococcaceae, Streptosporangiaceae, Bifidobacteriaceae, Fusobacteriaceae, and Lactobacillaceae.

In further embodiments, isolated microbial species may be selected from genera of *Prevotella, Megamonas, Ruminococcus, Clostridium, Clostridium* sensu *stricto*, Lachnospiraceae, *Anaerobiospirillum, Catenibacterium, Eubacterium, Holdemanella, Clostridium* cluster XI, *Allobaculum, Morganella, Acidicaldus, Parasutterella, Collinsella, Blautia, Bacteroides, Bacillus, Lactonifactor, Brevundimonas, Dialister, Actinomyces, Coprococcus, Cellulsilyticum, Acetanaerobacterium, Faecalibacterium, Murimonas, Clostridium* cluster XIVa, *Parabacteroides, Cetobacterium, Clostridium* cluster XVIII, *Odoribacter, Terrisporobacter, Turicibacter, Fusicatenibacter, Kandleria, Butyricicoccus, Veillonella, Acinetobacter, Enterococcus, Paraprevotella, Thermaerobacter, Bulleidia, Aerococcus, Robinsoniella, Erysipelotrichaceae, Streptosporangium, Bifidobacterium, Clostridium* cluster III, *Pediococcus, Fusobacterium, Glautia, Sarcina, Jeotgalibaca*, and *Megasphaera.*

Furthermore, the disclosure relates to microbes having characteristics substantially similar to that of a microbe identified in Table 1.

The isolated microbial species, and novel strains of said species, identified in the present disclosure, are able to impart beneficial properties or traits to canines.

For instance, the isolated microbes described in Table 1, or microbial ensemble of said microbes, are able to facilitate a decrease in the incidence of gastrointestinal dysbiosis, a decrease in the severity of gastrointestinal dysbiosis, a decrease in the incidence of diarrhea, a decrease in the severity of diarrhea, a decrease in the incidence of irritable bowel disease (IBD), a decrease in the severity of irritable or inflammatory bowel disease, a decrease in the incidence of chronic enteropathy, a decrease in the severity of chronic enteropathy, a decrease in the incidence of gastrointestinal pathogen colonization, a decrease in the incidence of gastrointestinal pathogen-induced disease, a decrease in the incidence of gastrointestinal pathogen carriage, a decrease in the amount of primary bile acids present in the feces, an increase in the secondary bile acids present in the feces, an increase in fatty acid production in the GI tract, an increase in fat, starch, and/or protein digestion, an increase in pH balance, an increase in vitamin availability, a reduced likelihood or incidence of mortality, a reduced likelihood or incidence of morbidity, an increased production of antimicrobials, an increase in mammalian and/or microbial synthesis of vitamins; a reduction of alpha diversity of the gastrointestinal microbiome; and/or combinations thereof; and wherein said increase or decrease is determined by comparing against an animal not having been administered said composition.

Heinken et al. (2019. Microbiome. 7:75; 18 pgs) identified a link between secondary bile acid metabolism in gut microbes and the distinct metabolic capabilities of these gut microbes in inflammatory bowel disease. The gut microbiome appears to be capable of modulating overall bile acid production and secondary bile acid production.

In some embodiments, the isolated microbial strains are microbes of the present disclosure that have been genetically modified. In some embodiments, the genetically modified or recombinant microbes comprise polynucleotide sequences which do not naturally occur in said microbes. In some embodiments, the microbes may comprise heterologous polynucleotides. In further embodiments, the heterologous polynucleotides may be operably linked to one or more polynucleotides native to the microbes.

In some embodiments, the heterologous polynucleotides may be reporter genes or selectable markers. In some embodiments, reporter genes may be selected from any of the family of fluorescence proteins (e.g., GFP, RFP, YFP, and the like), β-galactosidase, or luciferase. In some embodiments, selectable markers may be selected from neomycin phosphotransferase, hygromycin phosphotransferase, aminoglycoside adenyltransferase, dihydrofolate reductase, acetolactase synthase, bromoxynil nitrilase, β-glucuronidase, dihydrogolate reductase, and chloramphenicol acetyltransferase. In some embodiments, the heterologous polynucleotide may be operably linked to one or more promoter.

In some embodiments the isolated microbial strains express transgenic or native polypeptides selected from cellulases (e.g., endocellulases, exocellulases, and glucosidases), pectinases, amylases, amylopectinases, ligninases, and phytases.

Microbial Compositions

In some aspects, the disclosure provides microbial compositions comprising a combination of at least any two microbes selected from amongst the microbes identified in Table 1. In some aspects, the disclosure provides microbial compositions comprising at least one microbe selected from amongst the microbes identified in Table 1.

In certain embodiments, the compositions of the present disclosure comprise two microbes, or three microbes, or four microbes, or five microbes, or six microbes, or seven microbes, or eight microbes, or nine microbes, or ten or more microbes. Said microbes of the compositions are different microbial species, or different strains of a microbial species.

In some embodiments, the disclosure provides microbial compositions, comprising: at least one or at least two isolated microbial species belonging to genera of: *Prevotella, Megamonas, Ruminococcus, Clostridium, Clostridium* sensu *stricto*, Lachnospiraceae, *Anaerobiospirillum, Catenibacterium, Eubacterium, Holdemanella, Clostridium* cluster XI, *Allobaculum, Morganella, Acidicaldus, Parasutterella, Collinsella, Blautia, Bacteroides, Bacillus, Lactonifactor, Brevundimonas, Dialister, Actinomyces, Coprococcus, Cellulsilyticum, Acetanaerobacterium, Faecalibacterium, Murimonas, Clostridium* cluster XIVa, *Parabacteroides, Cetobacterium, Clostridium* cluster XVIII, *Odoribacter, Terrisporobacter, Turicibacter, Fusicatenibacter, Kandleria, Butyricicoccus, Veillonella, Acinetobacter, Enterococcus, Paraprevotella, Thermaerobacter, Bulleidia, Aerococcus, Robinsoniella, Erysipelotrichaceae, Streptosporangium, Bifidobacterium, Clostridium* cluster III, *Pediococcus, Fusobacterium, Glautia, Sarcina, Jeotgalibaca*, and *Megasphaera*. Particular novel strains of species of these aforementioned genera can be found in Table 1.

In some embodiments, the disclosure provides microbial compositions, comprising: at least one or at least two isolated microbial species belonging to the family of: Prevotellaceae, Veillonellaceae, Lachnospiraceae, Clostridiaceae, Succinivibrionaceae, Erysipelotrichaceae, Eubacteriaceae, Peptostreptococcaceae, Enterobacteriaceae, Acetobacteraceae, Sutterellaceae, Coriobacteriaceae, Bacteroidaceae, Bacillaceae, Caulobacteraceae, Actinomycetaceae, Ruminococcaceae, Porphyromonadaceae, Fusobacteriaceae, Moraxellaceae, Carnobacteriaceae, Clostridiales, Aerococcaceae, Streptosporangiaceae, Bifidobacteriaceae, Fusobacteriaceae, and Lactobacillaceae.

Particular novel strains of species of these aforementioned genera can be found in Table 1.

In particular aspects, the disclosure provides microbial compositions, comprising species as grouped in Tables 2-8. With respect to Tables 2-8, the letters A through I represent a non-limiting selection of microbes of the present disclosure, defined as:

A=Strain designation Ascusk9_546A identified in Table 1;
B=Strain designation Ascusk9_672A identified in Table 1;
C=Strain designation Ascusk9_210B identified in Table 1;
D=Strain designation Ascusk9_2A identified in Table 1;
E=Strain designation Ascusk9_33E identified in Table 1;
F=Strain designation Ascusk9_51G identified in Table 1;
G=Strain designation Ascusk9_0G identified in Table 1;
H=Strain designation Ascusk9_38A identified in Table 1; and
I=Strain designation Ascusk9_17A identified in Table 1.

TABLE 2

| Eight and Nine Strain Compositions | | | | | |
|---|---|---|---|---|---|
| A, B, C, D, E, F, G, H | A, B, C, D, E, F, G, I | A, B, C, D, E, F, H, I | A, B, C, D, E, G, H, I | A, B, C, D, F, G, H, I | A, B, C, E, F, G, H, I |
| A, B, D, E, F, G, H, I | A, C, D, E, F, G, H, I | B, C, D, E, F, G, H, I | A, B, C, D, E, F, G, H, I | | |

TABLE 3

| Seven Strain Compositions | | | | | |
|---|---|---|---|---|---|
| A, B, C, D, E, F, G | A, B, C, D, E, F, H | A, B, C, D, E, F, I | A, B, C, D, E, G, H | A, B, C, D, E, G, I | A, B, C, D, E, H, I |
| A, B, C, D, F, G, H | A, B, C, D, F, G, I | A, B, C, D, F, H, I | A, B, C, D, G, H, I | A, B, C, E, F, G, H | A, B, C, E, F, G, I |
| A, B, C, E, F, H, I | A, B, C, E, G, H, I | A, B, C, F, G, H, I | A, B, D, E, F, G, H | A, B, D, E, F, G, I | A, B, D, E, F, H, I |
| A, B, D, E, G, H, I | A, B, D, F, G, H, I | A, B, E, F, G, H, I | A, C, D, E, F, G, H | A, C, D, E, F, G, I | A, C, D, E, F, H, I |
| A, C, D, E, G, H, I | A, C, D, F, G, H, I | A, C, E, F, G, H, I | A, D, E, F, G, H, I | B, C, D, E, F, G, H | B, C, D, E, F, G, I |
| B, C, D, E, F, H, I | B, C, D, E, G, H, I | B, C, D, F, G, H, I | B, C, E, F, G, H, I | B, D, E, F, G, H, I | C, D, E, F, G, H, I |

TABLE 4

| Six Strain Compositions | | | | | | |
|---|---|---|---|---|---|---|
| A,B,C,D,E,F | A,B,C,D,E,G | A,B,C,D,E,H | A,B,C,D,E,I | A,B,C,D,F,G | A,B,C,D,F,H | A,B,C,D,F,I |
| A,B,C,D,G,H | A,B,C,D,G,I | A,B,C,D,H,I | A,B,C,E,F,G | A,B,C,E,F,H | A,B,C,E,F,I | A,B,C,E,G,H |
| A,B,C,E,G,I | A,B,C,E,H,I | A,B,C,F,G,H | A,B,C,F,G,I | A,B,C,F,H,I | A,B,C,G,H,I | A,B,D,E,F,G |
| A,B,D,E,F,H | A,B,D,E,F,I | A,B,D,E,G,H | A,B,D,E,G,I | A,B,D,E,H,I | A,B,D,F,G,H | A,B,D,F,G,I |
| D,E,F,G,H,I | C,E,F,G,H,I | A,B,D,F,H,I | A,B,D,G,H,I | A,B,E,F,G,H | A,B,E,F,G,I | A,B,E,F,H,I |
| A,B,E,G,H,I | A,B,F,G,H,I | A,C,D,E,F,G | A,C,D,E,F,H | A,C,D,E,F,I | A,C,D,E,G,H | A,C,D,E,G,I |
| A,C,D,E,H,I | A,C,D,F,G,H | A,C,D,F,G,I | A,C,D,F,H,I | A,C,D,G,H,I | A,C,E,F,G,H | A,C,E,F,G,I |
| A,C,E,F,H,I | A,C,E,G,H,I | A,C,F,G,H,I | A,D,E,F,G,H | A,D,E,F,G,I | A,D,E,F,H,I | A,D,E,G,H,I |
| A,D,F,G,H,I | A,E,F,G,H,I | B,C,D,E,F,G | B,C,D,E,F,H | B,C,D,E,F,I | B,C,D,E,G,H | B,C,D,E,G,I |
| B,C,D,E,H,I | B,C,D,F,G,H | B,C,D,F,G,I | B,C,D,F,H,I | B,C,D,G,H,I | B,C,E,F,G,H | B,C,E,F,G,I |
| B,C,E,F,H,I | B,C,E,G,H,I | B,C,F,G,H,I | B,D,E,F,G,H | B,D,E,F,G,I | B,D,E,F,H,I | B,D,E,G,H,I |
| B,D,F,G,H,I | B,E,F,G,H,I | C,D,E,F,G,H | C,D,E,F,G,I | C,D,E,F,H,I | C,D,E,G,H,I | C,D,F,G,H,I |

TABLE 5

| Five Strain Compositions | | | | | | | |
|---|---|---|---|---|---|---|---|
| A,B,C,D,E | A,B,C,D,F | A,B,C,D,G | A,B,C,D,H | A,B,C,D,I | A,B,C,E,F | A,B,C,E,G | A,B,C,E,H |
| A,B,C,F,H | A,B,C,F,G | A,B,C,F,I | A,B,C,G,H | A,B,C,G,I | A,B,C,H,I | A,B,D,E,F | A,B,D,E,G |
| A,B,D,E,I | A,B,D,F,G | A,B,D,F,H | A,B,D,F,I | A,B,D,G,H | A,B,D,G,I | A,B,D,H,I | A,B,E,F,G |
| A,B,E,F,I | A,B,E,G,H | A,B,E,G,I | A,B,E,H,I | A,B,F,G,H | A,B,F,G,I | A,B,F,H,I | A,B,G,H,I |
| A,C,D,E,G | A,C,D,E,H | A,C,D,E,I | A,C,D,F,G | A,C,D,F,H | A,C,D,F,I | A,C,D,G,H | A,C,D,G,I |
| A,C,E,F,G | A,C,E,F,H | A,C,E,F,I | A,C,E,G,H | A,C,E,G,I | A,C,E,H,I | A,C,F,G,H | A,C,F,G,I |
| A,C,G,H,I | A,D,E,F,G | A,D,E,F,H | A,D,E,F,I | A,D,E,G,H | A,D,E,G,I | A,D,E,H,I | A,D,F,G,H |
| A,D,F,H,I | A,D,G,H,I | A,E,F,G,H | A,E,F,G,I | A,E,F,H,I | A,E,G,H,I | A,F,G,H,I | B,C,D,E,F |
| B,C,D,E,H | B,C,D,E,I | B,C,D,F,G | B,C,D,F,H | B,C,D,F,I | B,C,D,G,H | B,C,D,G,I | B,C,D,H,I |
| B,C,E,F,H | B,C,E,F,I | B,C,E,G,H | B,C,E,G,I | B,C,E,H,I | B,C,F,G,H | B,C,F,G,I | B,C,F,H,I |
| B,D,E,F,G | B,D,E,F,H | B,D,E,F,I | B,D,E,G,H | B,D,E,G,I | B,D,E,H,I | B,D,F,G,H | B,D,F,G,I |
| B,D,G,H,I | B,E,F,G,H | B,E,F,G,I | B,E,F,H,I | B,E,G,H,I | B,F,G,H,I | C,D,E,F,G | C,D,E,F,H |
| C,D,E,G,H | C,D,E,G,I | C,D,E,H,I | C,D,F,G,H | C,D,F,G,I | C,D,F,H,I | C,D,G,H,I | C,E,F,G,H |
| C,E,F,H,I | C,E,G,H,I | C,F,G,H,I | D,E,F,G,H | D,E,F,G,I | D,E,F,H,I | D,E,G,H,I | D,F,G,H,I |
| A,B,C,E,I | A,B,D,E,H | A,B,E,F,H | A,C,D,E,F | A,C,D,H,I | A,C,F,H,I | A,D,F,G,I | B,C,D,E,G |
| B,C,E,F,G | B,C,G,H,I | B,D,F,H,I | C,D,E,F,I | C,E,F,G,I | E,F,G,H,I | | |

TABLE 6

| Four Strain Compositions | | | | | | | | |
|---|---|---|---|---|---|---|---|---|
| A,B,C,D | A,B,C,E | A,B,C,F | A,B,C,G | A,B,C,H | A,B,C,I | A,B,D,E | A,B,D,F | D,G,H,I |
| A,B,D,G | A,B,D,H | A,B,D,I | A,B,E,F | A,B,E,G | A,B,E,H | A,B,E,I | A,B,F,G | E,F,G,H |
| A,B,F,H | A,D,F,H | A,D,F,l | A,D,G,H | A,D,G,I | A,D,H,I | A,E,F,G | A,E,F,H | E,F,G,I |
| A,B,F,I | A,B,G,H | A,B,G,I | A,B,H,I | A,C,D,E | A,C,D,F | A,C,D,G | A,C,D,H | E,F,H,I |
| A,C,D,I | A,C,E,F | A,C,E,G | A,C,E,H | A,C,E,I | A,C,F,G | A,C,F,H | A,C,F,l | E,G,H,I |
| A,C,G,H | A,C,G,I | A,C,H,l | A,D,E,F | A,D,E,G | A,D,E,H | A,D,E,I | A,D,F,G | F,G,H,I |
| A,E,F,I | A,E,G,H | A,E,G,I | A,E,H,l | A,F,G,H | A,F,G,I | A,F,H,I | A,G,H,I | D,E,F,H |
| B,C,D,E | B,C,D,F | B,C,D,G | B,C,D,H | B,C,D,I | B,C,E,F | B,C,E,G | B,C,E,H | D,E,F,I |
| B,C,E,I | B,C,F,G | B,C,F,H | B,C,F,I | B,C,G,H | B,C,G,I | B,C,H,I | B,D,E,F | D,E,G,H |
| B,D,E,G | B,D,E,H | B,D,E,I | B,D,F,G | B,D,F,H | B,D,F,l | B,D,G,H | B,D,G,I | D,E,G,I |
| B,D,H,I | B,E,F,G | B,E,F,H | B,E,F,l | B,E,G,H | B,E,G,I | B,E,H,I | B,F,G,H | D,E,H,I |
| B,F,G,I | B,F,H,I | B,G,H,I | C,D,E,F | C,D,E,G | C,D,E,H | C,D,E,I | C,D,F,G | D,F,G,H |
| C,D,F,H | C,D,F,l | C,D,G,H | C,D,G,I | C,D,H,l | C,E,F,G | C,E,F,H | C,E,F,I | D,F,G,I |
| C,E,G,H | C,E,G,I | C,E,H,I | C,F,G,H | C,F,G,I | C,F,H,I | C,G,H,I | D,E,F,G | D,F,H,I |

TABLE 7

| Three Strain Compositions | | | | | | | | | | |
|---|---|---|---|---|---|---|---|---|---|---|
| A,B,C | A,B,D | A,B,E | A,B,F | A,B,G | A,B,H | A,B,I | A,C,D | A,C,E | G,H,I | E,F,H |
| A,C,F | A,C,G | A,C,H | A,C,I | A,D,E | A,D,F | A,D,G | A,D,H | A,D,I | F,H,I | E,F,G |
| A,E,F | A,E,G | A,E,H | A,E,I | A,F,G | A,F,H | A,F,I | A,G,H | A,G,I | F,G,I | D,H,I |
| A,H,I | B,C,D | B,C,E | B,C,F | B,C,G | B,C,H | B,C,I | B,D,E | B,D,F | F,G,H | D,G,I |
| B,D,G | B,D,H | B,D,I | B,E,F | B,E,G | B,E,H | B,E,I | B,F,G | B,F,H | E,H,I | E,F,I |
| B,F,I | B,G,H | B,G,I | B,H,I | C,D,E | C,D,F | C,D,G | C,D,H | C,D,I | E,G,I | D,G,H |
| C,E,F | C,E,G | C,E,H | C,E,I | C,F,G | C,F,H | C,F,I | C,G,H | C,G,I | E,G,H | D,F,I |
| C,H,I | D,E,F | D,E,G | D,E,H | D,E,I | D,F,G | D,F,H | | | | |

TABLE 8

| Two Strain Compositions | | | | | | | | | | | | | | | |
|---|---|---|---|---|---|---|---|---|---|---|---|---|---|---|---|
| A,B | A,C | A,D | A,E | A,F | A,G | A,H | A,I | B,C | B,D | B,E | B,F | B,G | B,H | B,I | C,D |
| C,E | C,F | C,G | C,H | C,I | D,E | D,F | D,G | D,H | D,I | E,F | E,G | E,H | E,I | F,G | F,H |
| F,I | G,H | G,I | H,I | | | | | | | | | | | | |

In some embodiments, the microbial compositions may be selected from any member group from Tables 2-8.

Isolated Microbes—Source Material

In particular embodiments, the microbes of the present compositions are not naturally found in association with the same animal. In some aspects, the microbial species or strains are not found in the same breed of canine. In some aspects, the microbial species or strains are not found in canines of the same age or same approximate age. In some aspects, the microbial species or strains are not found in canines fed the same diet. In some aspects, the microbial species or strains are not found in canines that have the same approximate activity level. In some aspects, the microbial species forming the microbial community are all found in association with animals from the same geographic location. In other aspects, each microbial species forming the composition is from a different geographic location. A geographic location can be defined based upon the predominant soil type in a region, the predominant climate in a region, the predominant plant community present in a region, the predominant plant community present in a region, the distance between regions, the average rainfall in a region, among others.

In some embodiments, the microbes of the present compositions are not naturally found in association with the same species of animal. In some embodiments, the microbes of the present compositions are found in the same species of animal, but separated by geographic region.

In a particular embodiment, at least one microbial species that is a member of the microbial community derived by the disclosed method is native to, or was acquired from, a geographic region at least about 1 m, 10 m, 100 m, 1 km, 10 km, 100 km, 1,000 km, 10,000 km, 20,000 km, 30,000 km, or 40,000 km from the location of the animal upon which a phenotypic trait is to be increased based upon the taught methods.

The microbes of the present disclosure were obtained, among other places, at various locales in the United States from the gastrointestinal tract of canines.

Isolated Microbes—Microbial Culture Techniques

The microbes of Table 1 were matched to their nearest taxonomic groups by utilizing classification tools of the Ribosomal Database Project (RDP) for 16s rRNA sequences and the User-friendly Nordic ITS Ectomycorrhiza (UNITE) database for ITS rRNA sequences. Examples of matching microbes to their nearest taxa may be found in Lan et al. (2012. PLOS one. 7(3):e32491), Schloss and Westcott (2011. *Appl. Environ. Microbiol.* 77(10):3219-3226), and Koljalg et al. (2005. *New Phytologist.* 166(3):1063-1068).

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium (e.g., nutrient agar plates) to obtain a single colony, which is characterized by the phenotypic traits described herein (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for microbes of the disclosure, biologically pure isolates can be obtained through repeated subculture of biological samples, each subculture followed by streaking onto solid media to obtain individual colonies or colony forming units. Methods of preparing, thawing, and growing lyophilized bacteria are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present disclosure.

The microbes of the disclosure can be propagated in a liquid medium under aerobic conditions, or alternatively anaerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the microbes include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present disclosure include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 gram(s) per liter of medium. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 gram(s) per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the microbial strains, essentially, between 20° C. and 46° C. In some aspects, a temperature range is 30° C.-39° C. For optimal growth, in some embodiments, the medium can be adjusted to pH 6.0-7.4. It will be appreciated that commercially available media may also be used to culture the microbial strains, such as Nutrient Broth or Nutrient Agar available from Difco, Detroit, MI. It will be appreciated that cultivation time may differ depending on the type of culture medium used and the concentration of sugar as a major carbon source.

In some aspects, cultivation lasts between 24-96 hours. Microbial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. In some aspects, microbial multistrain cultures may be obtained by propagating two or more of the strains described hereinabove. It will be appreciated that the microbial strains may be cultured together when compatible culture conditions can be employed.

Isolated Microbes—Microbial Strains

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. *Microbiol Rev* 1996, 60:407-438). One accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species. Thus, populations that share greater than the aforementioned 70% threshold can be considered to be variants of the same species. Another accepted genotypic method for defining species is to isolate marker genes of the present disclosure, sequence these genes, and align these sequenced genes from multiple isolates or variants. The microbes are interpreted as belonging to the same species if one or more of the sequenced genes share at least 97% sequence identity.

The 16S or 18S rRNA sequences or ITS sequences are often used for making distinctions between species and strains, in that if one of the aforementioned sequences shares less than a specified % sequence identity from a reference sequence, then the two organisms from which the sequences were obtained are said to be of different species or strains.

Thus, one could consider microbes to be of the same species, if they share at least 80%, 85%, 90%, 95%, 97%, 98%, or 99% sequence identity across the 16S or 18S rRNA sequence, or the ITS1 or ITS2 sequence.

Further, one could define microbial strains of a species, as those that share at least 80%, 85%, 90%, 95%, 97%, 98%, or 99% sequence identity across the 16S or 18S rRNA sequence, or the ITS1 or ITS2 sequence.

In one embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 95.1%, 95.2%, 95.3%, 95.4%, 95.5%, 95.6%, 95.7%, 95.8%, 95.9%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% sequence identity with any one of SEQ ID NOs:1-333.

In a further embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 95.1%, 95.2%, 95.3%, 95.4%, 95.5%, 95.6%, 95.7%, 95.8%, 95.9%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% sequence identity with any one of SEQ ID NOs:1-333.

Comparisons may also be made with 23S rRNA sequences against reference sequences.

Unculturable microbes often cannot be assigned to a definite species in the absence of a phenotype determination, the microbes can be given a candidatus designation within a genus provided their 16S or 18S rRNA sequences or ITS sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure.

In one embodiment, the microbes taught herein were identified utilizing 16S rRNA gene sequences and ITS sequences. It is known in the art that 16S rRNA contains hypervariable regions that can provide species/strain-specific signature sequences useful for bacterial identification, and that ITS sequences can also provide species/strain-specific signature sequences useful for fungal identification.

Phylogenetic analysis using the rRNA genes and/or ITS sequences are used to define "substantially similar" species belonging to common genera and also to define "substantially similar" strains of a given taxonomic species. Furthermore, physiological and/or biochemical properties of the isolates can be utilized to highlight both minor and significant differences between strains that could lead to advantageous behavior or outcomes in canines.

Compositions of the present disclosure may include combinations of fungal spores and bacterial spores, fungal spores and bacterial vegetative cells, fungal vegetative cells and bacterial spores, fungal vegetative cells and bacterial vegetative cells. In some embodiments, compositions of the present disclosure comprise bacteria only in the form of spores. In some embodiments, compositions of the present disclosure comprise bacteria only in the form of vegetative cells. In some embodiments, compositions of the present disclosure comprise bacteria in the absence of fungi. In some embodiments, compositions of the present disclosure comprise fungi in the absence of bacteria. In some embodiments, compositions of the present disclosure comprise VBNC bacteria and/or fungi. In some embodiments, compositions of the present disclosure comprise bacteria and/or fungi in a quiescent state. In some embodiments, compositions of the present disclosure include dormant bacteria and/or fungi.

Bacterial spores may include endospores and akinetes. Fungal spores may include statismospores, ballistospores, autospores, aplanospores, zoospores, mitospores, megaspores, microspores, meiospores, chlamydospores, urediniospores, teliospores, oospores, carpospores, tetraspores, sporangiospores, zygospores, ascospores, basidiospores, ascospores, and asciospores.

In some embodiments, spores of the composition germinate upon administration to animals of the present disclosure. In some embodiments, spores of the composition germinate only upon administration to animals of the present disclosure.

Microbial Compositions

In some embodiments, the microbes of the disclosure are combined into microbial compositions.

In some embodiments, the microbial compositions include animal feed, such as grain and grain byproducts (barley, maize, oats, sorghum, wheat, distillers grains, sweet bran, and the like)); starches (tapioca and the like); protein (oilseed cakes, vegetable wastes, corn by-products, wheat by-products, and the like); lean animal protein (chicken, turkey, duck, beef, buffalo, boar, pig, fish, lamb, rabbit, and the like); animal meal (chicken meal, beef meal, boar meal, pig meal, buffalo meal, bone meal, fish meal, rabbit meal, lamb meal, turkey meal, duck meal, and the like); animal fats (beef fat, chicken fat, tallow, and the like); and/or non-nitrogen protein. Animal feed for microbial compositions may further include commercial dry animal feed or wet animal feed. In some embodiments, the microbial compositions include vitamins and/or metabolites thereof, minerals, urea, trace elements, emulsifiers, aromatizing products, binders, colorants, odorants, thickening agents, antibiotics, and the like. In some embodiments, the microbial compositions include one or more of an ionophore; vaccine, antibiotic; antihelmintic; virucide; nematicide; amino acids such as methionine, glutamine, valine, glycine, cysteine, homocysteine, aspartic acid, and arginine; fish oil; oregano; carnitine, pantoate, pantothenate, aspartate, and biologically active molecules such as enzymes.

In some embodiments, the vitamins include vitamin B5, B1, B2, B3, B6, B9, B12, H, C, A, D, E, or K; and combinations thereof. In some embodiments, the microbial compositions include microbes that synthesize vitamin B5, B1, B2, B3, B6, B9, B12, H, C, A, D, E, and/or K. In some embodiments, the microbial compositions include microbes that synthesize vitamin B5. In some embodiments, the metabolites of vitamin B5, B1, B2, B3, B6, B9, B12, H, C, A, D, E, or K are contemplated as one or more components of a microbial composition of the present disclosure. In one embodiment, pantothenate is a component of a microbial composition of the present disclosure. In one embodiment, a component of a microbial composition of the present disclosure includes one or more precursors utilized by mammalian or microbial biosynthesis of vitamins.

In some embodiments, the microbial compositions of the present disclosure are solid. Where solid compositions are used, it may be desired to include one or more carrier materials including, but not limited to mineral earth carriers, food-grade carriers, and/or carriers of vegetable origin. Examples of such carriers include, but are not limited to: silicas, talc, kaolin, limestone, chalk, clay, dolomite, diatomaceous earth, activated charcoal, calcium sulfate, magnesium sulfate, magnesium oxide, zeolites, calcium carbonate, magnesium carbonate, trehalose, chitosan, shellac, albumins, starches, yucca root, skim milk powder, sweet whey powder, maltodextrin, lactose, inulin, dextrose, whey protein, flours (e.g., chickpea flour, sweet potato flour, or soy flour), yucca, sugar, soybean meal, maltodextrin, spices, herbs, cereal meals, tree bark meal, wood meal, and nutshell meal.

In some embodiments, the microbial compositions of the present disclosure are liquid. In further embodiments, the liquid comprises a solvent that may include water or an alcohol or a saline or carbohydrate solution, and other animal-safe solvents. In some embodiments, the microbial compositions of the present disclosure include binders such as animal-safe polymers, carboxymethylcellulose, starch, polyvinyl alcohol, and the like.

In some embodiments, the microbial compositions of the present disclosure comprise thickening agents such as silica, clay, natural extracts of seeds or seaweed, synthetic derivatives of cellulose, guar gum, locust bean gum, alginates, and methylcelluloses. In some embodiments, the microbial compositions comprise anti-settling agents such as modified starches, polyvinyl alcohol, xanthan gum, and the like.

In some embodiments, the microbial compositions of the present disclosure comprise flavoring agents, such as dried yeast, cheese flavoring, fish flavoring, pork flavoring, chicken flavoring, and/or beef flavoring.

In some embodiments, the microbial compositions of the present disclosure comprise colorants including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. In some embodiments, the microbial compositions of the present disclosure comprise trace nutrients such as salts of iron, manganese, boron, copper, cobalt, molybdenum and zinc. In some embodiments, the microbial compositions comprise dyes, both natural and artificial. In some embodiments, the dye is green in color.

In some embodiments, the microbial compositions of the present disclosure comprise an animal-safe virucide, parasiticide, bacteriocide, fungicide, or nematicide.

In some embodiments, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In a further embodiment, microbial compositions comprise polymers of agar, agarose, gelrite, gellan gum, and the like. In some embodiments, microbial compositions comprise plastic capsules, emulsions (e.g., water and oil), membranes, and artificial membranes. In some embodiments, emulsions or linked polymer solutions may comprise microbial compositions of the present disclosure. See Harel and Bennett (U.S. Pat. No. 8,460,726 B2).

In some embodiments, microbial compositions of the present disclosure comprise one or more oxygen scavengers, denitrifies, nitrifiers, heavy metal chelators, and/or dechlorinators; and combinations thereof. In one embodiment, the one or more oxygen scavengers, denitrifiers, nitrifiers, heavy metal chelators, and/or dechlorinators are not chemically active once the microbial compositions are mixed with food and/or water to be administered to the animal. In one embodiment, the one or more oxygen scavengers, denitrifiers, nitrifiers, heavy metal chelators, and/or dechlorinators are not chemically active when administered to the animal.

In some embodiments, microbial compositions of the present disclosure occur in a solid form (e.g., dispersed lyophilized spores) or a liquid form (microbes interspersed in a storage medium). In some embodiments, microbial compositions of the present disclosure are added in dry form to a liquid to a liquid to form a suspension immediately prior to administration In some embodiments, microbial compositions of the present disclosure comprise one or more preservatives. The preservatives may be in liquid or gas formulations. The preservatives may be selected from one or more of monosaccharide, disaccharide, trisaccharide, polysaccharide, acetic acid, ascorbic acid, calcium ascorbate, erythorbic acid, iso-ascorbic acid, erythrobic acid, potassium nitrate, sodium ascorbate, sodium erythorbate, sodium iso-ascorbate, sodium nitrate, sodium nitrite, nitrogen, benzoic acid, calcium sorbate, ethyl lauroyl arginate, methyl-p-hydroxy benzoate, methyl paraben, potassium acetate, potassium benzoiate, potassium bisulphite, potassium diacetate, potassium lactate, potassium metabisulphite, potassium sorbate, propyl-p-hydroxy benzoate, propyl paraben, sodium acetate, sodium benzoate, sodium bisulphite, sodium nitrite, sodium diacetate, sodium lactate, sodium metabisulphite, sodium salt of methyl-p-hydroxy benzoic acid, sodium salt of propyl-p-hydroxy benzoic acid, sodium sulphate, sodium sulfite, sodium dithionite, sulphurous acid, calcium propionate, dimethyl dicarbonate, natamycin, potassium sorbate, potassium bisulfite, potassium metabisulfite, propionic acid, sodium diacetate, sodium propionate, sodium sorbate, sorbic acid, ascorbic acid, ascorbyl palmitate, ascorbyl stearate, butylated hydro-xyanisole, butylated hydroxytoluene (BHT), butylated hydroxyl anisole (BHA), citric acid, citric acid esters of mono- and/or diglycerides, L-cysteine, L-cysteine hydrochloride, gum guaiacum, gum guaiac, lecithin, lecithin citrate, monoglyceride citrate, monoisopropyl citrate, propyl gallate, sodium metabisulphite, tartaric acid, tertiary butyl hydroquinone, stannous chloride, thiodipropionic acid, dilauryl thiodipropionate, distearyl thiodipropionate, ethoxyquin, sulfur dioxide, formic acid, or tocopherol(s).

In some embodiments, the microbial compositions of the present disclosure comprise carriers that reduce fecal odor. In some embodiments, the microbial composition comprises activated charcoal to reduce fecal odor. In some embodiments, the microbial composition comprises yucca root to reduce fecal odor.

In some embodiments, the microbial compositions of the present disclosure include bacterial and/or fungal cells in spore form, vegetative cell form, and/or lysed cell form. In one embodiment, the lysed cell form acts as a mycotoxin binder, e.g. mycotoxins binding to dead cells.

In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks. In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 years.

In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks. In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 years.

In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks. In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 years.

In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks. In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 years.

In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks. In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 years.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 100, about 1 to 95, about 1 to 90, about 1 to 85, about 1 to 80, about 1 to 75, about 1 to 70, about 1 to 65, about 1 to 60, about 1 to 55, about 1 to 50, about 1 to 45, about 1 to 40, about 1 to 35, about 1 to 30, about 1 to 25, about 1 to 20, about 1 to 15, about 1 to 10, about 1 to 5, about 5 to 100, about 5 to 95, about 5 to 90, about 5 to 85, about 5 to 80, about 5 to 75, about 5 to 70, about 5 to 65, about 5 to 60, about 5 to 55, about 5 to 50, about 5 to 45, about 5 to 40, about 5 to 35, about 5 to 30, about 5 to 25, about 5 to 20, about 5 to 15, about 5 to 10, about 10 to 100, about 10 to 95, about 10 to 90, about 10 to 85, about 10 to 80, about 10 to 75, about 10 to 70, about 10 to 65, about 10 to 60, about 10 to 55, about 10 to 50, about 10 to 45, about 10 to 40, about 10 to 35, about 10 to 30, about 10 to 25, about 10 to 20, about 10 to 15, about 15 to 100, about 15 to 95, about 15 to 90, about 15 to 85, about 15 to 80, about 15 to 75, about 15 to 70, about 15 to 65, about 15 to 60, about 15 to 55, about 15 to 50, about 15 to 45, about 15 to 40, about 15 to 35, about 15 to 30, about 15 to 25, about 15 to 20, about 20 to 100, about 20 to 95, about 20 to 90, about 20 to 85, about 20 to 80, about 20 to 75, about 20 to 70, about 20 to 65, about 20 to 60, about 20 to 55, about 20 to 50, about 20 to 45, about 20 to 40, about 20 to 35, about 20 to 30, about 20 to 25, about 25 to 100, about 25 to 95, about 25 to 90, about 25 to 85, about 25 to 80, about 25 to 75, about 25 to 70, about 25 to 65, about 25 to 60, about 25 to 55, about 25 to 50, about 25 to 45, about 25 to 40, about 25 to 35, about 25 to 30, about 30 to 100, about 30 to 95, about 30 to 90, about 30 to 85, about 30 to 80, about 30 to 75, about 30 to 70, about 30 to 65, about 30 to 60, about 30 to 55, about 30 to 50, about 30 to 45, about 30 to 40, about 30 to 35, about 35 to 100, about 35 to 95, about 35 to 90, about 35 to 85, about 35 to 80, about 35 to 75, about 35 to 70, about 35 to 65, about 35 to 60, about 35 to 55, about 35 to 50, about 35 to 45, about 35 to 40, about 40 to 100, about 40 to 95, about 40 to 90, about 40 to 85, about 40 to 80, about 40 to 75, about 40 to 70, about 40 to 65, about 40 to 60, about 40 to 55, about 40 to 50, about 40 to 45, about 45 to 100, about 45 to 95, about 45 to 90, about 45 to 85, about 45 to 80, about 45 to 75, about 45 to 70, about 45 to 65, about 45 to 60, about 45 to 55, about 45 to 50, about 50 to 100, about 50 to 95, about 50 to 90, about 50 to 85, about 50 to 80, about 50 to 75, about 50 to 70, about 50 to 65, about 50 to 60, about 50 to 55, about 55 to 100, about 55 to 95, about 55 to 90, about 55 to 85, about 55 to 80, about 55 to 75, about 55 to 70, about 55 to 65, about 55 to 60, about 60 to 100, about 60 to 95, about 60 to 90, about 60 to 85, about 60 to 80, about 60 to 75, about 60 to 70, about 60 to 65, about 65 to 100, about 65 to 95, about 65 to 90, about 65 to 85, about 65 to 80, about 65 to 75, about 65 to 70, about 70 to 100, about 70 to 95, about 70 to 90, about 70 to 85, about 70 to 80, about 70 to 75, about 75 to 100, about 75 to 95, about 75 to 90, about 75 to 85, about 75 to 80, about 80 to 100, about 80 to 95, about 80 to 90, about 80 to 85, about 85 to 100, about 85 to 95, about 85 to 90, about 90 to 100, about 90 to 95, or 95 to 100 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 100, 1 to 95, 1 to 90, 1 to 85, 1 to 80, 1 to 75, 1 to 70, 1 to 65, 1 to 60, 1 to 55, 1 to 50, 1 to 45, 1 to 40, 1 to 35, 1 to 30, 1 to 25, 1 to 20, 1 to 15, 1 to 10, 1 to 5, 5 to 100, 5 to 95, 5 to 90, 5 to 85, 5 to 80, 5 to 75, 5 to 70, 5 to 65, 5 to 60, 5 to 55, 5 to 50, 5 to 45, 5 to 40, 5 to 35, 5 to 30, 5 to 25, 5 to 20, 5 to 15, 5 to 10, 10 to 100, 10 to 95, 10 to 90, 10 to 85, 10 to 80, 10 to 75, 10 to 70, 10 to 65, 10 to 60, 10 to 55, 10 to 50, 10 to 45, 10 to 40, 10 to 35, 10 to 30, 10 to 25, 10 to 20, 10 to 15, 15 to 100, 15 to 95, 15 to 90, 15 to 85, 15 to 80, 15 to 75, 15 to 70, 15 to 65, 15 to 60, 15 to 55, 15 to 50, 15 to 45, 15 to 40, 15 to 35, 15 to 30, 15 to 25, 15 to 20, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, 20 to 30, 20 to 25, 25 to 100, 25 to 95, 25 to 90, 25 to 85, 25 to 80, 25 to 75, 25 to 70, 25 to 65, 25 to 60, 25 to 55, 25 to 50, 25 to 45, 25 to 40, 25 to 35, 25 to 30, 30 to 100, 30 to 95, 30 to 90, 30 to 85, 30 to 80, 30 to 75, 30 to 70, 30 to 65, 30 to 60, 30 to 55, 30 to 50, 30 to 45, 30 to 40, 30 to 35, 35 to 100, 35 to 95, 35 to 90, 35 to 85, 35 to 80, 35 to 75, 35 to 70, 35 to 65, 35 to 60, 35 to 55, 35 to 50, 35 to 45, 35 to 40, 40 to 100, 40 to 95, 40 to 90, 40 to 85, 40 to 80, 40 to 75, 40 to 70, 40 to 65, 40 to 60, 40 to 55, 40 to 50, 40 to 45, 45 to 100, 45 to 95, 45 to 90, 45 to 85, 45 to 80, 45 to 75, 45 to 70, 45 to 65, 45 to 60, 45 to 55, 45 to 50, 50 to 100, 50 to 95, 50 to 90, 50 to 85, 50 to 80, 50 to 75, 50 to 70, 50 to 65, 50 to 60, 50 to 55, 55 to 100, 55 to 95, 55 to 90, 55 to 85, 55 to 80, 55 to 75, 55 to 70, 55 to 65, 55 to 60, 60 to 100, 60 to 95, 60 to 90, 60 to 85, 60 to 80, 60 to 75, 60 to 70, 60 to 65, 65 to 100, 65 to 95, 65 to 90, 65 to 85, 65 to 80, 65 to 75, 65 to 70, 70 to 100, 70 to 95, 70 to 90, 70 to 85, 70 to 80, 70 to 75, 75 to 100, 75 to 95, 75 to 90, 75 to 85, 75 to 80, 80 to 100, 80 to 95, 80 to 90, 80 to 85, 85 to 100, 85 to 95, 85 to 90, 90 to 100, 90 to 95, or 95 to 100 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 36, about 1 to 34, about 1 to 32, about 1 to 30, about 1 to 28, about 1 to 26, about 1 to 24, about 1 to 22, about 1 to 20, about 1 to 18, about 1 to 16, about 1 to 14, about 1 to 12, about 1 to 10, about 1 to 8, about 1 to 6, about 1 one 4, about 1 to 2, about 4 to 36, about 4 to 34, about 4 to 32, about 4 to 30, about 4 to 28, about 4 to 26, about 4 to 24, about 4 to 22, about 4 to 20, about 4 to 18, about 4 to 16, about 4 to 14, about 4 to 12, about 4 to 10, about 4 to 8, about 4 to 6, about 6 to 36, about 6 to 34, about 6 to 32, about 6 to 30, about 6 to 28, about 6 to 26, about 6 to 24, about 6 to 22, about 6 to 20, about 6 to 18, about 6 to 16, about 6 to 14, about 6 to 12, about 6 to 10, about 6 to 8, about 8 to 36, about 8 to 34, about 8 to 32, about 8 to 30, about 8 to 28, about 8 to 26, about 8 to 24, about 8 to 22, about 8 to 20, about 8 to 18, about 8 to 16, about 8 to 14, about 8 to 12, about 8 to 10, about 10 to 36, about 10 to 34, about 10 to 32, about 10 to 30, about 10 to 28, about 10 to 26, about 10 to 24, about 10 to 22, about 10 to 20, about 10 to 18, about 10 to 16, about 10 to 14, about 10 to 12, about 12 to 36, about 12 to 34, about 12 to 32, about 12 to 30, about 12 to 28, about 12 to 26, about 12 to 24, about 12 to 22, about 12 to 20, about 12 to 18, about 12 to 16, about 12 to 14, about 14 to 36, about 14 to 34, about 14 to 32, about 14 to 30, about 14 to 28, about 14 to 26, about 14 to 24, about 14 to 22, about 14 to 20, about 14 to 18, about 14 to 16, about 16 to 36, about 16 to 34, about 16 to 32, about 16 to 30, about 16 to 28, about 16 to 26, about 16 to 24, about 16 to 22, about 16 to 20, about 16 to 18, about 18 to 36, about 18 to 34, about 18 to 32, about 18 to 30, about 18 to 28, about 18 to 26, about 18 to 24, about 18 to 22, about 18 to 20, about 20 to 36, about 20 to 34, about 20 to 32, about 20 to 30, about 20 to 28, about 20 to 26, about 20 to 24, about 20 to 22, about 22 to 36, about 22 to 34, about 22 to 32, about 22 to 30, about 22 to 28, about 22 to 26, about 22 to 24, about 24 to 36, about 24 to 34, about 24 to 32, about 24 to 30, about 24 to 28, about 24 to 26, about 26 to 36, about 26 to 34, about 26 to 32, about 26 to 30, about 26 to 28, about 28 to 36, about 28 to 34, about 28 to 32, about 28 to 30, about 30 to 36, about 30 to 34, about 30 to 32, about 32 to 36, about 32 to 34, or about 34 to 36 months.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 36, 1 to 34, 1 to 32, 1 to 30, 1 to 28, 1 to 26, 1 to 24, 1 to 22, 1 to 20, 1 to 18, 1 to 16, 1 to 14, 1 to 12, 1 to 10, 1 to 8, 1 to 6, 1 to 4, 1 to 2, 4 to 36, 4 to 34, 4 to 32, 4 to 30, 4 to 28, 4 to 26, 4 to 24, 4 to 22, 4 to 20, 4 to 18, 4 to 16, 4 to 14, 4 to 12, 4 to 10, 4 to 8, 4 to 6, 6 to 36, 6 to 34, 6 to 32, 6 to 30, 6 to 28, 6 to 26, 6 to 24, 6 to 22, 6 to 20, 6 to 18, 6 to 16, 6 to 14, 6 to 12, 6 to 10, 6 to 8, 8 to 36, 8 to 34, 8 to 32, 8 to 30, 8 to 28, 8 to 26, 8 to 24, 8 to 22, 8 to 20, 8 to 18, 8 to 16, 8 to 14, 8 to 12, 8 to 10, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 36, 14 to 34, 14 to 32, 14 to 30, 14 to 28, 14 to 26, 14 to 24, 14 to 22, 14 to 20, 14 to 18, 14 to 16, 16 to 36, 16 to 34, 16 to 32, 16 to 30, 16 to 28, 16 to 26, 16 to 24, 16 to 22, 16 to 20, 16 to 18, 18 to 36, 18 to 34, 18 to 32, 18 to 30, 18 to 28, 18 to 26, 18 to 24, 18 to 22, 18 to 20, 20 to 36, 20 to 34, 20 to 32, 20 to 30, 20 to 28, 20 to 26, 20 to 24, 20 to 22, 22 to 36, 22 to 34, 22 to 32, 22 to 30, 22 to 28, 22 to 26, 22 to 24, 24 to 36, 24 to 34, 24 to 32, 24 to 30, 24 to 28, 24 to 26, 26 to 36, 26 to 34, 26 to 32, 26 to 30, 26 to 28, 28 to 36, 28 to 34, 28 to 32, 28 to 30, 30 to 36, 30 to 34, 30 to 32, 32 to 36, 32 to 34, or 34 to 36 months.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 36, about 1 to 34, about 1 to 32, about 1 to 30, about 1 to 28, about 1 to 26, about 1 to 24, about 1 to 22, about 1 to 20, about 1 to 18, about 1 to 16, about 1 to 14, about 1 to 12, about 1 to 10, about 1 to 8, about 1 to 6, about 1 one 4, about 1 to 2, about 4 to 36, about 4 to 34, about 4 to 32, about 4 to 30, about 4 to 28, about 4 to 26, about 4 to 24, about 4 to 22, about 4 to 20, about 4 to 18, about 4 to 16, about 4 to 14, about 4 to 12, about 4 to 10, about 4 to 8, about 4 to 6, about 6 to 36, about 6 to 34, about 6 to 32, about 6 to 30, about 6 to 28, about 6 to 26, about 6 to 24, about 6 to 22, about 6 to 20, about 6 to 18, about 6 to 16, about 6 to 14, about 6 to 12, about 6 to 10, about 6 to 8, about 8 to 36, about 8 to 34, about 8 to 32, about 8 to 30, about 8 to 28, about 8 to 26, about 8 to 24, about 8 to 22, about 8 to 20, about 8 to 18, about 8 to 16, about 8 to 14, about 8 to 12, about 8 to 10, about 10 to 36, about 10 to 34, about 10 to 32, about 10 to 30, about 10 to 28, about 10 to 26, about 10 to 24, about 10 to 22, about 10 to 20, about 10 to 18, about 10 to 16, about 10 to 14, about 10 to 12, about 12 to 36, about 12 to 34, about 12 to 32, about 12 to 30, about 12 to 28, about 12 to 26, about 12 to 24, about 12 to 22, about 12 to 20, about 12 to 18, about 12 to 16, about 12 to 14, about 14 to 36, about 14 to 34, about 14 to 32, about 14 to 30, about 14 to 28, about 14 to 26, about 14 to 24, about 14 to 22, about 14 to 20, about 14 to 18, about 14 to 16, about 16 to 36, about 16 to 34, about 16 to 32, about 16 to 30, about 16 to 28, about 16 to 26, about 16 to 24, about 16 to 22, about 16 to 20, about 16 to 18, about 18 to 36, about 18 to 34, about 18 to 32, about 18 to 30, about 18 to 28, about 18 to 26, about 18 to 24, about 18 to 22, about 18 to 20, about 20 to 36, about 20 to 34, about 20 to 32, about 20 to 30, about 20 to 28, about 20 to 26, about 20 to 24, about 20 to 22, about 22 to 36, about 22 to 34, about 22 to 32, about 22 to 30, about 22 to 28, about 22 to 26, about 22 to 24, about 24 to 36, about 24 to 34, about 24 to 32, about 24 to 30, about 24 to 28, about 24 to 26, about 26 to 36, about 26 to 34, about 26 to 32, about 26 to 30, about 26 to 28, about 28 to 36, about 28 to 34, about 28 to 32, about 28 to 30, about 30 to 36, about 30 to 34, about 30 to 32, about 32 to 36, about 32 to 34, or about 34 to 36 years.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 36, 1 to 34, 1 to 32, 1 to 30, 1 to 28, 1 to 26, 1 to 24, 1 to 22, 1 to 20, 1 to 18, 1 to 16, 1 to 14, 1 to 12, 1 to 10, 1 to 8, 1 to 6, 1 to 4, 1 to 2, 4 to 36, 4 to 34, 4 to 32, 4 to 30, 4 to 28, 4 to 26, 4 to 24, 4 to 22, 4 to 20, 4 to 18, 4 to 16, 4 to 14, 4 to 12, 4 to 10, 4 to 8, 4 to 6, 6 to 36, 6 to 34, 6 to 32, 6 to 30, 6 to 28, 6 to 26, 6 to 24, 6 to 22, 6 to 20, 6 to 18, 6 to 16, 6 to 14, 6 to 12, 6 to 10, 6 to 8, 8 to 36, 8 to 34, 8 to 32, 8 to 30, 8 to 28, 8 to 26, 8 to 24, 8 to 22, 8 to 20, 8 to 18, 8 to 16, 8 to 14, 8 to 12, 8 to 10, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 36, 14 to 34, 14 to 32, 14 to 30, 14 to 28, 14 to 26, 14 to 24, 14 to 22, 14 to 20, 14 to 18, 14 to 16, 16 to 36, 16 to 34, 16 to 32, 16 to 30, 16 to 28, 16 to 26, 16 to 24, 16 to 22, 16 to 20, 16 to 18, 18 to 36, 18 to 34, 18 to 32, 18 to 30, 18 to 28, 18 to 26, 18 to 24, 18 to 22, 18 to 20, 20 to 36, 20 to 34, 20 to 32, 20 to 30, 20 to 28, 20 to 26, 20 to 24, 20 to 22, 22 to 36, 22 to 34, 22 to 32, 22 to 30, 22 to 28, 22 to 26, 22 to 24, 24 to 36, 24 to 34, 24 to 32, 24 to 30, 24 to 28, 24 to 26, 26 to 36, 26 to 34, 26 to 32, 26 to 30, 26 to 28, 28 to 36, 28 to 34, 28 to 32, 28 to 30, 30 to 36, 30 to 34, 30 to 32, 32 to 36, 32 to 34, or 34 to 36 years.

In some embodiments, the microbial compositions of the present disclosure are shelf stable at any of the disclosed temperatures and/or temperature ranges and spans of time at a relative humidity of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98%.

In some embodiments, the microbial composition of the present disclosure possesses a water activity ($a_w$) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some embodiments, the microbial composition of the present disclosure possesses a water activity ($a_w$) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

The water activity values are determined by the method of Saturated Aqueous Solutions (Multon, "Techniques d'Analyse E De Controle Dans Les Industries Agroalimentaires" APRIA (1981)) or by direct measurement using a viable Robotronic BT hygrometer or other hygrometer or hygroscope.

In some embodiments, the microbial composition comprises at least two different microbes, and wherein the at least two microbes are present in the composition at a ratio of 1:2, 1:3, 1:3, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:40, 1:50, 1:60, 1:100, 1:125, 1:150, 1:175, or 1:200 or the inverse thereof. In some embodiments, the microbial composition comprises at least three different microbes, and wherein the three microbes are present in the composition at a ratio of 1:2:1, 1:1:2, 2:2:1, 1:3:1, 1:1:3, 3:1:1, 3:3:1, 1:5:1, 1:1:5, 5:1:1, 5:5:1, or 1:5:5.

In some aspects, the microbial compositions comprise probiotic microbes. In some aspects, the microbial compositions comprise prebiotic substances. In some aspects, probiotic microbes are known to competitively exclude gut pathogens.

Encapsulation Compositions

In some embodiments, the microbes or microbial compositions of the disclosure are encapsulated in an encapsulating composition. An encapsulating composition protects the microbes from external stressors prior to entering the gastrointestinal tract of canines. In some embodiments, external stressors include thermal and physical stressors associated with pelleting and extrusion. In some embodiments, external stressors include chemicals present in the compositions. Encapsulating compositions further create an environment that may be beneficial to the microbes, such as minimizing the oxidative stresses of an aerobic environment on anaerobic microbes. See Kalsta et al. (U.S. Pat. No. 5,104,662A), Ford (U.S. Pat. No. 5,733,568A), and Mosbach and Nilsson (U.S. Pat. No. 4,647,536A) for encapsulation compositions of microbes, and methods of encapsulating microbes.

In one embodiment, the compositions of the present disclosure exhibit a thermal tolerance, which is used interchangeably with heat tolerance and heat resistance. In one embodiment, thermal tolerant compositions of the present disclosure are tolerant of the high temperatures associated with feed manufacturing, mixing of feed and compositions of the present disclosure, storage in high heat environments, etc. In one embodiment, thermal tolerant compositions of the present disclosure are resistant to heat-killing and denaturation of the cell wall components and the intracellular environment.

In one embodiment, the compositions of the present disclosure exhibit a pH tolerance, which is used interchangeably with acid tolerance and base tolerance. In one embodiment, pH tolerant compositions of the present disclosure are tolerant of the low pH associated with one or more steps of feed preparation. In one embodiment, pH tolerant compositions of the present disclosure are tolerant of the low pH associated with one or more environments in the gastrointestinal tract of the animal, such as the stomach, duodenum, jejunum, ileum, cecum, proximal colon, distal colon, and rectum. In one embodiment, pH tolerant compositions of the present disclosure are tolerant of the high pH associated with one or more steps of feed preparation. In one embodiment, pH tolerant compositions of the present disclosure are tolerant of the rapid swings in pH (high to low, low to high, high to neutral, low to neutral, neutral to high, and neutral to low) associated with one or more steps of feed preparation. In one embodiment, pH tolerant compositions of the present disclosure are tolerant of the low pH associated with one or more environments in the gastrointestinal tract of the animal, such as the stomach.

In one embodiments, the encapsulation is a reservoir-type encapsulation. In one embodiment, the encapsulation is a matrix-type encapsulation. In one embodiment, the encapsulation is a coated matrix-type encapsulation. Burgain et al. (2011. J. Food Eng. 104:467-483) discloses numerous encapsulation embodiments and techniques, all of which are incorporated by reference.

In some embodiments, the compositions of the present disclosure are encapsulated in one or more of the following: gellan gum, xanthan gum, K-Carrageenan, cellulose acetate phthalate, chitosan, starch, milk fat, whey protein, Ca-alginate, raftilose, raftiline, pectin, saccharide, glucose, maltodextrin, gum arabic, guar, seed flour, alginate, dextrins, dextrans, celluloase, gelatin, gelatin, albumin, casein, gluten, acacia gum, tragacanth, wax, paraffin, stearic acid, monodiglycerides, and diglycerides. In some embodiments, the compositions of the present disclosure are encapsulated by one or more of a polymer, carbohydrate, sugar, plastic, glass, polysaccharide, lipid, wax, oil, fatty acid, or glyceride. In one embodiment, the microbial composition is encapsulated by glucose. In one embodiment, the microbial composition is encapsulated by a glucose-containing composition. In one embodiment, formulations of the microbial composition comprise a glucose encapsulant. In one embodiment, formulations of the microbial composition comprise a glucose-encapsulated composition.

In some embodiments, the encapsulation of the compositions of the present disclosure is carried out by an extrusion, emulsification, coating, agglomeration, lyophilization, vitrification, foam drying, preservation by vaporization, vacuum-drying, or spray-drying.

In some embodiments, the encapsulated compositions of the present disclosure are vitrified. In some embodiments, encapsulation involves a process of drying a composition of the present disclosure in the presence of a substance which forms a glassy, amorphous solid state, a process known as vitrification, and in doing so encapsulates the composition. In some embodiments, the vitrified composition is protected from degradative conditions that would typically destroy or degrade microbes. Many common substances have the property of vitrification; that is, they will form a glassy solid state under certain conditions. Among these substances are several sugars, including sucrose and maltose, and other more complex compounds, such as polyvinylpyrrolidone (PVP). As any solution dries down, the molecules in the solution can either crystalize, or they can vitrify. A solute which has an extensive asymmetry may be a superior vitrifier, because of the hindrances to nucleation of crystals during drying. A substance that inhibits the crystallization of another substance may result in the combined substances forming a superior vitrification, such as raffinose in the presence of sucrose. See U.S. Pat. Nos. 5,290,765 and 9,469,835.

In some embodiments, a microbial composition is produced that is encapsulated in a vitrified substance. The vitrified composition may be created by selecting a mixture including cells; combining said mixture with sufficient quantity of one or more vitrifying solutes to protect said mixture during drying and to inhibit destructive reactions; and drying said combination by exposing said combination to a desiccant, or desiccating conditions, at a temperature above that which said combination will freeze and below that at which said vitrifying solutes achieve the vitrified state, at approximately normal atmospheric pressure, until said combination is substantially dry.

In one embodiment, the encapsulating composition comprises microcapsules having a multiplicity of liquid cores encapsulated in a solid shell material. For purposes of the disclosure, a "multiplicity" of cores is defined as two or more.

A first category of useful fusible shell materials is that of normally solid fats, including fats which are already of suitable hardness and animal or vegetable fats and oils which are hydrogenated until their melting points are sufficiently high to serve the purposes of the present disclosure. Depending on the desired process and storage temperatures and the specific material selected, a particular fat can be either a normally solid or normally liquid material. The terms "normally solid" and "normally liquid" as used herein refer to the state of a material at desired temperatures for storing the resulting microcapsules. Since fats and hydrogenated oils do not, strictly speaking, have melting points, the term "melting point" is used herein to describe the minimum temperature at which the fusible material becomes sufficiently softened or liquid to be successfully emulsified and spray cooled, thus roughly corresponding to the maximum temperature at which the shell material has sufficient integrity to prevent release of the choline cores. "Melting point" is similarly defined herein for other materials which do not have a sharp melting point.

Specific examples of fats and oils useful herein (some of which require hardening) are as follows: animal oils and fats, such as beef tallow, mutton tallow, lamb tallow, lard or pork fat, fish oil, and sperm oil; vegetable oils, such as canola oil, cottonseed oil, peanut oil, corn oil, olive oil, soybean oil, sunflower oil, safflower oil, coconut oil, palm oil, linseed oil, tung oil, and castor oil; fatty acid monoglycerides and diglycerides; free fatty acids, such as stearic acid, palmitic acid, and oleic acid; and mixtures thereof. The above listing of oils and fats is not meant to be exhaustive, but only exemplary.

Specific examples of fatty acids include linoleic acid, γ-linoleic acid, dihomo-γ-linolenic acid, arachidonic acid, docosatetraenoic acid, vaccenic acid, nervonic acid, mead acid, erucic acid, gondoic acid, elaidic acid, oleic acid, palitoleic acid, stearidonic acid, eicosapentaenoic acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecyclic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, and octatriacontanoic acid.

Another category of fusible materials useful as encapsulating shell materials is that of waxes. Representative waxes contemplated for use herein are as follows: animal waxes, such as beeswax, lanolin, shell wax, and Chinese insect wax; vegetable waxes, such as carnauba, candelilla, bayberry, and sugar cane; mineral waxes, such as paraffin, microcrystalline petroleum, ozocerite, ceresin, and montan; synthetic waxes, such as low molecular weight polyolefin (e.g., CARBOWAX), and polyol ether-esters (e.g., sorbitol); Fischer-Tropsch process synthetic waxes; and mixtures thereof. Water-soluble waxes, such as CARBOWAX and sorbitol, are not contemplated herein if the core is aqueous.

Still other fusible compounds useful herein are fusible natural resins, such as rosin, balsam, shellac, and mixtures thereof.

In some embodiments, the microbes or microbial composition is embedded in a wax, such as the waxes described in the present disclosure.

In some embodiments, the microbes or microbial composition is embedded in wax balls. In some embodiments, the microbes or microbial composition is already encapsulated prior to being embedded in wax balls. In some embodiments, the wax balls are 10 microbes, 20 microns, 30 microns, 40 microns, 50 microns, 60 microns, 70 microns, 80 microns, 90 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, 850 microns, 900 microns, 950 microns, or 1,000 microns.

In some embodiments, the wax balls are about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the wax balls are between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the wax balls are between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

Various adjunct materials are contemplated for incorporation in fusible materials according to the present disclosure. For example, antioxidants, light stabilizers, dyes and lakes, flavors, essential oils, anti-caking agents, fillers, pH stabilizers, sugars (monosaccharides, disaccharides, trisaccharides, and polysaccharides) and the like can be incorporated in the fusible material in amounts which do not diminish its utility for the present disclosure.

The core material contemplated herein constitutes from about 0.1% to about 50%, about 1% to about 35%, or about 5% to about 30% by weight of the microcapsules. In some embodiments, the core material contemplated herein constitutes no more than about 30% by weight of the microcapsules. In some embodiments, the core material contemplated herein constitutes about 5% by weight of the microcapsules. The core material is contemplated as either a liquid or solid at contemplated storage temperatures of the microcapsules.

The cores may include other additives well-known in the pharmaceutical art, including edible sugars, such as sucrose, glucose, maltose, fructose, lactose, cellobiose, monosaccharides, disaccharides, trisaccharides, and polysaccharides, and mixtures thereof; artificial sweeteners, such as aspartame, saccharin, cyclamate salts, and mixtures thereof; edible acids, such as acetic acid (vinegar), citric acid, ascorbic acid, tartaric acid, and mixtures thereof; edible starches, such as corn starch; hydrolyzed vegetable protein; water-soluble vitamins, such as Vitamin C; water-soluble medicaments; water-soluble nutritional materials, such as ferrous sulfate; flavors; salts; monosodium glutamate; antimicrobial agents, such as sorbic acid; antimycotic agents, such as potassium sorbate, sorbic acid, sodium benzoate, and benzoic acid; food grade pigments and dyes; and mixtures thereof. Other potentially useful supplemental core materials will be apparent to those of ordinary skill in the art.

Emulsifying agents may be employed to assist in the formation of stable emulsions. Representative emulsifying agents include glyceryl monostearate, polysorbate esters, ethoxylated mono- and diglycerides, and mixtures thereof.

For ease of processing, and particularly to enable the successful formation of a reasonably stable emulsion, the viscosities of the core material and the shell material should be similar at the temperature at which the emulsion is formed. In particular, the ratio of the viscosity of the shell to the viscosity of the core, expressed in centipoise or comparable units, and both measured at the temperature of the emulsion, should be from about 22:1 to about 1:1, desirably from about 8:1 to about 1:1, and preferably from about 3:1 to about 1:1. A ratio of 1:1 would be ideal, but a viscosity ratio within the recited ranges is useful.

Encapsulating compositions are not limited to microcapsule compositions as disclosed above. In some embodiments encapsulating compositions encapsulate the microbial compositions in an adhesive polymer that can be natural or synthetic without toxic effect. In some embodiments, the encapsulating composition may be a matrix selected from sugar matrix, gelatin matrix, polymer matrix, silica matrix, starch matrix, foam matrix, glass/glassy matrix etc. See Pirzio et al. (U.S. Pat. No. 7,488,503). In some embodiments, the encapsulating composition may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; monosaccharides; fats; fatty acids, including oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

In some embodiments, the encapsulating compositions comprise at least one layer of encapsulation. In some embodiments, the encapsulating compositions comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 layers of encapsulation/encapsulants.

In some embodiments, the encapsulating compositions comprise at least two layers of encapsulation. In some embodiments, each layer of encapsulation confers a different characteristic to the composition. In some embodiments, no two consecutive layers confer the same characteristic. In some embodiments, at least one layer of the at least two layers of encapsulation confers thermostability, shelf stability, ultraviolet resistance, moisture resistance, hydrophobicity, hydrophilicity, lipophobicity, lipophilicity, pH stability, acid resistance, and base resistance.

In some embodiments, the encapsulating compositions comprise two layers of encapsulation; the first layer confers thermostability and/or shelf stability, and the second layer provides pH resistance.

In some embodiments, the encapsulating layers confer a timed release of the microbial composition held in the center of the encapsulating layers. In some embodiments, the greater the number of layers confers a greater amount of time before the microbial composition is exposed, post administration.

In some embodiments, the encapsulating shell of the present disclosure can be up to 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330

μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, 510 μm, 520 μm, 530 μm, 540 μm, 550 μm, 560 μm, 570 μm, 580 μm, 590 μm, 600 μm, 610 μm, 620 μm, 630 μm, 640 μm, 650 μm, 660 μm, 670 μm, 680 μm, 690 μm, 700 μm, 710 μm, 720 μm, 730 μm, 740 μm, 750 μm, 760 μm, 770 μm, 780 μm, 790 μm, 800 μm, 810 μm, 820 μm, 830 μm, 840 μm, 850 μm, 860 μm, 870 μm, 880 μm, 890 μm, 900 μm, 910 μm, 920 μm, 930 μm, 940 μm, 950 μm, 960 μm, 970 μm, 980 μm, 990 μm, 1000 μm, $10^{10}$ μm, 1020 μm, 1030 μm, 1040 μm, 1050 μm, 1060 μm, 1070 μm, 1080 μm, 1090 μm, 1100 μm, 1110 μm, 1120 μm, 1130 μm, 1140 μm, 1150 μm, 1160 μm, 1170 μm, 1180 μm, 1190 μm, 1200 μm, 1210 μm, 1220 μm, 1230 μm, 1240 μm, 1250 μm, 1260 μm, 1270 μm, 1280 μm, 1290 μm, 1300 μm, 1310 μm, 1320 μm, 1330 μm, 1340 μm, 1350 μm, 1360 μm, 1370 μm, 1380 μm, 1390 μm, 1400 μm, 1410 μm, 1420 μm, 1430 μm, 1440 μm, 1450 μm, 1460 μm, 1470 μm, 1480 μm, 1490 μm, 1500 μm, 1510 μm, 1520 μm, 1530 μm, 1540 μm, 1550 μm, 1560 μm, 1570 μm, 1580 μm, 1590 μm, 1600 μm, 1610 μm, 1620 μm, 1630 μm, 1640 μm, 1650 μm, 1660 μm, 1670 μm, 1680 μm, 1690 μm, 1700 μm, 1710 μm, 1720 μm, 1730 μm, 1740 μm, 1750 μm, 1760 μm, 1770 μm, 1780 μm, 1790 μm, 1800 μm, 1810 μm, 1820 μm, 1830 μm, 1840 μm, 1850 μm, 1860 μm, 1870 μm, 1880 μm, 1890 μm, 1900 μm, 1910 μm, 1920 μm, 1930 μm, 1940 μm, 1950 μm, 1960 μm, 1970 μm, 1980 μm, 1990 μm, 2000 μm, 2010 μm, 2020 μm, 2030 μm, 2040 μm, 2050 μm, 2060 μm, 2070 μm, 2080 μm, 2090 μm, 2100 μm, 2110 μm, 2120 μm, 2130 μm, 2140 μm, 2150 μm, 2160 μm, 2170 μm, 2180 μm, 2190 μm, 2200 μm, 2210 μm, 2220 μm, 2230 μm, 2240 μm, 2250 μm, 2260 μm, 2270 μm, 2280 μm, 2290 μm, 2300 μm, 2310 μm, 2320 μm, 2330 μm, 2340 μm, 2350 μm, 2360 μm, 2370 μm, 2380 μm, 2390 μm, 2400 μm, 2410 μm, 2420 μm, 2430 μm, 2440 μm, 2450 μm, 2460 μm, 2470 μm, 2480 μm, 2490 μm, 2500 μm, 2510 μm, 2520 μm, 2530 μm, 2540 μm, 2550 μm, 2560 μm, 2570 μm, 2580 μm, 2590 μm, 2600 μm, 2610 μm, 2620 μm, 2630 μm, 2640 μm, 2650 μm, 2660 μm, 2670 μm, 2680 μm, 2690 μm, 2700 μm, 2710 μm, 2720 μm, 2730 μm, 2740 μm, 2750 μm, 2760 μm, 2770 μm, 2780 μm, 2790 μm, 2800 μm, 2810 μm, 2820 μm, 2830 μm, 2840 μm, 2850 μm, 2860 μm, 2870 μm, 2880 μm, 2890 μm, 2900 μm, 2910 μm, 2920 μm, 2930 μm, 2940 μm, 2950 μm, 2960 μm, 2970 μm, 2980 μm, 2990 μm, or 3000 μm thick.

In some embodiments, the encapsulation composition of the present disclosure possesses a water activity ($a_w$) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some embodiments, the encapsulation composition of the present disclosure possesses a water activity ($a_w$) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

In one embodiment, the microbe(s) are first dried by spray dry, lyophilization, or foam drying along with excipients that may include one or more sugars, sugar alcohols, disaccharides, trisaccharides, polysaccharides, salts, amino acids, amino acid salts, or polymers.

In some embodiments, the microbes or compositions comprising the microbes are milled to a size of 10 microns, 20 microns, 30 microns, 40 microns, 50 microns, 60 microns, 70 microns, 80 microns, 90 microns, 100 microns, 150 microns, 200 microns, 250 microns, 300 microns, 350 microns, 400 microns, 450 microns, 500 microns, 550 microns, 600 microns, 650 microns, 700 microns, 750 microns, 800 microns, 850 microns, 900 microns, 950 microns, or 1,000 microns.

In some embodiments, the microbes or compositions comprising the microbes are milled to a size of about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the microbes or compositions comprising the microbes are milled to a size of between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the microbes or compositions comprising the microbes are milled to a size of between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

In some embodiments, the microbes or compositions comprising the microbes are combined with a wax, fat, oil, fatty acid, or fatty alcohol, and spray congealed into beads of about 10 microbes, about 20 microns, about 30 microns, about 40 microns, about 50 microns, about 60 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, or about 1,000 microns.

In some embodiments, the microbes or compositions comprising the microbes are combined with a wax, fat, oil, fatty acid, or fatty alcohol, and spray congealed into beads of between 10-20 microns, 10-30 microns, 10-40 microns, 10-50 microns, 10-60 microns, 10-70 microns, 10-80 microns, 10-90 microns, 10-100 microns, 10-250 microns, 10-500 microns, 10-750 microns, 10-1,000 microns, 20-30 microns, 20-40 microns, 20-50 microns, 20-60 microns, 20-70 microns, 20-80 microns, 20-90 microns, 20-100 microns, 20-250 microns, 20-500 microns, 20-750 microns, 20-1,000 microns, 30-40 microns, 30-50 microns, 30-60 microns, 30-70 microns, 30-80 microns, 30-90 microns, 30-100 microns, 30-250 microns, 30-500 microns, 30-750 microns, 30-1,000 microns, 40-50 microns, 40-60 microns, 40-70 microns, 40-80 microns, 40-90 microns, 40-100 microns, 40-250 microns, 40-500 microns, 40-750 microns, 40-1,000 microns, 50-60 microns, 50-70 microns, 50-80 microns, 50-90 microns, 50-100 microns, 50-250 microns, 50-500 microns, 50-750 microns, 50-1,000 microns, 60-70 microns, 60-80 microns, 60-90 microns, 60-100 microns, 60-250 microns, 60-500 microns, 60-750 microns, 60-1,000 microns, 70-80 microns 70-90 microns, 70-90 microns, 70-100 microns, 70-250 microns, 70-500 microns, 70-750 microns, 70-1,000 microns, 80-90 microns, 80-100 microns, 80-250 microns, 80-500 microns, 80-500 microns, 80-750 microns, 80-1,000 microns, 90-100 microns, 90-250 microns, 90-500 microns, 90-750 microns, 90-1,000 microns, 100-250 microns, 100-500 microns, 100-750 microns, 100-1,000 microns, 250-500 microns, 250-750 microns, 250-1,000 microns, 500-750 microns, 500-1,000 microns, or 750-1,000 microns.

In some embodiments, the microbes or compositions comprising the microbes are combined with a wax, fat, oil, fatty acid, or fatty alcohol, and spray congealed into beads of between about 10-20 microns, about 10-30 microns, about 10-40 microns, about 10-50 microns, about 10-60 microns, about 10-70 microns, about 10-80 microns, about 10-90 microns, about 10-100 microns, about 10-250 microns, about 10-500 microns, about 10-750 microns, about 10-1,000 microns, about 20-30 microns, about 20-40 microns, about 20-50 microns, about 20-60 microns, about 20-70 microns, about 20-80 microns, about 20-90 microns, about 20-100 microns, about 20-250 microns, about 20-500 microns, about 20-750 microns, about 20-1,000 microns, about 30-40 microns, about 30-50 microns, about 30-60 microns, about 30-70 microns, about 30-80 microns, about 30-90 microns, about 30-100 microns, about 30-250 microns, about 30-500 microns, about 30-750 microns, about 30-1,000 microns, about 40-50 microns, about 40-60 microns, about 40-70 microns, about 40-80 microns, about 40-90 microns, about 40-100 microns, about 40-250 microns, about 40-500 microns, about 40-750 microns, about 40-1,000 microns, about 50-60 microns, about 50-70 microns, about 50-80 microns, about 50-90 microns, about 50-100 microns, about 50-250 microns, about 50-500 microns, about 50-750 microns, about 50-1,000 microns, about 60-70 microns, about 60-80 microns, about 60-90 microns, about 60-100 microns, about 60-250 microns, about 60-500 microns, about 60-750 microns, about 60-1,000 microns, about 70-80 microns about 70-90 microns, about 70-90 microns, about 70-100 microns, about 70-250 microns, about 70-500 microns, about 70-750 microns, about 70-1,000 microns, about 80-90 microns, about 80-100 microns, about 80-250 microns, about 80-500 microns, about 80-500 microns, about 80-750 microns, about 80-1,000 microns, about 90-100 microns, about 90-250 microns, about 90-500 microns, about 90-750 microns, about 90-1,000 microns, about 100-250 microns, about 100-500 microns, about 100-750 microns, about 100-1,000 microns, about 250-500 microns, about 250-750 microns, about 250-1,000 microns, about 500-750 microns, about 500-1,000 microns, or about 750-1,000 microns.

In some embodiments, the microbes or compositions comprising the microbes are combined with a wax, fat, oil, fatty acid, or fatty alcohol as well as a water-soluble polymer, salt, polysaccharide, sugar, polypeptide, protein, or sugar alcohol and spray congealed into beads, the size of which are described herein. In some embodiments, the water-soluble polymer, salt, polysaccharide, sugar, or sugar alcohol serves as a disintegrant. In some embodiments, the disintegrant forms pores once the beads are dispersed in the GI tract of the animal.

In some embodiments, the composition of the water-soluble polymer, salt, polysaccharide, sugar, polypeptide, protein, or sugar alcohol is modified such that the disintegrant dissolves within 1, 5, 10, 15, 20, 25, 30, 35, 40, 45, 50, 55, 60 minutes of being administered. In some embodiments, the composition of the water-soluble polymer, salt, polysaccharide, sugar, polypeptide, protein, or sugar alcohol is modified such that the disintegrant dissolves within about 1, about 5, about 10, about 15, about 20, about 25, about 30, about 35, about 40, about 45, about 50, about 55, or about 60 minutes of being administered.

In some embodiments, the composition of the water-soluble polymer, salt, polysaccharide, sugar, polypeptide, protein, or sugar alcohol is modified such that the disintegrant dissolves within 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours of being administered. In some embodiments, the composition of the water-soluble polymer, salt, polysaccharide, sugar, polypeptide, protein, or sugar alcohol is modified such that the disintegrant dissolves within about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, or about 12 hours of being administered.

In some embodiments, the composition of the water-soluble polymer, salt, polysaccharide, sugar, polypeptide, protein, or sugar alcohol is modified such that the disintegrant dissolves at a temperature of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. In some embodiments, the composition of the water-soluble polymer, salt, polysaccharide, sugar, polypeptide, protein, or sugar alcohol is modified such that the disintegrant dissolves at a temperature of at least about 10, least about 11, least about 12, least about 13, least about 14, least about 15, least about 16, least about 17, least about 18, least about 19, least about 20, least about 21, least about 22, least about 23, least about 24, least about 25, least about 26, least about 27, least about 28, least about 29, least about 30, least about 31, least about 32, least about 33, least about 34, about 35, about 36, about 37, about 38, about 39, about 40, about 41, about 42, about 43, about 44, least about 45, least about 46, least about 47, least about 48, least about 49, or least about 50° C.

In some embodiments, the composition of the water-soluble polymer, salt, polysaccharide, sugar, polypeptide, protein, or sugar alcohol is modified such that the disintegrant dissolves at a pH of at least 3.8, 3.9, 4. 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In some embodiments, the composition of the water-soluble polymer, salt, polysaccharide, sugar, polypeptide, protein, or sugar alcohol is modified such that the disintegrant dissolves at a pH of at least about 3.8, least about 3.9, least about 4. least about 4.1, least about 4.2, least about 4.3, least about 4.4, least about 4.5, least about 4.6, least about 4.7, least about 4.8, least about 4.9, least about 5.0, least about 5.1, least about 5.2, least about 5.3, least about 5.4, least about 5.5, least about 5.6, least about 5.7, least about 5.8, least about 5.9, least about 6.0, least about 6.2, least about 6.3, least about 6.4, least about 6.5, least about 6.6, least about 6.7, least about 6.8, least about 6.9, least about 7.0, least about 7.1, least about 7.2, least about 7.3, least about 7.4, least about 7.5, least about 7.6, least about 7.7, least about 7.8, least about 7.9, least about 8.0, least about 8.1, least about 8.2, least about 8.3, least about 8.4, least about 8.5, least about 8.6, least about 8.7, least about 8.8, least about 8.9, least about 9.0, least about 9.1, least about 9.2, least about 9.3, least about 9.4, least about 9.5, least about 9.6, least about 9.7, least about 9.8, least about 9.9, or least about 10.0.

In some embodiments, the microbes or compositions comprising the microbes are coated with a polymer, a polysaccharide, sugar, sugar alcohol, gel, wax, fat, fatty alcohol, or fatty acid In some embodiments, the microbes or compositions comprising the microbes are coated with a polymer, a polysaccharide, sugar, sugar alcohol, gel, wax, fat, fatty alcohol, or fatty acid.

In some embodiments, the coating of the microbes or compositions comprising the microbes is modified such that the coating dissolves within 1, 5, 10, 15, 20, 25, 30, 35, 40, 45, 50, 55, 60 minutes of being administered. In some embodiments, the coating of the microbes or compositions comprising the microbes is modified such that the coating dissolves within about 1, about 5, about 10, about 15, about 20, about 25, about 30, about 35, about 40, about 45, about 50, about 55, or about 60 minutes of being administered.

In some embodiments, the coating of the microbes or compositions comprising the microbes is modified such that the coating dissolves within 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours of being administered. In some embodiments, the coating of the microbes or compositions comprising the microbes is modified such that the coating dissolves within about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, or about 12 hours of being administered.

In some embodiments, the coating of the microbes or compositions comprising the microbes is modified such that the coating dissolves at a temperature of at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. In some embodiments, the coating of the microbes or compositions comprising the microbes is modified such that the coating dissolves at a temperature of at least about 10, least about 11, least about 12, least about 13, least about 14, least about 15, least about 16, least about 17, least about 18, least about 19, least about 20, least about 21, least about 22, least about 23, least about 24, least about 25, least about 26, least about 27, least about 28, least about 29, least about 30, least about 31, least about 32, least about 33, least about 34, about 35, about 36, about 37, about 38, about 39, about 40, about 41, about 42, about 43, about 44, least about 45, least about 46, least about 47, least about 48, least about 49, or least about 50° C.

In some embodiments, the coating of the microbes or compositions comprising the microbes is modified such that the coating dissolves at a pH of at least 3.8, 3.9, 4. 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In some embodiments, the coating of the microbes or compositions comprising the microbes is modified such that the coating dissolves at a pH of at least about 3.8, least about 3.9, least about 4. least about 4.1, least about 4.2, least about 4.3, least about 4.4, least about 4.5, least about 4.6, least about 4.7, least about 4.8, least about 4.9, least about 5.0, least about 5.1, least about 5.2, least about 5.3, least about 5.4, least about 5.5, least about 5.6, least about 5.7, least about 5.8, least about 5.9, least about 6.0, least about 6.2, least about 6.3, least about 6.4, least about 6.5, least about 6.6, least about 6.7, least about 6.8, least about 6.9, least about 7.0, least about 7.1, least about 7.2, least about 7.3, least about 7.4, least about 7.5, least about 7.6, least about 7.7, least about 7.8, least about 7.9, least about 8.0, least about 8.1, least about 8.2, least about 8.3, least about 8.4, least about 8.5, least about 8.6, least about 8.7, least about 8.8, least about 8.9, least about 9.0, least about 9.1, least about 9.2, least about 9.3, least about 9.4, least about 9.5, least about 9.6, least about 9.7, least about 9.8, least about 9.9, or least about 10.0.

Animal Feed

In some aspects, animal feed includes dry food, kibble, wet food, treats, cookies, biscuits, frozen food, fresh food, preserved food, dehydrated food, pasteurized food, raw food, freeze dried food, and home cooked food. In some aspects, animal feed is pet food.

In some embodiments, compositions of the present disclosure are mixed with animal feed. In some embodiments, compositions of the present disclosure are sprinkled on top of animal feed. In some embodiments, animal feed may be present in various forms such as kibble, wet food, dry food, raw food, etc.

In some embodiments, compositions of the present disclosure are mixed into the feed itself. In one embodiment, the compositions of the present disclosure are mixed into the feed at the feed mill. In one embodiment, the compositions of the present disclosure are mixed into or onto the feed just prior to feeding.

In some embodiments, feed of the present disclosure may be supplemented with water, premix or premixes, commercially available formula feeds, and mixtures thereof.

In some embodiments, microbial compositions of the present disclosure may be mixed with animal feed. Individual components of the animal feed may be mixed with the microbial compositions prior to feeding to animals. The microbial compositions of the present disclosure may be mixed with feed and pelleted into kibble.

In some embodiments, microbial compositions of the present disclosure may be mixed with animal feed at various stages of animal development.

Administration of Microbial Compositions

In some embodiments, the microbial compositions of the present disclosure are administered to animals via the oral route. In some embodiments the microbial compositions are administered via a direct injection route into the gastrointestinal tract. In further embodiments, the direct injection administration delivers the microbial compositions directly to the stomach. In some embodiments, the microbial composition are administered to the buccal cavity, mouth, stomach, duodenum, jejunum, ileum, cecum, proximal colon, distal colon, and rectum. In some embodiments, the microbial compositions of the present disclosure are administered to animals via the anus. In some embodiments, the microbial compositions are directed to the animals' buccal cavity, mouth, stomach, duodenum, jejunum, ileum, cecum, proximal colon, distal colon, and rectum. In further embodiments, anal administration is in the form of an inserted suppository.

In some embodiments, the microbial composition is administered in a dose volume comprising a total of, or at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, 35 mL, 36 mL, 37 mL, 38 mL, 39 mL, 40 mL, 41 mL, 42 mL, 43 mL, 44 mL, 45 mL, 46 mL, 47 mL, 48 mL, 49 mL, 50 mL, 60 mL, 70 mL, 80 mL, 90 mL, 100 mL, 200 mL, 300 mL, 400 mL, 500 mL, 600 mL, 700 mL, 800 mL, 900 mL, or 1,000 mL.

In some embodiments, the microbial composition is administered in a dose comprising a total of, or at least, $10^{18}$, $10^{17}$, $10^{16}$, $10^{15}$, $10^{14}$, $10^{13}$, $10^{12}$, $10^{11}$, $10^{10}$, $10^{9}$, $10^{8}$, $10^{7}$, $10^{6}$, $10^{5}$, $10^{4}$, $10^{3}$, or $10^{2}$ microbial cells.

In some embodiments, the microbial compositions are mixed with feed, and the administration occurs through the ingestion of the microbial compositions along with the feed. In some embodiments, the dose of the microbial composition is administered such that there exists $10^{2}$ to $10^{12}$, $10^{3}$ to $10^{12}$, $10^{4}$ to $10^{12}$, $10^{5}$ to $10^{12}$, $10^{6}$ to $10^{12}$, $10^{7}$ to $10^{12}$, $10^{8}$ to $10^{12}$, $10^{9}$ to $10^{12}$, $10^{10}$ to $10^{12}$, $10^{11}$ to $10^{12}$, $10^{2}$ to $10^{11}$, $10^{3}$ to $10^{11}$, $10^{4}$ to $10^{11}$, $10^{5}$ to $10^{11}$, $10^{6}$ to $10^{11}$, $10^{7}$ to $10^{11}$, $10^{8}$ to $10^{11}$, $10^{9}$ to $10^{11}$, $10^{10}$ to $10^{11}$, $10^{2}$ to $10^{10}$, $10^{3}$ to $10^{10}$, $10^{4}$ to $10^{10}$, $10^{5}$ to $10^{10}$, $10^{6}$ to $10^{10}$, $10^{7}$ to $10^{10}$, $10^{8}$ to $10^{10}$, $10^{9}$ to $10^{10}$, $10^{2}$ to $10^{9}$, $10^{3}$ to $10^{9}$, $10^{4}$ to $10^{9}$, $10^{5}$ to $10^{9}$, $10^{6}$ to $10^{9}$, $10^{7}$ to $10^{9}$, $10^{8}$ to $10^{9}$, $10^{2}$ to $10^{8}$, $10^{3}$ to $10^{8}$, $10^{4}$ to $10^{8}$, $10^{5}$ to $10^{8}$, $10^{6}$ to $10^{8}$, $10^{7}$ to $10^{8}$, $10^{2}$ to $10^{7}$, $10^{3}$ to $10^{7}$, $10^{4}$ to $10^{7}$, $10^{5}$ to $10^{7}$, $10^{6}$ to $10^{7}$, $10^{2}$ to $10^{6}$, $10^{3}$ to $10^{6}$, $10^{4}$ to $10^{6}$, $10^{5}$ to $10^{6}$, $10^{2}$ to $10^{5}$, $10^{3}$ to $10^{5}$, $10^{4}$ to $10^{5}$, $10^{2}$ to $10^{4}$, $10^{3}$ to $10^{4}$, $10^{2}$ to $10^{3}$, $10^{12}$, $10^{11}$, $10^{10}$, $10^{9}$, $10^{8}$, $10^{7}$, $10^{6}$, $10^{5}$, $10^{4}$, $10^{3}$, or $10^{2}$ total microbial cells per gram or milliliter of the composition.

In some embodiments, the administered dose of the microbial composition comprises $10^{2}$ to $10^{18}$, $10^{3}$ to $10^{18}$, $10^{4}$ to $10^{18}$, $10^{5}$ to $10^{18}$, $10^{6}$ to $10^{18}$, $10^{7}$ to $10^{18}$, $10^{8}$ to $10^{18}$, $10^{9}$ to $10^{18}$, $10^{10}$ to $10^{18}$, $10^{1}$ to $10^{18}$, $10^{12}$ to $10^{18}$, $10^{13}$ to $10^{18}$, $10^{14}$ to $10^{18}$, $10^{15}$ to $10^{18}$, $10^{16}$ to $10^{18}$, $10^{17}$ to $10^{18}$, $10^{2}$ to $10^{12}$, $10^{3}$ to $10^{12}$, $10^{4}$ to $10^{12}$, $10^{5}$ to $10^{12}$, $10^{6}$ to $10^{12}$, $10^{7}$ to $10^{12}$, $10^{8}$ to $10^{12}$, $10^{9}$ to $10^{12}$, $10^{10}$ to $10^{12}$, $10^{1}$ to $10^{12}$, $10^{2}$ to $10^{11}$, $10^{3}$ to $10^{11}$, $10^{4}$ to $10^{11}$, $10^{5}$ to $10^{11}$, $10^{6}$ to $10^{11}$, $10^{7}$ to $10^{11}$, $10^{8}$ to $10^{11}$, $10^{9}$ to $10^{11}$, $10^{10}$ to $10^{11}$, $10^{2}$ to $10^{10}$, $10^{3}$ to $10^{10}$, $10^{4}$ to $10^{10}$, $10^{5}$ to $10^{10}$, $10^{6}$ to $10^{10}$, $10^{7}$ to $10^{10}$, $10^{8}$ to $10^{10}$, $10^{9}$ to $10^{10}$, $10^{2}$ to $10^{9}$, $10^{3}$ to $10^{9}$, $10^{4}$ to $10^{9}$, $10^{5}$ to $10^{9}$, $10^{6}$ to $10^{9}$, $10^{7}$ to $10^{9}$, $10^{8}$ to $10^{9}$, $10^{2}$ to $10^{8}$, $10^{3}$ to $10^{8}$, $10^{4}$ to $10^{8}$, $10^{5}$ to $10^{8}$, $10^{6}$ to $10^{8}$, $10^{7}$ to $10^{8}$, $10^{2}$ to $10^{7}$, $10^{3}$ to $10^{7}$, $10^{4}$ to $10^{7}$, $10^{5}$ to $10^{7}$, $10^{6}$ to $10^{7}$, $10^{2}$ to $10^{6}$, $10^{3}$ to $10^{6}$, $10^{4}$ to $10^{6}$, $10^{5}$ to $10^{6}$, $10^{2}$ to $10^{5}$, $10^{3}$ to $10^{5}$, $10^{4}$ to $10^{5}$, $10^{2}$ to $10^{4}$, $10^{3}$ to $10^{4}$, $10^{2}$ to $10^{3}$, $10^{18}$, $10^{17}$, $10^{16}$, $10^{15}$, $10^{14}$, $10^{13}$, $10^{12}$, $10^{11}$, $10^{10}$, $10^{9}$, $10^{8}$, $10^{7}$, $10^{6}$, $10^{5}$, $10^{4}$, $10^{3}$, or $10^{2}$ total microbial cells.

In some embodiments, the microbial composition comprises one or more bacteria comprising a 16S nucleic acid sequence selected from SEQ ID NOs: 1-333. In some embodiments, the one or more bacteria are present in the microbial composition at a concentration of $10^{2}$ to $10^{12}$, $10^{3}$ to $10^{12}$, $10^{4}$ to $10^{12}$, $10^{5}$ to $10^{12}$, $10^{6}$ to $10^{12}$, $10^{7}$ to $10^{12}$, $10^{8}$ to $10^{12}$, $10^{9}$ to $10^{12}$, $10^{10}$ to $10^{12}$, $10^{11}$ to $10^{12}$, $10^{2}$ to $10^{11}$, $10^{3}$ to $10^{11}$, $10^{4}$ to $10^{11}$, $10^{5}$ to $10^{11}$, $10^{6}$ to $10^{11}$, $10^{7}$ to $10^{11}$, $10^{8}$ to $10^{11}$, 10 to $10^{11}$, $10^{10}$ to $10^{11}$, $10^{2}$ to $10^{10}$, $10^{3}$ to $10^{10}$, $10^{4}$ to $10^{10}$, $10^{5}$ to $10^{10}$, $10^{6}$ to $10^{10}$, $10^{7}$ to $10^{10}$, $10^{8}$ to $10^{10}$, $10^{9}$ to $10^{10}$, $10^{2}$ to $10^{9}$, $10^{3}$ to $10^{9}$, $10^{4}$ to $10^{9}$, $10^{5}$ to $10^{9}$, $10^{6}$ to $10^{9}$, $10^{7}$ to $10^{9}$, $10^{8}$ to $10^{9}$, $10^{2}$ to $10^{8}$, $10^{3}$ to $10^{8}$, $10^{4}$ to $10^{8}$, $10^{5}$ to $10^{8}$, $10^{6}$ to $10^{8}$, $10^{7}$ to $10^{8}$, $10^{2}$ to $10^{7}$, $10^{3}$ to $10^{7}$, $10^{4}$ to $10^{7}$, $10^{5}$ to $10^{7}$, $10^{6}$ to $10^{7}$, $10^{2}$ to $10^{6}$, $10^{3}$ to $10^{6}$, $10^{4}$ to $10^{6}$, $10^{5}$ to $10^{6}$, $10^{2}$ to $10^{5}$, $10^{3}$ to $10^{5}$, $10^{4}$ to $10^{5}$, $10^{2}$ to $10^{4}$, $10^{3}$ to $10^{4}$, $10^{2}$ to $10^{3}$, $10^{12}$, $10^{11}$, $10^{10}$, $10^{9}$, $10^{8}$, $10^{7}$, $10^{6}$, $10^{5}$, $10^{4}$, $10^{3}$, or $10^{2}$ cells per gram or milliliter of said composition. In some embodiments, the one or more bacteria are present in the microbial composition at a concentration of at least, $10^{2}$, $10^{3}$, $10^{4}$, $10^{5}$, $10^{6}$, $10^{7}$, $10^{8}$, $10^{9}$, $10^{10}$, $10^{12}$, $10^{11}$, $10^{13}$, $10^{14}$, $10^{15}$ cells per gram or milliliter of said composition.

In some embodiments, the composition is administered 1 or more times per day. In some aspects, the composition is administered with food each time the animal is fed. In some embodiments, the composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per day. In some embodiments, the composition is administered once per day. In some embodiments, the composition is administered twice per day.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per week.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per month.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per year.

In some embodiments, the microbial composition is administered to animals throughout their lifetime. In some embodiments, the microbial composition is administered to animals only as juveniles. In some embodiments, the microbial composition is administered to animals only as adults. In some embodiments, the microbial composition is administered to animals only as seniors. In some aspects, the microbial composition is administered to animals during the first 5%, 10%, 15%, 20% or 25% of their expected life span. In some aspects, the microbial composition is administered to animals during the last 5%, 10%, 15%, 20% or 25% of their expected life span.

In some embodiments, the microbial composition is chronically administered to animals to improve overall health. In some embodiments, the microbial composition is administered once per day, twice per day, three times per day, once per week, twice per week, three times per week, once every two weeks, or once per month throughout the lifetime of the animal to improve overall health. In some embodiments, chronic administration with the microbial compositions described herein improves one or more traits in the canine. In some embodiments, chronic administration with the microbial compositions described herein reduces diarrhea, improves fecal consistency, reduces incidence of infectious or non-infectious disease, increases lifespan, and/or improves performance of the animal. In some embodiments, chronic administration with the microbial compositions described herein improves gastrointestinal health, reduces inflammation, and/or stabilizes the gastrointestinal microbiome.

In some embodiments, the microbial composition is acutely administered to animals to improve overall health. In some embodiments, the microbial composition is administered once per day, twice per day, three times per day, once per week, twice per week, three times per week, once every two weeks, or once per month over a one month period, two month period, three month period, six month period, or twelve month period to improve overall health of the animal. In some embodiments, the microbial composition is administered once per day over a one month period. In some embodiments, acute administration with the microbial compositions described herein improves one or more traits in the canine. In some embodiments, acute administration with the microbial compositions described herein reduces diarrhea, reduces dysbiosis, reduces enteropathy, decreases incidence of infectious or non-infectious disease, increases lifespan, and/or improves performance of the animal. In some embodiments, acute administration with the microbial compositions described herein improves gastrointestinal health, reduces inflammation, and/or stabilizes the gastrointestinal microbiome.

In some embodiments, the type of diet fed to the animal corresponds with the type of microbial composition administered to the animal. In some embodiments, an animal exhibiting GI dysbiosis or GI enteropathy will receive a first microbial composition. In some embodiments, the animal that was receiving the first microbial composition is administered a second microbial composition (different from the first) due to a decrease in the severity of the GI dysbiosis or GI enteropathy. In some embodiments, the animal that was receiving the first microbial composition is administered a third microbial composition (different from the first and second) due to a decrease in the severity of the GI dysbiosis or GI enteropathy. In some embodiments, the animal that was receiving at least a first, at least a second, or at least a third microbial composition is administered a subsequent microbial composition (different from the previous administered microbial compositions) for maintaining a healthy microflora state in the gastrointestinal tract.

In some embodiments, an animal exhibiting GI dysbiosis or GI enteropathy will receive a first microbial composition. In further embodiments, the same animal fed a different diet will receive a second microbial composition, wherein the first microbial composition is different from the second microbial composition. In some embodiments, the same animal fed yet a different diet will receive a third microbial composition, wherein the first microbial composition is different from the second and third microbial compositions. In some embodiments, the same animal fed yet a different diet will receive a fourth microbial composition, wherein the first microbial composition is different from the second, third, and fourth microbial compositions. In some embodiments, the same animal fed yet a different diet will receive a fifth microbial composition, wherein the first microbial composition is different from the second, third, fourth, and fifth microbial compositions.

In some embodiments, the feed can be uniformly coated with one or more layers of the microbes and/or microbial compositions disclosed herein, using conventional methods of mixing, spraying, or a combination thereof through the use of treatment application equipment that is specifically designed and manufactured to accurately, safely, and efficiently apply coatings. Such equipment uses various types of coating technology such as rotary coaters, drum coaters, fluidized bed techniques, spouted beds, rotary mists, or a combination thereof. Liquid treatments such as those of the present disclosure can be applied via either a spinning "atomizer" disk or a spray nozzle, which evenly distributes the microbial composition onto the feed as it moves though the spray pattern. In some aspects, the feed is then mixed or tumbled for an additional period of time to achieve additional treatment distribution and drying.

In some embodiments, the feed coats of the present disclosure can be up to 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340

μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, 510 μm, 520 μm, 530 μm, 540 μm, 550 μm, 560 μm, 570 μm, 580 μm, 590 μm, 600 μm, 610 μm, 620 μm, 630 μm, 640 μm, 650 μm, 660 μm, 670 μm, 680 μm, 690 μm, 700 μm, 710 μm, 720 μm, 730 μm, 740 μm, 750 μm, 760 μm, 770 μm, 780 μm, 790 μm, 800 μm, 810 μm, 820 μm, 830 μm, 840 μm, 850 μm, 860 μm, 870 μm, 880 μm, 890 μm, 900 μm, 910 μm, 920 μm, 930 μm, 940 μm, 950 μm, 960 μm, 970 μm, 980 μm, 990 μm, 1000 μm, $10^{10}$ μm, 1020 μm, 1030 μm, 1040 μm, 1050 μm, 1060 μm, 1070 μm, 1080 μm, 1090 μm, 1100 μm, 1110 μm, 1120 μm, 1130 μm, 1140 μm, 1150 μm, 1160 μm, 1170 μm, 1180 μm, 1190 μm, 1200 μm, 1210 μm, 1220 μm, 1230 μm, 1240 μm, 1250 μm, 1260 μm, 1270 μm, 1280 μm, 1290 μm, 1300 μm, 1310 μm, 1320 μm, 1330 μm, 1340 μm, 1350 μm, 1360 μm, 1370 μm, 1380 μm, 1390 μm, 1400 μm, 1410 μm, 1420 μm, 1430 μm, 1440 μm, 1450 μm, 1460 μm, 1470 μm, 1480 μm, 1490 μm, 1500 μm, 1510 μm, 1520 μm, 1530 μm, 1540 μm, 1550 μm, 1560 μm, 1570 μm, 1580 μm, 1590 μm, 1600 μm, 1610 μm, 1620 μm, 1630 μm, 1640 μm, 1650 μm, 1660 μm, 1670 μm, 1680 μm, 1690 μm, 1700 μm, 1710 μm, 1720 μm, 1730 μm, 1740 μm, 1750 μm, 1760 μm, 1770 μm, 1780 μm, 1790 μm, 1800 μm, 1810 μm, 1820 μm, 1830 μm, 1840 μm, 1850 μm, 1860 μm, 1870 μm, 1880 μm, 1890 μm, 1900 μm, 1910 μm, 1920 μm, 1930 μm, 1940 μm, 1950 μm, 1960 μm, 1970 μm, 1980 μm, 1990 μm, 2000 μm, 2010 μm, 2020 μm, 2030 μm, 2040 μm, 2050 μm, 2060 μm, 2070 μm, 2080 μm, 2090 μm, 2100 μm, 2110 μm, 2120 μm, 2130 μm, 2140 μm, 2150 μm, 2160 μm, 2170 μm, 2180 μm, 2190 μm, 2200 μm, 2210 μm, 2220 μm, 2230 μm, 2240 μm, 2250 μm, 2260 μm, 2270 μm, 2280 μm, 2290 μm, 2300 μm, 2310 μm, 2320 μm, 2330 μm, 2340 μm, 2350 μm, 2360 μm, 2370 μm, 2380 μm, 2390 μm, 2400 μm, 2410 μm, 2420 μm, 2430 μm, 2440 μm, 2450 μm, 2460 μm, 2470 μm, 2480 μm, 2490 μm, 2500 μm, 2510 μm, 2520 μm, 2530 μm, 2540 μm, 2550 μm, 2560 μm, 2570 μm, 2580 μm, 2590 μm, 2600 μm, 2610 μm, 2620 μm, 2630 μm, 2640 μm, 2650 μm, 2660 μm, 2670 μm, 2680 μm, 2690 μm, 2700 μm, 2710 μm, 2720 μm, 2730 μm, 2740 μm, 2750 μm, 2760 μm, 2770 μm, 2780 μm, 2790 μm, 2800 μm, 2810 μm, 2820 μm, 2830 μm, 2840 μm, 2850 μm, 2860 μm, 2870 μm, 2880 μm, 2890 μm, 2900 μm, 2910 μm, 2920 μm, 2930 μm, 2940 μm, 2950 μm, 2960 μm, 2970 μm, 2980 μm, 2990 μm, or 3000 μm thick.

In some embodiments, the microbial cells can be coated freely onto any number of compositions or they can be formulated in a liquid or solid composition before being coated onto a composition. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, minerals, vitamins, prebiotics, oligosaccharides, fiber, and other agents capable of improving the quality of the products or a combination thereof.

Methods of coating and compositions in use of said methods that are known in the art can be particularly useful when they are modified by the addition of one of the embodiments of the present disclosure. Such coating methods and apparatus for their application are disclosed in, for example: U.S. Pat. Nos. 8,097,245 and 7,998,502; and PCT Pat. App. Pub. Nos. WO 2008/076975, WO 2010/138522, WO 2011/094469, WO 2010/111347, and WO 2010/111565 each of which is incorporated by reference herein.

In some embodiments, the microbes or microbial compositions of the present disclosure exhibit a synergistic effect, on one or more of the traits described herein, in the presence of one or more of the microbes or microbial compositions coming into contact with one another. The synergistic effect obtained by the taught methods can be quantified, for example, according to Colby's formula (i.e., (E)=X+Y−(X*Y/100)). See Colby, R. S., "Calculating Synergistic and Antagonistic Responses of Herbicide Combinations," 1967. Weeds. Vol. 15, pp. 20-22, incorporated herein by reference in its entirety. Thus, "synergistic" is intended to reflect an outcome/parameter/effect that has been increased by more than an additive amount.

In some embodiments, the microbes or microbial compositions of the present disclosure may be administered via drench. In one embodiment, the drench is an oral drench. A drench administration comprises utilizing a drench kit/applicator/syringe that injects/releases a liquid comprising the microbes or microbial compositions into the buccal cavity and/or esophagus of the animal.

In some embodiments, the microbes or microbial compositions of the present disclosure may be administered in a time-released fashion. The composition may be coated in a chemical composition, or may be contained in a mechanical device or capsule that releases the microbes or microbial compositions over a period of time instead all at once. In one embodiment, the microbes or microbial compositions are administered to an animal in a time-release capsule. In one embodiment, the composition may be coated in a chemical composition, or may be contained in a mechanical device or capsule that releases the microbes or microbial compositions all at once a period of time hours post ingestion.

In some embodiments, the microbes or microbial compositions are administered in a time-released fashion between 1 to 5, 1 to 10, 1 to 15, 1 to 20, 1 to 24, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, or 1 to 100 hours.

In some embodiments, the microbes or microbial compositions are administered in a time-released fashion between 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, or 1 to 30 days.

In some embodiments, the compositions of the present disclosure may employ various formulations for administration to the canines included formulations as tablets, compressed tablets, pills, powders, granules, solutions, suspensions, emulsions, elixirs, lotions, creams, gels, ointments, tinctures, pastes, foams, aerosols, irrigations, sprays, suppositories, or bandages. The form of the resulting formulation depends upon a number of factors, including the intended mode of administration (e.g. oral administration, enteral administration, parenteral administration, and topical administration to the skin, nasal passages, or buccal cavity).

In some embodiments, oral administration of the microbes or microbial compositions can be in the form of a solid or liquid composition. The solid dosage forms can be tablets, capsules, granules, and bulk powders. Types of oral tablets include compressed, chewable lozenges and tablets which can be enteric-coated, sugar-coated, or film-coated. Capsules can be hard or soft gelatin capsules, while granules and powders can be provided in non-effervescent or effervescent form with the combination of other ingredients known to those skilled in the art. In further embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets. Pharmaceutically acceptable carriers utilized in tablets include binders, lubricants, diluents, disintegrating agents, coloring agents, flavoring agents, and wetting agents.

In some embodiments, liquid oral dosage forms include aqueous solutions, emulsions, suspensions, solutions, and/or suspensions reconstituted from non-effervescent granules and effervescent preparations reconstituted from effervescent granules. Aqueous solutions include, for example, elixirs and syrups. Elixirs are clear, sweetened, hydroalcoholic preparations. Pharmaceutically acceptable carriers used in elixirs include solvents. Syrups can be concentration aqueous solutions of a sugar, for example, sucrose, and can contain a preservative. An emulsion is a two-phase system in which one liquid is dispersed in the form of small globules throughout another liquid, typically oil-in-water or water-in-oil. Pharmaceutically acceptable carriers used in emulsions are non-aqueous liquids, emulsifying agents, and preservatives. Suspensions can use pharmaceutically acceptable suspending agents and preservatives. Pharmaceutically acceptable substances used in non-effervescent granules, to be reconstituted into a liquid oral dosage form, include diluents, sweeteners, and wetting agents. Pharmaceutically acceptable substances used in effervescent granules to be reconstituted into a liquid oral dosage from can include organic acids and a source of carbon dioxide. Coloring and flavoring agents can be used in all of the above dosage forms.

Microorganisms

As used herein the term "microorganism" should be taken broadly. It includes, but is not limited to, the two prokaryotic domains, Bacteria and Archaea, as well as eukaryotic fungi, protozoa, and viruses.

By way of example, the microorganisms may include species of the genera of: *Prevotella, Megamonas, Ruminococcus, Clostridium, Clostridium* sensu *stricto, Lachnospiraceae, Anaerobiospirillum, Catenibacterium, Eubacterium, Holdemanella, Clostridium* cluster XI, *Allobaculum, Morganella, Acidicaldus, Parasutterella, Collinsella, Blautia, Bacteroides, Bacillus, Lactonifactor, Brevundimonas, Dialister, Actinomyces, Coprococcus, Cellulsilyticum, Acetanaerobacterium, Faecalibacterium, Murimonas, Clostridium* cluster XIVa, *Parabacteroides, Cetobacterium, Clostridium* cluster XVIII, *Odoribacter, Terrisporobacter, Turicibacter, Fusicatenibacter, Kandleria, Butyricicoccus, Veillonella, Acinetobacter, Enterococcus, Paraprevotella, Thermaerobacter, Bulleidia, Aerococcus, Robinsoniella, Erysipelotrichaceae, Streptosporangium, Bifidobacterium, Clostridium* cluster III, *Pediococcus, Fusobacterium, Glautia, Sarcina, Jeotgalibaca*, and *Megasphaera.*

In certain embodiments, the microorganism is unculturable. This should be taken to mean that the microorganism is not known to be culturable or is difficult to culture using methods known to one skilled in the art.

In one embodiment, the microbes are obtained from animals (e.g., mammals, reptiles, birds, and the like), soil (e.g., rhizosphere), air, water (e.g., marine, freshwater, wastewater sludge), sediment, oil, plants (e.g., roots, leaves, stems), agricultural products, and extreme environments (e.g., acid mine drainage or hydrothermal systems). In a further embodiment, microbes obtained from marine or freshwater environments such as an ocean, river, or lake. In a further embodiment, the microbes can be from the surface of the body of water, or any depth of the body of water (e.g., a deep sea sample).

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either administered to the GI tract of canines, or concentrated by filtering or centrifugation, diluted to an appropriate concentration and administered to the GI tract of canines with the bulk of the salt removed. By way of further example, microorganisms from mineralized or toxic sources may be similarly treated to recover the microbes for application to canines to minimize the potential for damage to the animal.

In another embodiment, the microorganisms are used in a crude form, in which they are not isolated from the source material in which they naturally reside. For example, the microorganisms are provided in combination with the source material in which they reside; for example, fecal matter, other composition found in the gastrointestinal tract. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

While not essential, in one embodiment, the material containing the microorganisms may be pre-treated prior to the isolation process in order to either multiply all microorganisms in the material, remove certain microorganisms in the material, and/or shift the distribution of microorganisms in the material. Microorganisms can then be isolated from the enriched materials as disclosed above.

In certain embodiments, as mentioned herein before, the microorganism(s) may be used in crude form and need not be isolated from an animal or a media. For example, feces, or growth media which includes the microorganisms identified to be of benefit to decrease GI dysbiosis may be obtained and used as a crude source of microorganisms for the next round of the method or as a crude source of microorganisms at the conclusion of the method. For example, fresh feces could be obtained and optionally processed.

Microbiome Shift and Abundance of Microbes

In some embodiments, the microbiome of canines, including the gastrointestinal microbiome comprises a diverse arrive of microbes with a wide variety of metabolic capabilities. The microbiome is influenced by a range of factors including diet, variations in animal metabolism, and breed, among others. The end products of primary degradation sustain a chain of microbes that ultimately produce a range of organic acids together with hydrogen and carbon dioxide. Because of the complex and interlinked nature of the microbiome, changing the diet and thus substrates for primary degradation may have a cascading effect on gut microbial metabolism, with changes in both the organic acid profiles.

In some aspects, the present disclosure is drawn to administering microbial compositions described herein to modulate or shift the microbiome of canines. Additional methods of administering microbial compositions to modulate microbiomes are described in International PCT Application Publication No. WO 2018/218211, which is incorporated by reference herein in its entirety.

In some embodiments, the microbiome is shifted through the administration of one or more microbes to one or more sections of the gastrointestinal tract. In some embodiments, the microbiome is shifted through the administration of one or more microbes to the gastrointestinal tract. In further embodiments, the one or more microbes are those selected from Table 1. In some embodiments, the microbiome shift or modulation includes a decrease or loss of specific microbes that were present prior to the administration of one or more microbes of the present disclosure. In some embodiments, the microbiome shift or modulation includes an increase in microbes that were present prior to the administration of one or more microbes of the present disclosure. In some embodiments, the microbiome shift or modulation includes a gain of one or more microbes that were not present prior to the administration of one or more microbes of the present disclosure. In a further embodiment, the gain of one or more microbes is a microbe that was not specifically included in the administered microbial composition.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 0, 7 to 9, 7 to 8, 8 to 10, 8 to 9, 9 to 10, 1, 2, 3, 4, 5, 6, 7, 8, 9, or 10 days.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 weeks.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, 10, 11, or 12 months.

In some embodiments, the presence of the administered microbes are detected by sampling the gastrointestinal tract and using primers to amplify the 16S or 18S rDNA sequences, or the ITS rDNA sequences of the administered microbes. In some embodiments, the administered microbes are one or more of those selected from Table 1. In some embodiments, the administered microbes are one or more of those comprising rDNA sequences selected from SEQ ID NO: 1-331.

In some embodiments, the microbiome of canines are measured by amplifying polynucleotides collected from gastrointestinal samples, wherein the polynucleotides may be 16S or 18S rDNA fragments, or ITS rDNA fragments of microbial rDNA. In one embodiment, the microbiome is fingerprinted by a method of denaturing gradient gel electrophoresis (DGGE) wherein the amplified rDNA fragments are sorted by where they denature, and form a unique banding pattern in a gel that may be used for comparing the microbiome of the same canine over time or the microbiomes of multiple. In another embodiment, the microbiome is fingerprinted by a method of terminal restriction fragment length polymorphism (T-RFLP), wherein labelled PCR fragments are digested using a restriction enzyme and then sorted by size. In a further embodiment, the data collected from the T-RFLP method is evaluated by nonmetric multidimensional scaling (nMDS) ordination and PERMANOVA statistics identify differences in microbiomes, thus allowing for the identification and measurement of shifts in the microbiome. See Coelho et al. (2018. *BMC Microbiome,* 6:12).

In some embodiments, administration of one or more microbial compositions results in a shift in the microbiome that increases the number and/or type of microbes belonging to one or more of the following taxonomic groups: Bacteroidales, Selenomonadales, Clostridiales, Aeromonadales, Erysipelotrichales, Enterobacteriales, Rhodospirillales, Burkholderiales, Coriobacteriales, Bacillales, Caulobacterales, Actinomycetales, Fusobacteriales, Pseudomonadales, Lactobacillales, Bifidobacteriales, Prevotellaceae, Veillonellaceae, Lachnospiraceae, Clostridiaceae, Succinivibrionaceae, Erysipelotrichaceae, Eubacteriaceae, Peptostreptococcaceae, Enterobacteriaceae, Acetobacteraceae, Sutterellaceae, Coriobacteriaceae, Bacteroidaceae, Bacillaceae, Caulobacteraceae, Actinomycetacea, Ruminococcaceae, Porphyromonadaceae, Fusobacteriaceae, Moraxellaceae, Carnobacteriaceae, Clostridiales cluster XVII, Aerococcaceae, Streptosporangiaceae, Bifidobacteriaceae, Lactobacillaceae, *Prevotella, Megamonas, Ruminococcus, Clostridium, Clostridium* sensu *stricto*, Lacnospiracea, *Anaerobiospirillum, Catenibacterium, Eubacterium, Holdemanella, Clostridium* cluster XI, *Allobaculum, Morganella, Acidicaldus, Parasutterella, Collinsella, Blautia, Bacteroides, Bacillus, Lactonifactor, Brevundimonas, Dialister, Actinomyces, Coprococcus, Ruminococcus, Cellulosilyticum, Acetanaerobacterium, Faecalibacterium, Murimonas, Clostridium* cluster XIVa, *Parabacteroides, Cetobacterium, Clostridium* cluster XVIII, *Odoribacter, Terrisporobacter, Turicibacter, Fusicatenibacter, Kandleria, Butyricicoccus, Beillonella, Acinetobacter, Enterococcus, Paraprevotella, Thermaerobacter, Bulleidia, Aerococcus, Robinsoniella, Erysipelotrichaceae, Streptosporangium, Bifidobacterium, Clostridium* cluster III, *Pediococcus*, and *Megasphaera.*

In some embodiments, administration of one or more microbial composition results in a shift in the microbiome that increases the number and/or type of microbes belonging to one or more of the taxonomic groups disclosed herein by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of microbes belonging to one or more of the taxonomic groups disclosed herein by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that decreases the number and/or type of microbes belonging to one or more of the taxonomic groups disclosed herein. In some embodiments, administration of one or more microbial composition results in a shift in the microbiome that reduces the number and/or type of microbes belonging to one or more of the taxonomic groups disclosed herein by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, administration of one or more microbial composition results in a shift in the microbiome that decreases the number and/or type of microbes belonging to one or more of the taxonomic groups disclosed herein by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, administration of one or more microbial compositions results in a shift in the microbiome that decreases the number and/or type of microbes belonging to one or more of the taxonomic groups disclosed herein. In some embodiments, administration of one or more microbial composition results in a shift in the microbiome that reduces the number and/or type of microbes belonging to one or more of the taxonomic groups disclosed herein by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, administration of one or more microbial composition results in a shift in the microbiome that decreases the number and/or type of microbes belonging to one or more of the taxonomic groups disclosed herein by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In some embodiments, administration of one or more microbial compositions results in a shift in the microbiome that increases the number and/or type of microbes belonging to one or more of the taxonomic groups disclosed herein. In some embodiments, administration of one or more microbial composition results in a shift in the microbiome that increases the number and/or type of microbes belonging to one or more of the taxonomic groups disclosed herein by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of microbes belonging to one or more of the taxonomic groups disclosed herein by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that increases the number and/or type of volatile fatty acid (VFA)-producing microbes. In some embodiments, the VFAs include acetate, butyrate, propionate, isobutyrate, isovalerate, and valerate. In some embodiments, administration of one or more microbial composition results in a shift in the microbiome that increases the number and/or type of VFA-producing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of VFA-producing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that increases the number and/or type of microbes that are utilized as protein sources for the animal. In some embodiments, administration of one or more microbial composition results in a shift in the microbiome that increases the number and/or type of microbes that are utilized as protein sources for the animal by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of microbes that are utilized as protein sources for the animal by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions to canines result in a shift in the microbiome that increases the number, type, and/or relative abundance of microbes in the GI tract, but the increase in number, type, and/or relative abundance of the microbes is not exhibited in the hind gut of the canines.

In some embodiments, administration of one or more microbial compositions results in a shift in the microbiome that increases the number and/or type of vitamin synthesizing microbes. In some embodiments, administration of one or more microbial composition results in a shift in the microbiome that increases the number and/or type of vitamin synthesizing microbes by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that increases the number and/or type of vitamin synthesizing microbes by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, administration of one or more microbial compositions results in a shift in the microbiome that reduces the overall alpha diversity of the microbial community. In some embodiments, administration of one or more microbial composition results in a shift in the microbiome that reduces the overall alpha diversity of the microbial community by at least 0.5%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 200%, at least 300%, at least 400%, at least 500%, at least 600%, or at least 700%. In some embodiments, administration of one or more microbial composition results in a shift in the microbiome that reduces the overall alpha diversity of the microbial community by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, or at least about 700%.

In some embodiments, the administration of microbes of the present disclosure results in a modulation or shift of the microbiome which further results in a desired phenotype or improved trait.

Canine Microbial Compositional Diversity

Canines have been found to exhibit a high degree of animal-to-animal variability in terms of the microbial diversity of the GI tract. The increased variability of the microbial compositions of the GI tract may lead to a lower ability to reach a stable microbial composition. Lower variability in turn results in a considerable difference in health, weight, and other attributes that affect viability of the animal. See Shabat S K B et al. (ISME J 10:2958-2972.)

In some embodiments, the administration of one or more microbes and/or microbial compositions of the present disclosure decreases the variability of the gut microbiome in canines and further establishes a stable canine microbiome.

In some embodiments, the variability of the gut microbiome is measured as the total number of species present in the gastrointestinal tract at one or more locations.

In some embodiments, the administration of one or more microbes and/or microbial compositions of the present disclosure reduces the amount of time required for the gastrointestinal microbiome to reach a stabilized state.

In some embodiments, the administration of one or more microbes and/or microbial compositions of the present disclosure results in canines of the present disclosure reaching a stabilized state of the gastrointestinal microbiome; a reduction in the variability of the GI microbiome.

In some embodiments, the stabilized state of the GI microbiome is reached when the GI microbiome of a canine contains about 10, about 20, about, 30, about 40, about 50, about 60, about 70, about 80, about 90, about 100, about 120, about 130, about 140, about 150, about 160, about 170, about 180, about 190, about 200, about 250, about 300, about 400, about 500, about 600, about 700, about 800, about 900, about 1,000, about 1,500, about 2,000, about 2,500, about 3,000, about 3,500, about 4,000, about 4,500, about 5,000, about 5,500, about 6,000, about 6,500, about 7,000, about 7,500, about 8,000, about 8,500, about 9,000, about 9,500, or about 10,000 different species.

In some embodiments, the stabilized state of the canine gut microbiome is reached when the GI microbiome of canine contains between about 10 to about 50, about 10 to about 100, about 50 to about 100, about 50 to about 200, about 100 to about 150, about 100 to about 200, about 100 to about 400, about 200 to about 500, about 200 to about 700, about 400 to about 800, about 500 to about 1,000, about 500 to about 2,000, about 1,000 to about 2,000, about 1,000 to about 5,000, about 5,000 to about 7,000, about 5,000 to about 10,000, or about 8,000 to about 10,000 different species.

In some embodiments, at least 5%, at least 10%, at least 20%, at least 30%, at least 40%, at least 50%, at least 60%, at least 70%, at least 80%, at least 90%, or at least 95% of the canines in a feed transition reach a stabilized state after administration of one or more microbes and/or bioensembles of the present disclosure.

MIC Scoring

According to the methods provided herein, a sample is processed to detect the presence of one or more microorganism types in the sample (FIG. 1, 1001; FIG. 2, 2001). The absolute number of one or more microorganism organism type in the sample is determined (FIG. 1, 1002; FIG. 2, 2002). The determination of the presence of the one or more organism types and the absolute number of at least one organism type can be conducted in parallel or serially. For example, in the case of a sample comprising a microbial community comprising bacteria (i.e., one microorganism type) and fungi (i.e., a second microorganism type), the user in one embodiment detects the presence of one or both of the organism types in the sample (FIG. 1, 1001; FIG. 2, 2001). The user, in a further embodiment, determines the absolute number of at least one organism type in the sample—in the case of this example, the number of bacteria, fungi or combination thereof, in the sample (FIG. 1, 1002; FIG. 2, 2002).

In one embodiment, the sample, or a portion thereof is subjected to flow cytometry (FC) analysis to detect the presence and/or number of one or more microorganism types (FIG. 1, 1001, 1002; FIG. 2, 2001, 2002). In one flow cytometer embodiment, individual microbial cells pass through an illumination zone, at a rate of at least about $300*s^{-1}$, or at least about $500*s^{-1}$, or at least about $1000*s^{-1}$. However, one of ordinary skill in the art will recognize that this rate can vary depending on the type of instrument is employed. Detectors which are gated electronically measure the magnitude of a pulse representing the extent of light scattered. The magnitudes of these pulses are sorted electronically into "bins" or "channels," permitting the display of histograms of the number of cells possessing a certain quantitative property (e.g., cell staining property, diameter, cell membrane) versus the channel number. Such analysis allows for the determination of the number of cells in each "bin" which in embodiments described herein is an "microorganism type" bin, e.g., a bacteria, fungi, nematode, protozoan, archaea, algae, dinoflagellate, virus, viroid, etc.

In one embodiment, a sample is stained with one or more fluorescent dyes wherein a fluorescent dye is specific to a particular microorganism type, to enable detection via a flow cytometer or some other detection and quantification method that harnesses fluorescence, such as fluorescence microscopy. The method can provide quantification of the number of cells and/or cell volume of a given organism type in a sample. In a further embodiment, as described herein, flow cytometry is harnessed to determine the presence and quantity of a unique first marker and/or unique second marker of the organism type, such as enzyme expression, cell surface protein expression, etc. Two- or three-variable histograms or contour plots of, for example, light scattering versus fluorescence from a cell membrane stain (versus fluorescence from a protein stain or DNA stain) may also be generated, and thus an impression may be gained of the distribution of a variety of properties of interest among the cells in the population as a whole. A number of displays of such multiparameter flow cytometric data are in common use and are amenable for use with the methods described herein.

In one embodiment of processing the sample to detect the presence and number of one or more microorganism types, a microscopy assay is employed (FIG. 1, 1001, 1002). In one embodiment, the microscopy is optical microscopy, where visible light and a system of lenses are used to magnify images of small samples. Digital images can be captured by a charge-couple device (CCD) camera. Other microscopic techniques include, but are not limited to, scanning electron microscopy and transmission electron microscopy. Microorganism types are visualized and quantified according to the aspects provided herein.

In another embodiment of the disclosure, in order to detect the presence and number of one or more microorganism types, each sample, or a portion thereof is subjected to fluorescence microscopy. Different fluorescent dyes can be used to directly stain cells in samples and to quantify total cell counts using an epifluorescence microscope as well as flow cytometry, described above. Useful dyes to quantify microorganisms include but are not limited to acridine orange (AO), 4,6-di-amino-2 phenylindole (DAPI) and 5-cyano-2,3 Dytolyl Tetrazolium Chloride (CTC). Viable cells can be estimated by a viability staining method such as the LIVE/DEAD® Bacterial Viability Kit (Bac-Light™) which contains two nucleic acid stains: the green-fluorescent SYTO 9™ dye penetrates all membranes and the red-fluorescent propidium iodide (PI) dye penetrates cells with damaged membranes. Therefore, cells with compromised membranes will stain red, whereas cells with undamaged membranes will stain green. Fluorescent in situ hybridization (FISH) extends epifluorescence microscopy, allowing for the fast detection and enumeration of specific organisms. FISH uses fluorescent labelled oligonucleotides probes (usually 15-25 base pairs) which bind specifically to organism DNA in the sample, allowing the visualization of the cells using an epifluorescence or confocal laser scanning microscope (CLSM). Catalyzed reporter deposition fluorescence in situ hybridization (CARD-FISH) improves upon the FISH method by using oligonucleotide probes labelled with a horse radish peroxidase (HRP) to amplify the intensity of the signal obtained from the microorganisms being studied. FISH can be combined with other techniques to characterize microorganism communities. One combined technique is high affinity peptide nucleic acid (PNA)-FISH, where the probe has an enhanced capability to penetrate through the Extracellular Polymeric Substance (EPS) matrix. Another example is LIVE/DEAD-FISH which combines the cell viability kit with FISH and has been used to assess the efficiency of disinfection in drinking water distribution systems.

In another embodiment, each sample, or a portion thereof is subjected to Raman micro-spectroscopy in order to determine the presence of a microorganism type and the absolute number of at least one microorganism type (FIG. 1, 1001-1002; FIG. 2, 2001-2002). Raman micro-spectroscopy is a non-destructive and label-free technology capable of detecting and measuring a single cell Raman spectrum (SCRS). A typical SCRS provides an intrinsic biochemical "fingerprint" of a single cell. A SCRS contains rich information of the biomolecules within it, including nucleic acids, proteins, carbohydrates and lipids, which enables characterization of different cell species, physiological changes and cell phenotypes. Raman microscopy examines the scattering of laser light by the chemical bonds of different cell biomarkers. A SCRS is a sum of the spectra of all the biomolecules in one single cell, indicating a cell's phenotypic profile. Cellular phenotypes, as a consequence of gene expression, usually reflect genotypes. Thus, under identical growth conditions, different microorganism types give distinct SCRS corresponding to differences in their genotypes and can thus be identified by their Raman spectra.

In yet another embodiment, the sample, or a portion thereof is subjected to centrifugation in order to determine the presence of a microorganism type and the number of at least one microorganism type (FIG. 1, 1001-1002; FIG. 2, 2001-2002). This process sediments a heterogeneous mixture by using the centrifugal force created by a centrifuge. More dense components of the mixture migrate away from the axis of the centrifuge, while less dense components of the mixture migrate towards the axis. Centrifugation can allow fractionation of samples into cytoplasmic, membrane and extracellular portions. It can also be used to determine localization information for biological molecules of interest. Additionally, centrifugation can be used to fractionate total microbial community DNA. Different prokaryotic groups differ in their guanine-plus-cytosine (G+C) content of DNA, so density-gradient centrifugation based on G+C content is a method to differentiate organism types and the number of cells associated with each type. The technique generates a fractionated profile of the entire community DNA and indicates abundance of DNA as a function of G+C content. The total community DNA is physically separated into highly purified fractions, each representing a different G+C content that can be analyzed by additional molecular techniques such as denaturing gradient gel electrophoresis (DGGE)/amplified ribosomal DNA restriction analysis (ARDRA) (see discussion herein) to assess total microbial community diversity and the presence/quantity of one or more microorganism types.

In another embodiment, the sample, or a portion thereof is subjected to staining in order to determine the presence of a microorganism type and the number of at least one microorganism type (FIG. 1, 1001-1002; FIG. 2, 2001-2002). Stains and dyes can be used to visualize biological tissues, cells or organelles within cells. Staining can be used in conjunction with microscopy, flow cytometry or gel electrophoresis to visualize or mark cells or biological molecules that are unique to different microorganism types. In vivo staining is the process of dyeing living tissues, whereas in vitro staining involves dyeing cells or structures that have been removed from their biological context. Examples of specific staining techniques for use with the methods described herein include, but are not limited to: gram staining to determine gram status of bacteria, endospore staining to identify the presence of endospores, Ziehl-Neelsen staining, haematoxylin and eosin staining to examine thin sections of tissue, papanicolaou staining to examine cell samples from various bodily secretions, periodic acid-Schiff staining of carbohydrates, Masson's trichome employing a three-color staining protocol to distinguish cells from the surrounding connective tissue, Romanowsky stains (or common variants that include Wright's stain, Jenner's stain, May-Grunwald stain, Leishman stain and Giemsa stain) to examine blood or bone marrow samples, silver staining to reveal proteins and DNA, Sudan staining for lipids and Conklin's staining to detect true endospores. Common biological stains include acridine orange for cell cycle determination; bismarck brown for acid mucins; carmine for glycogen; carmine alum for nuclei; Coomassie blue for proteins; Cresyl violet for the acidic components of the neuronal cytoplasm; Crystal violet for cell walls; DAPI for nuclei; eosin for cytoplasmic material, cell membranes, some extracellular structures and red blood cells; ethidium bromide for DNA; acid fuchsine for collagen, smooth muscle or mitochondria; haematoxylin for nuclei; Hoechst stains for DNA; iodine for starch; malachite green for bacteria in the Gimenez staining technique and for spores; methyl green for chromatin; methylene blue for animal cells; neutral red for Nissl substance; Nile blue for nuclei; Nile red for lipohilic entities; osmium tetroxide for lipids; rhodamine is used in fluorescence microscopy; safranin for nuclei. Stains are also used in transmission electron microscopy to enhance contrast and include phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, and vanadyl sulfate.

In another embodiment, the sample, or a portion thereof is subjected to mass spectrometry (MS) in order to determine the presence of a microorganism type and the number of at least one microorganism type (FIG. 1, 1001-1002; FIG. 2, 2001-2002). MS, as discussed below, can also be used to detect the presence and expression of one or more unique markers in a sample (FIG. 1, 1003-1004; FIG. 2, 2003-2004). MS is used for example, to detect the presence and quantity of protein and/or peptide markers unique to microorganism types and therefore to provide an assessment of the number of the respective microorganism type in the sample. Quantification can be either with stable isotope labelling or label-free. De novo sequencing of peptides can also occur directly from MS/MS spectra or sequence tagging (produce a short tag that can be matched against a database). MS can also reveal post-translational modifications of proteins and identify metabolites. MS can be used in conjunction with chromatographic and other separation techniques (such as gas chromatography, liquid chromatography, capillary electrophoresis, ion mobility) to enhance mass resolution and determination.

In another embodiment, the sample, or a portion thereof is subjected to lipid analysis in order to determine the presence of a microorganism type and the number of at least one microorganism type (FIG. 1, 1001-1002; FIG. 2, 2001-2002). Fatty acids are present in a relatively constant proportion of the cell biomass, and signature fatty acids exist in microbial cells that can differentiate microorganism types within a community. In one embodiment, fatty acids are extracted by saponification followed by derivatization to give the respective fatty acid methyl esters (FAMEs), which are then analyzed by gas chromatography. The FAME profile in one embodiment is then compared to a reference FAME database to identify the fatty acids and their corresponding microbial signatures by multivariate statistical analyses.

In the aspects of the methods provided herein, the number of unique first makers in the sample, or portion thereof (e.g., sample aliquot) is measured, as well as the abundance of each of the unique first markers (FIG. 1, 1003; FIG. 2, 2003). A unique marker is a marker of a microorganism strain. It should be understood by one of ordinary skill in the art that depending on the unique marker being probed for and measured, the entire sample need not be analyzed. For example, if the unique marker is unique to bacterial strains, then the fungal portion of the sample need not be analyzed. As described above, in some embodiments, measuring the absolute abundance of one or more organism types in a sample comprises separating the sample by organism type, e.g., via flow cytometry.

Any marker that is unique to an organism strain can be employed herein. For example, markers can include, but are not limited to, small subunit ribosomal RNA genes (16S/18S rDNA), large subunit ribosomal RNA genes (23S/25S/28S rDNA), intercalary 5.8S gene, cytochrome c oxidase, beta-tubulin, elongation factor, RNA polymerase and internal transcribed spacer (ITS).

Ribosomal RNA genes (rDNA), especially the small subunit ribosomal RNA genes, i.e., 18S rRNA genes (18S rDNA) in the case of eukaryotes and 16S rRNA (16S rDNA) in the case of prokaryotes, have been the predominant target for the assessment of organism types and strains in a microbial community. However, the large subunit ribosomal RNA genes, 28S rDNAs, have been also targeted. rDNAs are suitable for taxonomic identification because: (i) they are ubiquitous in all known organisms; (ii) they possess both conserved and variable regions; (iii) there is an exponentially expanding database of their sequences available for comparison. In community analysis of samples, the conserved regions serve as annealing sites for the corresponding universal PCR and/or sequencing primers, whereas the variable regions can be used for phylogenetic differentiation. In addition, the high copy number of rDNA in the cells facilitates detection from environmental samples.

The internal transcribed spacer (ITS), located between the 18S rDNA and 28S rDNA, has also been targeted. The ITS is transcribed but spliced away before assembly of the ribosomes. The ITS region is composed of two highly variable spacers, ITS1 and ITS2, and the intercalary 5.8S gene. This rDNA operon occurs in multiple copies in genomes. Because the ITS region does not code for ribosome components, it is highly variable.

In one embodiment, the unique RNA marker can be an mRNA marker, an siRNA marker or a ribosomal RNA marker.

Protein-coding functional genes can also be used herein as a unique first marker. Such markers include but are not limited to: the recombinase A gene family (bacterial RecA, archaea RadA and RadB, eukaryotic Rad51 and Rad57, phage UvsX); RNA polymerase R subunit (RpoB) gene, which is responsible for transcription initiation and elongation; chaperonins. Candidate marker genes have also been identified for bacteria plus archaea: ribosomal protein S2 (rpsB), ribosomal protein S10 (rpsJ), ribosomal protein L1 (rplA), translation elongation factor EF-2, translation initiation factor IF-2, metalloendopeptidase, ribosomal protein L22, ffh signal recognition particle protein, ribosomal protein L4/Lle (rplD), ribosomal protein L2 (rplB), ribosomal protein S9 (rpsI), ribosomal protein L3 (rplC), phenylalanyl-tRNA synthetase beta subunit, ribosomal protein L14b/L23e (rplN), ribosomal protein S5, ribosomal protein S19 (rpsS), ribosomal protein S7, ribosomal protein L16/L10E (rplP), ribosomal protein S13 (rpsM), phenylalanyl-tRNA synthetase $\alpha$ subunit, ribosomal protein L15, ribosomal protein L25/L23, ribosomal protein L6 (rplF), ribosomal protein L11 (rplK), ribosomal protein L5 (rplE), ribosomal protein S12/S23, ribosomal protein L29, ribosomal protein S3 (rpsC), ribosomal protein S11 (rpsK), ribosomal protein L10, ribosomal protein S8, tRNA pseudouridine synthase B, ribosomal protein L18P/L5E, ribosomal protein S15P/S13e, Porphobilinogen deaminase, ribosomal protein S17, ribosomal protein L13 (rplM), phosphoribosylformylglycinamidine cyclo-ligase (rpsE), ribonuclease HII and ribosomal protein L24. Other candidate marker genes for bacteria include: transcription elongation protein NusA (nusA), rpoB DNA-directed RNA polymerase subunit beta (rpoB), GTP-binding protein EngA, rpoC DNA-directed RNA polymerase subunit beta', priA primosome assembly protein, transcription-repair coupling factor, CTP synthase (pyrG), secY preprotein translocase subunit SecY, GTP-binding protein Obg/CgtA, DNA polymerase I, rpsF 30S ribosomal protein S6, poA DNA-directed RNA polymerase subunit alpha, peptide chain release factor 1, rplI 50S ribosomal protein L9, polyribonucleotide nucleotidyltransferase, tsf elongation factor Ts (tsf), rplQ 50S ribosomal protein L17, tRNA (guanine-N(1)-)-methyltransferase (rplS), rplY probable 50S ribosomal protein L25, DNA repair protein RadA, glucose-inhibited division protein A, ribosome-binding factor A, DNA mismatch repair protein MutL, smpB SsrA-binding protein (smpB), N-acetylglucosaminyl transferase, S-adenosyl-methyltransferase MraW, UDP-N-acetylmuramoylalanine-D-glutamate ligase, rplS 50S ribosomal protein L19, rplT 50S ribosomal protein L20 (rplT), ruvA Holliday junction DNA helicase, ruvB Holliday junction DNA helicase B, serS seryl-tRNA synthetase, rplU 50S ribosomal protein L21, rpsR 30S ribosomal protein S18, DNA mismatch repair protein MutS, rpsT 30S ribosomal protein S20, DNA repair protein RecN, frr ribosome recycling factor (frr), recombination protein RecR, protein of unknown function UPF0054, miaA tRNA isopentenyltransferase, GTP-binding protein YchF, chromosomal replication initiator protein DnaA, dephospho-CoA kinase, 16S rRNA processing protein RimM, ATP-cone domain protein, 1-deoxy-D-xylulose 5-phosphate reductoisomerase, 2C-methyl-D-erythritol 2,4-cyclodiphosphate synthase, fatty acid/phospholipid synthesis protein PlsX, tRNA(Ile)-lysidine synthetase, dnaG DNA primase (dnaG), ruvC Holliday junction resolvase, rpsP 30S ribosomal protein S16, Recombinase A recA, riboflavin biosynthesis protein RibF, glycyl-tRNA synthetase beta subunit, trmU tRNA (5-methylaminomethyl-2-thiouridylate)-methyltransferase, rpmI 50S ribosomal protein L35, hemE uroporphyrinogen decarboxylase, Rod shape-determining protein, rpmA 50S ribosomal protein L27 (rpmA), peptidyl-tRNA hydrolase, translation initiation factor IF-3 (infC), UDP-N-acetylmuramyl-tripeptide synthetase, rpmF 50S ribosomal protein L32, rpIL 50S ribosomal protein L7/L12 (rpIL), leuS leucyl-tRNA synthetase, ligA NAD-dependent DNA ligase, cell division protein FtsA, GTP-binding protein TypA, ATP-dependent Clp protease, ATP-binding subunit ClpX, DNA replication and repair protein RecF and UDP-N-acetylenolpyruvoylglucosamine reductase.

Phospholipid fatty acids (PLFAs) may also be used as unique first markers according to the methods described herein. Because PLFAs are rapidly synthesized during microbial growth, are not found in storage molecules and degrade rapidly during cell death, it provides an accurate census of the current living community. All cells contain fatty acids (FAs) that can be extracted and esterified to form fatty acid methyl esters (FAMEs). When the FAMEs are analyzed using gas chromatography-mass spectrometry, the resulting profile constitutes a 'fingerprint' of the microorganisms in the sample. The chemical compositions of membranes for organisms in the domains Bacteria and Eukarya are comprised of fatty acids linked to the glycerol by an ester-type bond (phospholipid fatty acids (PLFAs)). In contrast, the membrane lipids of Archaea are composed of long and branched hydrocarbons that are joined to glycerol by an ether-type bond (phospholipid ether lipids (PLELs)). This is one of the most widely used non-genetic criteria to distinguish the three domains. In this context, the phospholipids derived from microbial cell membranes, characterized by different acyl chains, are excellent signature molecules, because such lipid structural diversity can be linked to specific microbial taxa.

As provided herein, in order to determine whether an organism strain is active, the level of expression of one or more unique second markers, which can be the same or different as the first marker, is measured (FIG. 1, 1004; FIG. 2, 2004). Unique first markers are described above. The unique second marker is a marker of microorganism activity. For example, in one embodiment, the mRNA or protein expression of any of the first markers described above is considered a unique second marker for the purposes of this disclosure.

In one embodiment, if the level of expression of the second marker is above a threshold level (e.g., a control level) or at a threshold level, the microorganism is considered to be active (FIG. 1, 1005; FIG. 2, 2005). Activity is determined in one embodiment, if the level of expression of the second marker is altered by at least about 5%, at least about 10%, at least about 15%, at least about 20%, at least about 25%, or at least about 30%, as compared to a threshold level, which in some embodiments, is a control level.

Second unique markers are measured, in one embodiment, at the protein, RNA or metabolite level. A unique second marker is the same or different as the first unique marker.

As provided above, a number of unique first markers and unique second markers can be detected according to the methods described herein. Moreover, the detection and quantification of a unique first marker is carried out according to methods known to those of ordinary skill in the art (FIG. 1, 1003-1004, FIG. 2, 2003-2004).

Nucleic acid sequencing (e.g., gDNA, cDNA, rRNA, mRNA) in one embodiment is used to determine absolute cell count of a unique first marker and/or unique second marker. Sequencing platforms include, but are not limited to, Sanger sequencing and high-throughput sequencing methods available from Roche/454 Life Sciences, Illumina/Solexa, Pacific Biosciences, Ion Torrent and Nanopore. The sequencing can be amplicon sequencing of particular DNA or RNA sequences or whole metagenome/transcriptome shotgun sequencing.

Traditional Sanger sequencing (Sanger et al. (1977) DNA sequencing with chain-terminating inhibitors. Proc Natl. Acad. Sci. USA, 74, pp. 5463-5467, incorporated by reference herein in its entirety) relies on the selective incorporation of chain-terminating dideoxynucleotides by DNA polymerase during in vitro DNA replication and is amenable for use with the methods described herein.

In another embodiment, the sample, or a portion thereof is subjected to extraction of nucleic acids, amplification of DNA of interest (such as the rRNA gene) with suitable primers and the construction of clone libraries using sequencing vectors. Selected clones are then sequenced by Sanger sequencing and the nucleotide sequence of the DNA of interest is retrieved, allowing calculation of the number of unique microorganism strains in a sample.

454 pyrosequencing from Roche/454 Life Sciences yields long reads and can be harnessed in the methods described herein (Margulies et al. (2005) Nature, 437, pp. 376-380; U.S. Pat. Nos. 6,274,320; 6,258,568; 6,210,891, each of which is herein incorporated in its entirety for all purposes). Nucleic acid to be sequenced (e.g., amplicons or nebulized genomic/metagenomic DNA) have specific adapters affixed on either end by PCR or by ligation. The DNA with adapters is fixed to tiny beads (ideally, one bead will have one DNA fragment) that are suspended in a water-in-oil emulsion. An emulsion PCR step is then performed to make multiple copies of each DNA fragment, resulting in a set of beads in which each bead contains many cloned copies of the same DNA fragment. Each bead is then placed into a well of a fiber-optic chip that also contains enzymes necessary for the sequencing-by-synthesis reactions. The addition of bases (such as A, C, G, or T) trigger pyrophosphate release, which produces flashes of light that are recorded to infer the sequence of the DNA fragments in each well. About 1 million reads per run with reads up to 1,000 bases in length can be achieved. Paired-end sequencing can be done, which produces pairs of reads, each of which begins at one end of a given DNA fragment. A molecular barcode can be created and placed between the adapter sequence and the sequence of interest in multiplex reactions, allowing each sequence to be assigned to a sample bioinformatically.

Illumina/Solexa sequencing produces average read lengths of about 25 base pairs (bp) to about 300 bp (Bennett et al. (2005) Pharmacogenomics, 6:373-382; Lange et al. (2014). BMC Genomics 15, p. 63; Fadrosh et al. (2014) Microbiome 2, p. 6; Caporaso et al. (2012) ISME J, 6, p. 1621-1624; Bentley et al. (2008) Accurate whole human genome sequencing using reversible terminator chemistry. Nature, 456:53-59). This sequencing technology is also sequencing-by-synthesis but employs reversible dye terminators and a flow cell with a field of oligos attached. DNA fragments to be sequenced have specific adapters on either end and are washed over a flow cell filled with specific oligonucleotides that hybridize to the ends of the fragments. Each fragment is then replicated to make a cluster of identical fragments. Reversible dye-terminator nucleotides are then washed over the flow cell and given time to attach. The excess nucleotides are washed away, the flow cell is imaged, and the reversible terminators can be removed so that the process can repeat and nucleotides can continue to be added in subsequent cycles. Paired-end reads that are 300 bases in length each can be achieved. An Illumina platform can produce 4 billion fragments in a paired-end fashion with 125 bases for each read in a single run. Barcodes can also be used for sample multiplexing, but indexing primers are used.

The SOLiD (Sequencing by Oligonucleotide Ligation and Detection, Life Technologies) process is a "sequencing-by-ligation" approach, and can be used with the methods described herein for detecting the presence and abundance of a first marker and/or a second marker (FIG. 1, 1003-1004; FIG. 2,2003-2004) (Peckham et al. SOLiD™ Sequencing and 2-Base Encoding. San Diego, CA: American Society of Human Genetics, 2007; Mitra et al. (2013) Analysis of the intestinal microbiota using SOLiD 16S rRNA gene sequencing and SOLiD shotgun sequencing. BMC Genomics, 14(Suppl 5): S16; Mardis (2008) Next-generation DNA sequencing methods. Annu Rev Genomics Hum Genet, 9:387-402; each incorporated by reference herein in its entirety). A library of DNA fragments is prepared from the sample to be sequenced, and are used to prepare clonal bead populations, where only one species of fragment will be present on the surface of each magnetic bead. The fragments attached to the magnetic beads will have a universal P1 adapter sequence so that the starting sequence of every fragment is both known and identical. Primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. The SOLiD platform can produce up to 3 billion reads per run with reads that are 75 bases long. Paired-end sequencing is available and can be used herein, but with the second read in the pair being only 35 bases long. Multiplexing of samples is possible through a system akin to the one used by Illumina, with a separate indexing run.

The Ion Torrent system, like 454 sequencing, is amenable for use with the methods described herein for detecting the presence and abundance of a first marker and/or a second marker (FIG. 1, 1003-1004; FIG. 2, 2003-2004). It uses a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, and they record when these changes occur. The different bases (A, C, G, T) are washed sequentially through the wells, allowing the sequence from each well to be inferred. The Ion Proton platform can produce up to 50 million reads per run that have read lengths of 200 bases. The Personal Genome Machine platform has longer reads at 400 bases. Bidirectional sequencing is available. Multiplexing is possible through the standard in-line molecular barcode sequencing.

Pacific Biosciences (PacBio) SMRT sequencing uses a single-molecule, real-time sequencing approach and in one embodiment, is used with the methods described herein for detecting the presence and abundance of a first marker and/or a second marker (FIG. 1, 1003-1004; FIG. 2, 2003-2004). The PacBio sequencing system involves no amplification step, setting it apart from the other major next-generation sequencing systems. In one embodiment, the sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. The PacBio system yields very long read lengths (averaging around 4,600 bases) and a very high number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In one embodiment, where the first unique marker is the ITS genomic region, automated ribosomal intergenic spacer analysis (ARISA) is used in one embodiment to determine the number and identity of microorganism strains in a sample (FIG. 1, 1003, FIG. 2, 2003) (Ranjard et al. (2003). Environmental Microbiology 5, pp. 1111-1120, incorporated by reference in its entirety for all purposes). The ITS region has significant heterogeneity in both length and nucleotide sequence. The use of a fluorescence-labeled forward primer and an automatic DNA sequencer permits high resolution of separation and high throughput. The inclusion of an internal standard in each sample provides accuracy in sizing general fragments.

In another embodiment, fragment length polymorphism (RFLP) of PCR-amplified rDNA fragments, otherwise known as amplified ribosomal DNA restriction analysis (ARDRA), is used to characterize unique first markers and the abundance of the same in samples (FIG. 1, 1003, FIG. 2, 2003) (for additional detail, see Massol-Deya et al. (1995). Mol. Microb. Ecol. Manual. 3.3.2, pp. 1-18, the entirety of which is herein incorporated by reference for all purposes). rDNA fragments are generated by PCR using general primers, digested with restriction enzymes, electrophoresed in agarose or acrylamide gels, and stained with ethidium bromide or silver nitrate.

One fingerprinting technique used in detecting the presence and abundance of a unique first marker is single-stranded-conformation polymorphism (SSCP) (see Lee et al. (1996). Appl Environ Microbiol 62, pp. 3112-3120; Scheinert et al. (1996). J. Microbiol. Methods 26, pp. 103-117; Schwieger and Tebbe (1998). Appl. Environ. Microbiol. 64, pp. 4870-4876, each of which is incorporated by reference herein in its entirety). In this technique, DNA fragments such as PCR products obtained with primers specific for the 16S rRNA gene, are denatured and directly electrophoresed on a non-denaturing gel. Separation is based on differences in size and in the folded conformation of single-stranded DNA, which influences the electrophoretic mobility. Reannealing of DNA strands during electrophoresis can be prevented by a number of strategies, including the use of one phosphorylated primer in the PCR followed by specific digestion of the phosphorylated strands with lambda exonuclease and the use of one biotinylated primer to perform magnetic separation of one single strand after denaturation. To assess the identity of the predominant populations in a given microbial composition, in one embodiment, bands are excised and sequenced, or SSCP-patterns can be hybridized with specific probes. Electrophoretic conditions, such as gel matrix, temperature, and addition of glycerol to the gel, can influence the separation.

In addition to sequencing based methods, other methods for quantifying expression (e.g., gene, protein expression) of a second marker are amenable for use with the methods provided herein for determining the level of expression of one or more second markers (FIG. 1, 1004; FIG. 2, 2004). For example, quantitative RT-PCR, microarray analysis, linear amplification techniques such as nucleic acid sequence based amplification (NASBA) are all amenable for use with the methods described herein, and can be carried out according to methods known to those of ordinary skill in the art.

In another embodiment, the sample, or a portion thereof is subjected to a quantitative polymerase chain reaction (PCR) for detecting the presence and abundance of a first marker and/or a second marker (FIG. 1, 1003-1004; FIG. 2,2003-2004). Specific microorganism strains activity is measured by reverse transcription of transcribed ribosomal and/or messenger RNA (rRNA and mRNA) into complementary DNA (cDNA), followed by PCR (RT-PCR).

In another embodiment, the sample, or a portion thereof is subjected to PCR-based fingerprinting techniques to detect the presence and abundance of a first marker and/or a second marker (FIG. 1, 1003-1004; FIG. 2, 2003-2004). PCR products can be separated by electrophoresis based on the nucleotide composition. Sequence variation among the different DNA molecules influences the melting behavior, and therefore molecules with different sequences will stop migrating at different positions in the gel. Thus electrophoretic profiles can be defined by the position and the relative intensity of different bands or peaks and can be translated to numerical data for calculation of diversity indices. Bands can also be excised from the gel and subsequently sequenced to reveal the phylogenetic affiliation of the community members. Electrophoresis methods can include, but are not limited to: denaturing gradient gel electrophoresis (DGGE), temperature gradient gel electrophoresis (TGGE), single-stranded-conformation polymorphism (SSCP), restriction fragment length polymorphism analysis (RFLP) or amplified ribosomal DNA restriction analysis (ARDRA), terminal restriction fragment length polymorphism analysis (T-RFLP), automated ribosomal intergenic spacer analysis (ARISA), randomly amplified polymorphic DNA (RAPD), DNA amplification fingerprinting (DAF) and Bb-PEG electrophoresis.

In another embodiment, the sample, or a portion thereof is subjected to a chip-based platform such as microarray or microfluidics to determine the abundance of a unique first marker and/or presence/abundance of a unique second marker (FIG. 1, 1003-1004, FIG. 2, 2003-2004). The PCR products are amplified from total DNA in the sample and directly hybridized to known molecular probes affixed to microarrays. After the fluorescently labeled PCR amplicons are hybridized to the probes, positive signals are scored by the use of confocal laser scanning microscopy. The microarray technique allows samples to be rapidly evaluated with replication, which is a significant advantage in microbial community analyses. In general the hybridization signal intensity on microarrays can be directly proportional to the abundance of the target organism. The universal high-density 16S microarray (e.g., PHYLOCHIP) contains about 30,000 probes of 16SrRNA gene targeted to several cultured microbial species and "candidate divisions". These probes target all 121 demarcated prokaryotic orders and allow simultaneous detection of 8,741 bacterial and archaeal taxa. Another microarray in use for profiling microbial communities is the Functional Gene Array (FGA). Unlike PHYLOCHIPs, FGAs are designed primarily to detect specific metabolic groups of bacteria. Thus, FGA not only reveal the community structure, but they also shed light on the in situ community metabolic potential. FGA contain probes from genes with known biological functions, so they are useful in linking microbial community composition to ecosystem functions. An FGA termed GEOCHIP contains>24,000 probes from all known metabolic genes involved in various biogeochemical, ecological, and environmental processes such as ammonia oxidation, methane oxidation, and nitrogen fixation.

A protein expression assay, in one embodiment, is used with the methods described herein for determining the level of expression of one or more second markers (FIG. 1, 1004; FIG. 2, 2004). For example, in one embodiment, mass spectrometry or an immunoassay such as an enzyme-linked immunosorbant assay (ELISA) is utilized to quantify the level of expression of one or more unique second markers, wherein the one or more unique second markers is a protein.

In one embodiment, the sample, or a portion thereof is subjected to Bromodeoxyuridine (BrdU) incorporation to determine the level of a second unique marker (FIG. 1, 1004; FIG. 2, 2004). BrdU, a synthetic nucleoside analog of thymidine, can be incorporated into newly synthesized DNA of replicating cells. Antibodies specific for BRdU can then be used for detection of the base analog. Thus BrdU incorporation identifies cells that are actively replicating their DNA, a measure of activity of a microorganism according to one embodiment of the methods described herein. BrdU incorporation can be used in combination with FISH to provide the identity and activity of targeted cells.

In one embodiment, the sample, or a portion thereof is subjected to microautoradiography (MAR) combined with FISH to determine the level of a second unique marker (FIG. 1, 1004; FIG. 2, 2004). MAR-FISH is based on the incorporation of radioactive substrate into cells, detection of the active cells using autoradiography and identification of the cells using FISH. The detection and identification of active cells at single-cell resolution is performed with a microscope. MAR-FISH provides information on total cells, probe targeted cells and the percentage of cells that incorporate a given radiolabelled substance. The method provides an assessment of the in situ function of targeted microorganisms and is an effective approach to study the in vivo physiology of microorganisms. A technique developed for quantification of cell-specific substrate uptake in combination with MAR-FISH is known as quantitative MAR (QMAR).

In one embodiment, the sample, or a portion thereof is subjected to stable isotope Raman spectroscopy combined with FISH (Raman-FISH) to determine the level of a second unique marker (FIG. 1, 1004; FIG. 2, 2004). This technique combines stable isotope probing, Raman spectroscopy and FISH to link metabolic processes with particular organisms. The proportion of stable isotope incorporation by cells affects the light scatter, resulting in measurable peak shifts for labelled cellular components, including protein and mRNA components. Raman spectroscopy can be used to identify whether a cell synthesizes compounds including, but not limited to: oil (such as alkanes), lipids (such as triacylglycerols (TAG)), specific proteins (such as heme proteins, metalloproteins), cytochrome (such as P450, cytochrome c), chlorophyll, chromophores (such as pigments for light harvesting carotenoids and rhodopsins), organic polymers (such as polyhydroxyalkanoates (PHA), polyhydroxybutyrate (PHB)), hopanoids, steroids, starch, sulfide, sulfate and secondary metabolites (such as vitamin B12).

In one embodiment, the sample, or a portion thereof is subjected to DNA/RNA stable isotope probing (SIP) to determine the level of a second unique marker (FIG. 1, 1004; FIG. 2, 2004). SIP enables determination of the microbial diversity associated with specific metabolic pathways and has been generally applied to study microorganisms involved in the utilization of carbon and nitrogen compounds. The substrate of interest is labelled with stable isotopes (such as $^{3}$C or $^{15}$N) and added to the sample. Only microorganisms able to metabolize the substrate will incorporate it into their cells. Subsequently, $^{13}$C-DNA and $^{15}$N-DNA can be isolated by density gradient centrifugation and used for metagenomic analysis. RNA-based SIP can be a responsive biomarker for use in SIP studies, since RNA itself is a reflection of cellular activity.

In one embodiment, the sample, or a portion thereof is subjected to isotope array to determine the level of a second unique marker (FIG. 1, 1004; FIG. 2, 2004). Isotope arrays allow for functional and phylogenetic screening of active microbial communities in a high-throughput fashion. The technique uses a combination of SIP for monitoring the substrate uptake profiles and microarray technology for determining the taxonomic identities of active microbial communities. Samples are incubated with a $^{14}$C-labeled substrate, which during the course of growth becomes incorporated into microbial biomass. The $^{14}$C-labeled rRNA is separated from unlabeled rRNA and then labeled with fluorochromes. Fluorescent labeled rRNA is hybridized to a phylogenetic microarray followed by scanning for radioactive and fluorescent signals. The technique thus allows simultaneous study of microbial community composition and specific substrate consumption by metabolically active microorganisms of complex microbial communities.

In one embodiment, the sample, or a portion thereof is subjected to a metabolomics assay to determine the level of a second unique marker (FIG. 1, 1004; FIG. 2, 2004). Metabolomics studies the metabolome which represents the collection of all metabolites, the end products of cellular processes, in a biological cell, tissue, organ or organism. This methodology can be used to monitor the presence of microorganisms and/or microbial mediated processes since it allows associating specific metabolite profiles with different microorganisms. Profiles of intracellular and extracellular metabolites associated with microbial activity can be obtained using techniques such as gas chromatography-mass spectrometry (GC-MS). The complex mixture of a metabolomic sample can be separated by such techniques as gas chromatography, high performance liquid chromatography and capillary electrophoresis. Detection of metabolites can be by mass spectrometry, nuclear magnetic resonance (NMR) spectroscopy, ion-mobility spectrometry, electrochemical detection (coupled to HPLC) and radiolabel (when combined with thin-layer chromatography).

According to the embodiments described herein, the presence and respective number of one or more active microorganism strains in a sample are determined (FIG. 1, 1006; FIG. 2, 2006). For example, strain identity information obtained from assaying the number and presence of first markers is analyzed to determine how many occurrences of a unique first marker are present, thereby representing a unique microorganism strain (e.g., by counting the number of sequence reads in a sequencing assay). This value can be represented in one embodiment as a percentage of total sequence reads of the first maker to give a percentage of unique microorganism strains of a particular microorganism type. In a further embodiment, this percentage is multiplied by the number of microorganism types (obtained at step 1002 or 2002, see FIG. 1 and FIG. 2) to give the absolute abundance of the one or more microorganism strains in a sample and a given volume.

The one or more microorganism strains are considered active, as described above, if the level of second unique marker expression is at a threshold level, higher than a threshold value, e.g., higher than at least about 5%, at least about 10%, at least about 20% or at least about 30% over a control level.

In another aspect of the disclosure, a method for determining the absolute abundance of one or more microorganism strains is determined in a plurality of samples (FIG. 2, see in particular, 2007). For a microorganism strain to be classified as active, it need only be active in one of the samples. The samples can be taken over multiple time points from the same source, or can be from different environmental sources (e.g., different animals).

The absolute abundance values over samples are used in one embodiment to relate the one or more active microorganism strains, with an environmental parameter (FIG. 2, 2008). In one embodiment, the environmental parameter is the presence of a second active microorganism strain. Relating the one or more active microorganism strains to the environmental parameter, in one embodiment, is carried out by determining the co-occurrence of the strain and parameter by correlation or by network analysis.

In one embodiment, determining the co-occurrence of one or more active microorganism strains with an environmental parameter comprises a network and/or cluster analysis method to measure connectivity of strains or a strain with an environmental parameter within a network, wherein the network is a collection of two or more samples that share a common or similar environmental parameter. In another embodiment, the network and/or cluster analysis method may be applied to determining the co-occurrence of two or more active microorganism strains in a sample (FIG. 2, 2008). In another embodiment, the network analysis comprises nonparametric approaches including mutual information to establish connectivity between variables. In another embodiment, the network analysis comprises linkage analysis, modularity analysis, robustness measures, betweenness measures, connectivity measures, transitivity measures, centrality measures or a combination thereof (FIG. 2, 2009). In another embodiment, the cluster analysis method comprises building a connectivity model, subspace model, distribution model, density model, or a centroid model and/or using community detection algorithms such as the Louvain, Bron-Kerbosch, Girvan-Newman, Clauset-Newman-Moore, Pons-Latapy, and Wakita-Tsurumi algorithms (FIG. 2, 2010).

In one embodiment, the cluster analysis method is a heuristic method based on modularity optimization. In a further embodiment, the cluster analysis method is the Louvain method (See, e.g., the method described by Blondel et al. (2008) Fast unfolding of communities in large networks. Journal of Statistical Mechanics: Theory and Experiment, Volume 2008, October 2008, incorporated by reference herein in its entirety for all purposes).

In another embodiment, the network analysis comprises predictive modeling of network through link mining and prediction, collective classification, link-based clustering, relational similarity, or a combination thereof. In another embodiment, the network analysis comprises differential equation based modeling of populations. In another embodiment, the network analysis comprises Lotka-Volterra modeling.

In one embodiment, relating the one or more active microorganism strains to an environmental parameter (e.g., determining the co-occurrence) in the sample comprises creating matrices populated with linkages denoting environmental parameter and microorganism strain associations.

In one embodiment, the multiple sample data obtained at step 2007 (e.g., over two or more samples which can be collected at two or more time points where each time point corresponds to an individual sample) is compiled. In a further embodiment, the number of cells of each of the one or more microorganism strains in each sample is stored in an association matrix (which can be in some embodiments, an abundance matrix). In one embodiment, the association matrix is used to identify associations between active microorganism strains in a specific time point sample using rule mining approaches weighted with association (e.g., abundance) data. Filters are applied in one embodiment to remove insignificant rules.

In one embodiment, the absolute abundance of one or more, or two or more active microorganism strains is related to one or more environmental parameters (FIG. 2, 2008), e.g., via co-occurrence determination. Environmental parameters are chosen by the user depending on the sample(s) to be analyzed and are not restricted by the methods described herein. The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. In one embodiment, the environmental parameter is the presence, activity and/or abundance of a second microorganism strain in the microbial community, present in the same sample.

In some embodiments described herein, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

For example, according to one embodiment, microorganism strain number changes are calculated over multiple samples according to the method of FIG. 2 (i.e., at 2001-2007). Strain number changes of one or more active strains over time is compiled (e.g., one or more strains that have initially been identified as active according to step 2006), and the directionality of change is noted (i.e., negative values denoting decreases, positive values denoting increases). The number of cells over time is represented as a network, with microorganism strains representing nodes and the abundance weighted rules representing edges. Markov chains and random walks are leveraged to determine connectivity between nodes and to define clusters. Clusters in one embodiment are filtered using metadata in order to identify clusters associated with desirable metadata (FIG. 2, 2008).

In a further embodiment, microorganism strains are ranked according to importance by integrating cell number changes over time and strains present in target clusters, with the highest changes in cell number ranking the highest.

Canine Pathogen Resistance and Clearance

In some aspects, the present disclosure is drawn to administering one or more microbial compositions described herein to canines to clear the gastrointestinal tract of pathogenic microbes. In some embodiments, the present disclosure is further drawn to administering microbial compositions described herein to prevent colonization of pathogenic microbes in the gastrointestinal tract. In some embodiments, the administration of microbial compositions described herein further clear pathogens from the integument and the respiratory tract of canines, and/or prevent colonization of pathogens on the integument and in the respiratory tract. In some embodiments, the administration of microbial compositions described herein reduce leaky gut/intestinal permeability, levels of histamine, production of lipopolysaccharides (LPS), inflammation, bloat, diarrhea, GI dysbiosis, GI enteropathy, hemorrhagic diarrhea, and/or incidence of GI pathogen-induced disease.

In some embodiments, microbes of the present disclosure colonize the gastrointestinal tract of canines, which may prevent colonization of the pathogenic microbes. In some embodiments, microbes of the present disclosure colonize the hindgut of the canines, which may prevent colonization of the pathogenic microbes.

In some embodiments, the microbial compositions of the present disclosure comprise one or more microbes that are present in the gastrointestinal tract of canines at a relative abundance of less than 15%, 14%, 13%, 12%, 11%, 10%, 9%, 8%, 7%, 6%, 5%, 4%, 3%, 2%, 1%, 0.5%, 0.1%, or 0.01%.

In some embodiments, after administration of microbial compositions of the present disclosure the one or more microbes are present in the gastrointestinal tract of the canine at a relative abundance of at least 0.5%, 1%, 5%, 10%, 15%, 20%, 25%, 30%, 35%, 40%, 45%, 50%, 55%, 60%, 65%, 70%, 75%, 80%, 85%, 90%, or 95%.

Pathogenic microbes of canines include the following: *Clostridium perfringens, Clostridium botulinum, Salmonella typi, Salmonella typhimurium, Salmonella enterica, Salmonella pullorum, Erysipelothrix insidiosa, Campylobacter jejuni, Campylobacter coli, Campylobacter lari, Listeria monocytogenes, Streptococcus agalactiae, Streptococcus dysgalactiae, Clostridium difficile, Corynebacterium bovis, Mycoplasma* sp., *Citrobacter* sp., *Enterobacter* sp., *Pseudomonas aeruginosa, Pasteurella* sp., *Bacillus cereus, Bacillus licheniformis, Streptococcus uberis, Staphylococcus aureus*, and pathogenic strains of enteropathogenic, enteroinvasive, or enterohemorrhagic *Escherichia coli, Staphylococcus aureus, Pasteurella multocida, Mannheimia haemolytica, Histophilus somni, Proteus* sp., *Klebsiella* sp, *Shigella* sp., and *Aspergillus* sp.

In some embodiments, the pathogenic microbes include viral pathogens. In some embodiments, the pathogenic microbes are pathogenic to both canines and humans. In some embodiments, the pathogenic microbes are pathogenic to either canines or humans.

In some embodiments, the administration of compositions of the present disclosure to canines modulate the makeup of the gastrointestinal microbiome such that the administered microbes outcompete microbial pathogens present in the gastrointestinal tract. In some embodiments, the administration of compositions of the present disclosure to canine harboring microbial pathogens outcompetes the pathogens and clears the canine of the pathogens. In some embodiments, the administration of compositions of the present disclosure stimulate host immunity, and aids in clearance of the microbial pathogens. In some embodiments, the administration of compositions of the present disclosure introduce microbes that produce bacteriostatic and/or bactericidal components that decrease or clear canines of the microbial pathogens. (U.S. Pat. No. 8,345,010).

In some aspects, the microbes of the present disclosure outcompete pathogens, preventing pathogens from colonizing the GI tract, attaching to attachment sites on the GI epithelia or GI mucosa. In some aspects, the microbes of the present disclosure prevent pathogens from colonizing due to the production of antimicrobials that inhibit the growth of the pathogens. In some aspects, the microbes of the present disclosure reduce the state of inflammation of the GI tract. In some aspects, the microbes of the present disclosure reduce the state of inflammation of the epithelia of the GI tract. In some aspects, the microbes of the present disclosure reduce the state of inflammation of the sub-epithelial cells and tissues of the gastrointestinal tract.

In some aspects, administration of the microbes of the present disclosure results in a protection of the mucosal layers in the GI tract. In some aspects, administration of the microbes of the present disclosure results in an increase in the mucosa produced by the GI tract. In some aspects, administration of the microbes of the present disclosure results in a decrease in the incidence of biochemical degradation of the GI mucosa. In some aspects, administration of the microbes of the present disclosure results in a decreased ability of pathogens to pass through the mucosal layer(s) of the GI tract to localize to the GI endothelial cells. In some aspects, the microbes of the present disclosure create a mucosal shield that prevents or decreases incidence of pathogens from gaining access to the GI endothelial cells.

In some aspects, the microbes of the present disclosure outcompete one or more canine GI pathogens for binding sites in the GI tract, thus preventing colonization of the pathogen or intracellular or intercellular access to the pathogen.

In some aspects, microbes of the present disclosure are capable of correcting or maintaining typical physiological pH of the various subcompartments or sections of the gastrointestinal tract to prevent pH shifts that would favor pathogen colonization. In some aspects, microbes of the present disclosure include microbes that utilize carbon dioxide and/or hydrogen that contribute to the pH/redox balance of the GI tract. In some aspects, microbes of the present disclosure include VFA-producing microbes that contribute to the pH/redox balance of the GI tract.

In some embodiments, challenging canines with a microbial colonizer or microbial pathogen after administering one or more compositions of the present disclosure prevents the microbial colonizer or microbial pathogen from growing to a relative abundance of greater than 15%, 14%, 13%, 12%, 11%, 10%, 9%, 8%, 7%, 6%, 5%, 4%, 3%, 2%, 1%, 0.5%, 0.1%, or 0.01%. In further embodiments, challenging canines with a microbial colonizer or microbial pathogen after administering one or more compositions of the present disclosure prevents the microbial colonizer or microbial pathogen from colonizing canines.

In some embodiments, clearance of the microbial colonizer or microbial pathogen occurs in less than 25 days, less than 24 days, less than 23 days, less than 22 days, less than 21 days, less than 20 days, less than 19 days, less than 18 days, less than 17 days, less than 16 days, less than 15 days, less than 14 days, less than 13 days, less than 12 days, less than 11 days, less than 10 days, less than 9 days, less than 8 days, less than 7 days, less than 6 days, less than 5 days, less than 4 days, less than 3 days, or less than 2 days post administration of the one or more compositions of the present disclosure.

In some embodiments, clearance of the microbial colonizer or microbial pathogen occurs within 1-30 days, 1-25 days, 1-20 day, 1-15 days, 1-10 days, 1-5 days, 5-30 days, 5-25 days, 5-20 days, 5-15 days, 5-10 days, 10-30 days, 10-25 days, 10-20 days, 10-15 days, 15-30 days, 15-25 days, 15-20 days, 20-30 days, 20-25 days, or 25-30 days post administration of the one or more compositions of the present disclosure.

Improved Traits

A diverse microbial population inhabits the canine gastrointestinal tract. The enzymatic activity of the microbes in the gastrointestinal tract are critical to break down the chemicals and molecules in the feed into simple sugars and volatile fatty acids. This enzymatic activity is critical to the extraction of energy from feed, and more efficient degradation ultimately provides more energy to the animal. Some of the soluble sugars found in the feed are converted to volatile fatty acids such as butyrate, propionate, and acetate. Volatile fatty acids arise from the digestion of both the fibrous and non-fibrous components of the feed.

In some aspects, the present disclosure is drawn to administering microbial compositions described herein to canines to improve one or more traits through the modulation of aspects of weight, gastrointestinal health, digestive chemistry, feed digestibility, fecal output, prevention of colonization of pathogenic microbes, and clearance of pathogenic microbes. In some aspects, the present disclosure is further drawn to administering microbial compositions herein to canines to achieve a decrease in the incidence of gastrointestinal dysbiosis, a decrease in the severity of gastrointestinal dysbiosis, a decrease in the incidence of diarrhea, a decrease in the severity of diarrhea, a decrease in the incidence of irritable bowel disease (IBD), a decrease in the severity of irritable bowel disease, a decrease in the severity of enteropathy, a decrease in the incidence of enteropathy, a decrease in the incidence of gastrointestinal pathogen colonization, a decrease in the incidence of gastrointestinal pathogen-induced disease, a decrease in the incidence of gastrointestinal pathogen carriage, a decrease in the amount of primary bile acids present in the feces, an increase in the secondary bile acids present in the feces; and/or combinations thereof.

In some embodiments, administering the microbial compositions described herein improve at least one trait in a canine. In some embodiments, the at least one improved trait is selected from the group consisting of: a decrease in the incidence of gastrointestinal dysbiosis, a decrease in the severity of gastrointestinal dysbiosis, a decrease in the incidence of diarrhea, a decrease in the severity of diarrhea, a decrease in the incidence of irritable bowel disease (IBD), a decrease in the severity of irritable bowel disease, a decrease in the severity of enteropathy, a decrease in the incidence of enteropathy, a decrease in the incidence of gastrointestinal pathogen colonization, a decrease in the incidence of gastrointestinal pathogen-induced disease, a decrease in the incidence of gastrointestinal pathogen carriage, a decrease in the amount of primary bile acids present in the feces, an increase in the secondary bile acids present in the feces, an increase in fatty acid production in the GI tract, an increase in polysaccharide and lignin degradation; an increase in fat, starch, and/or protein digestion, an increase in pH balance, an increase in vitamin availability, a reduced likelihood or incidence of mortality, a reduced likelihood or incidence of morbidity, an increased production of antimicrobials, an increase in mammalian and/or microbial synthesis of vitamins; a reduction of alpha diversity of the gastrointestinal microbiome; improved fecal consistency; increased regular bowel movements; reduced straining during defecation; improved dental health, reduced side-effects from antibiotics; brighter eyes; increased energy; increased appetite; improved fur and coat quality; increased lifespan; and/or combinations thereof; and wherein said increase or decrease is determined by comparing against an animal not having been administered said composition.

In some embodiments, the number of canine dysbiotic events is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the incidence of hemorrhagic diarrhea in the GI is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the occurrence of secondary bile acids is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure. In some aspects, secondary bile acids include deoxycholic acid and lithocholic acid.

In some embodiments, the occurrence of primary bile acids is decreased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure. In some aspects, primary bile acids include cholic acid and chenodeoxycholic acid.

In some embodiments, the canine having been administered one or more microbes of the present disclosure have an increased buffering capacity in the GI tract by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the incidence of irritable bowel disease is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the colonization of microbial pathogens in the GI tract is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the alpha diversity of the microorganisms of the gastrointestinal tract is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the production of antimicrobials in the gastrointestinal tract is increased by at least than 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the production of vitamins in the gastrointestinal tract is increased by at least than 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the incidence of bloat is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the synthesis of one or more volatile fatty acids is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the body weight of the animals is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the rate of weight gain of the animals is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the lipopolysaccharide production in the animals is decreased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, improving the efficiency and digestibility of animal feed is desirable. In some embodiments, increasing the degradation of lignocellulosic components from animal feed is desirable. Lignocellulosic components include lignin, cellulose, and hemicellulose.

In some embodiments, increasing the concentration of fatty acids in the gastrointestinal tract is desirable. Fatty acids include acetic acid, propionic acid, and butyric acid. In some embodiments, maintaining the pH balance in the gastrointestinal tract to prevent destruction of beneficial microbial compositions is desirable.

In some embodiments, decreasing the amount of methane and manure produced by canines is desirable In some embodiments, a decrease in the amount of primary bile acids is desirable. In further embodiments, an increase in the amount of secondary bile acids is desirable.

In some embodiments, improving the dry matter intake is desirable. In some embodiments, improving the feed intake is desirable. In some embodiments, improving the efficiency of nitrogen utilization of the feed and/or dry matter ingested by canines is desirable.

In some embodiments, the improved traits of the present disclosure are the result of the administration of the presently described microbial compositions. It is thought that the microbial compositions modulate the GI microbiome of canines such that the biochemistry of the GI tract is changed in such a way that the gastrointestinal liquid and solid substratum are more efficiently and more completely degraded into subcomponents and metabolites than the gastrointestinal tract of canines not having been administered microbial compositions of the present disclosure.

In some embodiments, the increase in efficiency and the increase of degradation of the gastrointestinal substratum result in an increase in improved traits of the present disclosure.

In some embodiments, the administration of one or more compositions of the present disclosure result in a decrease in the severity of GI dysbiosis and/or diarrhea.

In some embodiments, the administration of one or more compositions of the present disclosure result in a decrease in likelihood of developing colon cancer, inflammatory bowel disease, chronic diarrhea, obesity, enteropathy, and intestinal disorders such as malabsorption of nutrients such as vitamins and fats. In some embodiments, the administration of one or more compositions of the present disclosure result in a decrease in severity of inflammatory bowel disease, chronic diarrhea, obesity, enteropathy, and intestinal disorders such as malabsorption of nutrients such as vitamins and fats.

In some embodiments, the administration of one or more compositions of the present disclosure result in an improved feed efficiency in the presence or absence of antibiotic agents.

Ziese et al., Sindern et al., Hooda et al., and Barko et al. provide a general state of knowledge pertaining to the testing of probiotic microbes in canines. See Ziese et al. (2018. PLOS ONE. 13(9): e0204691; Sindern et al. (2019. J Vet Intern Med. 33:100-10[5]); Hooda et al. (2012. Animal health Research Reviews. 13(1):78-88); and Barko et al. (2018. J Vet Intern Med. 32:9-25).

In some embodiments, the administration of one or more compositions of the present disclosure result in a reduced body temperature in canines, as compared to those not having been administered the one or more compositions. In further embodiments, the reduction in temperature is at least 0.2° F., at least 0.4° F., at least 0.6° F., at least 0.8° F., at least 1° F., at least 1.2° F., at least 1.4° F., at least 1.6° F., at least 1.8° F., at least 2° F., at least 2.2° F., at least 2.4° F., at least 2.6° F., at least 2.8° F., at least 3° F., at least 3.2° F., at least 3.4° F., at least 3.6° F., at least 3.8° F., at least 4° F., at least 4.2° F., at least 4.4° F., at least 4.6° F., at least 4.8° F., at least 5° F., at least 5.2° F., at least 5.4° F., at least 5.6° F., at least 5.8° F., or at least 6° F.

In further embodiments, the reduction in temperature is at about 0.2° F., about 0.4° F., about 0.6° F., about 0.8° F., about 1° F., about 1.2° F., about 1.4° F., about 1.6° F., about 1.8° F., about 2° F., about 2.2° F., about 2.4° F., about 2.6° F., about 2.8° F., about 3° F., about 3.2° F., about 3.4° F., about 3.6° F., about 3.8° F., about 4° F., about 4.2° F., about 4.4° F., about 4.6° F., about 4.8° F., about 5° F., about 5.2° F., about 5.4° F., about 5.6° F., about 5.8° F., or about 6° F.

In some embodiments, the increase of any one or more of the traits of the present disclosure is an increase of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to an animal not having been administered one or more microbial compositions of the present disclosure.

In some embodiments, the increase of any one or more of the traits of the present disclosure is an increase of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to an animal not having been administered one or more microbial compositions of the present disclosure.

In some embodiments, the decrease of any one or more of the traits of the present disclosure is a decrease of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to an animal not having been administered one or more microbial compositions of the present disclosure.

In some embodiments, the decrease of any one or more of the traits of the present disclosure is a decrease of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to an animal not having been administered one or more microbial compositions of the present disclosure In some aspects, administration of one or more microbes of the present disclosure result in a fold change, increase or decrease, of any one or more species of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to canines that were not administered the one or more microbes.

In some aspects, administration of one or more microbes of the present disclosure result in a fold change, increase or decrease, of any one or more genera of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to canines that were not administered the one or more microbes.

In some aspects, administration of one or more microbes of the present disclosure result in a fold change, increase or decrease, of any one or more family of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to caninese that were not administered the one or more microbes.

In some aspects, administration of one or more microbes of the present disclosure result in a fold change, increase or decrease, of any one or more class of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to canines that were not administered the one or more microbes.

In some aspects, administration of one or more microbes of the present disclosure result in a fold change, increase or decrease, of any one or more order of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to canines that were not administered the one or more microbes.

In some aspects, administration of one or more microbes of the present disclosure result in a fold change, increase or decrease, of any one or more phyla of the present disclosure by at least 0.1, at least 0.2, at least 0.3, at least 0.4, at least 0.5, at least 0.6, at least 0.8, at least 0.9, at least 1, at least 1.2, at least 1.4, at least 1.6, at least 1.8, at least 2, at least 2.2, at least 2.4, at least 2.6, at least 2.8, at least 3, at least 3.2, at least 3.4, at least 3.6, at least 3.8, at least 4, at least 4.2, at least 4.4, at least 4.6, at least 4.8, at least 5, at least 5.5, at least 6, at least 6.5, at least 7, at least 7.5, at least 8, at least 8.5, at least 9, at least 9.5, at least 10, at least 11, at least 12, at least 13, at least 14, at least 15, at least 16, at least 17, at least 18, at least 19, or at least 20 fold relative to canines that were not administered the one or more microbes.

In some aspects, administration of one or more microbes of the present disclosure results in a change in the relative abundance of any one or more types of microbes belonging to one or more of the taxonomic groups disclosed herein such that the any or more types of microbes belonging to the one or more taxonomic groups disclosed herein are present in the GI tract at a relative abundance of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some aspects, administration of one or more microbes of the present disclosure results in a change in the relative abundance of any one or more types of microbes belonging to one or more of the taxonomic groups disclosed herein such that the any or more types of microbes belonging to the one or more taxonomic groups disclosed herein are present in the GI tract at a relative abundance of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some aspects, administration of one or more microbes of the present disclosure results in a change in the relative abundance of any one or more types of microbes belonging to one or more of the taxonomic groups disclosed herein such that the any or more types of microbes belonging to the one or more taxonomic groups disclosed herein are present in the GI tract at a relative abundance of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some aspects, administration of one or more microbes of the present disclosure results in a change in the relative abundance of any one or more types of microbes belonging to one or more of the taxonomic groups disclosed herein such that the any or more types of microbes belonging to the one or more taxonomic groups disclosed herein are present in the GI tract at a relative abundance of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some aspects, administration of one or more microbes of the present disclosure results in a change in the relative abundance of any one or more types of microbes belonging to one or more of the taxonomic groups disclosed herein such that the any or more types of microbes belonging to the one or more taxonomic groups disclosed herein are present in the GI tract at a relative abundance of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some aspects, administration of one or more microbes of the present disclosure results in a change in the relative abundance of Bacteroidales such that bacteria of order Bacteroidales are present in the GI tract at a relative abundance of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some aspects, administering one or microbes of the present disclosure to canines results in a shift in the population of microbes present (species, genera, families, orders, classes, phyla) such that a first population of microbes present in the GI tract prior to administration increases in abundance after administration; wherein a second population of microbes present in the GI tract prior to administration increases in abundance after administration; wherein a third population of microbes present in the GI tract prior to administration increases in abundance after administration; wherein a fourth population of microbes present in the GI tract prior to administration increases in abundance after administration; wherein a fifth population of microbes present in the GI tract prior to administration increases in abundance after administration; wherein a sixth population of microbes present in the GI tract prior to administration increases in abundance after administration; and/or wherein a seventh population of microbes present in the GI tract prior to administration increases in abundance after administration.

In some aspects, the fold change, microbiome shift, and/or change in relative abundance regarding any one or more of the above one or more microbes or one or more microbial compositions occurs in week 1, week 2, week 3, week 4, week 5, week 6, week 7, week 8, week 9, week 10, week 11, week 12, week 13, week 14, week 15, week 16, week 17, week 18, week 19, or week 20 post-administration.

In some aspects, the fold change, microbiome shift, and/or change in relative abundance regarding any one or more of the above one or more microbes or one or more microbial compositions occurs in week 1, week 2, week 3, week 4, week 5, week 6, week 7, week 8, week 9, week 10, week 11, week 12, week 13, week 14, week 15, week 16, week 17, week 18, week 19, or week 20 post first administration, while continuing successive administrations daily, weekly, or monthly.

Network Analysis

A network and/or cluster analysis method, in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises mutual information, maximal information coefficient (MIC) calculations, or other nonparametric methods between variables to establish connectivity. In another embodiment, network analysis comprises differential equation based modeling of populations. In yet another embodiment, network analysis comprises Lotka-Volterra modeling.

The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. In one embodiment, the environmental parameter is the presence, activity and/or abundance of a second microorganism strain in the microbial community, present in the same sample. In some embodiments, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

A cluster analysis method comprises building a connectivity model, subspace model, distribution model, density model, or a centroid model.

Network and cluster based analysis, for example, to carry out method step 2008 of FIG. 2, can be carried out via a module. As used herein, a component and/or module can be, for example, any assembly, instructions and/or set of operatively-coupled electrical components, and can include, for example, a memory, a processor, electrical traces, optical connectors, software (executing in hardware) and/or the like.

Diagnostics

In some embodiments, a sample (serum, fecal, GI fluid, tissue, blood, etc.) is collected from a canine. In some embodiments, the sample is assayed for the presence and/or quantity of one or more chemical substances or populations of microbes. In some embodiments the presence or absence of the one or more chemical substances or populations of microbes are diagnostic of a desirable trait described in the present disclosure. In some aspects, the makeup of the microbial population is diagnostic of a particular state, such as a disease state or a healthy state. In some aspects, the disease state is hemorrhagic enteropathy, diarrheal enteropathy, pre-hemorrhagic enteropathy, pre-diarrheal enteropathy, and simple GI dysbiosis.

In some embodiments, the present disclosure is drawn to a method of determining the disease state of an animal. In some embodiments, the method comprises collecting a first sample of blood, blood serum, feces, and/or GI mucosa at a first time point and collecting a second sample of blood, blood serum, feces, and/or GI mucosa at a second time point, assaying the samples for the presence and concentration of a chemical or population of microbes in the blood, blood serum, feces, and/or GI mucosa.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

The following examples are given for the purpose of illustrating the methods and compositions described herein. These examples are not meant to limit the present disclosure to the embodiments shown. Changes therein and other uses which are encompassed within the disclosure will be recognized by those skilled in the art.

Example 1. Canine Cereal Diet Trial

The objective of this study is to determine the microbial population during and in between the diet periods.

Experimental groups of canines are placed on one of three diets: control diet, high cereal content diet, and recovery diet. Each of the three groups are on a different diet at the same time, and each group is switched to the subsequence diet at the same time.

Fecal samples are collected daily to determine the composition of the gut microbiome and how it changes across the various diets and the transitions between the various diets.

The results are expected to at least identify the types or classes of microbes that increase or decrease in abundance during the various diets, providing insight on microbes or microbial populations that may assist canines in more efficiently adapting to different diets.

Example 2. Household Canine Survey

The objective of this study is to determine the microbial populations of canines exhibiting GI dysbiosis during and after administration of microbial compositions of the present disclosure, including healthy control canines, and to evaluate the efficacy of the administered microbial compositions in returning the canines to a non-GI dysbiotic state.

Study will include data from canines in households with multiple canines in an attempt to control for variations in lifestyle and diet.

Example 3. Household Canine Survey

The objective of this study is to determine the microbial populations of canines exhibiting GI dysbiosis such as irritable bowel disease and/or hemorrhagic diarrhea, and to determine the microbial populations of canines as they are being administered microbial compositions of the present disclosure. Data collection will include colonoscopy samples in order to sample from multiple sites within the colon instead of simply relying on feces output. Data collection will further include tissue histology on samples taken during colonoscopies. Samples from healthy canines will be utilized as controls.

Example 4. Microbial Supplementation Study in Canines with Gastrointestinal Disorders The objective of this study is to determine the efficacy of microbial supplementation in canines diagnosed with a gastrointestinal disorder such as chronic enteropathy.

Canines in the experimental group will be administered one or more microbes selected from: Ascusk9_546A (SEQ ID NO: 326), Ascusk9_672A (SEQ ID NO: 327), Ascusk9_210B (SEQ ID NO: 237), Ascusk9_51G (SEQ ID NO: 19), Ascusk9_33E (SEQ ID NO: 328), Ascusk9_0G (SEQ ID NO: 172), Ascusk9_38A (SEQ ID NO: 329), Ascusk9_17A (SEQ ID NO: 330), or Ascusk9_2A (SEQ ID NO: 331) over a 30 day period. Canines in the control group will either not receive treatment or will receive a placebo over the 30 day period.

Canines that received microbial supplementation over the 30 day period are expected to exhibit an improvement in stool condition, frequency of bowel movements, appetite, and overall health.

Example 5. Microbial Supplementation Study in Healthy Canines

The objective of this study is to determine the efficacy of microbial supplementation in healthy canines, i.e., canines without diagnosed gastrointestinal disorders.

Canines in the experimental group will be administered one or more microbes selected from: Ascusk9_546A (SEQ ID NO: 326), Ascusk9_672A (SEQ ID NO: 327), Ascusk9_210B (SEQ ID NO: 237), Ascusk9_51G (SEQ ID NO: 19), Ascusk9_33E (SEQ ID NO: 328), Ascusk9_0G (SEQ ID NO: 172), Ascusk9_38A (SEQ ID NO: 329), Ascusk9_17A (SEQ ID NO: 330), or Ascusk9_2A (SEQ ID NO: 331) over a 30 day period. Canines in the control group will either not receive treatment or will receive a placebo over the 30 day period.

Canines that received microbial supplementation over the 30 day period are expected to exhibit an improvement in stool condition, frequency of bowel movements, appetite, and overall health. It is expected that canines that receive microbial supplementation will exhibit reduced incidence of diarrhea.

Example 6. Analysis of Canine Microorganisms for Volatile Fatty Acid Production and Carbon Source Identification This example assesses the ability of microbial isolates or enrichments to produce volatile fatty acids. HPLC was used to measure the concentrations of acetate, butyrate, and propionate in spent media.

For pure isolates, a single colony from each of the desired strains (on solid anaerobic media) was inoculated into the strain's preferred rich media. Enrichments were inoculated from fresh canine fecal samples into a desired media. Various media recipes were used mimic the canine gastrointestinal tract under a variety of relevant physiological conditions. Cultures and medium blanks were incubated at their optimal conditions until significant growth was visible in the cultures. Absorbance reads were taken at 600 nm and 420 nm to determine the growth of each culture.

Pure culture strain IDs were confirmed with Illumina sequencing. Enrichments and their corresponding sample inocula were Illumina sequenced to determine the presence or absence of target strains. These sequencing datasets were integrated with cell count data to determine if target strains grew in vitro.

An aliquot of each culture was sterile filtered through 0.22 μm polyethersulfone membrane into a sterile acid washed 15 mL glass sample vial to be analyzed by HPLC. HPLC reactions were performed at Michigan State University Bioeconomy Institute. HPLC parameters: The column is BioRad Aminex HPX-87H, 60° C., 0.5 mL/min mobile phase 0.00325 N $H_2SO_4$, 500 psi, 35C RI detector, 45 min run time, injection volume 5 μL. Production of various compounds was assessed by comparison of the sample's readings to the appropriate blank. Concentrations of acetate, butyrate, and propionate were quantified for the cultures and media blanks.

The results of the HPLC analysis are shown in Table 9 below. The "+" represents consumption; the "−" represents production; and the "0" indicates no change.

TABLE 9

HPLC Analysis of Microbial Isolates or Enrichments

| StrainID | Media Recipe | Succinate | Lactate | Acetate | Propionate | Ethanol | Butyrate |
|---|---|---|---|---|---|---|---|
| Ascusk9_OB | 1 | 0 | + | + | + | − | + |
| Ascusk9_OB | 3 | + | + | + | + | + | + |
| Ascusk9_OB | 4 | + | + | + | + | + | 0 |
| Ascusk9_OB | 5 | + | − | + | + | 0 | + |
| Ascusk9_OB | 5 | 0 | + | + | + | + | 0 |
| Ascusk9_OD | 4 | + | + | + | + | + | 0 |
| Ascusk9_OD | 5 | + | − | + | + | 0 | + |
| Ascusk9_OD | 5 | 0 | + | + | + | + | 0 |
| Ascusk9_OF | 1 | 0 | + | + | + | − | + |
| Ascusk9_OF | 3 | + | + | + | + | + | + |
| Ascusk9_OF | 4 | + | + | + | + | + | 0 |
| Ascusk9_OF | 5 | + | − | + | + | 0 | + |
| Ascusk9_OF | 5 | 0 | + | + | + | + | 0 |
| Ascusk9_OG | 6 | 0 | 0 | + | 0 | + | 0 |
| Ascusk9_OG | 1 | 0 | + | + | + | − | + |
| Ascusk9_OG | 3 | + | + | + | + | + | + |

TABLE 9-continued

| HPLC Analysis of Microbial Isolates or Enrichments | | | | | | | |
|---|---|---|---|---|---|---|---|
| StrainID | Media Recipe | Succinate | Lactate | Acetate | Propionate | Ethanol | Butyrate |
| Ascusk9_OG | 4 | + | + | + | + | + | 0 |
| Ascusk9_OG | 5 | + | | + | + | 0 | + |
| Ascusk9_OG | 5 | 0 | + | + | + | + | 0 |
| Ascusk9_OI | 1 | 0 | + | + | + | − | + |
| Ascusk9_OI | 3 | + | + | + | + | + | + |
| Ascusk9_OI | 4 | + | + | + | + | + | 0 |
| Ascusk9_OI | 5 | + | − | + | + | 0 | + |
| Ascusk9_OI | 5 | 0 | + | + | + | + | 0 |
| Ascusk9_10B | 1 | 0 | + | + | + | − | + |
| Ascusk9_10B | 3 | + | + | + | + | + | + |
| Ascusk9_10B | 5 | + | − | + | + | 0 | + |
| Ascusk9_10F | 1 | 0 | + | + | + | − | + |
| Ascusk9_10F | 3 | + | + | + | + | + | + |
| Ascusk9_10F | 5 | + | − | + | + | 0 | + |
| Ascusk9_10G | 1 | 0 | + | + | + | − | + |
| Ascusk9_10G | 3 | + | + | + | + | + | + |
| Ascusk9_10G | 5 | + | − | + | + | 0 | + |
| Ascusk9_116C | 3 | + | + | + | + | + | + |
| Ascusk9_11B | 1 | 0 | + | + | + | − | + |
| Ascusk9_11B | 3 | + | + | + | + | + | + |
| Ascusk9_11B | 4 | + | + | + | + | + | 0 |
| Ascusk9_11B | 5 | + | − | + | + | 0 | + |
| Ascusk9_11B | 5 | 0 | + | + | + | + | 0 |
| Ascusk9_11G | 1 | 0 | + | + | + | − | + |
| Ascusk9_11G | 3 | + | + | + | + | + | + |
| Ascusk9_11G | 4 | + | + | + | + | + | 0 |
| Ascusk9_11G | 5 | + | − | + | + | 0 | + |
| Ascusk9_11G | 5 | 0 | + | + | + | + | 0 |
| Ascusk9_11I | 1 | 0 | + | + | + | − | + |
| Ascusk9_11I | 3 | + | + | + | + | + | + |
| Ascusk9_11I | 4 | + | + | + | + | + | 0 |
| Ascusk9_11I | 5 | + | − | + | + | 0 | + |
| Ascusk9_11I | 5 | 0 | + | + | + | + | 0 |
| Ascusk9_12A | 1 | 0 | + | + | + | − | + |
| Ascusk9_12A | 3 | + | + | + | + | + | + |
| Ascusk9_12A | 4 | + | + | + | + | + | 0 |
| Ascusk9_12A | 5 | + | − | + | + | 0 | + |
| Ascusk9_12A | 5 | 0 | + | + | + | + | 0 |
| Ascusk9_12B | 1 | 0 | + | + | + | − | + |
| Ascusk9_12B | 3 | + | + | + | + | + | + |
| Ascusk9_12B | 4 | + | + | + | + | + | 0 |
| Ascusk9_12B | 5 | + | − | + | + | 0 | + |
| Ascusk9_12B | 5 | 0 | + | + | + | + | 0 |
| Ascusk9_12F | 1 | 0 | + | + | + | − | + |
| Ascusk9_12F | 3 | + | + | + | + | + | + |
| Ascusk9_12F | 4 | + | + | + | + | + | 0 |
| Ascusk9_12F | 5 | + | − | + | + | 0 | + |
| Ascusk9_12F | 5 | 0 | + | + | + | + | 0 |
| Ascusk9_12H | 4 | + | + | + | + | + | 0 |
| Ascusk9_12H | 5 | + | | + | + | 0 | + |
| Ascusk9_12H | 5 | 0 | + | + | + | + | 0 |
| Ascusk9_144G | 1 | 0 | + | + | + | − | + |
| Ascusk9_144G | 3 | + | + | + | + | + | + |
| Ascusk9_144G | 4 | + | + | + | + | + | 0 |
| Ascusk9_144G | 5 | + | − | + | + | 0 | + |
| Ascusk9_144A | 4 | + | + | + | + | + | 0 |
| Ascusk9_144A | 5 | + | − | + | + | 0 | + |
| Ascusk9_148B | 2 | + | + | + | + | + | + |
| Ascusk9_148E | 2 | + | + | + | + | + | + |
| Ascusk9_148E | 4 | + | + | + | + | + | 0 |
| Ascusk9_148E | 5 | + | − | + | + | 0 | + |
| Ascusk9_148F | 4 | + | + | + | + | + | 0 |
| Ascusk9_148F | 5 | + | − | + | + | 0 | + |
| Ascusk9_148G | 2 | + | + | + | + | + | + |
| Ascusk9_148H | 2 | + | + | + | + | + | + |
| Ascusk9_148I | 4 | + | + | + | + | + | 0 |
| Ascusk9_148I | 5 | + | − | + | + | 0 | + |
| Ascusk9_14D | 1 | 0 | + | + | + | − | + |
| Ascusk9_14D | 3 | + | + | + | + | + | + |
| Ascusk9_14G | 1 | 0 | + | + | + | − | + |
| Ascusk9_14G | 3 | + | + | + | + | + | + |
| Ascusk9_14H | 1 | 0 | + | + | + | − | + |
| Ascusk9_14H | 3 | + | + | + | + | + | + |
| Ascusk9_15A | 5 | 0 | + | + | + | + | 0 |
| Ascusk9_15B | 4 | + | + | + | + | + | 0 |

TABLE 9-continued

HPLC Analysis of Microbial Isolates or Enrichments

| StrainID | Media Recipe | Succinate | Lactate | Acetate | Propionate | Ethanol | Butyrate |
|---|---|---|---|---|---|---|---|
| Ascusk9_15B | 5 | + | − | + | + | 0 | + |
| Ascusk9_15E | 4 | + | + | + | + | + | 0 |
| Ascusk9_15E | 5 | + | − | + | + | 0 | + |
| Ascusk9_15F | 1 | 0 | + | + | + | − | + |
| Ascusk9_15F | 3 | + | + | + | + | + | + |
| Ascusk9_15F | 4 | + | + | + | + | + | 0 |
| Ascusk9_15F | 5 | + | − | + | + | 0 | + |
| Ascusk9_15F | 5 | 0 | + | + | + | + | 0 |
| Ascusk9_16F | 3 | + | − | + | + | 0 | + |
| Ascusk9_16F | 4 | + | + | + | + | + | 0 |
| Ascusk9_16F | 5 | + | − | + | + | 0 | + |
| Ascusk9_16G | 4 | + | + | + | + | + | 0 |
| Ascusk9_16G | 5 | + | − | + | + | 0 | + |
| Ascusk9_16H | 4 | + | + | + | + | + | 0 |
| Ascusk9_16H | 5 | + | − | + | + | 0 | + |
| Ascusk9_176D | 3 | + | + | + | + | + | + |
| Ascusk9_17A | 6 | 0 | + | + | 0 | 0 | 0 |
| Ascusk9_210B | 6 | + | + | + | + | 0 | 0 |
| Ascusk9_210B | 5 | + | − | + | + | 0 | + |
| Ascusk9_217A | 1 | 0 | + | + | + | − | + |
| Ascusk9_25B | 1 | 0 | + | + | + | − | + |
| Ascusk9_288E | 5 | + | − | + | + | 0 | + |
| Ascusk9_30D | 1 | 0 | + | + | + | − | + |
| Ascusk9_30D | 3 | + | + | + | + | + | + |
| Ascusk9_33B | 3 | + | − | + | + | 0 | + |
| Ascusk9_33C | 5 | + | − | + | + | 0 | + |
| Ascusk9_33D | 3 | + | − | + | + | 0 | + |
| Ascusk9_33E | 6 | 0 | 0 | + | 0 | + | 0 |
| Ascusk9_35D | 1 | 0 | + | + | + | − | + |
| Ascusk9_35D | 3 | + | + | + | + | + | + |
| Ascusk9_38A | 6 | 0 | + | + | 0 | 0 | 0 |
| Ascusk9_39B | 4 | + | + | + | + | + | 0 |
| Ascusk9_39B | 5 | + | − | + | + | 0 | + |
| Ascusk9_39D | 4 | + | + | + | + | + | 0 |
| Ascusk9_39D | 5 | + | − | + | + | 0 | + |
| Ascusk9_39F | 4 | + | + | + | + | + | 0 |
| Ascusk9_39F | 5 | + | − | + | + | 0 | + |
| Ascusk9_3E | 1 | 0 | + | + | + | − | + |
| Ascusk9_3E | 3 | + | + | + | + | + | + |
| Ascusk9_3F | 1 | 0 | + | + | + | − | + |
| Ascusk9_3F | 3 | + | + | + | + | + | + |
| Ascusk9_3F | 5 | + | − | + | + | 0 | + |
| Ascusk9_3G | 1 | 0 | + | + | + | − | + |
| Ascusk9_3G | 3 | + | + | + | + | + | + |
| Ascusk9_3G | 5 | + | − | + | + | 0 | + |
| Ascusk9_3G | 5 | 0 | + | + | + | + | 0 |
| Ascusk9_3H | 1 | 0 | + | + | + | − | + |
| Ascusk9_3H | 3 | + | + | + | + | + | + |
| Ascusk9_429C | 1 | 0 | + | + | + | − | + |
| Ascusk9_429C | 3 | + | + | + | + | + | + |
| Ascusk9_429E | 3 | + | − | + | + | 0 | + |
| Ascusk9_429H | 3 | + | − | + | + | 0 | + |
| Ascusk9_467B | 1 | 0 | + | + | + | − | + |
| Ascusk9_467B | 3 | + | + | + | + | + | + |
| Ascusk9_4F | 1 | 0 | + | + | + | − | + |
| Ascusk9_4F | 3 | + | + | + | + | + | + |
| Ascusk9_4G | 1 | 0 | + | + | + | − | + |
| Ascusk9_4G | 3 | + | + | + | + | + | + |
| Ascusk9_510C | 5 | + | − | + | + | 0 | + |
| Ascusk9_51A | 1 | 0 | + | + | + | - | + |
| Ascusk9_51A | 3 | + | + | + | + | + | + |
| Ascusk9_51A | 4 | + | + | + | + | + | 0 |
| Ascusk9_51A | 5 | + | − | + | + | 0 | + |
| Ascusk9_51D | 1 | 0 | + | + | + | − | + |
| Ascusk9_51D | 3 | + | + | + | + | + | + |
| Ascusk9_51E | 1 | 0 | + | + | + | − | + |
| Ascusk9_51E | 3 | + | + | + | + | + | + |

TABLE 9-continued

| HPLC Analysis of Microbial Isolates or Enrichments | | | | | | | |
|---|---|---|---|---|---|---|---|
| StrainID | Media Recipe | Succinate | Lactate | Acetate | Propionate | Ethanol | Butyrate |
| Ascusk9_51E | 4 | + | + | + | + | + | 0 |
| Ascusk9_51E | 5 | + | − | + | + | 0 | + |
| Ascusk9_51F | 1 | 0 | + | + | + | − | + |
| Ascusk9_51F | 3 | + | + | + | + | + | + |
| Ascusk9_51F | 4 | + | + | + | + | + | 0 |
| Ascusk9_51F | 5 | + | − | + | + | 0 | + |
| Ascusk9_51G | 6 | 0 | + | + | + | 0 | 0 |
| Ascusk9_51G | 1 | 0 | + | + | + | - | + |
| Ascusk9_51G | 3 | + | + | + | + | + | + |
| Ascusk9_51G | 4 | + | + | + | + | + | 0 |
| Ascusk9_51G | 5 | + | − | + | + | 0 | + |
| Ascusk9_51G | 5 | 0 | + | + | + | + | 0 |
| Ascusk9_51I | 1 | 0 | + | + | + | − | + |
| Ascusk9_51I | 3 | + | + | + | + | + | + |
| Ascusk9_51J | 1 | 0 | + | + | + | − | + |
| Ascusk9_51J | 3 | + | + | + | + | + | + |
| Ascusk9_51J | 4 | + | + | + | + | + | 0 |
| Ascusk9_51J | 5 | + | − | + | + | 0 | + |
| Ascusk9_52A | 2 | + | + | + | + | + | + |
| Ascusk9_546A | 6 | 0 | + | + | 0 | 0 | 0 |
| Ascusk9_58D | 3 | + | − | + | + | 0 | + |
| Ascusk9_59A | 1 | 0 | + | + | + | − | + |
| Ascusk9_59A | 3 | + | + | + | + | + | + |
| Ascusk9_59G | 1 | 0 | + | + | + | − | + |
| Ascusk9_59G | 3 | + | + | + | + | + | + |
| Ascusk9_59G | 4 | + | + | + | + | + | 0 |
| Ascusk9_59G | 5 | + | − | + | + | 0 | + |
| Ascusk9_59G | 5 | 0 | + | + | + | + | 0 |
| Ascusk9_59J | 1 | 0 | + | + | + | − | + |
| Ascusk9_59J | 3 | + | + | + | + | + | + |
| Ascusk9_6A | 1 | 0 | + | + | + | − | + |
| Ascusk9_6A | 3 | + | + | + | + | + | + |
| Ascusk9_82C | 1 | 0 | + | + | + | − | + |
| Ascusk9_82C | 3 | + | + | + | + | + | + |
| Ascusk9_82C | 4 | + | + | + | + | + | 0 |
| Ascusk9_82C | 5 | + | − | + | + | 0 | + |
| Ascusk9_82C | 5 | 0 | + | + | + | + | 0 |
| Ascusk9_82D | 5 | 0 | + | + | + | + | 0 |
| Ascusk9_88C | 5 | 0 | + | + | + | + | 0 |
| Ascusk9_88D | 1 | 0 | + | + | + | − | + |
| Ascusk9_88D | 3 | + | + | + | + | + | + |
| Ascusk9_88D | 4 | + | + | + | + | + | 0 |
| Ascusk9_88D | 5 | + | − | + | + | 0 | + |
| Ascusk9_88D | 5 | 0 | + | + | + | + | 0 |
| Ascusk9_8A | 1 | 0 | + | + | + | − | + |
| Ascusk9_8A | 3 | + | + | + | + | + | + |
| Ascusk9_8A | 4 | + | + | + | + | + | 0 |
| Ascusk9_8A | 5 | + | − | + | + | 0 | + |
| Ascusk9_9D | 5 | + | − | + | + | 0 | + |
| Ascusk9_9E | 5 | 0 | + | + | + | + | 0 |

Example 7. Microbial Supplementation Study in Healthy Canines

The objective of this study is to determine the efficacy of microbial supplementation in healthy canines, i.e., canines without diagnosed gastrointestinal disorders. Specifically, this study examines the efficacy of microbial supplementation in improving fecal consistency and supporting gastrointestinal health.

Methods

Forty canine received one dose of a microbial consortia (Ascusk9_51G, Ascusk9_546A, Ascusk9_0G) daily for 30 days. The microbial consortia was formulated as a powder, and was administered once daily by sprinkling over the dog's food. The microbial composition is provided in Table 10 below.

TABLE 10

| Microbial Supplement for Healthy Canines | | |
|---|---|---|
| Formulation | Doses to be packaged as a dry powder in a foil sachet. | |
| Microorganisms/ CFU Per Day | Ascus9_51G (SEQ ID NO: 19) | 1.00E+07 |
| | Ascus9_546A (SEQ ID NO: 326) | 1.00E+08 |
| | Ascus9_0G (SEQ ID NO: 172) | 2.00E+05 |
| Storage | Powder will be refrigerated at 4° C. after opening. | |

The dog's owner received a survey to complete before and after the 30-day period to assess various aspects of the dog's health and fecal consistency. Health Observations were performed by the owner throughout the 30-day administration period. Additional observations were made if necessary.

Fecal quality was quantified using the Purina Fecal Scoring system. A fecal score of 1 was considered constipation, a fecal score of 2 or 3 represented the ideal fecal consistency, and a fecal score of 4 or greater represented various stages of diarrhea.

Results

Thirty-three survey responses were received after the 30-day administration period. One dog experienced an unrelated health event and stopped consuming supplementation halfway through the 30-day administration period. This canine was removed subsequent analysis.

Administration of native microorganisms (Ascusk9_51G, Ascusk9_546A, Ascusk9_0G) was found to support or improve the fecal consistency of 29 out of 32 canines. Eleven canines started at a less ideal score (i.e. constipation or diarrhea score) and shifted to a 2 or 3 at the end of the 30 day period. Of the three canines reporting worse fecal consistency, two canines shifted from a score of 2 or 3 to a score of 5. The third canine began the trial with diarrhea and showed no change after administration of the microbial supplement.

In addition to improvement in fecal quality, other benefits were reported, including: more regular bowel movements and better fecal consistency; less straining during defecation; improved dental health; eased side-effects of antibiotics; brighter eyes; more energy; better appetite; and improved fur and coat quality.

These results demonstrate that daily microbial supplementation with Ascus9_51G, Ascus9_546A, and Ascus9_0G support or improve fecal consistency in most canines, and provides additional health benefits. Daily supplementation with these microorganisms was therefore shown to support overall health and wellbeing in canines.

Example 8. Case Study of Microbial Supplementation in a Healthy Canine (Dog #1)

The objective of this study is to test the efficacy of microbial supplementation in improving fecal consistency and supporting gastrointestinal health in a healthy canine.

Methods

A healthy canine was enrolled in a 30-day test (Dog #1). The canine received one dose of a microbial consortia (Ascusk9_51G, Ascusk9_546A, Ascusk9_0G) daily for 30 days. The microbial consortia was formulated as a powder containing calcium carbonate and inulin as a carrier. The microbial composition is provided in Table 11 below.

TABLE 11

Microbial Supplementation for Dog #1

| Formulation | Doses to be packaged as a dry powder in a foil sachet. | |
|---|---|---|
| Microorganisms/ CFU Per Day | Ascus9_51G (SEQ ID NO: 19) | 1.00E+07 |
| | Ascus9_546A (SEQ ID NO: 326) | 1.00E+08 |
| | Ascus9_0G (SEQ ID NO: 172) | 2.00E+05 |
| Storage | Powder will be refrigerated at 4° C. after opening. | |

The dog's owner received a survey to complete before and after the 30-day period to assess various aspects of the dog's health and fecal consistency. Health Observations were also performed by the owner throughout the 30-day administration period. Additional observations were made if necessary.

Fecal quality was quantified using the Purina Fecal Scoring system. A fecal score of 1 was considered constipation, a fecal score of 2 or 3 represented the ideal fecal consistency, and a fecal score of 4 or greater represented various stages of diarrhea. Fecal samples were also collected prior to and after the 30-day administration period for microbiome analysis.

Results

Administration of Ascusk9_51G, Ascusk9_546A, and Ascusk9_0G to the canine did not cause any abnormal health observations. No gastrointestinal distress was noted during the administration period nor during follow-up period. The canine's owner reported that fecal consistency was a 2 both before and after administration of microbes based on the Purina Scoring System.

The pre-administration fecal microbiome of Dog #1 was compared to the post-administration fecal microbiome to assess efficacy of microbial supplementation in shifting the overall microbial community towards a more healthy state.

Figure 5B:
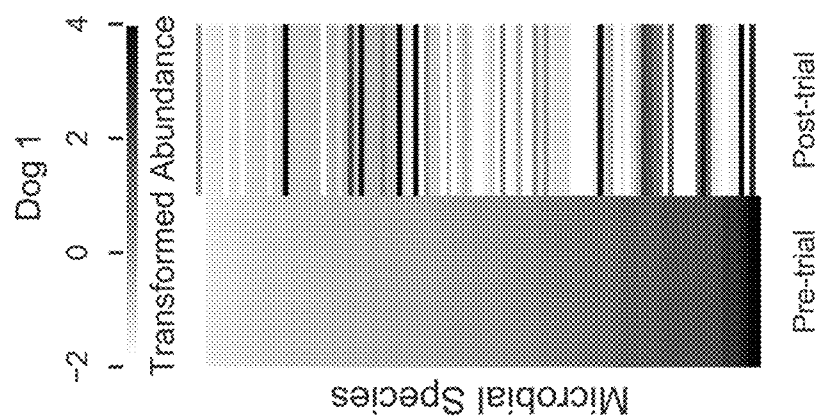
FIG. 5B shows the taxonomic diversity of the fecal microbiome of Dog #1 before and after daily administration of a microbial supplement for a 30-day period.
Figure 5A:
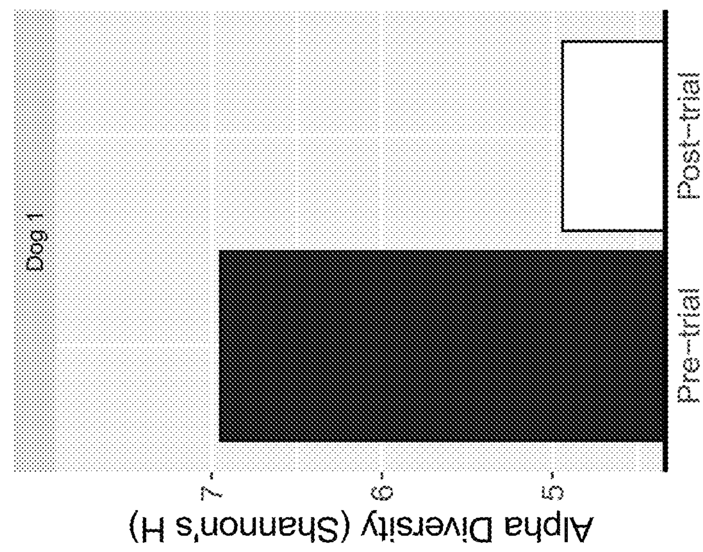
FIG. 5A shows the alpha diversity of the fecal microbiome of Dog #1 before and after daily administration of a microbial supplement for a 30-day period.

Previous studies have found that reduced alpha diversity is a common characteristic of healthy microbiomes. FIG. 5A depicts the alpha diversity of the fecal microbiome of Dog #1 prior to administration (left) and after administration (right). Lower alpha diversity in canines has been previously observed in healthier canines. After administration, the fecal microbiome of Dog #1 exhibited a reduction in alpha diversity, suggesting that the post-administration state of the fecal microbiome is more optimal than the pre-administration state.

Figure 5C:
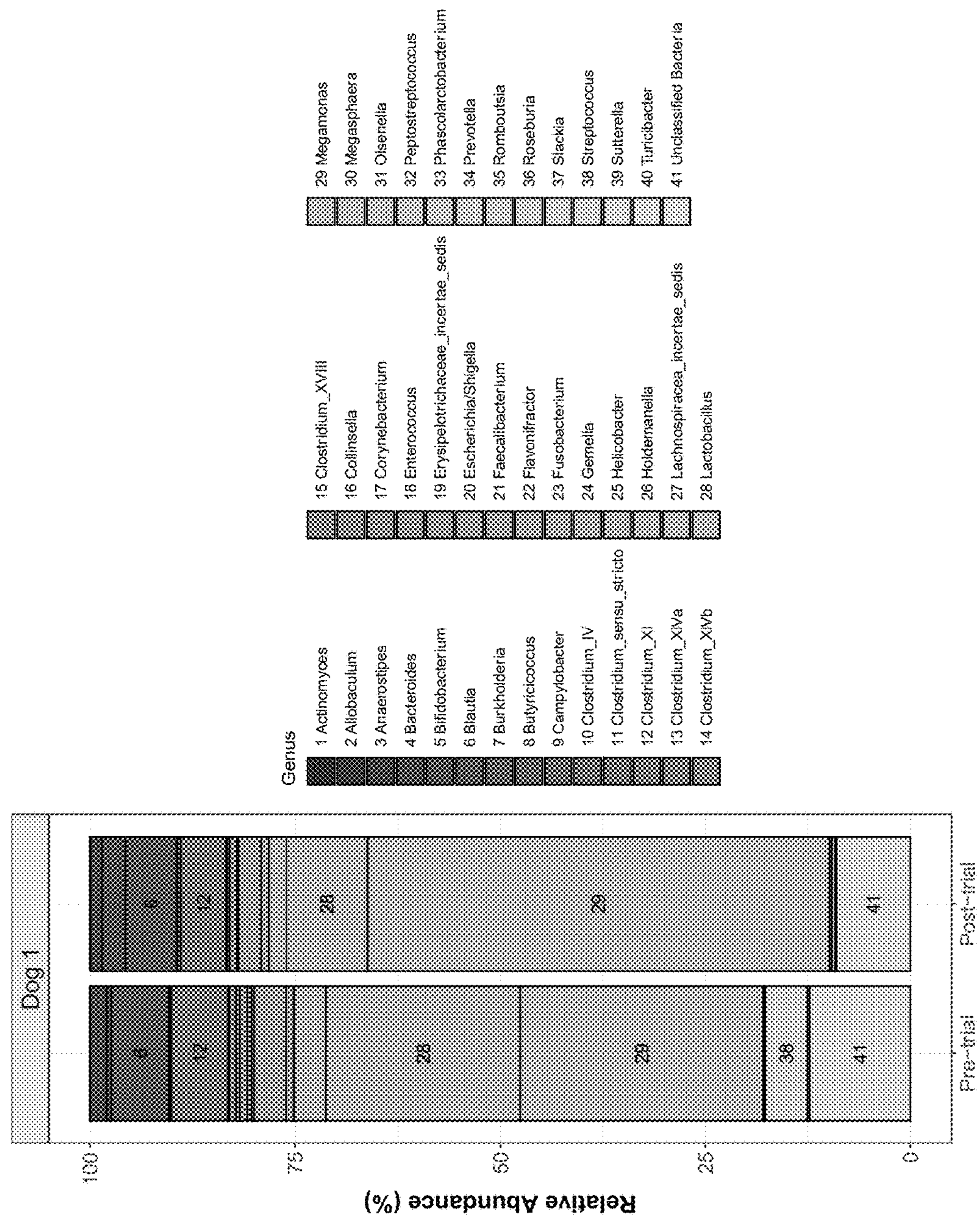
FIG. 5C shows the taxonomic groups at the genus level of the fecal microbiome of Dog #1 before and after daily administration of a microbial supplement for a 30-day period. The microbial supplement comprised Ascusk9_51G, Ascusk9_546A, and Ascusk9_0G (FIG. 5A-5C).
Figure 6:
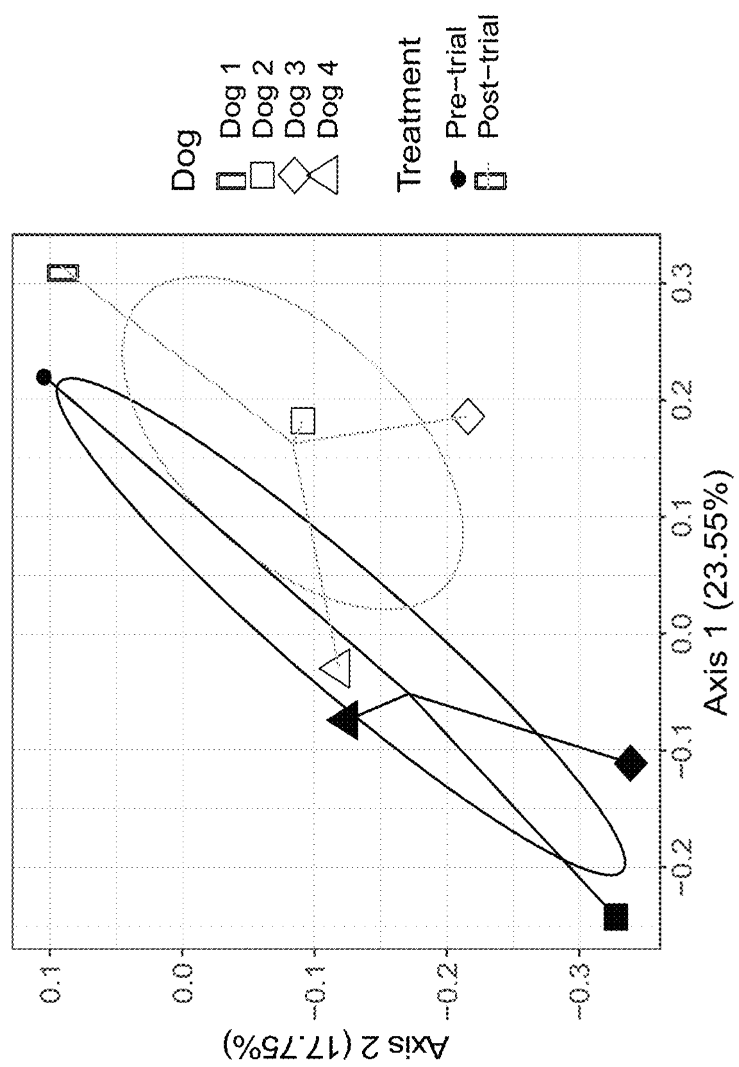
FIG. 6 shows principal coordinates analysis (PCoA) of the four individual case studies in canines. Dogs #1 and #4 were healthy canines supplemented with Ascusk9_5IG, Ascusk9_546A, and Ascusk9_0G for a 30-day period. Dogs #2 and #3 were canines diagnosed with chronic enteropathy and were supplemented with Ascusk9_51G, Ascusk9_546A, Ascusk9_0G, Ascusk9_210B, Ascusk9_17A, Ascusk9_2A, and Ascusk9_33E for a 30-day period.

The taxonomic diversity of the microbiome was also investigated before and after daily administration of Ascusk9_51G, Ascusk9_546A, and Ascusk9_0G for a 30-day period. As shown in FIG. 5B, the microbiome composition of Dog #1 shifted after administration of microorganisms. Based on taxonomic information, one of the genera that shifted the most after the 30-day period was *Megamonas* (Ascusk9_51G) (FIG. 5C). PCoA analysis of all four case study dogs (discussed herein and in the Examples below) suggested that the microbiome of Dog #1 remained similar to the healthy-state after microbial supplementation (FIG. 6).

Collectively, the fecal microbiome data obtained from this case study suggests that administration of Ascusk9_51G, Ascusk9_546A, and Ascusk9_0G for a 30-day period can support the stability of the microbiome in a healthy canine. In the event of an acute dysbiotic event, daily administration of microorganisms may reduce the health impacts of severe microbiome shifts by promoting compositional stability and robustness.

Example 9. Case Study of Microbial Supplementation in a Canine with Chronic Enteropathy (Dog #2)

The objective of this study is to test the efficacy of microbial supplementation in improving fecal consistency and supporting gastrointestinal health in a canine with chronic enteropathy.

Methods

A canine diagnosed chronic enteropathy was enrolled in a 30-day test (Dog #2). The canine received one dose of a microbial consortia (Ascusk9_51G, Ascusk9_546A, Ascusk9_0G, Ascusk9_210B, Ascusk9_17A, Ascusk9_2A, and Ascusk9_33E) daily for 30 days. The microbial consortia was formulated as a powder containing calcium carbonate and inulin as a carrier. The microbial composition is provided in Table 12 below.

TABLE 12

| Microbial Supplementation for Dog #2 | | |
|---|---|---|
| Formulation | Doses to be packaged as a dry powder in a foil sachet. | |
| Microorganisms/ CFU Per Day | Ascus9_51G (SEQ ID NO: 19) | 1.00E+08 |
| | Ascus9_546A (SEQ ID NO: 326) | 1.00E+08 |
| | Ascus9_0G (SEQ ID NO: 172) | 1.00E+06 |
| | Ascusk9_210B (SEQ ID NO: 237) | 1.00E+07 |
| | Ascusk9_17A (SEQ ID NO: 330) | 1.00E+06 |
| | Ascusk9_2A (SEQ ID NO: 331) | 1.00E+06 |
| | Ascusk9_33E (SEQ ID NO: 328) | 1.00E+05 |
| Storage | Powder will be refrigerated at 4° C. after opening. | |

The dog's owner received a survey to complete before and after the 30-day period to assess various aspects of the dog's health and fecal consistency. Health Observations were also performed by the owner throughout the 30-day administration period. Additional observations were made if necessary.

Fecal quality was quantified using the Purina Fecal Scoring system. A fecal score of 1 was considered constipation, a fecal score of 2 or 3 represented the ideal fecal consistency, and a fecal score of 4 or greater represented various stages of diarrhea. Fecal samples were also collected prior to and after the 30-day administration period for microbiome analysis.

Results

Administration of the microbial supplement (Ascusk9_51G, Ascusk9_546A, Ascusk9_0G, Ascusk9_210B, Ascusk9_17A, Ascusk9_2A, and Ascusk9_33E) to Dog #2 did not cause any abnormal health observations. No gastrointestinal distress was noted during the administration period nor during the follow-up period. The canine's owner reported a shift in fecal consistency from a 2 to a 3 based on the Purina Scoring System. He also defecated more regularly and had more energy as well as an increased appetite. The owner observed that the administration of microorganisms improved the dog's alopecia and reduced dark pigmentation spots on the skin.

The pre-administration fecal microbiome of Dog #2 was compared to the post-administration fecal microbiome to assess efficacy of microbial supplementation in shifting the overall microbial community towards a more healthy state.

Figure 7A:
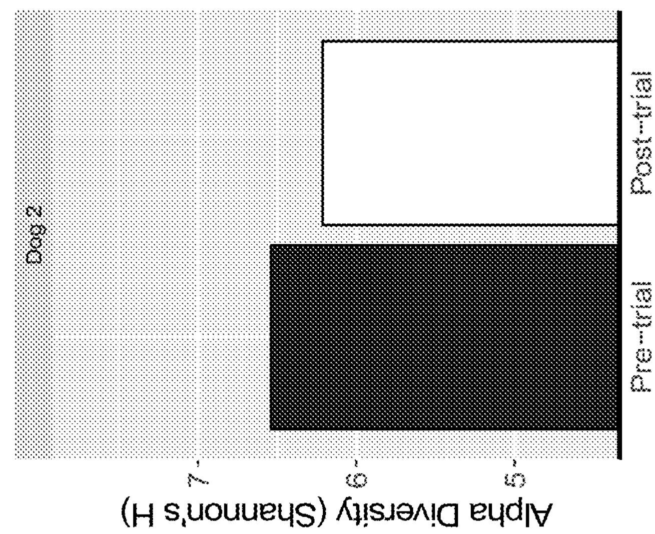
FIG. 7A shows the alpha diversity of the fecal microbiome of Dog #2 before and after daily administration of a microbial supplement for a 30-day period.

FIG. 7A depicts the alpha diversity of the fecal microbiome of Dog #2 before and after daily administration of the microbial supplement containing Ascusk9_51G, Ascusk9_546A, Ascusk9_0G, Ascusk9_210B, Ascusk9_17A, Ascusk9_2A, and Ascusk9_33E. Previous studies have found that reduced alpha diversity is a common characteristic of healthy microbiomes. The fecal microbiome of Dog #2 exhibited a reduction in alpha diversity, suggesting that the post-administration state of the fecal microbiome is more optimal than the pre-administration state.

Figure 7B:
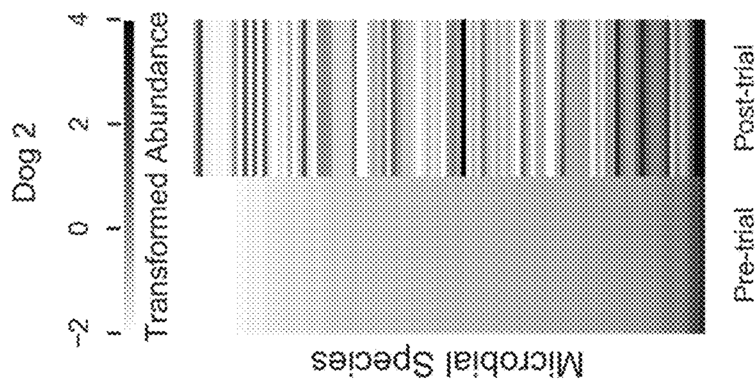
FIG. 7B shows the taxonomic diversity of the fecal microbiome of Dog #2 before and after daily administration of the microbial supplement for a 30-day period.
Figure 7C:
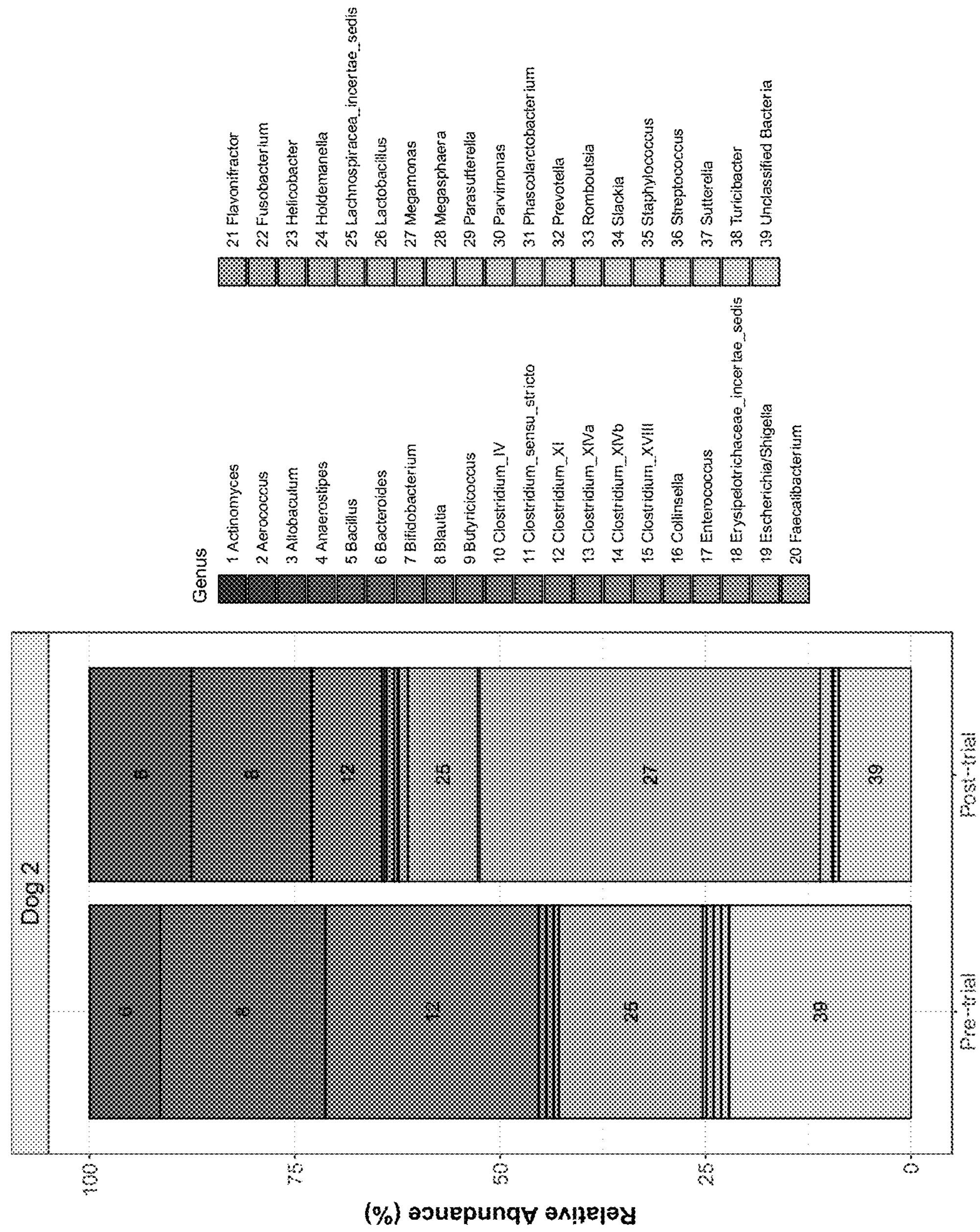
FIG. 7C shows the taxonomic groups at the genus level of the fecal microbiome of Dog #2 before and after daily administration of the microbial supplement for a 30-day period. The microbial supplement comprised Ascusk9_51G, Ascusk9_546A, Ascusk9_0G, Ascusk9_210B, Ascusk9_17A, Ascusk9_2A, and Ascusk9_33E (FIG. 7A-7C).

The taxonomic diversity of the microbiome was also investigated before and after administration of the microbial supplement. The microbiome of Dog #2 shifted after administration of microorganisms (FIG. 7B). Based on taxonomic information, one of the genera that shifted the most after the 30-day period was *Megamonas* (Ascusk9_51G) (FIG. 7C). PCoA analysis of all four case study dogs suggested that the microbiome of Dog #2 shifted and was more similar to the healthy microbiome state following microbial supplementation (FIG. 6).

Collectively, the fecal microbiome data obtained from this case study suggests that administration of a microbial supplement containing Ascusk9_51G, Ascusk9_546A, Ascusk9_0G, Ascusk9_210B, Ascusk9_17A, Ascusk9_2A, and Ascusk9_33E for a 30-day period can support the microbiome of a canine with chronic enteropathy, and shift the composition such that the microbiome is more similar to a healthy microbiome state. Daily administration of microorganisms may reduce the severity of chronic enteropathy.

Example 10. Case Study of Microbial Supplementation in a Canine with Chronic Enteropathy (Dog #3)

The objective of this study is to test the efficacy of microbial supplementation in improving fecal consistency and supporting gastrointestinal health in a canine with chronic enteropathy.

Methods

A canine with diagnosed chronic enteropathy was enrolled in the 30-day test (Dog #3). The canine received one dose of a microbial consortia (Ascusk9_51G, Ascusk9_546A, Ascusk9_0G, Ascusk9_210B, Ascusk9_17A, Ascusk9_2A, and Ascusk9_33E) daily for 30 days. The microbial consortia was formulated as a powder containing calcium carbonate and inulin as a carrier. The microbial composition is provided in Table 13 below.

TABLE 13

| Microbial Supplementation for Dog #3 | | |
|---|---|---|
| Formulation | Doses to be packaged as a dry powder in a foil sachet. | |
| Microorganisms/ CFU Per Day | Ascus9_51G (SEQ ID NO: 19) | 1.00E+08 |
| | Ascus9_546A (SEQ ID NO: 326) | 1.00E+08 |
| | Ascus9_0G (SEQ ID NO: 172) | 1.00E+06 |
| | Ascusk9_210B (SEQ ID NO: 237) | 1.00E+07 |
| | Ascusk9_17A (SEQ ID NO: 330) | 1.00E+06 |
| | Ascusk9_2A (SEQ ID NO: 331) | 1.00E+06 |
| | Ascusk9_33E (SEQ ID NO: 328) | 1.00E+05 |
| Storage | Powder will be refrigerated at 4° C. after opening. | |

The dog's owner received a survey to complete before and after the 30-day period to assess various aspects of the dog's health and fecal consistency. Health Observations were also performed by the owner throughout the 30-day administration period. Additional observations were made if necessary.

Fecal quality was quantified using the Purina Fecal Scoring system. A fecal score of 1 was considered constipation, a fecal score of 2 or 3 represented the ideal fecal consistency, and a fecal score of 4 or greater represented various stages of diarrhea. Fecal samples were also collected prior to and after the 30-day administration period for microbiome analysis.

Results

Administration of the microbial supplement (Ascusk9_51G, Ascusk9_546A, Ascusk9_0G, Ascusk9_210B, Ascusk9_17A, Ascusk9_2A, and Ascusk9_33E) to Dog #3 did not cause any abnormal health observations. Dog #3 began an antibiotic regimen halfway through the administration period due to an unrelated health event. The canine's owner reported that the microorganisms helped alleviate the side effects of antibiotic administration.

The pre-administration fecal microbiome of Dog #3 was compared to the post-administration fecal microbiome to assess efficacy of native microorganisms in shifting the overall microbial community towards a more healthy state.

Figure 8B:
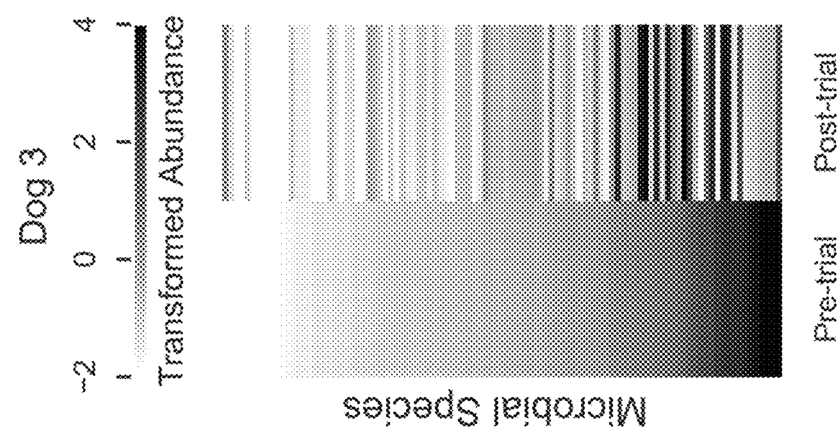
FIG. 8B shows the taxonomic diversity of the fecal microbiome of Dog #3 before and after daily administration of a for a 30-day period.
Figure 8A:
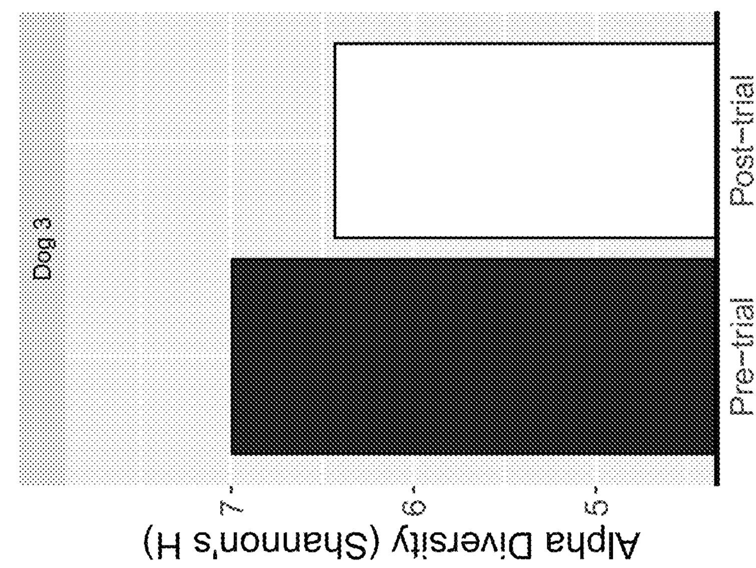
FIG. 8A shows the alpha diversity of the fecal microbiome of Dog #3 before and after daily administration of a microbial supplement for a 30-day period.

FIG. 8A depicts the alpha diversity of Dog #3's fecal microbiome before and after daily administration of the microbial supplement containing Ascusk9_51G, Ascusk9_546A, Ascusk9_0G, Ascusk9_210B, Ascusk9_17A, Ascusk9_2A, and Ascusk9_33E. Previous studies have found that reduced alpha diversity is a common characteristic of healthy microbiomes. After microbial administration, the fecal microbiome of Dog #3 exhibited a reduction in alpha diversity, suggesting that the post-administration state of the fecal microbiome is more optimal than the pre-administration state.

Figure 8C:
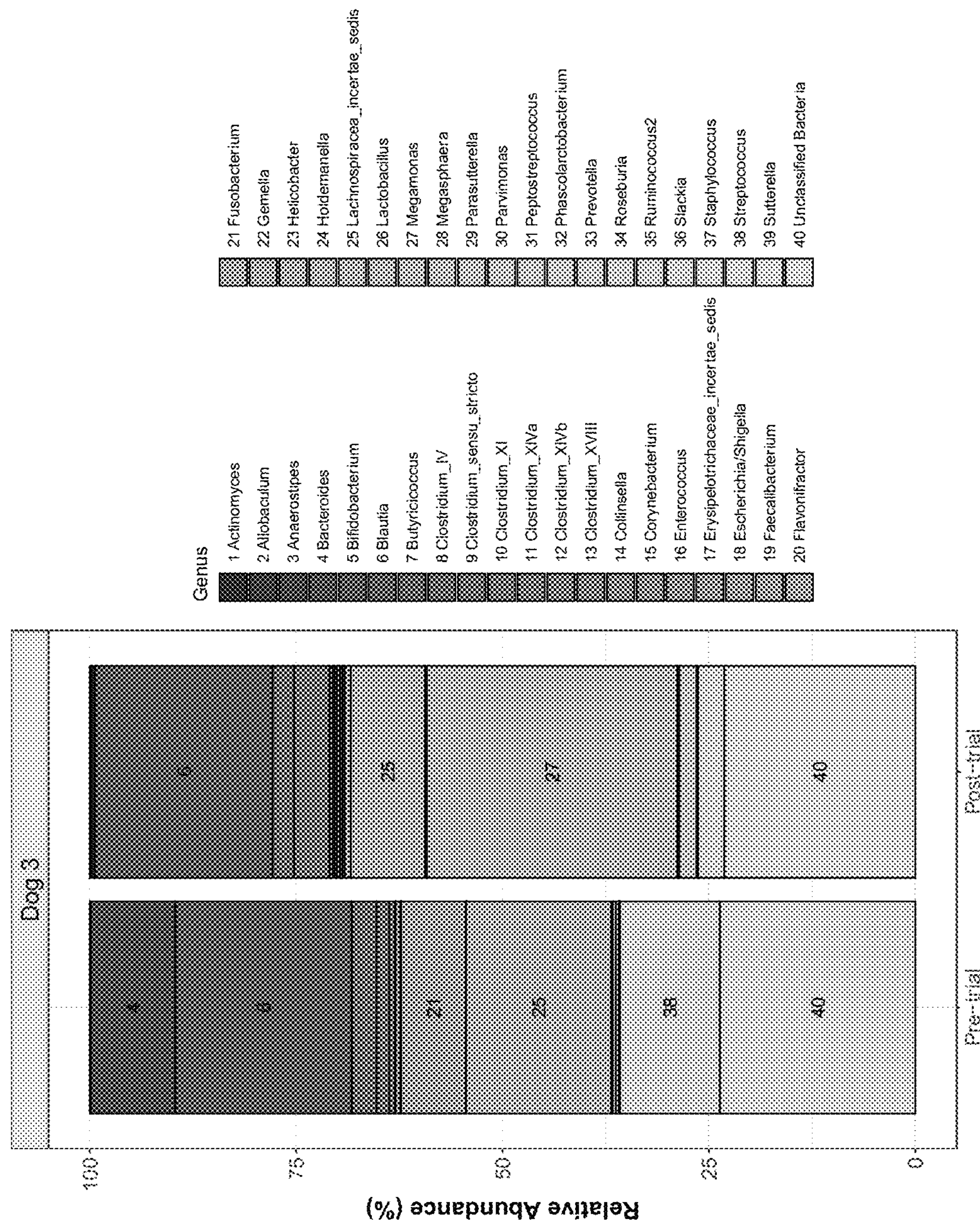
FIG. 8C shows the taxonomic groups at the genus level of the fecal microbiome of Dog #3 before and after daily administration of a microbial supplement for a 30-day period. The microbial supplement comprised Ascusk9_51G, Ascusk9_546A, Ascusk9_0G, Ascusk9_210B, Ascusk9_17A, Ascusk9_2A, and Ascusk9_33E (FIG. 8A-8C).

The taxonomic diversity of the microbiome was also investigated before and after administration of microorganisms. The microbiome composition did shift after administration of microorganisms (FIG. 8B). Some of this shift may be due to antibiotic use. Investigation into taxonomic level information revealed that several microbial groups dramatically reduced in abundance, including *Bacteroides, Fusobacterium*, and *Streptococcus*. Similar to the other case studies, one of the genera that increased the most after the 30-day period was *Megamonas* (Ascusk9_51G) (FIG. 8C). PCoA analysis of all four case study dogs suggested that the microbiome of Dog #3 shifted and was more similar to the healthy microbiome state after microbial supplementation (FIG. 6).

Collectively, the fecal microbiome data obtained from this case study suggests that administration of native microorganisms for a 30-day period can support the microbiome of a canine with chronic enteropathy, and shift the composition such that the microbiome is more similar to a healthy microbiome state. Antibiotic use may have enabled the microbiome to shift more rapidly to the healthy state by destabilizing the existing microbiome. Daily administration of microorganisms may reduce the severity of chronic enteropathy.

Example 11. Case Study of Microbial Supplementation in a Healthy Canine (Dog #4)

The objective of this study is to test the efficacy of microbial supplementation in improving fecal consistency and supporting gastrointestinal health in a healthy canine.

Methods

One healthy canine was enrolled in a 30-day test (Dog #4). The canine received one dose of a microbial consortia (Ascusk9_51G, Ascusk9_546A, and Ascusk9_0G) daily for 30 days. The microbial consortia was formulated as a powder containing calcium carbonate and inulin as a carrier. The microbial composition is provided in Table 14 below.

TABLE 14

Microbial Supplementation for Dog #4

| Formulation | Doses to be packaged as a dry powder in a foil sachet. | |
|---|---|---|
| Microorganisms/ CFU Per Day | Ascus9_51G (SEQ ID NO: 19) | 1.00E+07 |
| | Ascus9_546A (SEQ ID NO: 326) | 1.00E+08 |
| | Ascus9_0G (SEQ ID NO: 172) | 2.00E+05 |
| Storage | Powder will be refrigerated at 4° C. after opening. | |

The dog's owner received a survey to complete before and after the 30-day period to assess various aspects of the dog's health and fecal consistency. Health Observations were also performed by the owner throughout the 30-day administration period. Additional observations were made if necessary.

Fecal quality was quantified using the Purina Fecal Scoring system. A fecal score of 1 was considered constipation, a fecal score of 2 or 3 represented the ideal fecal consistency, and a fecal score of 4 or greater represented various stages of diarrhea. Fecal samples were also collected prior to and after the 30-day administration period for microbiome analysis.

Results

Administration of the microorganisms Ascusk9_51G, Ascusk9_546A, and Ascusk9_0G to the canine did not cause any abnormal health observations. No gastrointestinal distress was noted during the administration period nor during the follow-up period. The canine's owner reported that fecal consistency was a 2 both before and after administration of microbes based on the Purina Scoring System.

The pre-administration fecal microbiome of Dog #4 was compared to the post-administration fecal microbiome to assess efficacy of microbial supplementation in shifting the overall microbial community towards a more healthy state.

Figure 9B:
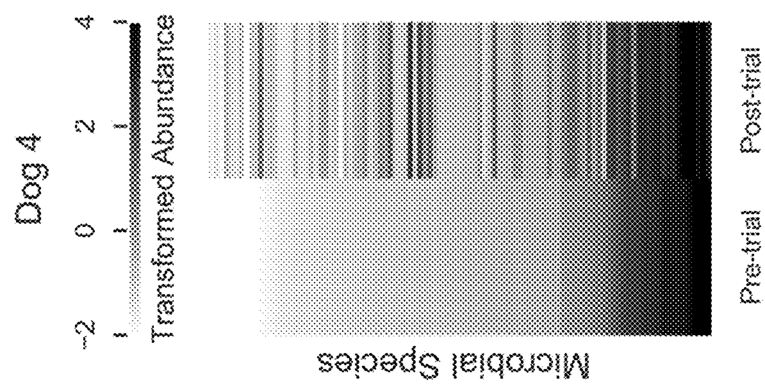
FIG. 9B shows the taxonomic diversity of the fecal microbiome of Dog #4 before and after daily administration of a microbial supplement for a 30-day period.
Figure 9A:
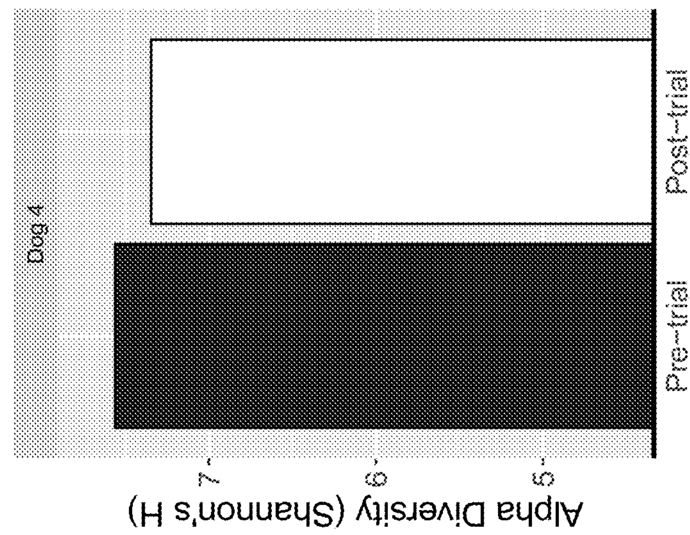
FIG. 9A shows the alpha diversity of the fecal microbiome of Dog #4 before and after daily administration of a microbial supplement for a 30-day period.

FIG. 9A depicts the alpha diversity of the fecal microbiome of Dog #4 before and after daily administration of Ascusk9_51G, Ascusk9_546A, and Ascusk9_0G for 30-days. Previous studies have found that reduced alpha diversity is a common characteristic of healthy microbiomes. The fecal microbiome of Dog #4 exhibited a reduction in alpha diversity following microbial supplementation, suggesting that the post-administration state of the fecal microbiome is more optimal than the pre-administration state (FIG. 9A).

Figure 9C:
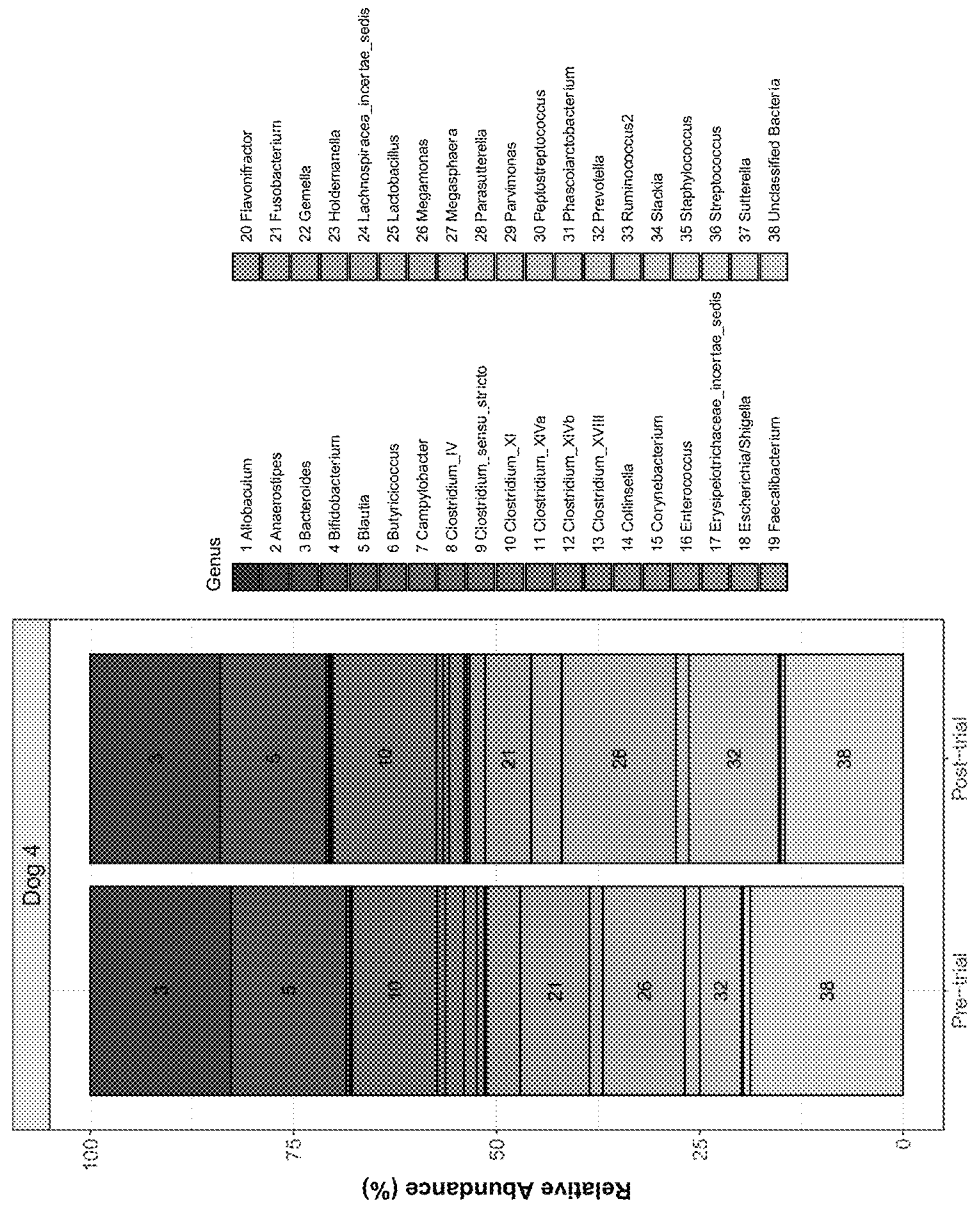
FIG. 9C shows the taxonomic groups at the genus level of the fecal microbiome of Dog #4 before and after daily administration of a microbial supplement for a 30-day period. The microbial supplement comprised Ascusk9_51G, Ascusk9_546A, and Ascusk9_0G (FIG. 9A-9C).

The taxonomic diversity of the microbiome was also investigated before and after microbial supplementation. The microbiome of Dog #4 shifted slightly after administration of the microorganisms (FIG. 9B). Based on taxonomic information, one of the genera that shifted the most after the 30-day period was *Megamonas* (Ascusk9_51G) (FIG. 9C). PCoA analysis of all four case study dogs suggested that the microbiome of Dog #4 remained similar to the healthy-state after microbial supplementation (FIG. 6).

Collectively, the fecal microbiome data obtained from this case study suggests that administration of Ascusk9_51G, Ascusk9_546A, and Ascusk9_0G for a 30-day period can support the stability of the microbiome in a healthy canine. In the event of an acute dysbiotic event, daily administration of microorganisms may reduce the health impacts of severe microbiome shifts by promoting compositional stability and robustness.

Example 12. Competitive Exclusion Against *E. coli*

Previous studies have shown that *Escherichia coli* (*E. coli*) overgrowth may be a causative agent of acute diarrhea in otherwise healthy dogs. The objective of this study was to test the ability of individual microbial isolates to compete against *E. coli* in the gastrointestinal tract.

An in vitro assay was designed to investigate potential antimicrobial activity against *E. coli*. Ascusk9_546A, Ascusk9_672A, Ascusk9_210B, Ascusk9_51G, Ascusk9_33E, Ascusk9_0G, Ascusk9_38A, Ascusk9_17A, and Ascusk9_2A were plated on solid TSB with non-pathogenic *E. coli*. The plates were cultured anaerobically overnight and observed the following day for zones of clearance.

Figure 10:
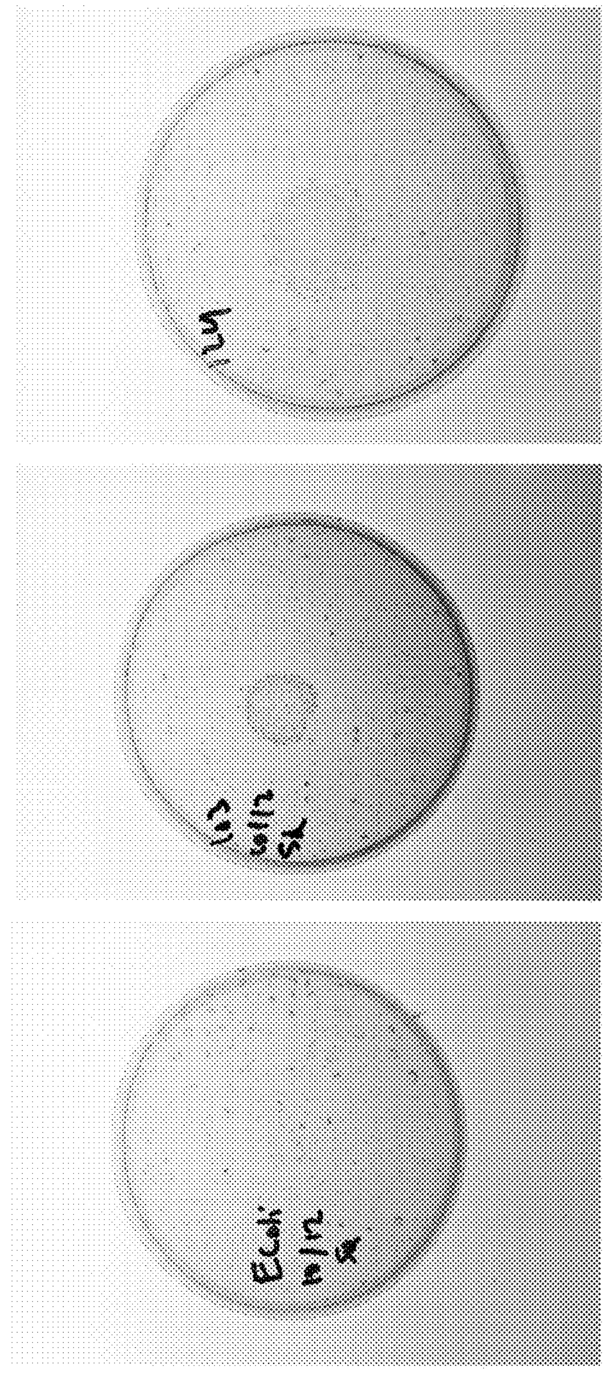
FIG. 10 shows the ability of individual microbial isolates (Ascusk9_546A and Ascusk9_17A) to compete against *E. coli* in vitro.

As shown in FIG. 10, two strains produced clear halos in the lawn of *E. coli*: Ascusk9_546A and Ascusk9_17A. These results indicate that microbial supplementation with these microorganisms will likely reduce the incidence and severity of diarrhea caused by *E. coli* overgrowth in the gastrointestinal tract of canines.

Further Embodiments of the Invention

Other subject matter contemplated by the present disclosure is set out in the following numbered embodiments:

1. A microbial composition comprising:
   (a) a purified microbial population that comprises one or more bacteria with a 16S nucleic acid sequence that shares at least 97% sequence identity with a nucleic acid sequence selected from SEQ ID NOs: 1-333; and
   (b) one or more carriers suitable for canine administration.
2. The microbial composition of embodiment 1, wherein the purified microbial population comprises a bacterium with a 16S nucleic acid sequence sharing at least 97% sequence identity with SEQ ID NO: 19.
3. The microbial composition of embodiment 1, wherein the purified microbial population comprises a bacterium with a 16S nucleic acid sequence comprising SEQ ID NO: 19.
4. The microbial composition of embodiment 1, wherein the purified microbial population comprises a bacterium with a 16S nucleic acid sequence sharing at least 97% sequence identity with SEQ ID NO: 172.
5. The microbial composition of embodiment 1, wherein the purified microbial population comprises a bacterium with a 16S nucleic acid sequence comprising SEQ ID NO: 172.
6. The microbial composition of embodiment 1, wherein the purified microbial population comprises a bacterium with a 16S nucleic acid sequence sharing at least 97% sequence identity with SEQ ID NO: 237.
7. The microbial composition of embodiment 1, wherein the purified microbial population comprises a bacterium with a 16S nucleic acid sequence comprising SEQ ID NO: 237.
8. The microbial composition of embodiment 1, wherein the purified microbial population comprises a bacterium with a 16S nucleic acid sequence sharing at least 97% sequence identity with SEQ ID NO: 326.
9. The microbial composition of embodiment 1, wherein the purified microbial population comprises a bacterium with a 16S nucleic acid sequence comprising SEQ ID NO: 326.
10. The microbial composition of embodiment 1, wherein the purified microbial population comprises a bacterium with a 16S nucleic acid sequence sharing at least 97% sequence identity with SEQ ID NO: 327.
11. The microbial composition of embodiment 1, wherein the purified microbial population comprises a bacterium with a 16S nucleic acid sequence comprising SEQ ID NO: 327.
12. The microbial composition of embodiment 1, wherein the purified microbial population comprises a bacterium with a 16S nucleic acid sequence sharing at least 97% sequence identity with SEQ ID NO: 328.
13. The microbial composition of embodiment 1, wherein the purified microbial population comprises a bacterium with a 16S nucleic acid sequence comprising SEQ ID NO: 328.
14. The microbial composition of embodiment 1, wherein the purified microbial population comprises a bacterium with a 16S nucleic acid sequence sharing at least 97% sequence identity with SEQ ID NO: 329.
15. The microbial composition of embodiment 1, wherein the purified microbial population comprises a bacterium with a 16S nucleic acid sequence comprising SEQ ID NO: 329.
16. The microbial composition of embodiment 1, wherein the purified microbial population comprises a bacterium with a 16S nucleic acid sequence sharing at least 97% sequence identity with SEQ ID NO: 330.
17. The microbial composition of embodiment 1, wherein the purified microbial population comprises a bacterium with a 16S nucleic acid sequence comprising SEQ ID NO: 330.
18. The microbial composition of embodiment 1, wherein the purified microbial population comprises a bacterium with a 16S nucleic acid sequence sharing at least 97% sequence identity with SEQ ID NO: 331.
19. The microbial composition of embodiment 1, wherein the purified microbial population comprises a bacterium with a 16S nucleic acid sequence comprising SEQ ID NO: 331.
20. The microbial composition of embodiment 1, wherein the one or more bacteria comprises a 16S nucleic acid sequence that shares at least 97% sequence identity with a nucleic acid sequence selected from SEQ ID NOs: 19, 172, 237, and 326-331.
21. The microbial composition of embodiment 1, wherein the one or more bacteria comprises a 16S nucleic acid sequence selected from SEQ ID NOs: 19, 172, 237, and 326-331.
22. The microbial composition of embodiment 1, wherein the one or more bacteria comprises a 16S nucleic acid sequence that shares at least 97% sequence identity with SEQ ID NOs: 19, 172, and 326.
23. The microbial composition of embodiment 1, wherein the one or more bacteria comprises a 16S nucleic acid sequence of SEQ ID NOs: 19, 172, and 326.
24. The microbial composition of embodiment 1, wherein the one or more bacteria comprises a 16S nucleic acid sequence that shares at least 97% sequence identity with SEQ ID NOs: 19, 172, 237, 326, 328, 330, and 331.
25. The microbial composition of embodiment 1, wherein the one or more bacteria comprises a 16S nucleic acid sequence of SEQ ID NOs: 19, 172, 237, 326, 328, 330, and 331.
26. The microbial composition of any one of embodiments 1-25, wherein the microbial composition is comprised of spores.
27. The microbial composition of any one of embodiments 1-25, wherein the microbial composition is embedded in a wax.
28. The microbial composition of any one of embodiments 1-25, wherein the microbial composition is encapsulated.
29. The microbial composition of embodiment 28, wherein the encapsulated microbial composition comprises a polymer selected from the group consisting of: a saccharide polymer, an agar polymer, an agarose polymer, a protein polymer, and a lipid polymer.
30. The microbial composition of embodiment 28, wherein the microbial composition is preserved in a glass matrix.
31. The microbial composition of any one of embodiments 1-30, wherein the one or more carriers are selected from the group consisting of: an edible feed grade material, an aluminosilicate-containing mineral, a zeolite, calcium carbonate, a prebiotic, and a flavoring agent.

32. The microbial composition of embodiment 31, wherein the prebiotic is an inulin, an oligosaccharide, and/or a vitamin.

33. The microbial composition of embodiment 32, wherein the one or more carriers are inulin, calcium carbonate, activated charcoal, and/or yucca.

34. The microbial composition of embodiment 31, wherein the flavoring agent is dried yeast, cheese flavoring, beef flavoring, fish flavoring, chicken flavoring, and/or pork flavoring.

35. The microbial composition of any one of embodiments 1-34, wherein the one or more bacteria is present in the composition at a concentration of about $10^2$ to about $10^{15}$ cells per gram of said composition.

36. The microbial composition of any one of embodiments 1-34, wherein the one or more bacteria is present in the composition at a concentration of at least $10^2$ cells per gram of said composition.

37. The microbial composition of any one of embodiments 1-36, wherein the microbial composition is mixed with or sprinkled on top of animal feed.

38. The microbial composition of any one of embodiments 1-36, wherein the microbial composition is formulated as a tablet, a pill, a capsule, a powder, a solution, a suspension, or an emulsion.

39. The microbial composition of embodiment 38, wherein the microbial composition is formulated as a pill.

40. The microbial composition of any one of embodiments 1-36, wherein the microbial composition is formulated as a food.

41. The microbial composition of embodiment 40, wherein the microbial composition is formulated as a dry food, a wet food, a kibble, or a raw food.

42. A microbial composition comprising:
   - (a) at least one isolated microbial strain selected from the group consisting of:
     - (i) Ascusk9_546A deposited as NRRL Accession Deposit No. B-67972;
     - (ii) Ascusk9_672A deposited as NRRL Accession Deposit No. B-67973;
     - (iii) Ascusk9_210B deposited as NRRL Accession Deposit No. B-67974;
     - (iv) Ascusk9_51G deposited as NRRL Accession Deposit No. B-67975;
     - (v) Ascusk9_33E deposited as NRRL Accession Deposit No. B-67976;
     - (vi) Ascusk9_0G deposited as NRRL Accession Deposit No. B-67977;
     - (vii) Ascusk9_38A deposited as NRRL Accession Deposit No. B-67987;
     - (viii) Ascusk9_17A deposited as NRRL Accession Deposit No. B-67986; and
     - (ix) Ascusk 9_2A deposited as NRRL Accession Deposit No. B-67985; and
   - (b) one or more carriers suitable for canine administration.

43. A method of imparting at least one desirable trait in a canine, the method comprising administration of the microbial composition of any one of embodiments 1-42 to the canine.

44. The method of embodiment 43, wherein the at least one desirable trait is selected from the group consisting of: improved fecal consistency, increased regular bowel movements, reduced incidence of diarrhea, reduced incidence of constipation, less straining during defecation, reduced side-effects from antibiotics, improved dental health, brighter eyes, increased energy, increased appetite, improved fur and coat quality, decreased incidence of infectious or non-infectious disease, increased lifespan, and/or improved performance of the canine.

45. A method of maintaining or improving gastrointestinal health in a canine, the method comprising administration of the microbial composition of any one of embodiments 1-42 to the canine.

46. A method of treating or preventing gastrointestinal dysbiosis or gastrointestinal enteropathy in a canine, the method comprising administration of the microbial composition of any one of embodiments 1-42 to the canine.

47. The method of embodiment 45 or 46, wherein the microbial composition reduces the incidence of diarrhea, improves fecal consistency, reduces straining during defecation, reduces constipation, increases regular bowel movements, reduces dysbiosis, and/or reduces enteropathy in the canine.

48. A method of modulating the microbiome of a canine, the method comprising administering the composition of any one of embodiments 1-42 to the canine.

49. The method of embodiment 48, wherein the modulation of the microbiome is an increase in the proportion of the one or more bacteria of the microbiome, wherein the increase is measured relative to a canine that did not have the one or more bacteria administered.

50. The method of embodiment 48, wherein the modulation of the microbiome is a decrease in the proportion of the one or more bacteria present in the microbiome prior to the administration of the composition, wherein the decrease is measured relative to the microbiome of the canine prior to the administration of the composition.

51. A method of increasing resistance of a canine to the colonization of pathogenic microbes, the method comprising the administration of the composition of any one of embodiments 1-42, wherein the pathogen's ability to colonize the gastrointestinal tract of the canine is reduced.

52. A method of treating a canine for the presence of at least one pathogenic microbe, the method comprising administration of the composition of any one of embodiments 1-42.

53. The method of embodiment 52, wherein after administration of the composition the relative abundance of the at least one pathogenic microbe decreases to less than 5% relative abundance in the gastrointestinal tract.

54. The method of embodiment 53, wherein the relative abundance of the at least one pathogenic microbe decreases to less than 1% relative abundance in the gastrointestinal tract.

55. The method of embodiment 53, wherein the at least one pathogenic microbe is undetectable in the gastrointestinal tract.

56. The method of any one of embodiments 43-55, wherein the microbial composition is administered once per day throughout the lifetime of a canine.

57. The method of any one of embodiments 43-55, wherein the microbial composition is administered twice per day throughout the lifetime of a canine.

58. The method of any one of embodiments 43-55, wherein the microbial composition is administered to the canine once per day, twice per day, three times per day, once per week, twice per week, three times per week, once every two weeks, or once per month over a one month period, two month period, three month period, six month period, or twelve month period.

59. A canine feed supplement capable of increasing a desirable phenotypic trait in a canine, the feed supplement comprising:
   (a) a microbial composition of any one of embodiments 1-30 present at a concentration that does not occur naturally in the canine; and
   (b) an acceptable carrier.

60. A canine feed supplement capable of increasing a desirable phenotypic trait in a canine, the feed supplement comprising:
   (a) one or more bacteria comprising a 16S nucleic acid sequence that shares at least 97% sequence identity with SEQ ID NOs: 19, 172, and 326; and
   (b) an acceptable carrier;

wherein the one or more bacteria are present in the canine feed supplement at a concentration of at least $10^2$ cells per gram of said composition.

61. A canine feed supplement for treating or preventing gastrointestinal dysbiosis or gastrointestinal enteropathy in a canine, the feed supplement comprising:
   (a) one or more bacteria comprising a 16S nucleic acid sequence that shares at least 97% sequence identity with SEQ ID NOs: 19, 172, 237, 326, 328, 330, and 331; and
   (b) an acceptable carrier;

wherein the one or more bacteria are present in the canine feed supplement at a concentration of at least $10^2$ cells per gram of said composition.

62. A canine feed supplement capable of increasing a desirable phenotypic trait in a canine, the feed supplement comprising a *Megamonas* sp. and an acceptable carrier;

wherein the *Megamonas* sp. is present in the canine feed supplement at a concentration of at least $10^2$ cells per gram of said composition.

63. A canine feed supplement for treating or preventing gastrointestinal dysbiosis or gastrointestinal enteropathy in a canine, the feed supplement comprising a *Megamonas* sp. and an acceptable carrier;

wherein the *Megamonas* sp. is present in the canine feed supplement at a concentration of at least $10^2$ cells per gram of said composition.

64. An isolated microbial strain selected from any one of the microbial strains in Table 1.

65. An isolated microbial strain selected from the group consisting of:
   (a) Ascusk9_546A deposited as NRRL Accession Deposit No. B-67972;
   (b) Ascusk9_672A deposited as NRRL Accession Deposit No. B-67973;
   (c) Ascusk9_210B deposited as NRRL Accession Deposit No. B-67974;
   (d) Ascusk9_51G deposited as NRRL Accession Deposit No. B-67975;
   (e) Ascusk9_33E deposited as NRRL Accession Deposit No. B-67976;
   (f) Ascusk9_0G deposited as NRRL Accession Deposit No. B-67977;
   (g) Ascusk9_38A deposited as NRRL Accession Deposit No. B-67987;
   (h) Ascusk9_17A deposited as NRRL Accession Deposit No. B-67986; and
   (i) Ascusk 9_2A deposited as NRRL Accession Deposit No. B-67985.

66. An isolated microbial strain comprising a polynucleotide sequence sharing at least 90% sequence identity with any one of SEQ ID NOs: 1-333.

67. A substantially pure culture of an isolated microbial strain according to any one of embodiments 64 to 66.

The invention claimed is:

1. A composition comprising:
(a) a purified population of bacteria comprising:
(i) a bacterium comprising a 16S nucleic acid sequence sharing at least 99.5% sequence identity to SEQ ID NO: 19;
(ii) a bacterium comprising a 16S nucleic acid sequence sharing at least 99.5% sequence identity to SEQ ID NO: 172; and
(iii) optionally, a bacterium comprising a 16S nucleic acid sequence sharing at least 99.5% sequence identity to SEQ ID NO: 326; and
(b) one or more carriers suitable for canine administration;
wherein the bacteria in the composition are lyophilized; and wherein the bacteria present in the composition are in an amount effective to improve one or more traits in a canine administered the composition.

2. The composition of claim 1, wherein the purified population of bacteria comprises: a bacterium having a 16S nucleic acid sequence of SEQ ID NO: 19; and a a bacterium having a 16S nucleic acid sequence of SEQ ID NO: 172; and optionally, a bacterium having a 16S nucleic acid sequence of SEQ ID NO: 326.

3. The composition of claim 1, wherein the purified population of bacteria comprises: a bacterium having a 16S nucleic acid sequence of SEQ ID NO: 19; a a bacterium having a 16S nucleic acid sequence of SEQ ID NO: 172; and a bacterium having a 16S nucleic acid sequence of SEQ ID NO: 326.

4. The composition of claim 1, wherein the purified population of bacteria comprises: a bacterium deposited as NRRL B-67972; a bacterium deposited as NRRL B-67975; and a bacterium deposited as NRRL B-67977.

5. The composition of claim 1, wherein the purified population further comprises one or more bacteria with a 16S nucleic acid sequence that shares at least 97% sequence identity with a nucleic acid sequence selected from: SEQ ID NOs: 237 and 327-331.

6. The composition of claim 1, wherein the one or more carriers are selected from the group consisting of: an edible feed grade material, an aluminosilicate-containing mineral, a zeolite, calcium carbonate, a prebiotic, and a flavoring agent.

7. The composition of claim 6, wherein the prebiotic is inulin, an oligosaccharide, and/or a vitamin.

8. The composition of claim 6, wherein the flavoring agent is dried yeast, cheese flavoring, beef flavoring, fish flavoring, chicken flavoring, and/or pork flavoring.

9. The composition of claim 1, wherein the one or more carriers are inulin and/or dried yeast.

10. The composition of claim 1, wherein the bacteria are present in the composition at a concentration of at least $10^2$ cells per gram of said composition.

11. The composition of claim 1, wherein the composition is mixed with or sprinkled on top of animal food.

12. The composition of claim 1, wherein the composition is formulated as a tablet, a pill, a capsule, a powder, a solution, a suspension, a food, or an emulsion.

13. The composition of claim 12, wherein the composition is formulated as a dry food, a wet food, a kibble, or a raw food.

14. The composition of claim 1, wherein the purified population of bacteria comprises: a bacterium deposited as NRRL B-67975; a bacterium deposited as NRRL B-67977, and optionally, a bacterium deposited as NRRL B-67972.

15. The composition of claim 1, wherein the purified population of bacteria comprises: a bacterium comprising a 16S nucleic acid sequence sharing at least 99.5% sequence identity to SEQ ID NO: 19; a bacterium comprising a 16S nucleic acid sequence sharing at least 99.5% sequence identity to SEQ ID NO: 172; and a bacterium comprising a 16S nucleic acid sequence sharing at least 99.5% sequence identity to SEQ ID NO: 326.

16. The composition of claim 1, wherein the one or more traits is an improvement in gastrointestinal health of the canine.

17. The composition of claim 1, wherein the improvement in gastrointestinal health of the canine is reduced incidence of diarrhea, reduced dysbiosis, reduced enteropathy, reduced inflammation, improved fecal consistency, an increase in regular bowel movements, reduced incidence of constipation, or less straining during defecation.

18. The composition of claim 1, wherein the one or more traits are selected from a group consisting of: reduced incidence of diarrhea, reduced dysbiosis, reduced enteropathy, reduced inflammation, decreased incidence of infectious or non-infectious disease, improved fecal consistency, increased regular bowel movements, improved fur or coat quality, increased appetite, increased energy, improved performance, and increased lifespan.

* * * * *

SEQUENCE LISTING

```
Sequence total quantity: 333
SEQ ID NO: 1            moltype = DNA  length = 90
FEATURE                 Location/Qualifiers
source                  1..90
                        mol_type = genomic DNA
                        organism = Prevotella copri
SEQUENCE: 1
tacggaaggt ccgggcgtta tccggattta ttgggtttaa agggagcgta ggccggagat  60
taagcgtgtt gtgaaatgta gacgctcaac                                   90

SEQ ID NO: 2            moltype = DNA  length = 225
FEATURE                 Location/Qualifiers
source                  1..225
                        mol_type = genomic DNA
                        organism = Prevotella copri
SEQUENCE: 2
gtgtcagccg ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcataga tatcacgcag aactccgatt gcgaaggcag cttac                  225

SEQ ID NO: 3            moltype = DNA  length = 225
FEATURE                 Location/Qualifiers
source                  1..225
                        mol_type = genomic DNA
                        organism = Prevotella copri
SEQUENCE: 3
gtgccagccg ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcttaga tatcacgaag aaccccgatt gcgaaggcag cacac                  225
```

```
SEQ ID NO: 4            moltype = DNA  length = 225
FEATURE                 Location/Qualifiers
source                  1..225
                        mol_type = genomic DNA
                        organism = Prevotella copri
SEQUENCE: 4
tgccagcctc cgcggtaata cggaaggtcc gggcgttatc cggatttatt gggtttaaag  60
ggagcgtagg ccggagatta agcgtgttgt gaaatgtaga cgctcaacgt ctgcactgca  120
gcgcgaactg gtttccttga gtacgcacaa agtgggcgga attcgtggtg tagcggtgaa  180
atgcttagat atcacgaaga actccgatcg cgaaggcagc tcact                  225

SEQ ID NO: 5            moltype = DNA  length = 225
FEATURE                 Location/Qualifiers
source                  1..225
                        mol_type = genomic DNA
                        organism = Prevotella copri
SEQUENCE: 5
gtgtcagcag cccggtaata cggaaggtcc gggcgttatc cggatttatt gggtttaaag  60
ggagcgtagg ccggagatta agcgtgttgt gaaatgtaga cgctcaacgt ctgcactgca  120
gcgcgaactg gtttccttga gtgcgcacaa agtgggcgga attcgtggtg tagcggtgaa  180
atgcctagat atcacgaaga actccgattg cgaaggcagc acact                  225

SEQ ID NO: 6            moltype = DNA  length = 225
FEATURE                 Location/Qualifiers
source                  1..225
                        mol_type = genomic DNA
                        organism = Prevotella copri
SEQUENCE: 6
gtgtcagcag ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcttaga tatcacgaag aactccgatt gcgaaggcgg ctttc                  225

SEQ ID NO: 7            moltype = DNA  length = 225
FEATURE                 Location/Qualifiers
source                  1..225
                        mol_type = genomic DNA
                        organism = Prevotella copri
SEQUENCE: 7
gtgccagcag ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtgcgcaca aagtgggcgg aattcgtggt gtagcggtga  180
aatgcttaga tatcacgaag aactccgatt gcgaaggcag ctcac                  225

SEQ ID NO: 8            moltype = DNA  length = 225
FEATURE                 Location/Qualifiers
source                  1..225
                        mol_type = genomic DNA
                        organism = Prevotella copri
SEQUENCE: 8
gtgtcagccg ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcttaga tatcacgaag aactccgatt gcgaaggcag ctcac                  225

SEQ ID NO: 9            moltype = DNA  length = 225
FEATURE                 Location/Qualifiers
source                  1..225
                        mol_type = genomic DNA
                        organism = Prevotella copri
SEQUENCE: 9
gttcagcagc cgcggtaata cggaaggtcc gggcgttatc cggatttatt gggtttaaag  60
ggagcgtagg ccggagatta agcgtgttgt gaaatgtaga cgctcaacgt ctgcactgca  120
gcgcgaactg gtttccttga gtacgcacaa agtgggcgga attcgtggtg tagcggtgaa  180
atgcttagat atcacgaaga actccgattg cgaaggcagc tcact                  225

SEQ ID NO: 10           moltype = DNA  length = 225
FEATURE                 Location/Qualifiers
source                  1..225
                        mol_type = genomic DNA
                        organism = Prevotella copri
SEQUENCE: 10
gtgccagccg ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcttaga tatcacgaag aactccgatt gcgaaggcag cttgc                  225

SEQ ID NO: 11           moltype = DNA  length = 225
```

```
FEATURE                 Location/Qualifiers
source                  1..225
                        mol_type = genomic DNA
                        organism = Prevotella copri
SEQUENCE: 11
gtgtcagcag ccgcggtaat acggaaggtc cgggcgttat ccggatttat tgggtttaaa  60
gggagcgtag gccggagatt aagcgtgttg tgaaatgtag acgctcaacg tctgcactgc  120
agcgcgaact ggtttccttg agtacgcaca aagtgggcgg aattcgtggt gtagcggtga  180
aatgcttaga tatcacgaag aaccccgatt gcgaaggcag cttgc                   225

SEQ ID NO: 12           moltype = DNA  length = 90
FEATURE                 Location/Qualifiers
source                  1..90
                        mol_type = genomic DNA
                        organism = Megamonas funiformis
SEQUENCE: 12
tacgtaggcg gcaagcgttg tccggaatta ttgggcgtaa agggagcgca ggcgggaaac  60
taagcggatc ttaaaagtgc ggggctcaac                                    90

SEQ ID NO: 13           moltype = DNA  length = 225
FEATURE                 Location/Qualifiers
source                  1..225
                        mol_type = genomic DNA
                        organism = Megamonas funiformis
SEQUENCE: 13
gtgccagccg ccgcggtaat acgtaggcgg caagcgttgt ccggaattat tgggcgtaaa  60
gggagcgcag gcgggaaact aagcggatct taaaagtgcg gggctcaacc ccgtgatggg  120
gtccgaactg gttttcttga gtgcaggaga ggaaagcgga attcccagtg tagcggtgaa  180
atgcgtagat attgggagga acaccagtag cgaaggcggc tttct                   225

SEQ ID NO: 14           moltype = DNA  length = 225
FEATURE                 Location/Qualifiers
source                  1..225
                        mol_type = genomic DNA
                        organism = Megamonas funiformis
SEQUENCE: 14
gtgccagccg ccgcggtaat acgtaggcgg caagcgttgt ccggaattat tgggcgtaaa  60
gggagcgcag gcgggaaact aagcggatct taaaagtgcg gggctcaacc ccgtgatggg  120
gtccgaactg gttttcttga gtgcaggaga ggaaagggga attcccagtg tagcggtgaa  180
atgcgtagat attgggagga acaccagtgg cgaaggcgcc tttct                   225

SEQ ID NO: 15           moltype = DNA  length = 225
FEATURE                 Location/Qualifiers
source                  1..225
                        mol_type = genomic DNA
                        organism = Megamonas funiformis
SEQUENCE: 15
gtgtcagcag ccgcggtaat acgtaggcgg caagcgttgt ccggaattat tgggcgtaaa  60
gggagcgcag gcgggaaact aagcggatct taaaagtgcg gggctcaacc ccgtgatggg  120
gtccgaactg gttttcttga gtgcaggaga ggaaagcgga attcccagtg tagcggtgaa  180
atgcgtagat attaggagga acaccagtgg cgaaggcggc ttact                   225

SEQ ID NO: 16           moltype = DNA  length = 225
FEATURE                 Location/Qualifiers
source                  1..225
                        mol_type = genomic DNA
                        organism = Megamonas funiformis
SEQUENCE: 16
gtgccagcag ccgcggtaat acgtaggcgg caagcgttgt ccggaattat tgggcgtaaa  60
gggagcgcag gcgggaaact aagcggatct taaaagtgcg gggctcaacc ccgtgatggg  120
gtccgaactg gttttcttga gtgcaggaga ggaaagcgga attcccagtg tagcggtgaa  180
atgcgtagat atcgggagga acaccagtgg cgaaggcggc ctact                   225

SEQ ID NO: 17           moltype = DNA  length = 225
FEATURE                 Location/Qualifiers
source                  1..225
                        mol_type = genomic DNA
                        organism = Megamonas funiformis
SEQUENCE: 17
gtgtcagcag ccgcggtaat acgtaggcgg caagcgttgt ccggaattat tgggcgtaaa  60
gggagcgcag gcgggaaact aagcggatct taaaagtgcg gggctcaacc ccgtgatggg  120
gtccgaactg gttttcttga gtgcaggaga ggaaagcgga attcccagtg tagcggtgaa  180
atgcgtagat attgggaaga acaccagtgg cgaaggcggc ctact                   225

SEQ ID NO: 18           moltype = DNA  length = 225
FEATURE                 Location/Qualifiers
source                  1..225
                        mol_type = genomic DNA
                        organism = Megamonas funiformis
```

```
SEQUENCE: 18
gtgtcagcag ccgcggtaat acgtaggcgg caagcgttgt ccggaattat tgggcgtaaa  60
gggagcgcag gcgggaaact aagcggatct taaaagtgcg ggctcaacc ccgtgatggg  120
gtccgaactg gttttcttga gtgcaggaga ggaaagcgga attcccagtg tagcggtgaa  180
atgcgtagat attgggagga acaccagtgg cgaaggcgcc tttct                  225

SEQ ID NO: 19          moltype = DNA  length = 225
FEATURE                Location/Qualifiers
source                 1..225
                       mol_type = genomic DNA
                       organism = Megamonas funiformis
SEQUENCE: 19
gtgtcagccg ccgcggtaat acgtaggcgg caagcgttgt ccggaattat tgggcgtaaa  60
gggagcgcag gcgggaaact aagcggatct taaaagtgcg ggctcaacc ccgtgatggg  120
gtccgaactg gttttcttga gtgcaggaga ggaaagcgga attcccagtg tagcggtgaa  180
atgcgtagat attgggaaga acaccagtgg cgaaggcggc tttct                  225

SEQ ID NO: 20          moltype = DNA  length = 225
FEATURE                Location/Qualifiers
source                 1..225
                       mol_type = genomic DNA
                       organism = Megamonas funiformis
SEQUENCE: 20
gtgtcagccg ccgcggtaat acgtaggcgg caagcgttgt ccggaattat tgggcgtaaa  60
gggagcgcag gcgggaaact aagcggatct taaaagtgcg ggctcaacc ccgtgatggg  120
gtccgaactg gttttcttga gtgcaggaga ggaaagcgga attcccagtg tagcggtgaa  180
atgcgtagat attaggagga acaccagtgg cgaaagcggc tttct                  225

SEQ ID NO: 21          moltype = DNA  length = 225
FEATURE                Location/Qualifiers
source                 1..225
                       mol_type = genomic DNA
                       organism = Megamonas funiformis
SEQUENCE: 21
gtgccagcag ccgcggtaat acgtaggcgg caagcgttgt ccggaattat tgggcgtaaa  60
gggagcgcag gcgggaaact aagcggatct taaaagtgcg ggctcaacc ccgtgatggg  120
gtccgaactg gttttcttga gtgcaggaga ggaaagcgga attcctagtg tagcggtgaa  180
atgcgtagat attaggagga acaccagtgg cgaaagcggc tttct                  225

SEQ ID NO: 22          moltype = DNA  length = 225
FEATURE                Location/Qualifiers
source                 1..225
                       mol_type = genomic DNA
                       organism = Megamonas funiformis
SEQUENCE: 22
gttcagcagc cgcggtaata cgtaggcggc aagcgttgtc cggaattatt gggcgtaaag  60
ggagcgcagg cgggaaacta agcggatctt aaaagtgcgg ggctcaaccc cgtgatgggg  120
tccgaactgg ttttcttgag tgcaggagag gaaagcggaa ttcccagtgt agcggtgaaa  180
tgcgtagata ttgggaagaa caccagtggc gaaggcggct ttctg                  225

SEQ ID NO: 23          moltype = DNA  length = 90
FEATURE                Location/Qualifiers
source                 1..90
                       mol_type = genomic DNA
                       organism = Ruminococcus faecis
SEQUENCE: 23
tacgtatggt gcaagcgtta tccggattta ctgggtgtaa agggagcgta gacggttgtg  60
taagtctgat gtgaaaaccc ggggctcaac                                    90

SEQ ID NO: 24          moltype = DNA  length = 90
FEATURE                Location/Qualifiers
source                 1..90
                       mol_type = genomic DNA
                       organism = Eubacterium nitritogenes
SEQUENCE: 24
tacggaggtg gcgagcgttg tccggattta ctgggcgtaa agggagcgta ggcggatttt  60
taagtgggat gtgaaatacc cgggctcaac                                    90

SEQ ID NO: 25          moltype = DNA  length = 90
FEATURE                Location/Qualifiers
source                 1..90
                       mol_type = genomic DNA
                       organism = Eubacterium hallii
SEQUENCE: 25
tacgtatgga gcaagcgtta tccggattta ctgggtgtaa agggtgcgta ggcggcaagg  60
caagtcagat gtgaaagacc ggggctcaac                                    90

SEQ ID NO: 26          moltype = DNA  length = 225
FEATURE                Location/Qualifiers
```

```
source                  1..225
                        mol_type = genomic DNA
                        organism = Eubacterium hallii
SEQUENCE: 26
gtgccagcag ccgcggtaat acgtatggag caagcgttat ccggatttac tgggtgtaaa  60
gggtgcgtag gcggcaaggc aagtcagatg tgaaagaccg gggctcaact ccggggctgc  120
atttgaaact gttttgctgg agtccaggag aggcaggcgg aattcctagt gtagcggtga  180
aatgcgtaga tattaggagg aacaccagtg gcgaaagcgg cctgc                  225

SEQ ID NO: 27           moltype = DNA  length = 225
FEATURE                 Location/Qualifiers
source                  1..225
                        mol_type = genomic DNA
                        organism = Eubacterium hallii
SEQUENCE: 27
gtgtcagcag ccgcggtaat acgtatggag caagcgttat ccggatttac tgggtgtaaa  60
gggtgcgtag gcggcaaggc aagtcagatg tgaaagaccg gggctcaact ccggggctgc  120
atttgaaact gttttgctgg agtccaggag aggcaggcgg aattcctagt gtagcggtga  180
aatgcgtaga tattaggagg aacaccagtg gcgaaggcag ctcac                  225

SEQ ID NO: 28           moltype = DNA  length = 225
FEATURE                 Location/Qualifiers
source                  1..225
                        mol_type = genomic DNA
                        organism = Eubacterium hallii
SEQUENCE: 28
gttcagcagc cgcggtaata cgtatggagc aagcgttatc cggatttact gggtgtaaag  60
ggtgcgtagg cggcaaggca agtcagatgt gaaagaccgg ggctcaactc cggggctgca  120
tttgaaactg ttttgctgga gtccaggaga ggcaggcgga attcctagtg tagcggtgaa  180
atgcgtagat attaggagga acaccagtgg cgaaggcggc ctgct                  225

SEQ ID NO: 29           moltype = DNA  length = 225
FEATURE                 Location/Qualifiers
source                  1..225
                        mol_type = genomic DNA
                        organism = Eubacterium hallii
SEQUENCE: 29
gtgtcagccg ccgcggtaat acgtatggag caagcgttat ccggatttac tgggtgtaaa  60
gggtgcgtag gcggcaaggc aagtcagatg tgaaagaccg gggctcaact ccggggctgc  120
atttgaaact gttttgctgg agtccaggag aggcaggcgg aattcctagt gtagcggtga  180
aatgcgtaga tattaggagg aacaccagtg gcgaaggcgg cctgc                  225

SEQ ID NO: 30           moltype = DNA  length = 225
FEATURE                 Location/Qualifiers
source                  1..225
                        mol_type = genomic DNA
                        organism = Eubacterium hallii
SEQUENCE: 30
gtgtcagcag ccgcggtaat acgtatggag caagcgttat ccggatttac tgggtgtaaa  60
gggtgcgtag gcggcaaggc aagtcagatg tgaaagaccg gggctcaact ccggggctgc  120
atttgaaact gttttgctgg agtccaggag aggcaggcgg aattcctagt gtagcggtga  180
aatgcgtaga tattaggagg aacaccagtg gcgaaagcgg ctttc                  225

SEQ ID NO: 31           moltype = DNA  length = 225
FEATURE                 Location/Qualifiers
source                  1..225
                        mol_type = genomic DNA
                        organism = Eubacterium hallii
SEQUENCE: 31
gtgtcagcag ccgcggtaat acgtatggag caagcgttat ccggatttac tgggtgtaaa  60
gggtgcgtag gcggcaaggc aagtcagatg tgaaagaccg gggctcaact ccggggctgc  120
atttgaaact gttttgctgg agtccaggag aggcaggcgg aattcctagt gtagcggtga  180
aatgcgtaga tattgggagg aacaccagtg gcgaaggcgc ctttc                  225

SEQ ID NO: 32           moltype = DNA  length = 90
FEATURE                 Location/Qualifiers
source                  1..90
                        mol_type = genomic DNA
                        organism = Prevotella bryantii
SEQUENCE: 32
tacggaaggt ccgggcgtta tccggattta ttgggtttaa agggagcgca ggcggactct  60
taagtcagtt gtgaaatacg gcggctcaac                                   90

SEQ ID NO: 33           moltype = DNA  length = 225
FEATURE                 Location/Qualifiers
source                  1..225
                        mol_type = genomic DNA
                        organism = Prevotella bryantii
SEQUENCE: 33
```

```
gtgtcagccg ccgcggtaat acggaaggtc cgggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcatggt gtagcggtga  180
aatgctcaga tatcatgaag aactccgatc gcgaaggcag ctcac                 225

SEQ ID NO: 34          moltype = DNA  length = 90
FEATURE                Location/Qualifiers
source                 1..90
                       mol_type = genomic DNA
                       organism = Anaerobiospirillum succiniciproducens
SEQUENCE: 34
tacggagggt gcaagcgtta atcggaataa ctgggcgtaa agggcatgta ggcggaaagg  60
caagcaagat gtgaaagacc tgggctcaac                                  90

SEQ ID NO: 35          moltype = DNA  length = 90
FEATURE                Location/Qualifiers
source                 1..90
                       mol_type = genomic DNA
                       organism = Catenibacterium mitsuokai
SEQUENCE: 35
tacgtaggtg gcgagcgtta tccggaatca ttgggcataa agagggagca ggcggccgca  60
agggtctgtg gtgaaagacc gaagctaaac                                  90

SEQ ID NO: 36          moltype = DNA  length = 90
FEATURE                Location/Qualifiers
source                 1..90
                       mol_type = genomic DNA
                       organism = Eubacterium infirmum
SEQUENCE: 36
tacggagggg gcaagcgtta tccggaatta ttgggcgtaa agggtacgta ggtggtttac  60
caagcgcagg gtttaaggca atggctcaac                                  90

SEQ ID NO: 37          moltype = DNA  length = 90
FEATURE                Location/Qualifiers
source                 1..90
                       mol_type = genomic DNA
                       organism = Holdemanella biformis
SEQUENCE: 37
tacggaggtg gcgagcgtta tccggaatga ttgggcgtaa agggtgcgta ggtggcagat  60
caagtctgga gtaaaaggta tggctcaac                                   90

SEQ ID NO: 38          moltype = DNA  length = 90
FEATURE                Location/Qualifiers
source                 1..90
                       mol_type = genomic DNA
                       organism = Clostridium hiranonis
SEQUENCE: 38
tacggagggg gctagcgtta tccggattta ctgggcgtaa agggtgcgta ggcggtcttt  60
caagtcagga gttaaaggct acggctcaac                                  90

SEQ ID NO: 39          moltype = DNA  length = 90
FEATURE                Location/Qualifiers
source                 1..90
                       mol_type = genomic DNA
                       organism = Catenibacterium mitsuokai
SEQUENCE: 39
tacgtaggtg gcgagcgtta tccggaatca ttgggcgtaa agagggagca ggcggccgca  60
agggtctgcg gtgaaagacc gaagctaaac                                  90

SEQ ID NO: 40          moltype = DNA  length = 90
FEATURE                Location/Qualifiers
source                 1..90
                       mol_type = genomic DNA
                       organism = Allobaculum stercoricanis
SEQUENCE: 40
tacgtaggtg gcgagcgtta tccggaatga ttgggcgtaa agggtgcgca ggcggcatat  60
caagtctgaa gtgaaaggta cgggctcaac                                  90

SEQ ID NO: 41          moltype = DNA  length = 225
FEATURE                Location/Qualifiers
source                 1..225
                       mol_type = genomic DNA
                       organism = Allobaculum stercoricanis
SEQUENCE: 41
gtgccagccg ccgcggtaat acgtaggtgg cgagcgttat ccggaatgat tgggcgtaaa  60
gggtgcgcag gcggcatatc aagtctgaag tgaaaggtac gggctcaacc tgtacaggct  120
ttggaaactg gtatgctcga ggacaggaga gggcggtgga actccacgtg tagcggtaaa  180
atgcgtagag atgtggaaga acaccagtgg cgaaggcggc cgcct                 225
```

```
SEQ ID NO: 42          moltype = DNA  length = 90
FEATURE                Location/Qualifiers
source                 1..90
                       mol_type = genomic DNA
                       organism = Prevotella copri
SEQUENCE: 42
tacggaaggt ccgggcgtta tccggattta ttgggtttaa agggagcgta ggccggagat  60
taagcgtgtt gtgaaatgta gatgctcaac                                   90

SEQ ID NO: 43          moltype = DNA  length = 225
FEATURE                Location/Qualifiers
source                 1..225
                       mol_type = genomic DNA
                       organism = Prevotella copri
SEQUENCE: 43
tttttagctg ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcag ctcac                  225

SEQ ID NO: 44          moltype = DNA  length = 225
FEATURE                Location/Qualifiers
source                 1..225
                       mol_type = genomic DNA
                       organism = Prevotella copri
SEQUENCE: 44
gtgtcagcag ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgcag aactccgatt gcgaaggcag cttac                  225

SEQ ID NO: 45          moltype = DNA  length = 225
FEATURE                Location/Qualifiers
source                 1..225
                       mol_type = genomic DNA
                       organism = Prevotella copri
SEQUENCE: 45
gtgccagcag ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
agtgcttaga tatcatgaag aactccgatt gcgaaggcag ctcac                  225

SEQ ID NO: 46          moltype = DNA  length = 225
FEATURE                Location/Qualifiers
source                 1..225
                       mol_type = genomic DNA
                       organism = Prevotella copri
SEQUENCE: 46
gtgtcagccg ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcag gtatc                  225

SEQ ID NO: 47          moltype = DNA  length = 225
FEATURE                Location/Qualifiers
source                 1..225
                       mol_type = genomic DNA
                       organism = Prevotella copri
SEQUENCE: 47
gtgccagccg ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcgg ctttc                  225

SEQ ID NO: 48          moltype = DNA  length = 225
FEATURE                Location/Qualifiers
source                 1..225
                       mol_type = genomic DNA
                       organism = Prevotella copri
SEQUENCE: 48
gtgccagcag ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcag cacac                  225

SEQ ID NO: 49          moltype = DNA  length = 225
FEATURE                Location/Qualifiers
source                 1..225
                       mol_type = genomic DNA
```

```
                        organism = Prevotella copri
SEQUENCE: 49
gtgtcagccg ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcag ctcac                 225

SEQ ID NO: 50           moltype = DNA  length = 225
FEATURE                 Location/Qualifiers
source                  1..225
                        mol_type = genomic DNA
                        organism = Prevotella copri
SEQUENCE: 50
gtgtcagccg ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aaccccgatt gcgaaggcag cttgc                 225

SEQ ID NO: 51           moltype = DNA  length = 225
FEATURE                 Location/Qualifiers
source                  1..225
                        mol_type = genomic DNA
                        organism = Prevotella copri
SEQUENCE: 51
gtgccagcag ccgcggtaat acggaaggtc cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaaggcag cttgc                 225

SEQ ID NO: 52           moltype = DNA  length = 225
FEATURE                 Location/Qualifiers
source                  1..225
                        mol_type = genomic DNA
                        organism = Prevotella copri
SEQUENCE: 52
gttcagcagc cgcggtaata cggaaggtcc gggcgttatc cggatttatt gggtttaaag  60
ggagcgtagg ccggagatta agcgtgttgt gaaatgtaga tgctcaacat ctgaactgca  120
gcgcgaactg gtttccttga gtacgcacaa agtgggcgga attcgtggtg tagcggtgaa  180
atgcttagat atcacgaaga actccgattg cgaaggcagc tcact                 225

SEQ ID NO: 53           moltype = DNA  length = 90
FEATURE                 Location/Qualifiers
source                  1..90
                        mol_type = genomic DNA
                        organism = Morganella morganii
SEQUENCE: 53
tacggagggt gcaagcgtta atcggaatta ctgggcgtaa agcgcacgca ggcggttgat  60
tgagtcagat gtgaaatccc cgggcttaac                                  90

SEQ ID NO: 54           moltype = DNA  length = 90
FEATURE                 Location/Qualifiers
source                  1..90
                        mol_type = genomic DNA
                        organism = Acidicaldus organivorans
SEQUENCE: 54
tacgaagggg gctagcgttg ctcggaatga ctgggcgtaa agggcgcgta ggcggatcgg  60
acagtcgggc gtgaaattcc tgggctcaac                                  90

SEQ ID NO: 55           moltype = DNA  length = 90
FEATURE                 Location/Qualifiers
source                  1..90
                        mol_type = genomic DNA
                        organism = Eubacterium hallii
SEQUENCE: 55
tacgtatgga gcaagcgtta tccggattta ctgggtgtaa agggtgcgta ggtggcagtg  60
caagtcagat gtgaaaggcc ggggctcaac                                  90

SEQ ID NO: 56           moltype = DNA  length = 90
FEATURE                 Location/Qualifiers
source                  1..90
                        mol_type = genomic DNA
                        organism = Parasutterella excrementihominis
SEQUENCE: 56
tacgtagggt gcgagcgtta atcggaatta ctgggcgtaa agggtgcgca ggcggttgag  60
taagacagat gtgaaatccc cgagcttaac                                  90

SEQ ID NO: 57           moltype = DNA  length = 90
FEATURE                 Location/Qualifiers
source                  1..90
```

```
                        mol_type = genomic DNA
                        organism = Ruminococcus torques
SEQUENCE: 57
tacgtatggt gcaagcgtta tccggattta ctgggtgtaa agggagcgta gacggatggg  60
caagtctgat gtgaaaaccc ggggctcaac                                   90

SEQ ID NO: 58           moltype = DNA  length = 225
FEATURE                 Location/Qualifiers
source                  1..225
                        mol_type = genomic DNA
                        organism = Ruminococcus torques
SEQUENCE: 58
gtgtcagccg ccgcggtaat acgtatggtg caagcgttat ccggatttac tgggtgtaaa  60
gggagcgtag acggatgggc aagtctgatg tgaaaacccg gggctcaacc ccgggactgc  120
attggaaact gttcatctag agtgctggag aggtaagtgg aattcctagt gtagcggtga  180
aatgcgtaga tattgggagg aacaccagtg gcgaaggcgc ctttc                  225

SEQ ID NO: 59           moltype = DNA  length = 225
FEATURE                 Location/Qualifiers
source                  1..225
                        mol_type = genomic DNA
                        organism = Ruminococcus torques
SEQUENCE: 59
gtgccagccg ccgcggtaat acgtatggtg caagcgttat ccggatttac tgggtgtaaa  60
gggagcgtag acggatgggc aagtctgatg tgaaaacccg gggctcaacc ccgggactgc  120
attggaaact gttcatctag agtgctggag aggtaagtgg aattcctagt gtagcggtga  180
aatgcgtaga tattgggaag aacaccagtg gcgaaggcgg ctttc                  225

SEQ ID NO: 60           moltype = DNA  length = 225
FEATURE                 Location/Qualifiers
source                  1..225
                        mol_type = genomic DNA
                        organism = Ruminococcus torques
SEQUENCE: 60
gtgtcagcag ccgcggtaat acgtatggtg caagcgttat ccggatttac tgggtgtaaa  60
gggagcgtag acggatgggc aagtctgatg tgaaaacccg gggctcaacc ccgggactgc  120
attggaaact gttcatctag agtgctggag aggtaagtgg aattcctagt gtagcggtga  180
aatgcgtaga tattaggagg aacaccagtg gcgaaggcgg cttac                  225

SEQ ID NO: 61           moltype = DNA  length = 90
FEATURE                 Location/Qualifiers
source                  1..90
                        mol_type = genomic DNA
                        organism = Collinsella intestinalis
SEQUENCE: 61
tacgtagggg gcgagcgtta tccggattca ttgggagtaa agcgcgcgta ggcggcccgg  60
caggcagggg ggcaaatggc ggggctcaac                                   90

SEQ ID NO: 62           moltype = DNA  length = 90
FEATURE                 Location/Qualifiers
source                  1..90
                        mol_type = genomic DNA
                        organism = Blautia wexlerae
SEQUENCE: 62
tacgtagggg gcaagcgtta tccggattta ctgggtgtaa agggagcgta gacggtgttg  60
caagtctgat gtgaaaggcg ggggctcaac                                   90

SEQ ID NO: 63           moltype = DNA  length = 225
FEATURE                 Location/Qualifiers
source                  1..225
                        mol_type = genomic DNA
                        organism = Blautia wexlerae
SEQUENCE: 63
gtgccagccg ccgcggtaat acgtaggggg caagcgttat ccggatttac tgggtgtaaa  60
gggagcgtag acggtgttgc aagtctgatg tgaaaggcgg gggctcaacc cctggactgc  120
attggaaact gtgatactcg agtgccggag aggtaagcgg aattcctagt gtagcggtga  180
aatgcgtaga tattaggagg aacaccagtg gcgaaggcgg ccctc                  225

SEQ ID NO: 64           moltype = DNA  length = 225
FEATURE                 Location/Qualifiers
source                  1..225
                        mol_type = genomic DNA
                        organism = Blautia wexlerae
SEQUENCE: 64
gtgtcagcag ccgcggtaat acgtaggggg caagcgttat ccggatttac tgggtgtaaa  60
gggagcgtag acggtgttgc aagtctgatg tgaaaggcgg gggctcaacc cctggactgc  120
attggaaact gtgatactcg agtgtcggag aggaaagcgg aattcctagt gtagcggtga  180
aatgcgtaga tattaggagg aacaccagtg gcgaaagcgg ctttc                  225
```

```
SEQ ID NO: 65          moltype = DNA  length = 225
FEATURE                Location/Qualifiers
source                 1..225
                       mol_type = genomic DNA
                       organism = Blautia wexlerae
SEQUENCE: 65
gtgccagcag ccgcggtaat acgtaggggg caagcgttat ccggatttac tgggtgtaaa  60
gggagcgtag acggtgttgc aagtctgatg tgaaaggcgg gggctcaacc cctggactgc  120
attggaaact gtgatactcg agtgccggag aggtaagcgg aattcctagt gtagcggtga  180
aatgcgtaga tattaggagg aacaccagtg gcgaaagcgg ctttc                 225

SEQ ID NO: 66          moltype = DNA  length = 225
FEATURE                Location/Qualifiers
source                 1..225
                       mol_type = genomic DNA
                       organism = Blautia wexlerae
SEQUENCE: 66
gtgtcagccg ccgcggtaat acgtaggggg caagcgttat ccggatttac tgggtgtaaa  60
gggagcgtag acggtgttgc aagtctgatg tgaaaggcgg gggctcaacc cctggactgc  120
attggaaact gtgatactcg agtgccggag aggtaagcgg aattcctagt gtagcggtga  180
aatgcgtaga tattaggagg aacaccagtg gcgaaggcgg cttac                 225

SEQ ID NO: 67          moltype = DNA  length = 225
FEATURE                Location/Qualifiers
source                 1..225
                       mol_type = genomic DNA
                       organism = Blautia wexlerae
SEQUENCE: 67
gtgtcagcag ccgcggtaat acgtaggggg caagcgttat ccggatttac tgggtgtaaa  60
gggagcgtag acggtgttgc aagtctgatg tgaaaggcgg gggctcaacc cctggactgc  120
attggaaact gtgatactcg agtgccggag aggtaagcgg aattcctagt gtagcggtga  180
aatgcgtaga tattgggaag aacaccagtg gcgaaggcgg ctttc                 225

SEQ ID NO: 68          moltype = DNA  length = 90
FEATURE                Location/Qualifiers
source                 1..90
                       mol_type = genomic DNA
                       organism = Eubacterium tarantellae
SEQUENCE: 68
tacggaggtg gcgagcgtta tccggattta ctgggcgtaa agggagcgta ggcggatgat  60
taagtgggat gtgaaatacc cgggctcaac                                  90

SEQ ID NO: 69          moltype = DNA  length = 90
FEATURE                Location/Qualifiers
source                 1..90
                       mol_type = genomic DNA
                       organism = Bacteroides plebeius
SEQUENCE: 69
tacggaggat gcgagcgtta tccggattta ttgggtttaa agggagcgca gacgggtttt  60
taagtcagct gtgaaagttc ggggctcaac                                  90

SEQ ID NO: 70          moltype = DNA  length = 90
FEATURE                Location/Qualifiers
source                 1..90
                       mol_type = genomic DNA
                       organism = Prevotella oulorum
SEQUENCE: 70
tacggaaggt tcgggcgtta tccggattta ttgggtttaa agggagcgta ggccggagat  60
taagcgtgtt gtgaaatgta gatgctcaac                                  90

SEQ ID NO: 71          moltype = DNA  length = 225
FEATURE                Location/Qualifiers
source                 1..225
                       mol_type = genomic DNA
                       organism = Prevotella oulorum
SEQUENCE: 71
gtgtcagcag ccgcggtaat acggaaggtt cgggcgttat ccggatttat tgggtttaaa  60
gggagcgtag gccggagatt aagcgtgttg tgaaatgtag atgctcaaca tctgaactgc  120
agcgcgaact ggtttccttg agtacgcaca aagtgggcgg aattcgtggt gtagcggtga  180
aatgcttaga tatcacgaag aactccgatt gcgaagacag ctcac                 225

SEQ ID NO: 72          moltype = DNA  length = 225
FEATURE                Location/Qualifiers
source                 1..225
                       mol_type = genomic DNA
                       organism = Prevotella oulorum
SEQUENCE: 72
gtgtcagcag ccgcggtaat acggaaggtt cgggcgttat ccggatttat tgggtttaaa  60
gggagcgtag gccggagatt aagcgtgttg tgaaatgtag atgctcaaca tctgaactgc  120
```

```
agcgcgaact ggtttccttg agtacgcaca aagtgggcgg agttcgtggt gtagcggtga  180
aatgcttaga tatcacgaag aactccgatt gcgaaggcag cacac                  225

SEQ ID NO: 73          moltype = DNA  length = 90
FEATURE                Location/Qualifiers
source                 1..90
                       mol_type = genomic DNA
                       organism = Bacillus huizhouensis
SEQUENCE: 73
tacgtaggtg gcaagcgttg tccggaatta ttgggcgtaa agcgcgcgca ggtggttcct  60
taagtctgat gtgaaagccc acggctcaac                                   90

SEQ ID NO: 74          moltype = DNA  length = 90
FEATURE                Location/Qualifiers
source                 1..90
                       mol_type = genomic DNA
                       organism = Lactonifactor longoviformis
SEQUENCE: 74
tacgtagggg gcaagcgtta tccggattta ctgggtgtaa agggagcgta gacggacggg  60
caagtctgat gtgaaagccc ggggcttaac                                   90

SEQ ID NO: 75          moltype = DNA  length = 225
FEATURE                Location/Qualifiers
source                 1..225
                       mol_type = genomic DNA
                       organism = Lactonifactor longoviformis
SEQUENCE: 75
gtgccagccg ccgcggtaat acgtaggggg caagcgttat ccggatttac tgggtgtaaa  60
gggagcgtag acggacgggc aagtctgatg tgaaagcccg gggcttaacc ccgggactgt  120
atcggaaact gttcatcttg agtgccggag aggtaagcgg aattcctagt gtagcggtga  180
aatgcgtaga tattaggagg aacaccagtg gcgaaggcgg ctttc                  225

SEQ ID NO: 76          moltype = DNA  length = 225
FEATURE                Location/Qualifiers
source                 1..225
                       mol_type = genomic DNA
                       organism = Lactonifactor longoviformis
SEQUENCE: 76
gtgcagccgc cgcggtaata cgtagggggc aagcgttatc cggatttact gggtgtaaag  60
ggagcgtaga cggacgggca agtctgatgt gaaagcccgg ggcttaaccc cgggactgca  120
ttggaaactg tccatcttga gtgccggaga ggtaagcgga attcctagtg tagcggtgaa  180
atgcgtagat attaggagga acaccagtgg cgaaggcggc ttact                  225

SEQ ID NO: 77          moltype = DNA  length = 225
FEATURE                Location/Qualifiers
source                 1..225
                       mol_type = genomic DNA
                       organism = Lactonifactor longoviformis
SEQUENCE: 77
gtgtcagccg ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccaacttg agtgccggag aggtaagcgg aattcccagt gtagcggtga  180
aatgcgtaga tattgggagg aacaccagta gcgaaggcgg ctttc                  225

SEQ ID NO: 78          moltype = DNA  length = 225
FEATURE                Location/Qualifiers
source                 1..225
                       mol_type = genomic DNA
                       organism = Lactonifactor longoviformis
SEQUENCE: 78
gtgtcagcag ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgcaggag aggaaagcgg aattcccagt gtagcggtga  180
aatgcgtaga tattgggaag aacaccagtg gcgaaggcgg ctttc                  225

SEQ ID NO: 79          moltype = DNA  length = 225
FEATURE                Location/Qualifiers
source                 1..225
                       mol_type = genomic DNA
                       organism = Lactonifactor longoviformis
SEQUENCE: 79
gtgccagcag ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgccggag aggtaagcgg aattcctagt gtagcggtga  180
aatgcgtaga tattaggagg aacaccagtg gcgaaggcgg cctgc                  225

SEQ ID NO: 80          moltype = DNA  length = 225
FEATURE                Location/Qualifiers
source                 1..225
```

```
                         mol_type = genomic DNA
                         organism = Lactonifactor longoviformis
SEQUENCE: 80
gtgccagccg ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgccggag aggtaagcgg aattcctagt gtagcggtga  180
aatgcgtaga tattaggagg aacaccagtg gcgaaagcgg ctttc                 225

SEQ ID NO: 81            moltype = DNA  length = 225
FEATURE                  Location/Qualifiers
source                   1..225
                         mol_type = genomic DNA
                         organism = Lactonifactor longoviformis
SEQUENCE: 81
gtgtcagccg ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgccggag aggtaagcgg aattcctagt gtagcggtga  180
aatgcgtaga tattaggagg aacaccagtg gcgaaggcgg cttac                 225

SEQ ID NO: 82            moltype = DNA  length = 225
FEATURE                  Location/Qualifiers
source                   1..225
                         mol_type = genomic DNA
                         organism = Lactonifactor longoviformis
SEQUENCE: 82
gtgtcagccg ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgccggag aggtaagcgg aattcctagt gtagcggtga  180
aatgcgtaga tattgggaag aacaccagtg gcgaaggcgg ctttc                 225

SEQ ID NO: 83            moltype = DNA  length = 225
FEATURE                  Location/Qualifiers
source                   1..225
                         mol_type = genomic DNA
                         organism = Lactonifactor longoviformis
SEQUENCE: 83
gtgccagcag ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccatcttg agtgccggag aggtaagcgg aattcctagt gtagcggtga  180
aatgcgtaga tattgggagg aacaccagtg gcgaaggcgc ctttc                 225

SEQ ID NO: 84            moltype = DNA  length = 225
FEATURE                  Location/Qualifiers
source                   1..225
                         mol_type = genomic DNA
                         organism = Lactonifactor longoviformis
SEQUENCE: 84
gtgccagcag ccgcggtaat acgtaggggg caagcgttat ccggatttac tgggtgtaaa  60
gggagcgtag acggacgggc aagtctgatg tgaaagcccg gggcttaacc ccgggactgc  120
attggaaact gtccaacttg agtgccggag aggtaagcgg aattcctagt gtagcggtga  180
aatgcgtaga tattaggagg aacaccagtg gcgaaggcgg cttac                 225

SEQ ID NO: 85            moltype = DNA  length = 90
FEATURE                  Location/Qualifiers
source                   1..90
                         mol_type = genomic DNA
                         organism = Bacteroides plebeius
SEQUENCE: 85
tacggaggat gcgagcgtta tccggattta ttgggtttaa agggagcgca gacgggtttt  60
taagtcagct gtgaaagttt ggggctcaac                                  90

SEQ ID NO: 86            moltype = DNA  length = 225
FEATURE                  Location/Qualifiers
source                   1..225
                         mol_type = genomic DNA
                         organism = Bacteroides plebeius
SEQUENCE: 86
gtgtcagccg ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggtttccttg agtgcagttg aggcaggcgg aattcgtggt gtagcggtga  180
aatgcttaga tatcacgaag aaccccgatt gcgaaggcag cttgc                 225

SEQ ID NO: 87            moltype = DNA  length = 225
FEATURE                  Location/Qualifiers
source                   1..225
                         mol_type = genomic DNA
                         organism = Bacteroides plebeius
SEQUENCE: 87
gttcagcagc cgcggtaata cggaggatgc gagcgttatc cggatttatt gggtttaaag  60
```

```
ggagcgcaga cgggttttta agtcagctgt gaaagtttgg ggctcaacct taaaattgca  120
gttgatactg gagaccttga gtgcagttga ggcaggcgga attcgtggtg tagcggtgaa  180
atgcttagat atcacgaaga actccgattg cgaaggcagc ttgct                  225

SEQ ID NO: 88          moltype = DNA  length = 225
FEATURE                Location/Qualifiers
source                 1..225
                       mol_type = genomic DNA
                       organism = Bacteroides plebeius
SEQUENCE: 88
gtgtcagcag ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggcgtccttg agtgcggttg aggtgtgcgg aattcgtggt gtagcggtga  180
aatgcttaga tatcacgaag aactccgatt gcgaaggcag ctcac                  225

SEQ ID NO: 89          moltype = DNA  length = 225
FEATURE                Location/Qualifiers
source                 1..225
                       mol_type = genomic DNA
                       organism = Bacteroides plebeius
SEQUENCE: 89
gtgtcagcag ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcggttg aggtgtgcgg aattcgtggt gtagcggtga  180
aatgcttaga tatcacgaag aactccgatt gcgaaggcag cacac                  225

SEQ ID NO: 90          moltype = DNA  length = 225
FEATURE                Location/Qualifiers
source                 1..225
                       mol_type = genomic DNA
                       organism = Bacteroides plebeius
SEQUENCE: 90
gtgccagccg ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcagttg aggtgtgcgg aattcgtggt gtagcggtga  180
aatgcttaga tatcacgaag aactccgatt gcgaaggcag cacac                  225

SEQ ID NO: 91          moltype = DNA  length = 225
FEATURE                Location/Qualifiers
source                 1..225
                       mol_type = genomic DNA
                       organism = Bacteroides plebeius
SEQUENCE: 91
gtgtcagccg ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcagttg aggcaggcgg aattcgtggt gtagcggtga  180
aatgcttaga tatcacgaag aactccgatt gcgaaggcag cacac                  225

SEQ ID NO: 92          moltype = DNA  length = 225
FEATURE                Location/Qualifiers
source                 1..225
                       mol_type = genomic DNA
                       organism = Bacteroides plebeius
SEQUENCE: 92
gtgtcagccg ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcagttg aggcaggcgg aattcgtggt gtagcggtga  180
aatgcttaga tatcacgaag aactccgatt gcgaaggcag cttgc                  225

SEQ ID NO: 93          moltype = DNA  length = 225
FEATURE                Location/Qualifiers
source                 1..225
                       mol_type = genomic DNA
                       organism = Bacteroides plebeius
SEQUENCE: 93
gtgccagcag ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcagttg aggcaggcgg aattcgtggt gtagcggtga  180
aatgcttaga tatcacgaag aactccgatt gcgaaggcag ctcac                  225

SEQ ID NO: 94          moltype = DNA  length = 225
FEATURE                Location/Qualifiers
source                 1..225
                       mol_type = genomic DNA
                       organism = Bacteroides plebeius
SEQUENCE: 94
gtgccagcag ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggagaccttg agtgcagttg aggcaggcgg aattcgtggt gtagcggtga  180
```

```
aatgcttaga tatcacgaag aaccccgatt gcgaaggcag cttgc                 225

SEQ ID NO: 95          moltype = DNA  length = 225
FEATURE                Location/Qualifiers
source                 1..225
                       mol_type = genomic DNA
                       organism = Bacteroides plebeius
SEQUENCE: 95
gtgccagccg ccgcggtaat acggaggatg cgagcgttat ccggatttat tgggtttaaa  60
gggagcgcag acgggttttt aagtcagctg tgaaagtttg gggctcaacc ttaaaattgc  120
agttgatact ggcgtccttg agtgcggttg aggtgtgcgg aattcgtggt gtagcggtga  180
aatgcttaga tatcacgaag aactccgatt gcgaaggcag cacac                 225

SEQ ID NO: 96          moltype = DNA  length = 90
FEATURE                Location/Qualifiers
source                 1..90
                       mol_type = genomic DNA
                       organism = Brevundimonas faecalis
SEQUENCE: 96
tacggagggg gctagcgttg ctcggaatta ctgggcgtaa agggcgcgta ggcggatcgt  60
taagtcagag gtgaaatccc agggctcaac                                  90

SEQ ID NO: 97          moltype = DNA  length = 90
FEATURE                Location/Qualifiers
source                 1..90
                       mol_type = genomic DNA
                       organism = Murimonas intestini
SEQUENCE: 97
tacgtagggg gcaagcgtta tccggattta ctgggtgtaa agggagcgta gacggtgttg  60
caagtctgat gtgaaaggca ggggctcaac                                  90

SEQ ID NO: 98          moltype = DNA  length = 90
FEATURE                Location/Qualifiers
source                 1..90
                       mol_type = genomic DNA
                       organism = Dialister succinatiphilus
SEQUENCE: 98
tacgtaggtg gcaagcgttg tccggaatta ttgggcgtaa agcgcgcgca ggcggcttct  60
taagtccatc ttaaaagtgc ggggcttaac                                  90

SEQ ID NO: 99          moltype = DNA  length = 90
FEATURE                Location/Qualifiers
source                 1..90
                       mol_type = genomic DNA
                       organism = Actinomyces coleocanis
SEQUENCE: 99
tacgtagggt actagcgttg tccggaatta ttgggcgtaa agggcttgta ggtggtttgt  60
cgcgtctgtc gtgaaaaccc ggggcttaac                                  90

SEQ ID NO: 100         moltype = DNA  length = 90
FEATURE                Location/Qualifiers
source                 1..90
                       mol_type = genomic DNA
                       organism = Coprococcus comes
SEQUENCE: 100
tacgtagggg gcaagcgtta tccggattta ctgggtgtaa agggagcgta gacggctgtg  60
caagtctgaa gtgaaagccc ggggctcaac                                  90

SEQ ID NO: 101         moltype = DNA  length = 225
FEATURE                Location/Qualifiers
source                 1..225
                       mol_type = genomic DNA
                       organism = Coprococcus comes
SEQUENCE: 101
gtgccagccg ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattaggagg aacaccagtg gcgaaggcgc ctttc                 225

SEQ ID NO: 102         moltype = DNA  length = 225
FEATURE                Location/Qualifiers
source                 1..225
                       mol_type = genomic DNA
                       organism = Coprococcus comes
SEQUENCE: 102
gtgtcagcag ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattgggagg aacaccagtg gcgaaggcgc ctttc                 225
```

```
SEQ ID NO: 103          moltype = DNA  length = 225
FEATURE                 Location/Qualifiers
source                  1..225
                        mol_type = genomic DNA
                        organism = Coprococcus comes
SEQUENCE: 103
gtgtcagcag ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gttctgctag agtgctggag aggtaagtgg aattcctagt gtagcggtga  180
aatgcgtaga tattaggagg aacaccagtg gcgaaggcgg cttac                  225

SEQ ID NO: 104          moltype = DNA  length = 225
FEATURE                 Location/Qualifiers
source                  1..225
                        mol_type = genomic DNA
                        organism = Coprococcus comes
SEQUENCE: 104
gtgccagccg ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattgggaag aacaccagtg gcgaaggcgg ctttc                  225

SEQ ID NO: 105          moltype = DNA  length = 225
FEATURE                 Location/Qualifiers
source                  1..225
                        mol_type = genomic DNA
                        organism = Coprococcus comes
SEQUENCE: 105
gtgccagcag ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattaggagg aacaccagtg gcgaaggcga cttac                  225

SEQ ID NO: 106          moltype = DNA  length = 225
FEATURE                 Location/Qualifiers
source                  1..225
                        mol_type = genomic DNA
                        organism = Coprococcus comes
SEQUENCE: 106
gtgtcagccg ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattaggagg aacaccagtg gcgaaggcgg cttac                  225

SEQ ID NO: 107          moltype = DNA  length = 225
FEATURE                 Location/Qualifiers
source                  1..225
                        mol_type = genomic DNA
                        organism = Coprococcus comes
SEQUENCE: 107
gttcagcagc cgcggtaata cgtagggggc aagcgttatc cggatttact gggtgtaaag  60
ggagcgtaga cggctgtgca agtctgaagt gaaagcccgg ggctcaaccc cgggactgct  120
ttggaaactg tatagctaga gtgctggaga ggtaagtgga attcctagtg tagcggtgaa  180
atgcgtagat attaggagga acaccagtgg cgaaggcggc ttact                  225

SEQ ID NO: 108          moltype = DNA  length = 225
FEATURE                 Location/Qualifiers
source                  1..225
                        mol_type = genomic DNA
                        organism = Coprococcus comes
SEQUENCE: 108
gtgccagcag ccgcggtaat acgtaggggg caagcgttat ccggatttac tgggtgtaaa  60
gggagcgtag acggctgtgc aagtctgaag tgaaagcccg gggctcaacc ccgggactgc  120
tttggaaact gtatagctag agtgctggag aggtaagtgg aattcctagt gtagcggtga  180
aatgcgtaga tattaggagg aacaccagtg gcgaaagcgg ctttc                  225

SEQ ID NO: 109          moltype = DNA  length = 90
FEATURE                 Location/Qualifiers
source                  1..90
                        mol_type = genomic DNA
                        organism = Ruminococcus callidus
SEQUENCE: 109
tacgtaggga gcgagcgttg tccggaatta ctgggtgtaa agggagcgta ggcgggagat  60
caagtcagat gtgaaaacta tgggctcaac                                   90

SEQ ID NO: 110          moltype = DNA  length = 90
FEATURE                 Location/Qualifiers
source                  1..90
```

```
                        mol_type = genomic DNA
                        organism = Bacteroides dorei
SEQUENCE: 110
tacggaggat ccgagtgtta tccggattta ttgggtttaa agggagcgta gatggatgtt  60
taagtcagtt gtgaaagttt gcggctcaac                                   90

SEQ ID NO: 111          moltype = DNA  length = 90
FEATURE                 Location/Qualifiers
source                  1..90
                        mol_type = genomic DNA
                        organism = Clostridium septicum
SEQUENCE: 111
tacgtaggtg gcgagcgttg tccggattta ctgggcgtaa agggagtgta ggcggacttt  60
taagtgagat gtgaaatacc caggctcaac                                   90

SEQ ID NO: 112          moltype = DNA  length = 90
FEATURE                 Location/Qualifiers
source                  1..90
                        mol_type = genomic DNA
                        organism = Blautia schinkii
SEQUENCE: 112
tacgtagggg gcaagcgtta tccggattta ctgggtgtaa agggagcgta gacggttctg  60
caagtctgat gtgaaaggca gaggctcaac                                   90

SEQ ID NO: 113          moltype = DNA  length = 90
FEATURE                 Location/Qualifiers
source                  1..90
                        mol_type = genomic DNA
                        organism = Cellulosilyticum ruminicola
SEQUENCE: 113
tacgtaggga gcaagcgtta tccggattta ctgggtgtaa agggtgcgta ggcggccttt  60
taagtcggaa gtgaaatttc ggggctcaac                                   90

SEQ ID NO: 114          moltype = DNA  length = 225
FEATURE                 Location/Qualifiers
source                  1..225
                        mol_type = genomic DNA
                        organism = Cellulosilyticum ruminicola
SEQUENCE: 114
gtgtcagccg ccgcggtaat acgtagggag caagcgttat ccggatttac tgggtgtaaa  60
gggtgcgtag gcggcctttt aagtcggaag tgaaatttcg gggctcaacc ccggagctgc  120
taccgaaact gagaggctag agtgtgggag aggaaagtgg aactttgagt gtagcggtga  180
aatgcgtaga gattcaaagg aacaccagta gcgaaggcgg ctttc                  225

SEQ ID NO: 115          moltype = DNA  length = 90
FEATURE                 Location/Qualifiers
source                  1..90
                        mol_type = genomic DNA
                        organism = Acetanaerobacterium elongatum
SEQUENCE: 115
tacgtaggtg gcaagcgttg tccggaatta ctgggtgtaa agggagcgta ggcggggagg  60
caagttgaat gtctaaacta tcggctcaac                                   90

SEQ ID NO: 116          moltype = DNA  length = 90
FEATURE                 Location/Qualifiers
source                  1..90
                        mol_type = genomic DNA
                        organism = Faecalibacterium prausnitzii
SEQUENCE: 116
aacgtaggtc acaagcgttg tccggaatta ctgggtgtaa agggagcgca ggcgggaaga  60
caagttggaa gtgaaatcta tggctcaac                                    90

SEQ ID NO: 117          moltype = DNA  length = 225
FEATURE                 Location/Qualifiers
source                  1..225
                        mol_type = genomic DNA
                        organism = Faecalibacterium prausnitzii
SEQUENCE: 117
gtgccagccg ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tatcgggtgg aacaccggtg gcgaaggcgg ccctc                  225

SEQ ID NO: 118          moltype = DNA  length = 225
FEATURE                 Location/Qualifiers
source                  1..225
                        mol_type = genomic DNA
                        organism = Faecalibacterium prausnitzii
SEQUENCE: 118
```

```
gtgtcagcag ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tatcgggagg aacaccagtg gcgaaggcgg ccctc                  225

SEQ ID NO: 119         moltype = DNA  length = 225
FEATURE                Location/Qualifiers
source                 1..225
                       mol_type = genomic DNA
                       organism = Faecalibacterium prausnitzii
SEQUENCE: 119
gtgccagcag ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tattgggagg aacaccagtg gcgaaggcgc ctttc                  225

SEQ ID NO: 120         moltype = DNA  length = 225
FEATURE                Location/Qualifiers
source                 1..225
                       mol_type = genomic DNA
                       organism = Faecalibacterium prausnitzii
SEQUENCE: 120
gtgccagcag ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tattaggagg aacaccagtg gcgaaagcgg ctttc                  225

SEQ ID NO: 121         moltype = DNA  length = 225
FEATURE                Location/Qualifiers
source                 1..225
                       mol_type = genomic DNA
                       organism = Faecalibacterium prausnitzii
SEQUENCE: 121
gtgtcagccg ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccagt gtagcggtga  180
aatgcgtaga tattgggagg aacaccagtg gcgaaggcgc ctttc                  225

SEQ ID NO: 122         moltype = DNA  length = 225
FEATURE                Location/Qualifiers
source                 1..225
                       mol_type = genomic DNA
                       organism = Faecalibacterium prausnitzii
SEQUENCE: 122
gttcagcagc cgcggtaaaa cgtaggtcac aagcgttgtc cggaattact gggtgtaaag  60
ggagcgcagg cgggaagaca agttggaagt gaaatctatg ggctcaaccc ataaactgct  120
ttcaaaactg tttttcttga gtagtgcaga ggtaggcgga attcccggtg tagcggtgga  180
atgcgtagat atcgggagga acaccagtgg cgaaggcggc ctact                  225

SEQ ID NO: 123         moltype = DNA  length = 225
FEATURE                Location/Qualifiers
source                 1..225
                       mol_type = genomic DNA
                       organism = Faecalibacterium prausnitzii
SEQUENCE: 123
gtgtcagccg ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tatcgggagg aacaccagtg gcgaaggcgg cctac                  225

SEQ ID NO: 124         moltype = DNA  length = 225
FEATURE                Location/Qualifiers
source                 1..225
                       mol_type = genomic DNA
                       organism = Faecalibacterium prausnitzii
SEQUENCE: 124
gtgtcagccg ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tatcgggagg aacaccagtg gcgaaggcgc ctttc                  225

SEQ ID NO: 125         moltype = DNA  length = 225
FEATURE                Location/Qualifiers
source                 1..225
                       mol_type = genomic DNA
                       organism = Faecalibacterium prausnitzii
SEQUENCE: 125
gtgtcagcag ccgcggtaaa acgtaggtca caagcgttgt ccggaattac tgggtgtaaa  60
gggagcgcag gcgggaagac aagttggaag tgaaatctat gggctcaacc cataaactgc  120
```

```
tttcaaaact gtttttcttg agtagtgcag aggtaggcgg aattcccggt gtagcggtgg  180
aatgcgtaga tatcgggagg aacaccagtg gcgaaagcgg ctttc                  225

SEQ ID NO: 126         moltype = DNA  length = 225
FEATURE                Location/Qualifiers
source                 1..225
                       mol_type = genomic DNA
                       organism = Faecalibacterium prausnitzii
SEQUENCE: 126
gtgtcagcag ccgcggtaaa acgtaggtca caagcgttgt ccggaattac tgggtgtaaa  60
gggagcgcag gcgggaagac aagttggaag tgaaatctat gggctcaacc cataaactgc  120
tttcaaaact gtttttcttg agtagtgcag aggtaggcgg aattcccggt gtagcggtgg  180
aatgcgtaga tattgggaag aacaccagtg gcgaaggcgg ctttc                  225

SEQ ID NO: 127         moltype = DNA  length = 90
FEATURE                Location/Qualifiers
source                 1..90
                       mol_type = genomic DNA
                       organism = Murimonas intestini
SEQUENCE: 127
tacgtagggg gcaagcgtta tccggattta ctgggtgtaa agggagcgta gacggcatgg  60
caagtctgat gtgaaaggca ggggctcaac                                   90

SEQ ID NO: 128         moltype = DNA  length = 90
FEATURE                Location/Qualifiers
source                 1..90
                       mol_type = genomic DNA
                       organism = Clostridium nexile
SEQUENCE: 128
tacgtatggt gcaagcgtta tccggattta ctgggtgtaa agggagcgta gacggttgtg  60
taagtctggt gtgaaagccc ggggctcaac                                   90

SEQ ID NO: 129         moltype = DNA  length = 90
FEATURE                Location/Qualifiers
source                 1..90
                       mol_type = genomic DNA
                       organism = Ruminococcus torques
SEQUENCE: 129
tacgtatggt gcaagcgtta tccggattta ctgggtgtaa agggagcgta gacggatggg  60
caagtctgat gtgaaaaccc agggctcaac                                   90

SEQ ID NO: 130         moltype = DNA  length = 90
FEATURE                Location/Qualifiers
source                 1..90
                       mol_type = genomic DNA
                       organism = Parabacteroides merdae
SEQUENCE: 130
tacggaggat gcgagcgtta tccggattta ttgggtttaa agggtgcgta ggtggtgatt  60
taagtcagcg gtgaaagttt gtggctcaac                                   90

SEQ ID NO: 131         moltype = DNA  length = 225
FEATURE                Location/Qualifiers
source                 1..225
                       mol_type = genomic DNA
                       organism = Parabacteroides merdae
SEQUENCE: 131
gtgtcagcag ccgcggtaat acggaggatg cgagcgttat ccggatttat tgggtttaaa  60
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcataga tatcacgaag aactccgatt gcgaaggcag ctcac                  225

SEQ ID NO: 132         moltype = DNA  length = 225
FEATURE                Location/Qualifiers
source                 1..225
                       mol_type = genomic DNA
                       organism = Parabacteroides merdae
SEQUENCE: 132
gtgtcagcag ccgcggtaat acggaggatg cgagcgttat ccggatttat tgggtttaaa  60
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcataga tatcacgaag aaccccgatt gcgaaggcag cttgc                  225

SEQ ID NO: 133         moltype = DNA  length = 225
FEATURE                Location/Qualifiers
source                 1..225
                       mol_type = genomic DNA
                       organism = Parabacteroides merdae
SEQUENCE: 133
gtgccagccg ccgcggtaat acggaggatg cgagcgttat ccggatttat tgggtttaaa  60
```

```
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcttaga tatcacgaag aaccccgatt gcgaaggcag cttgc                  225

SEQ ID NO: 134         moltype = DNA  length = 225
FEATURE                Location/Qualifiers
source                 1..225
                       mol_type = genomic DNA
                       organism = Parabacteroides merdae
SEQUENCE: 134
gttcagcagc cgcggtaata cggaggatgc gagcgttatc cggatttatt gggtttaaag  60
ggtgcgtagg tggtgattta agtcagcggt gaaagtttgt ggctcaacca taaaattgcc  120
gttgaaactg ggttacttga gtgtgtttga ggtaggcgga atgcgtggtg tagcggtgaa  180
atgcatagat atcacgcaga actccgattg cgaaggcagc ttact                  225

SEQ ID NO: 135         moltype = DNA  length = 225
FEATURE                Location/Qualifiers
source                 1..225
                       mol_type = genomic DNA
                       organism = Parabacteroides merdae
SEQUENCE: 135
gtgtcagccg ccgcggtaat acggaggatg cgagcgttat ccggatttat tgggtttaaa  60
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcataga tatcacgcag aactccgatt gcgaaggcag cttac                  225

SEQ ID NO: 136         moltype = DNA  length = 225
FEATURE                Location/Qualifiers
source                 1..225
                       mol_type = genomic DNA
                       organism = Parabacteroides merdae
SEQUENCE: 136
gtgccagccg ccgcggtaat acggaggatg cgagcgttat ccggatttat tgggtttaaa  60
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcataga tatcacgcag aactccgatt gcgaaggcag cacac                  225

SEQ ID NO: 137         moltype = DNA  length = 225
FEATURE                Location/Qualifiers
source                 1..225
                       mol_type = genomic DNA
                       organism = Parabacteroides merdae
SEQUENCE: 137
gtgtcagccg ccgcggtaat acggaggatg cgagcgttat ccggatttat tgggtttaaa  60
gggtgcgtag gtggtgattt aagtcagcgg tgaaagtttg tggctcaacc ataaaattgc  120
cgttgaaact gggttacttg agtgtgtttg aggtaggcgg aatgcgtggt gtagcggtga  180
aatgcttaga tatcacgaag aactccgatt gcgaaggcag cacac                  225

SEQ ID NO: 138         moltype = DNA  length = 90
FEATURE                Location/Qualifiers
source                 1..90
                       mol_type = genomic DNA
                       organism = Clostridium hylemonae
SEQUENCE: 138
tacgtagggg gcaagcgtta tccggattta ctgggtgtaa agggagcgta gacggatgtg  60
caagtctgaa gtgaaagccc ggggctcaac                                   90

SEQ ID NO: 139         moltype = DNA  length = 225
FEATURE                Location/Qualifiers
source                 1..225
                       mol_type = genomic DNA
                       organism = Clostridium hylemonae
SEQUENCE: 139
gtgccagccg ccgcggtaat acgtaggggg caagcgttat ccggatttac tgggtgtaaa  60
gggagcgtag acggatgtgc aagtctgaag tgaaagcccg gggctcaacc ccgggactgc  120
tttggaaact gtgtatctag agtgccggag aggtaagcgg aattcccagt gtagcggtga  180
aatgcgtaga tattgggagg aacaccagtg gcgaaggcgc ctttc                  225

SEQ ID NO: 140         moltype = DNA  length = 225
FEATURE                Location/Qualifiers
source                 1..225
                       mol_type = genomic DNA
                       organism = Clostridium hylemonae
SEQUENCE: 140
gtgccagcag ccgcggtaat acgtaggggg caagcgttat ccggatttac tgggtgtaaa  60
gggagcgtag acggatgtgc aagtctgaag tgaaagcccg gggctcaacc ccgggactgc  120
tttggaaact gtgtatctag agtgccggag aggtaagcgg aattcccagt gtagcggtga  180
aatgcgtaga tattgggaag aacaccagtg gcgaaggcgg ctttc                  225
```

```
SEQ ID NO: 141          moltype = DNA  length = 225
FEATURE                 Location/Qualifiers
source                  1..225
                        mol_type = genomic DNA
                        organism = Clostridium hylemonae
SEQUENCE: 141
gtgtcagccg ccgcggtaat acgtaggggg caagcgttat ccggatttac tgggtgtaaa  60
gggagcgtag acggatgtgc aagtctgaag tgaaagcccg gggctcaacc ccgggactgc  120
tttggaaact gtgtatctag agtgccggag aggtaagcgg aattcccagt gtagcggtga  180
aatgcgtaga tattgggagg aacaccagtg gcgaaggcgg cttac                 225

SEQ ID NO: 142          moltype = DNA  length = 225
FEATURE                 Location/Qualifiers
source                  1..225
                        mol_type = genomic DNA
                        organism = Clostridium hylemonae
SEQUENCE: 142
gtgccagcag ccgcggtaat acgtaggggg caagcgttat ccggatttac tgggtgtaaa  60
gggagcgtag acggatgtgc aagtctgaag tgaaagcccg gggctcaacc ccgggactgc  120
tttggaaact gtgtatctag agtgccggag aggtaagcgg aattcctagt gtagcggtga  180
aatgcgtaga tattaggagg aacaccagtg gcgaaggcgg cttac                 225

SEQ ID NO: 143          moltype = DNA  length = 90
FEATURE                 Location/Qualifiers
source                  1..90
                        mol_type = genomic DNA
                        organism = Cetobacterium somerae
SEQUENCE: 143
tacgtatgtc gcaagcgtta tccggattta ttgggcgtaa agcgcgtcta ggcggaaaag  60
aaagtctgat gttaaaatgc ggggctcaac                                  90

SEQ ID NO: 144          moltype = DNA  length = 90
FEATURE                 Location/Qualifiers
source                  1..90
                        mol_type = genomic DNA
                        organism = Clostridium spiroforme
SEQUENCE: 144
tacgtaggtg gcgagcgtta tccggaatta ttgggcgtaa agagggagca ggcggcacta  60
agggtctgtg gtgaaagatc gaagcttaac                                  90

SEQ ID NO: 145          moltype = DNA  length = 225
FEATURE                 Location/Qualifiers
source                  1..225
                        mol_type = genomic DNA
                        organism = Clostridium spiroforme
SEQUENCE: 145
gtgtcagccg ccgcggtaat acgtaggtgg cgagcgttat ccggaattat tgggcgtaaa  60
gagggagcag gcggcactaa gggtctgtgg tgaaagatcg aagcttaact tcggtaagcc  120
atggaaaccg tagagctaga gtgtgtgaga ggatcgtgga attccatgtg tagcggtgaa  180
atgcgtagat atatggagga acaccagtgg cgaaggcggc tttct                 225

SEQ ID NO: 146          moltype = DNA  length = 225
FEATURE                 Location/Qualifiers
source                  1..225
                        mol_type = genomic DNA
                        organism = Clostridium spiroforme
SEQUENCE: 146
gtgtcagcag ccgcggtaat acgtaggtgg cgagcgttat ccggaattat tgggcgtaaa  60
gagggagcag gcggcactaa gggtctgtgg tgaaagatcg aagcttaact tcggtaagcc  120
atggaaaccg tagagctaga gtgtgtgaga ggatcgtgga attccatgtg tagcggtgaa  180
atgcgtagat atatggagga acaccagtgg cgaaggcgac gatct                 225

SEQ ID NO: 147          moltype = DNA  length = 90
FEATURE                 Location/Qualifiers
source                  1..90
                        mol_type = genomic DNA
                        organism = Odoribacter laneus
SEQUENCE: 147
tacggaggat gcgagcgtta tccggattta ttgggtttaa agggtgcgta ggcggttgat  60
taagttagtg gtaaaatgtc atggctaaac                                  90

SEQ ID NO: 148          moltype = DNA  length = 90
FEATURE                 Location/Qualifiers
source                  1..90
                        mol_type = genomic DNA
                        organism = Clostridium cocleatum
SEQUENCE: 148
tacgtaggtg gcaagcgtta tccggaatta ttgggcgtaa agagggagca ggcggcggca  60
aaggtctgtg gtgaaagact gaagcttaac                                  90
```

```
SEQ ID NO: 149          moltype = DNA  length = 225
FEATURE                 Location/Qualifiers
source                  1..225
                        mol_type = genomic DNA
                        organism = Clostridium cocleatum
SEQUENCE: 149
gtgtcagcag ccgcggtaat acgtaggtgg caagcgttat ccggaattat tgggcgtaaa  60
gagggagcag gcggcggcaa aggtctgtgg tgaaagactg aagcttaact tcagtaagcc  120
atagaaaccg ggcggctaga gtgcaggaga ggatcgtgga attccatgtg tagcggtgaa  180
atgcgtagat atatggagga acaccagtgg cgaaggcggc tttct                  225

SEQ ID NO: 150          moltype = DNA  length = 225
FEATURE                 Location/Qualifiers
source                  1..225
                        mol_type = genomic DNA
                        organism = Clostridium cocleatum
SEQUENCE: 150
gtgtcagcag ccgcggtaat acgtaggtgg caagcgttat ccggaattat tgggcgtaaa  60
gagggagcag gcggcggcaa aggtctgtgg tgaaagactg aagcttaact tcagtaagcc  120
atagaaaccg ggcggctaga gtgcaggaga ggatcgtgga attccatgtg tagcggtgaa  180
atgcgtagat atatggagga acaccagtgg cgaaggcgac ggtct                  225

SEQ ID NO: 151          moltype = DNA  length = 90
FEATURE                 Location/Qualifiers
source                  1..90
                        mol_type = genomic DNA
                        organism = Terrisporobacter glycolicus
SEQUENCE: 151
tacggagggg gctagcgtta tccggattta ctgggcgtaa agggtgcgta ggtggtttct  60
taagtcagga gtgaaaggct acggcttaac                                   90

SEQ ID NO: 152          moltype = DNA  length = 90
FEATURE                 Location/Qualifiers
source                  1..90
                        mol_type = genomic DNA
                        organism = Bacteroides eggerthii
SEQUENCE: 152
tacggaggat ccgagcgtta tccggattta ttgggtttaa agggagcgta ggcggaattt  60
taagtcagtt gtgaaagttt gcggctcaac                                   90

SEQ ID NO: 153          moltype = DNA  length = 90
FEATURE                 Location/Qualifiers
source                  1..90
                        mol_type = genomic DNA
                        organism = Turicibacter sanguinis
SEQUENCE: 153
tacgtaggtg gcaagcgtta tccggaatta ttgggcgtaa agagcgcgca ggtggttgat  60
taagtctgat gtgaaagccc acggcttaac                                   90

SEQ ID NO: 154          moltype = DNA  length = 225
FEATURE                 Location/Qualifiers
source                  1..225
                        mol_type = genomic DNA
                        organism = Turicibacter sanguinis
SEQUENCE: 154
gtgtcagccg ccgcggtaat acgtaggtgg caagcgttat ccggaattat tgggcgtaaa  60
gagcgcgcag gtggttgatt aagtctgatg tgaaagccca cggcttaacc gtggagggtc  120
attggaaact ggtcgacttg agtgcagaag agggaagtgg aattccatgt gtagcggtga  180
aatgcgtaga gatatggagg aacaccagtg gcgaaggcgg cttcc                  225

SEQ ID NO: 155          moltype = DNA  length = 90
FEATURE                 Location/Qualifiers
source                  1..90
                        mol_type = genomic DNA
                        organism = Eubacterium coprostanoligenes
SEQUENCE: 155
tacgtaggtg gcaagcgttg tccggaatta ctgggtgtaa agggagcgca ggcgggaagc  60
caagtcagct gtgaaaacta cgggcttaac                                   90

SEQ ID NO: 156          moltype = DNA  length = 90
FEATURE                 Location/Qualifiers
source                  1..90
                        mol_type = genomic DNA
                        organism = Fusicatenibacter saccarivorans
SEQUENCE: 156
tacgtagggg gcaagcgtta tccggattta ctgggtgtaa agggagcgta gacggcaagg  60
caagtctgat gtgaaaaccc agggcttaac                                   90
```

```
SEQ ID NO: 157          moltype = DNA  length = 90
FEATURE                 Location/Qualifiers
source                  1..90
                        mol_type = genomic DNA
                        organism = Blautia wexlerae
SEQUENCE: 157
tacgtagggg gcaagcgtta tccggattta ctgggtgtaa agggagcgta gacggtgtgg  60
caagtctgat gtgaaaggca tgggctcaac                                   90

SEQ ID NO: 158          moltype = DNA  length = 90
FEATURE                 Location/Qualifiers
source                  1..90
                        mol_type = genomic DNA
                        organism = Bacteroides sartorii
SEQUENCE: 158
tacggaggat ccgagcgtta tccggattta ttgggtttaa agggagcgta gatgggttgt  60
taagtcagtt gtgaaagttt gcggctcaac                                   90

SEQ ID NO: 159          moltype = DNA  length = 90
FEATURE                 Location/Qualifiers
source                  1..90
                        mol_type = genomic DNA
                        organism = Clostridium bolteae
SEQUENCE: 159
tacgtagggg gcaagcgtta tccggattta ctgggtgtaa agggagcgta gacggcgaag  60
caagtctgaa gtgaaagccc ggggcttaac                                   90

SEQ ID NO: 160          moltype = DNA  length = 225
FEATURE                 Location/Qualifiers
source                  1..225
                        mol_type = genomic DNA
                        organism = Clostridium bolteae
SEQUENCE: 160
gtgtcagcag ccgcggtaat acgtaggggg caagcgttat ccggatttac tgggtgtaaa  60
gggagcgtag acggcgaagc aagtctgaag tgaaagcccg gggcttaacc ccgggactgc  120
tttggaaact gttttgctag agtgctggag aggtaagtgg aattcctagt gtagcggtga  180
aatgcgtaga tattgggagg aacaccagtg gcgaaggcgc ctttc                  225

SEQ ID NO: 161          moltype = DNA  length = 225
FEATURE                 Location/Qualifiers
source                  1..225
                        mol_type = genomic DNA
                        organism = Clostridium bolteae
SEQUENCE: 161
gtgtcagccg ccgcggtaat acgtaggggg caagcgttat ccggatttac tgggtgtaaa  60
gggagcgtag acggcgaagc aagtctgaag tgaaagcccg gggcttaacc ccgggactgc  120
tttggaaact gttttgctag agtgctggag aggtaagtgg aattcctagt gtagcggtga  180
aatgcgtaga tattaggagg aacaccagtg gcgaaagcgg ctttc                  225

SEQ ID NO: 162          moltype = DNA  length = 225
FEATURE                 Location/Qualifiers
source                  1..225
                        mol_type = genomic DNA
                        organism = Clostridium bolteae
SEQUENCE: 162
gtgtcagccg ccgcggtaat acgtaggggg caagcgttat ccggatttac tgggtgtaaa  60
gggagcgtag acggcgaagc aagtctgaag tgaaagcccg gggcttaacc ccgggactgc  120
tttggaaact gttttgctag agtgctggag aggtaagtgg aattcctagt gtagcggtga  180
aatgcgtaga tattgggaag aacaccagtg gcgaaggcgg ctttc                  225

SEQ ID NO: 163          moltype = DNA  length = 225
FEATURE                 Location/Qualifiers
source                  1..225
                        mol_type = genomic DNA
                        organism = Clostridium bolteae
SEQUENCE: 163
gtgccagccg ccgcggtaat acgtaggggg caagcgttat ccggatttac tgggtgtaaa  60
gggagcgtag acggcgaagc aagtctgaag tgaaagcccg gggcttaacc ccgggactgc  120
tttggaaact gttttgctag agtgctggag aggtaagtgg aattcctagt gtagcggtga  180
aatgcgtaga tattaggagg aacaccagtg gcgaaggcgg cttac                  225

SEQ ID NO: 164          moltype = DNA  length = 225
FEATURE                 Location/Qualifiers
source                  1..225
                        mol_type = genomic DNA
                        organism = Clostridium bolteae
SEQUENCE: 164
gttcagccgc cgcggtaata cgtagggggc aagcgttatc cggatttact gggtgtaaag  60
ggagcgtaga cggcgaagca agtctgaagt gaaagcccgg ggcttaaccc cgggactgct  120
```

```
ttggaaactg ttttgctaga gtgctggaga ggtaagtgga attcctagtg tagcggtgaa  180
atgcgtagat attaggagga acaccagtgg cgaaggcggc ttact                  225

SEQ ID NO: 165         moltype = DNA  length = 90
FEATURE                Location/Qualifiers
source                 1..90
                       mol_type = genomic DNA
                       organism = Clostridium hiranonis
SEQUENCE: 165
tacgtagggg gctagcgtta tccggattta ctgggcgtaa agggtgcgta ggcggtcttt  60
caagtcagga gttaaaggct acggctcaac                                   90

SEQ ID NO: 166         moltype = DNA  length = 225
FEATURE                Location/Qualifiers
source                 1..225
                       mol_type = genomic DNA
                       organism = Clostridium hiranonis
SEQUENCE: 166
gtgtcagccg ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagggga attcccagtg tagcggtgaa  180
atgcgtagat attgggagga acaccagtgg cgaaggcgcc tttct                  225

SEQ ID NO: 167         moltype = DNA  length = 225
FEATURE                Location/Qualifiers
source                 1..225
                       mol_type = genomic DNA
                       organism = Clostridium hiranonis
SEQUENCE: 167
gttcagcagc cgcggtaata cgtagggggc tagcgttatc cggatttact gggcgtaaag  60
ggtgcgtagg cggtctttca agtcaggagt taaaggctac ggctcaaccg tagtaagctc  120
ctgatactgt ctgacttgag tgcaggagag gaaagcggaa ttcccagtgt agcggtgaaa  180
tgcgtagata ttgggaggaa caccagtagc gaaggcggct ttctg                  225

SEQ ID NO: 168         moltype = DNA  length = 225
FEATURE                Location/Qualifiers
source                 1..225
                       mol_type = genomic DNA
                       organism = Clostridium hiranonis
SEQUENCE: 168
gtgtcagcag ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcctagtg tagcggtgaa  180
atgcgtagat attaggagga acaccagtgg cgaaagcggc tttct                  225

SEQ ID NO: 169         moltype = DNA  length = 225
FEATURE                Location/Qualifiers
source                 1..225
                       mol_type = genomic DNA
                       organism = Clostridium hiranonis
SEQUENCE: 169
gtgccagccg ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
gtgcgtagat attgggaaga acaccagtgg cgaaggcggc tttct                  225

SEQ ID NO: 170         moltype = DNA  length = 225
FEATURE                Location/Qualifiers
source                 1..225
                       mol_type = genomic DNA
                       organism = Clostridium hiranonis
SEQUENCE: 170
gtgccagcag ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
atgcgtagat attaggagga acaccagtgg cgaaggcggc ttact                  225

SEQ ID NO: 171         moltype = DNA  length = 225
FEATURE                Location/Qualifiers
source                 1..225
                       mol_type = genomic DNA
                       organism = Clostridium hiranonis
SEQUENCE: 171
gtgtcagcag ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
atgcgtagat attgggaaga acaccagtgg cgaaggcggc tttct                  225

SEQ ID NO: 172         moltype = DNA  length = 225
```

```
FEATURE                  Location/Qualifiers
source                   1..225
                         mol_type = genomic DNA
                         organism = Clostridium hiranonis
SEQUENCE: 172
gtgtcagccg ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
atgcgtagat attgggagga acaccagtag cgaaggcggc tttct                  225

SEQ ID NO: 173           moltype = DNA  length = 225
FEATURE                  Location/Qualifiers
source                   1..225
                         mol_type = genomic DNA
                         organism = Clostridium hiranonis
SEQUENCE: 173
gtgccagcag ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
atgcgtagat attgggagga acaccagtgg cgaaggcgcc tttct                  225

SEQ ID NO: 174           moltype = DNA  length = 225
FEATURE                  Location/Qualifiers
source                   1..225
                         mol_type = genomic DNA
                         organism = Clostridium hiranonis
SEQUENCE: 174
gtgccagcag ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagtgga attcccagtg tagcggtgaa  180
atgcgtagat attgggagga acaccagtag cgaaggcggc tttct                  225

SEQ ID NO: 175           moltype = DNA  length = 225
FEATURE                  Location/Qualifiers
source                   1..225
                         mol_type = genomic DNA
                         organism = Clostridium hiranonis
SEQUENCE: 175
gtgccagccg ccgcggtaat acgtaggggg ctagcgttat ccggatttac tgggcgtaaa  60
gggtgcgtag gcggtctttc aagtcaggag ttaaaggcta cggctcaacc gtagtaagct  120
cctgatactg tctgacttga gtgcaggaga ggaaagcgga attcccagtg tagcggtgaa  180
atgcgtagat attaggagga acaccagtgg cgaaagcggc tttct                  225

SEQ ID NO: 176           moltype = DNA  length = 90
FEATURE                  Location/Qualifiers
source                   1..90
                         mol_type = genomic DNA
                         organism = Megamonas funiformis
SEQUENCE: 176
tacgtaggcg gcaagcgttg tccggaatta ttgggcgtaa agggagcgca ggcgggaaac  60
taagcggatc ttaaaagtgc ggggcttaac                                   90

SEQ ID NO: 177           moltype = DNA  length = 90
FEATURE                  Location/Qualifiers
source                   1..90
                         mol_type = genomic DNA
                         organism = Murimonas intestini
SEQUENCE: 177
tacgtagggg gcaagcgtta tccggattta ctgggtgtaa agggagcgta gacggaatgg  60
caagtctgat gtgaaaggca ggggctcaac                                   90

SEQ ID NO: 178           moltype = DNA  length = 225
FEATURE                  Location/Qualifiers
source                   1..225
                         mol_type = genomic DNA
                         organism = Murimonas intestini
SEQUENCE: 178
gtgccagccg ccgcggtaat acgtaggggg caagcgttat ccggatttac tgggtgtaaa  60
gggagcgtag acggaatggc aagtctgatg tgaaaggcag ggctcaacc cctggactgc  120
attggaaact gtcagtcttg agtaccggag gggtaagcgg aattcctagt gtagcggtga  180
aatgcgtaga tattaggagg aacaccagtg gcgaaagcgg ctttc                  225

SEQ ID NO: 179           moltype = DNA  length = 225
FEATURE                  Location/Qualifiers
source                   1..225
                         mol_type = genomic DNA
                         organism = Murimonas intestini
SEQUENCE: 179
gtgccagcag ccgcggtaat acgtaggggg caagcgttat ccggatttac tgggtgtaaa  60
```

```
gggagcgtag acggaatggc aagtctgatg tgaaaggcag gggctcaacc cctggactgc  120
attggaaact gtcagtcttg agtatcggag ggtaagcgg aattcctagt gtagcggtga  180
aatgcgtaga tattaggagg aacaccagtg gcgaaggcgg cttac                  225

SEQ ID NO: 180          moltype = DNA  length = 225
FEATURE                 Location/Qualifiers
source                  1..225
                        mol_type = genomic DNA
                        organism = Murimonas intestini
SEQUENCE: 180
gtgtcagccg ccgcggtaat acgtaggggg caagcgttat ccggatttac tgggtgtaaa  60
gggagcgtag acggaatggc aagtctgatg tgaaaggcag gggctcaacc cctggactgc  120
attggaaact gtcagtcttg agtaccggag ggtaagcgg aattcctagt gtagcggtga  180
aatgcgtaga tattaggagg aacaccagtg gcgaaggcgg cttac                  225

SEQ ID NO: 181          moltype = DNA  length = 90
FEATURE                 Location/Qualifiers
source                  1..90
                        mol_type = genomic DNA
                        organism = Kandleria vitulina
SEQUENCE: 181
tacgtaggtg gcgagcgtta tccggaatca ttgggcgtaa agagggagca ggtggccgca  60
aaggtctgtg gtgaaagacc gaagctaaac                                   90

SEQ ID NO: 182          moltype = DNA  length = 90
FEATURE                 Location/Qualifiers
source                  1..90
                        mol_type = genomic DNA
                        organism = Bacteroides coprocola
SEQUENCE: 182
tacggaggat gcgagcgtta tccggattta ttgggtttaa agggagcgca gacgggagat  60
taagtcagtt gtgaaagttt gcggctcaac                                   90

SEQ ID NO: 183          moltype = DNA  length = 225
FEATURE                 Location/Qualifiers
source                  1..225
                        mol_type = genomic DNA
                        organism = Bacteroides coprocola
SEQUENCE: 183
gtgccagcag ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttccttg agtgcagttg aggcaggcgg aattcgtggt gtagcggtga  180
aatgcttaga tatcacgaag aactccgatt gcgaaggcag cttgc                  225

SEQ ID NO: 184          moltype = DNA  length = 225
FEATURE                 Location/Qualifiers
source                  1..225
                        mol_type = genomic DNA
                        organism = Bacteroides coprocola
SEQUENCE: 184
gtgccagccg ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggcgtccttg agtgcggttg aggtgtgcgg aattcgtggt gtagcggtga  180
aatgcttaga tatcacgaag aactccgatt gcgaaggcag cacac                  225

SEQ ID NO: 185          moltype = DNA  length = 225
FEATURE                 Location/Qualifiers
source                  1..225
                        mol_type = genomic DNA
                        organism = Bacteroides coprocola
SEQUENCE: 185
gtgtcagcag ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttccttg agtgcagttg aggtgtgcgg aattcgtggt gtagcggtga  180
aatgcttaga tatcacgaag aactccgatt gcgaaggcag cacac                  225

SEQ ID NO: 186          moltype = DNA  length = 225
FEATURE                 Location/Qualifiers
source                  1..225
                        mol_type = genomic DNA
                        organism = Bacteroides coprocola
SEQUENCE: 186
gtgccagccg ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggttttcttg agtgcagtag aggtgggcgg aattcgtggt gtagcggtga  180
aatgcttaga tatcacgaag aactccgatt gcgaaggcag cacac                  225

SEQ ID NO: 187          moltype = DNA  length = 225
FEATURE                 Location/Qualifiers
```

```
source                  1..225
                        mol_type = genomic DNA
                        organism = Bacteroides coprocola
SEQUENCE: 187
gtgtcagcag ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggcgtccttg agtgcggttg aggtgtgcgg aattcgtggt gtagcggtga  180
aatgcttaga tatcacgaag aaccccgatt gcgaaggcag cacac                  225

SEQ ID NO: 188          moltype = DNA  length = 225
FEATURE                 Location/Qualifiers
source                  1..225
                        mol_type = genomic DNA
                        organism = Bacteroides coprocola
SEQUENCE: 188
gtgtcagccg ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttccttg agtgcagttg aggcaggcgg aattcgtggt gtagcggtga  180
aatgcttaga tatcacgaag aactccgatt gcgaaggcag ctcac                  225

SEQ ID NO: 189          moltype = DNA  length = 225
FEATURE                 Location/Qualifiers
source                  1..225
                        mol_type = genomic DNA
                        organism = Bacteroides coprocola
SEQUENCE: 189
gtgtcagccg ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttccttg agtgcagttg aggcaggcgg aattcgtggt gtagcggtga  180
aatgcttaga tatcacgaag aaccccgatt gcgaaggcag cttgc                  225

SEQ ID NO: 190          moltype = DNA  length = 225
FEATURE                 Location/Qualifiers
source                  1..225
                        mol_type = genomic DNA
                        organism = Bacteroides coprocola
SEQUENCE: 190
gtgccagcag ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttccttg agtgcagttg aggcaggcgg aattcgtggt gtagcggtga  180
aatgcttaga tatcacgaag aactccgatt gcgaaggcag cacac                  225

SEQ ID NO: 191          moltype = DNA  length = 225
FEATURE                 Location/Qualifiers
source                  1..225
                        mol_type = genomic DNA
                        organism = Bacteroides coprocola
SEQUENCE: 191
gtgtcagcag ccgcggtaat acggaggatg cgagcgttat ccggatttat tgggtttaaa  60
gggagcgcag acgggagatt aagtcagttg tgaaagtttg cggctcaacc gtaaaattgc  120
agttgatact ggtttttcttg agtgcagtag aggtgggcgg aattcgtggt gtagcggtga  180
aatgcttaga tatcacgaag aactccgatt gcgaaggcag ctcac                  225

SEQ ID NO: 192          moltype = DNA  length = 225
FEATURE                 Location/Qualifiers
source                  1..225
                        mol_type = genomic DNA
                        organism = Bacteroides coprocola
SEQUENCE: 192
gttcagcagc cgcggtaata cggaggatgc gagcgttatc cggatttatt gggtttaaag  60
ggagcgcaga cgggagatta agtcagttgt gaaagtttgc ggctcaaccg taaaattgca  120
gttgatactg gtttccttga gtgcagttga ggcaggcgga attcgtggtg tagcggtgaa  180
atgcttagat atcacgaaga accccgattg cgaaggcagc ttgct                  225

SEQ ID NO: 193          moltype = DNA  length = 90
FEATURE                 Location/Qualifiers
source                  1..90
                        mol_type = genomic DNA
                        organism = Clostridum nexile
SEQUENCE: 193
tacgtatggt gcaagcgtta tccggattta ctgggtgtaa agggagtgta gacggttgtg  60
taagtctgat gtgaaagccc ggggctcaac                                   90

SEQ ID NO: 194          moltype = DNA  length = 90
FEATURE                 Location/Qualifiers
source                  1..90
                        mol_type = genomic DNA
                        organism = Sarcina Maxima
SEQUENCE: 194
```

```
tacgtaggtg gcgagcgtta tccggattta ttgggcgtaa agggagcgta ggcggatact  60
taagtgggat gtgaaatact tgggctcaac                                    90

SEQ ID NO: 195         moltype = DNA  length = 90
FEATURE                Location/Qualifiers
source                 1..90
                       mol_type = genomic DNA
                       organism = Allobaculum stercoricanis
SEQUENCE: 195
tacgtaggtg gcgagcgtta tccggaatga ttgggcgtaa agggtgcgca ggcggcatat  60
caagtctgaa gtgaaaggta cgggcttaac                                    90

SEQ ID NO: 196         moltype = DNA  length = 90
FEATURE                Location/Qualifiers
source                 1..90
                       mol_type = genomic DNA
                       organism = Butyricicoccus pullicaecorum
SEQUENCE: 196
tacgtaggga gcaagcgtta tccggattta ctgggtgtaa agggcgcgca ggcgggccgg  60
taagttggaa gtgaaatcta tgggcttaac                                    90

SEQ ID NO: 197         moltype = DNA  length = 90
FEATURE                Location/Qualifiers
source                 1..90
                       mol_type = genomic DNA
                       organism = Veillonella ratti
SEQUENCE: 197
tacgtaggtg gcaagcgttg tccggaatta ttgggcgtaa agggcgcgca ggcggtttca  60
taagtctgtc ttaaaagtgc ggggcttaac                                    90

SEQ ID NO: 198         moltype = DNA  length = 90
FEATURE                Location/Qualifiers
source                 1..90
                       mol_type = genomic DNA
                       organism = Acinetobacter tjernbergiae
SEQUENCE: 198
tacagagggt gcgagcgtta atcggattta ctgggcgtaa agcgtgcgta ggcggcttct  60
taagtcggat gtgaaatccc tgagcttaac                                    90

SEQ ID NO: 199         moltype = DNA  length = 90
FEATURE                Location/Qualifiers
source                 1..90
                       mol_type = genomic DNA
                       organism = Kandleria vitulina
SEQUENCE: 199
tacgtaggtg gcgagcgtta tccggaatca ttgggcgtaa agagggagca ggcggccgca  60
aaggtctgtg gtgaaagacc gaagctaaac                                    90

SEQ ID NO: 200         moltype = DNA  length = 225
FEATURE                Location/Qualifiers
source                 1..225
                       mol_type = genomic DNA
                       organism = Kandleria vitulina
SEQUENCE: 200
gtgtcagagc cgcggtaata cgtaggtggc gagcgttatc cggaatcatt gggcgtaaag  60
agggagcagg cggccgcaaa ggtctgtggt gaaagaccga agctaaactt cggtaagcca  120
tggaaaccgg gcggctagag tgcggaagag gatcgtggaa ttccatgtgt agcggtgaaa  180
tgcgtagata tatggaggaa caccagtggc gaaggcgacg gtctg                  225

SEQ ID NO: 201         moltype = DNA  length = 225
FEATURE                Location/Qualifiers
source                 1..225
                       mol_type = genomic DNA
                       organism = Kandleria vitulina
SEQUENCE: 201
gtgtcagcag ccgcggtaat acgtaggtgg cgagcgttat ccggaatcat tgggcgtaaa  60
gagggagcag gcggccgcaa aggtctgtgg tgaaagaccg aagctaaact tcggtaagcc  120
atggaaaccg ggcggctaga gtgcggaaga ggatcgtgga attccatgtg tagcggtgaa  180
atgcgtagat atatggagga acaccagtgg cgaaggcgcc tttct                  225

SEQ ID NO: 202         moltype = DNA  length = 225
FEATURE                Location/Qualifiers
source                 1..225
                       mol_type = genomic DNA
                       organism = Kandleria vitulina
SEQUENCE: 202
gtgccagccg ccgcggtaat acgtaggtgg cgagcgttat ccggaatcat tgggcgtaaa  60
gagggagcag gcggccgcaa aggtctgtgg tgaaagaccg aagctaaact tcggtaagcc  120
atggaagccg ggcggctaga gtgcggaaga ggatcgtgga attccatgtg tagcggtgaa  180
```

```
atgcgtagat atatggagga acaccagtgg cgaaggcgac ggtct                225

SEQ ID NO: 203         moltype = DNA  length = 225
FEATURE                Location/Qualifiers
source                 1..225
                       mol_type = genomic DNA
                       organism = Kandleria vitulina
SEQUENCE: 203
gtgccagcag ccgggtaata cgtaggtggc gagcgttatc cggaatcatt gggcgtaaag  60
agggagcagg cggccgcaaa ggtctgtggt gaaagaccga agctaaactt cggtaagcca  120
tggaaaccgg gcggctagag tgcggaagag gatcgtggaa ttccatgtgt agcggtgaaa  180
tgcgtagata tatggaggaa caccagtggc gaaggcgacg gtctg                225

SEQ ID NO: 204         moltype = DNA  length = 90
FEATURE                Location/Qualifiers
source                 1..90
                       mol_type = genomic DNA
                       organism = Jeotgalibaca dankookensis
SEQUENCE: 204
tacgtaggtg gcaagtgttg tccggattta ttgggcgtaa agcgagcgca ggcggttctt  60
taagtctgat gtgaaagccc ccggctcaac                                 90

SEQ ID NO: 205         moltype = DNA  length = 90
FEATURE                Location/Qualifiers
source                 1..90
                       mol_type = genomic DNA
                       organism = Blautia glucerasea
SEQUENCE: 205
tacgtagggg gcaagcgtta tccggattta ctgggtgtaa agggagcgta gacggagcag  60
caagtctgat gtgaaagacg gggctcaac                                  90

SEQ ID NO: 206         moltype = DNA  length = 90
FEATURE                Location/Qualifiers
source                 1..90
                       mol_type = genomic DNA
                       organism = Paraprevotella clara
SEQUENCE: 206
tacggaagat gcgagcgtta tccggattta ttgggtttaa agggagcgta ggcggacgat  60
taagtcagcg gtaaaataga gtggctcaac                                 90

SEQ ID NO: 207         moltype = DNA  length = 90
FEATURE                Location/Qualifiers
source                 1..90
                       mol_type = genomic DNA
                       organism = Murimonas intestini
SEQUENCE: 207
tacggagggg gcaagcgtta tccggattta ctgggtgtaa agggagcgta gacggcatgg  60
caagtctgat gtgaaaggca ggggctcaac                                 90

SEQ ID NO: 208         moltype = DNA  length = 90
FEATURE                Location/Qualifiers
source                 1..90
                       mol_type = genomic DNA
                       organism = Thermaerobacter nagasakiensis
SEQUENCE: 208
aacatagggg gcaagcgttg tccggaatca ctgggcgtaa agggcgcgta ggcggtctgt  60
taagtcggat gtgaaatgta agggctcaac                                 90

SEQ ID NO: 209         moltype = DNA  length = 225
FEATURE                Location/Qualifiers
source                 1..225
                       mol_type = genomic DNA
                       organism = Thermaerobacter nagasakiensis
SEQUENCE: 209
gtgccagcag ccgcggtaaa acataggggg caagcgttgt ccggaatcac tgggcgtaaa  60
gggcgcgtag gcggtctgtt aagtcggatg tgaaatgtaa gggctcaacc cttaacgtgc  120
atccgatact ggcagacttg agtgcggaag aggcaagtgg aattcctagt gtagcggtga  180
aatgcgtaga tattaggagg aacaccagtg gcgaaggcgg cttac                225

SEQ ID NO: 210         moltype = DNA  length = 225
FEATURE                Location/Qualifiers
source                 1..225
                       mol_type = genomic DNA
                       organism = Thermaerobacter nagasakiensis
SEQUENCE: 210
gtgtcagcag ccgcggtaaa acataggggg caagcgttgt ccggaatcac tgggcgtaaa  60
gggcgcgtag gcggtctgtt aagtcggatg tgaaatgtaa gggctcaacc cttaacgtgc  120
atccgatact ggcagacttg agtgcggaag aggcaagtgg aattcctagt gtagcggtga  180
aatgcgtaga tattaggagg aacaccagtg gcgaaagcgg ctttc                225
```

```
SEQ ID NO: 211         moltype = DNA  length = 225
FEATURE                Location/Qualifiers
source                 1..225
                       mol_type = genomic DNA
                       organism = Thermaerobacter nagasakiensis
SEQUENCE: 211
gtgtcagccg ccgcggtaaa acatagggggg caagcgttgt ccggaatcac tgggcgtaaa  60
gggcgcgtag gcggtctgtt aagtcggatg tgaaatgtaa gggctcaacc cttaacgtgc  120
atccgatact ggcagacttg agtgcggaag aggcaagtgg aattcctagt gtagcggtga  180
aatgcgtaga tattaggagg aacaccagtg gcgaaggcga cttgc                  225

SEQ ID NO: 212         moltype = DNA  length = 90
FEATURE                Location/Qualifiers
source                 1..90
                       mol_type = genomic DNA
                       organism = Bulleidia extructa
SEQUENCE: 212
tacgtaggtg gcgagcgtta tccggaatta ttgggcgtaa agggtgcgta ggcggtctgc  60
taagtccatg gtgaaagcgt ggggctcaac                                   90

SEQ ID NO: 213         moltype = DNA  length = 90
FEATURE                Location/Qualifiers
source                 1..90
                       mol_type = genomic DNA
                       organism = Bacteroides rodentium
SEQUENCE: 213
tacggaggat ccgagcgtta tccggattta ttgggtttaa agggagcgta ggcggatgct  60
taagtcagtt gtgaaagttt gcggctcaac                                   90

SEQ ID NO: 214         moltype = DNA  length = 225
FEATURE                Location/Qualifiers
source                 1..225
                       mol_type = genomic DNA
                       organism = Bacteroides rodentium
SEQUENCE: 214
gccagcccgc ggtaatacgg aggatccgag cgttatccgg atttattggg tttaaaggga  60
gcgtaggcgg atgcttaagt cagttgtgaa agtttgcggc tcaaccgtaa aattgcagtt  120
gatactgggt gtcttgagta cagtagaggc aggcggaatt cgtggtgtag cggtgaaatg  180
cttagatatc acgaagaact ccgattgcga aggcagcttg ctgga                  225

SEQ ID NO: 215         moltype = DNA  length = 225
FEATURE                Location/Qualifiers
source                 1..225
                       mol_type = genomic DNA
                       organism = Bacteroides rodentium
SEQUENCE: 215
gtgtcagccg ccgcggtaat acggaggatc cgagcgttat ccggatttat tgggtttaaa  60
gggagcgtag gcggatgctt aagtcagttg tgaaagtttg cggctcaacc gtaaaattgc  120
agttgatact gggtgtcttg agtacagtag aggcaggcgg aattcgtggt gtagcggtga  180
aatgcttaga tatcacgaag aactccgatt gcgaaggcag cacac                  225

SEQ ID NO: 216         moltype = DNA  length = 225
FEATURE                Location/Qualifiers
source                 1..225
                       mol_type = genomic DNA
                       organism = Bacteroides rodentium
SEQUENCE: 216
gtgtcagccg ccgcggtaat acggaggatc cgagcgttat ccggatttat tgggtttaaa  60
gggagcgtag gcggatgctt aagtcagttg tgaaagtttg cggctcaacc gtaaaattgc  120
agttgatact gggtgtcttg agtacagtag aggcaggcgg aattcgtggt gtagcggtga  180
aatgcttaga tatcacgaag aactccgatt gcgaaggcag cttgc                  225

SEQ ID NO: 217         moltype = DNA  length = 90
FEATURE                Location/Qualifiers
source                 1..90
                       mol_type = genomic DNA
                       organism = Collinsella intestinalis
SEQUENCE: 217
tacgtagggg gcgagcgtta tccggattca ttgggcgtaa agcgcgcgta ggcggcccgg  60
caggcagggg gttaaatggc ggggctcaac                                   90

SEQ ID NO: 218         moltype = DNA  length = 90
FEATURE                Location/Qualifiers
source                 1..90
                       mol_type = genomic DNA
                       organism = Aerococcus urinaehominis
SEQUENCE: 218
tacgtaggtg gcaagcgttg tccggattta ttgggcgtaa agggagcgca ggtggtttct  60
```

```
taagtctgat gtgaaagccc acggcttaac                                90

SEQ ID NO: 219          moltype = DNA  length = 90
FEATURE                 Location/Qualifiers
source                  1..90
                        mol_type = genomic DNA
                        organism = Clostridium hylemonae
SEQUENCE: 219
tacgtagggg gcaagcgtta tccggattta ctgggtgtaa agggagtgta gacggcaagg  60
caagtctgaa gtgaaagccc ggtgctcaac                                90

SEQ ID NO: 220          moltype = DNA  length = 225
FEATURE                 Location/Qualifiers
source                  1..225
                        mol_type = genomic DNA
                        organism = Clostridium hylemonae
SEQUENCE: 220
gtgtcagccg ccgcggtaat acgtaggggg caagcgttat ccggatttac tgggtgtaaa  60
gggagtgtag acggcaaggc aagtctgaag tgaaagcccg gtgctcaacg ccgggactgc  120
tttggaaact gtttagctag agtgccggag aggtaagcgg aattcctagt gtagcggtga  180
aatgcgtaga tattgggagg aacaccagtg gcgaaggcgc ctttc                225

SEQ ID NO: 221          moltype = DNA  length = 225
FEATURE                 Location/Qualifiers
source                  1..225
                        mol_type = genomic DNA
                        organism = Clostridium hylemonae
SEQUENCE: 221
gtgccacagc cgcggtaata cgtagggggc aagcgttatc cggatttact gggtgtaaag  60
ggagtgtaga cggcaaggca agtctgaagt gaaagcccgg tgctcaacgc cgggactgct  120
ttggaaactg tttagctaga gtgccggaga ggtaagcgga attcctagtg tagcggtgaa  180
atgcgtagat attaggaaga acaccagtgg cgaaggcggc ttact                225

SEQ ID NO: 222          moltype = DNA  length = 225
FEATURE                 Location/Qualifiers
source                  1..225
                        mol_type = genomic DNA
                        organism = Clostridium hylemonae
SEQUENCE: 222
gtgccagcag ccgcggtaat acgtaggggg caagcgttat ccggatttac tgggtgtaaa  60
gggagtgtag acggcaaggc aagtctgaag tgaaagcccg gtgctcaacg ccgggactgc  120
tttggaaact gtttagctag agtgccggag aggtaagcgg aattcctagt gtagcggtga  180
aatgcgtaga tattaggaag aacaccagtg gcgaaagcgg ctttc                225

SEQ ID NO: 223          moltype = DNA  length = 225
FEATURE                 Location/Qualifiers
source                  1..225
                        mol_type = genomic DNA
                        organism = Clostridium hylemonae
SEQUENCE: 223
gtgtcagccg ccgcggtaat acgtaggggg caagcgttat ccggatttac tgggtgtaaa  60
gggagtgtag acggcaaggc aagtctgaag tgaaagcccg gtgctcaacg ccgggactgc  120
tttggaaact gtttagctag agtgccggag aggtaagcgg aattcctagt gtagcggtga  180
aatgcgtaga tattaggaag aacaccagtg gcgaaggcgg cttac                225

SEQ ID NO: 224          moltype = DNA  length = 225
FEATURE                 Location/Qualifiers
source                  1..225
                        mol_type = genomic DNA
                        organism = Clostridium hylemonae
SEQUENCE: 224
gtgtcagccg ccgcggtaat acgtaggggg caagcgttat ccggatttac tgggtgtaaa  60
gggagtgtag acggcaaggc aagtctgaag tgaaagcccg gtgctcaacg ccgggactgc  120
tttggaaact gtttagctag agtgccggag aggtaagcgg aattcctagt gtagcggtga  180
aatgcgtaga tattaggagg aacaccagtg gcgaaagcgg ctttc                225

SEQ ID NO: 225          moltype = DNA  length = 225
FEATURE                 Location/Qualifiers
source                  1..225
                        mol_type = genomic DNA
                        organism = Clostridium hylemonae
SEQUENCE: 225
gtgccagccg ccgcggtaat acgtaggggg caagcgttat ccggatttac tgggtgtaaa  60
gggagtgtag acggcaaggc aagtctgaag tgaaagcccg gtgctcaacg ccgggactgc  120
tttggaaact gtttagctag agtgccggag aggtaagcgg aattcctagt gtagcggtga  180
aatgcgtaga tattgggaag aacaccagtg gcgaaggcgg ctttc                225

SEQ ID NO: 226          moltype = DNA  length = 90
FEATURE                 Location/Qualifiers
```

```
source                  1..90
                        mol_type = genomic DNA
                        organism = Bacteroides eggerthii
SEQUENCE: 226
tacggaggat ccgagcgtta tccggattta ttgggtttaa agggagcgta ggcggaagtt  60
taagtcagtt gtgaaagttt gcggctcaac                                   90

SEQ ID NO: 227          moltype = DNA  length = 90
FEATURE                 Location/Qualifiers
source                  1..90
                        mol_type = genomic DNA
                        organism = Lactonifactor longoviformis
SEQUENCE: 227
tacgtagggg gcaagcgtta tccggattta ctgggtgtaa agggagcgta gacggaagtg  60
caagtctgat gtgaaaaccc gaggctcaac                                   90

SEQ ID NO: 228          moltype = DNA  length = 225
FEATURE                 Location/Qualifiers
source                  1..225
                        mol_type = genomic DNA
                        organism = Lactonifactor longoviformis
SEQUENCE: 228
gtgtcagccg ccgcggtaat acgtaggggg caagcgttat ccggatttac tgggtgtaaa  60
gggagcgtag acggaagtgc aagtctgatg tgaaaacccg aggctcaacc acgggactgc  120
attggaaact gtgcttctag agtgccggag aggtaagcgg aattcctagt gtagcggtga  180
aatgcgtaga tattgggaag aacaccagtg gcgaaggcgg ctttc                  225

SEQ ID NO: 229          moltype = DNA  length = 225
FEATURE                 Location/Qualifiers
source                  1..225
                        mol_type = genomic DNA
                        organism = Lactonifactor longoviformis
SEQUENCE: 229
gtgccagccg ccgcggtaat acgtaggggg caagcgttat ccggatttac tgggtgtaaa  60
gggagcgtag acggaagtgc aagtctgatg tgaaaacccg aggctcaacc acgggactgc  120
attggaaact gtgcttctag agtgccggag aggtaagcgg aattcctagt gtagcggtga  180
aatgcgtaga tattaggagg aacaccagtg gcgaaggcgg ccgtc                  225

SEQ ID NO: 230          moltype = DNA  length = 225
FEATURE                 Location/Qualifiers
source                  1..225
                        mol_type = genomic DNA
                        organism = Lactonifactor longoviformis
SEQUENCE: 230
gtgtcagccg ccgcggtaat acgtaggggg caagcgttat ccggatttac tgggtgtaaa  60
gggagcgtag acggaagtgc aagtctgatg tgaaaacccg aggctcaacc acgggactgc  120
attggaaact gtgcttctag agtgccggag aggtaagcgg aattcctagt gtagcggtga  180
aatgcgtaga tattaggagg aacaccagtg gcgaaggcgg cttac                  225

SEQ ID NO: 231          moltype = DNA  length = 225
FEATURE                 Location/Qualifiers
source                  1..225
                        mol_type = genomic DNA
                        organism = Lactonifactor longoviformis
SEQUENCE: 231
gtgccagcag ccgcggtaat acgtaggggg caagcgttat ccggatttac tgggtgtaaa  60
gggagcgtag acggaagtgc aagtctgatg tgaaaacccg aggctcaacc acgggactgc  120
attggaaact gtgcttctag agtgccggag aggtaagcgg aattcctagt gtagcggtga  180
aatgcgtaga tattaggagg aacaccagtg gcgaaagcgg ctttc                  225

SEQ ID NO: 232          moltype = DNA  length = 90
FEATURE                 Location/Qualifiers
source                  1..90
                        mol_type = genomic DNA
                        organism = Clostridum intestinale
SEQUENCE: 232
tacgtaggtg gcaagcgtta tccggattta ctgggcgtaa agggagcgta ggcggatact  60
taagtgggat gtgaaatacc tgggcttaac                                   90

SEQ ID NO: 233          moltype = DNA  length = 90
FEATURE                 Location/Qualifiers
source                  1..90
                        mol_type = genomic DNA
                        organism = Blautia wexlerae
SEQUENCE: 233
tacggagggg gcaagcgtta tccggattta ctgggtgtaa agggagcgta gacggtgtgg  60
caagtctgat gtgaaaggca tgggctcaac                                   90

SEQ ID NO: 234          moltype = DNA  length = 90
```

```
FEATURE                 Location/Qualifiers
source                  1..90
                        mol_type = genomic DNA
                        organism = Ruminococcus faecis
SEQUENCE: 234
tacggagggg gcaagcgtta tccggattta ctgggtgtaa agggagcgta gacggactgg  60
caagtctgat gtgaaaaccc ggggctcaac                                    90

SEQ ID NO: 235          moltype = DNA  length = 90
FEATURE                 Location/Qualifiers
source                  1..90
                        mol_type = genomic DNA
                        organism = Bacteroides dorei
SEQUENCE: 235
tacggaggat ccgagcgtta tccggattta ttgggtttaa agggagcgta gatggatgtt  60
taagtcagtt gtgaaagttt gcggctcaac                                    90

SEQ ID NO: 236          moltype = DNA  length = 225
FEATURE                 Location/Qualifiers
source                  1..225
                        mol_type = genomic DNA
                        organism = Bacteroides dorei
SEQUENCE: 236
gtgtcagcag ccgcggtaat acggaggatc cgagcgttat ccggatttat tgggtttaaa  60
gggagcgtag atggatgttt aagtcagttg tgaaagtttg cggctcaacc gtaaaattgc  120
agttgatact ggatatcttg agtgcagttg aggcaggcgg aattcgtggt gtagcggtga  180
aatgcttaga tatcacgaag aactccgatt gcgaaggcag ctcac                  225

SEQ ID NO: 237          moltype = DNA  length = 225
FEATURE                 Location/Qualifiers
source                  1..225
                        mol_type = genomic DNA
                        organism = Bacteroides dorei
SEQUENCE: 237
gtgtcagcag ccgcggtaat acggaggatc cgagcgttat ccggatttat tgggtttaaa  60
gggagcgtag atggatgttt aagtcagttg tgaaagtttg cggctcaacc gtaaaattgc  120
agttgatact ggatatcttg agtgcagttg aggcaggcgg aattcgtggt gtagcggtga  180
aatgcttaga tatcacgaag aactccgatt gcgaaggcag cctgc                  225

SEQ ID NO: 238          moltype = DNA  length = 90
FEATURE                 Location/Qualifiers
source                  1..90
                        mol_type = genomic DNA
                        organism = Robinsoniella peoriensis
SEQUENCE: 238
tacgtagggg gcaagcgtta tccggattta ctgggtgtaa agggagcgta gacggcatgg  60
caagcctgat gtgaaaggca ggggctcaac                                    90

SEQ ID NO: 239          moltype = DNA  length = 90
FEATURE                 Location/Qualifiers
source                  1..90
                        mol_type = genomic DNA
                        organism = Clostridium glycyrrhizinilyticum
SEQUENCE: 239
tacgtatggt gcaagcgtta tccggattta ctgggtgtaa agggagcgta gacggagagg  60
caagtctgat gtgaaaaccc ggggctcaac                                    90

SEQ ID NO: 240          moltype = DNA  length = 225
FEATURE                 Location/Qualifiers
source                  1..225
                        mol_type = genomic DNA
                        organism = Clostridium glycyrrhizinilyticum
SEQUENCE: 240
gtgtcagcag ccgcggtaat acgtatggtg caagcgttat ccggatttac tgggtgtaaa  60
gggagcgtag acggagaggc aagtctgatg tgaaaacccg gggctcaacc ccgggactgc  120
attggaaact gtttttctag agtgtcggag aggtaagtgg aattcctagt gtagcggtga  180
aatgcgtaga tattgggagg aacaccagtg gcgaaggcgc ctttc                  225

SEQ ID NO: 241          moltype = DNA  length = 225
FEATURE                 Location/Qualifiers
source                  1..225
                        mol_type = genomic DNA
                        organism = Clostridium glycyrrhizinilyticum
SEQUENCE: 241
gtgccagccg ccgcggtaat acgtatggtg caagcgttat ccggatttac tgggtgtaaa  60
gggagcgtag acggagaggc aagtctgatg tgaaaacccg gggctcaacc ccgggactgc  120
attggaaact gtttttctag agtgtcggag aggtaagtgg aattcctagt gtagcggtga  180
aatgcgtaga tattaggagg aacaccagtg gcgaaggcgc ctttc                  225
```

```
SEQ ID NO: 242          moltype = DNA  length = 225
FEATURE                 Location/Qualifiers
source                  1..225
                        mol_type = genomic DNA
                        organism = Clostridium glycyrrhizinilyticum
SEQUENCE: 242
gtgtcagccg ccgcggtaat acgtatggtg caagcgttat ccggatttac tgggtgtaaa  60
gggagcgtag acggagaggc aagtctgatg tgaaaacccg ggctcaacc ccgggactgc  120
attggaaact gtttttctag agtgtcggag aggtaagtgg aattcctagt gtagcggtga  180
aatgcgtaga tattaggagg aacaccagtg gcgaaggcgg cttac                 225

SEQ ID NO: 243          moltype = DNA  length = 225
FEATURE                 Location/Qualifiers
source                  1..225
                        mol_type = genomic DNA
                        organism = Clostridium glycyrrhizinilyticum
SEQUENCE: 243
gtgccagcag ccgcggtaat acgtatggtg caagcgttat ccggatttac tgggtgtaaa  60
gggagcgtag acggagaggc aagtctgatg tgaaaacccg ggctcaacc ccgggactgc  120
attggaaact gtttttctag agtgtcggag aggtaagtgg aattcctagt gtagcggtga  180
aatgcgtaga tattaggagg aacaccagtg gcgaaagcgg ctttc                 225

SEQ ID NO: 244          moltype = DNA  length = 90
FEATURE                 Location/Qualifiers
source                  1..90
                        mol_type = genomic DNA
                        organism = Bacteroides thetaiotaomicron
SEQUENCE: 244
tacggaggat ccgagcgtta tccggattta ttgggtttaa agggagcgta ggtggaagat  60
taagtcagcc tgtgaaagtt tgcggctcaa                                  90

SEQ ID NO: 245          moltype = DNA  length = 225
FEATURE                 Location/Qualifiers
source                  1..225
                        mol_type = genomic DNA
                        organism = Bacteroides thetaiotaomicron
SEQUENCE: 245
gtgccagcag ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgggcg gaattcgtgg tgtagcggtg  180
agatgcttag atatcacgaa gaactccgat tgcgaaggca gcaca                 225

SEQ ID NO: 246          moltype = DNA  length = 225
FEATURE                 Location/Qualifiers
source                  1..225
                        mol_type = genomic DNA
                        organism = Bacteroides thetaiotaomicron
SEQUENCE: 246
gtgccagcac cgcggtcata cggaggatcc gagcgttatc cggatttatt gggtttaaag  60
ggagcgtagg tggaagatta agtcagcctg tgaaagtttg cggctcaacc gtaaaattgc  120
agttgatact ggttttcttg agtgcagtag aggtgggcgg aattcgtggt gtagcggtga  180
aatgcttaga tatcacgaag aactccgatt gcgaaggcag ctcac                 225

SEQ ID NO: 247          moltype = DNA  length = 225
FEATURE                 Location/Qualifiers
source                  1..225
                        mol_type = genomic DNA
                        organism = Bacteroides thetaiotaomicron
SEQUENCE: 247
gtgccagccg cggtaatacg gaggatccga gcgttatccg gatttattgg gtttaaaggg  60
agcgtaggtg gaagattaag tcagcctgtg aaagtttgcg gctcaaccgt aaaattgcag  120
ttgatactgg ttttcttgag tgcagtagag gtgggcggaa ttcgtggtgt agcggtgaaa  180
tgcttagata tcacgaagaa ctccgattgc gaaggcagct cactg                 225

SEQ ID NO: 248          moltype = DNA  length = 225
FEATURE                 Location/Qualifiers
source                  1..225
                        mol_type = genomic DNA
                        organism = Bacteroides thetaiotaomicron
SEQUENCE: 248
gtgtcagcag ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgtgcg gaattcgtgg tgtagcggtg  180
aaatgcttag atatcacgaa gaactccgat tgcgaaggca gcaca                 225

SEQ ID NO: 249          moltype = DNA  length = 225
FEATURE                 Location/Qualifiers
source                  1..225
                        mol_type = genomic DNA
```

```
                        organism = Bacteroides thetaiotaomicron
SEQUENCE: 249
gtgtcagcag ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagtt gaggcaggcg gaattcgtgg tgtagcggtg  180
aaatgcttag atatcacgaa gaaccccgat tgcgaaggca gcttg                  225

SEQ ID NO: 250          moltype = DNA  length = 225
FEATURE                 Location/Qualifiers
source                  1..225
                        mol_type = genomic DNA
                        organism = Bacteroides thetaiotaomicron
SEQUENCE: 250
gtgtcagccg ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgggcg gaattcgtgg tgtagcggtg  180
aaatgcttag atatcacgaa gaaccccgat tgcgaaggca gcttg                  225

SEQ ID NO: 251          moltype = DNA  length = 225
FEATURE                 Location/Qualifiers
source                  1..225
                        mol_type = genomic DNA
                        organism = Bacteroides thetaiotaomicron
SEQUENCE: 251
gtgtcagccg ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgggcg gaattcgtgg tgtagcggtg  180
aaatgcttag atatcacgaa gaactccgat tgcgaaggca gctca                  225

SEQ ID NO: 252          moltype = DNA  length = 225
FEATURE                 Location/Qualifiers
source                  1..225
                        mol_type = genomic DNA
                        organism = Bacteroides thetaiotaomicron
SEQUENCE: 252
gttcagcagc cgcggtaata cggaggatcc gagcgttatc cggatttatt gggtttaaag  60
ggagcgtagg tggaagatta agtcagcctg tgaaagtttg cggctcaacc gtaaaattgc  120
agttgatact ggttttcttg agtgcagtag aggtgggcgg aattcgtggt gtagcggtga  180
aatgcttaga tatcacgaag aactccgatt gcgaaggcag ctcac                  225

SEQ ID NO: 253          moltype = DNA  length = 225
FEATURE                 Location/Qualifiers
source                  1..225
                        mol_type = genomic DNA
                        organism = Bacteroides thetaiotaomicron
SEQUENCE: 253
gtgccagccg ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgggcg gaattcgtgg tgtagcggtg  180
aaatgcttag atatcacgaa gaaccccgat tgcgaaggca gcaca                  225

SEQ ID NO: 254          moltype = DNA  length = 225
FEATURE                 Location/Qualifiers
source                  1..225
                        mol_type = genomic DNA
                        organism = Bacteroides thetaiotaomicron
SEQUENCE: 254
gtgccagcag ccgcggtaat acggaggatc cgagcgttat ccggatttat tgggtttaaa  60
gggagcgtag gtggaagatt aagtcagcct gtgaaagttt gcggctcaac cgtaaaattg  120
cagttgatac tggttttctt gagtgcagta gaggtgggcg gaattcgtgg tgtagcggtg  180
aaatgcttag atatcacgaa gaactccgat tgcgaaggca gcttg                  225

SEQ ID NO: 255          moltype = DNA  length = 90
FEATURE                 Location/Qualifiers
source                  1..90
                        mol_type = genomic DNA
                        organism = Eubacterium tortuosum
SEQUENCE: 255
tacgtaggtg gcgagcgtta tccggaatca ttgggcgtaa agggtgcgca ggtggtacat  60
taagtccgaa gtaaaaggca gcagctcaac                                   90

SEQ ID NO: 256          moltype = DNA  length = 90
FEATURE                 Location/Qualifiers
source                  1..90
                        mol_type = genomic DNA
                        organism = Bacteroides stercoris
SEQUENCE: 256
tacggaggat ccgagcgtta tccggattta ttgggtttaa agggagcgta ggcgggttgt  60
taagtcagtt gtgaaagttt gcggctcaac                                   90
```

```
SEQ ID NO: 257          moltype = DNA  length = 225
FEATURE                Location/Qualifiers
source                 1..225
                       mol_type = genomic DNA
                       organism = Bacteroides stercoris
SEQUENCE: 257
gttcagcagc cgcggtaata cggaggatcc gagcgttatc cggatttatt gggtttaaag  60
ggagcgtagg cgggttgtta agtcagttgt gaaagtttgc ggctcaaccg taaaattgca  120
gttgatactg gcgaccttga gtgcaacaga ggtaggcgga attcgtggtg tagcggtgaa  180
atgcttagat atcacgaaga actccgattg cgaaggcagc ttact                  225

SEQ ID NO: 258          moltype = DNA  length = 225
FEATURE                Location/Qualifiers
source                 1..225
                       mol_type = genomic DNA
                       organism = Bacteroides stercoris
SEQUENCE: 258
gtgccagcag ccgcggtaat acggaggatc cgagcgttat ccggatttat tgggtttaaa  60
gggagcgtag gcgggttgtt aagtcagttg tgaaagtttg cggctcaacc gtaaaattgc  120
agttgatact ggcgaccttg agtgcaacag aggtaggcgg aattcgtggt gtagcggtga  180
aatgcttaga tatcacgaag aactccgatt gcgaaggcgg ctttc                  225

SEQ ID NO: 259          moltype = DNA  length = 225
FEATURE                Location/Qualifiers
source                 1..225
                       mol_type = genomic DNA
                       organism = Bacteroides stercoris
SEQUENCE: 259
gtgccagcag ccgcggtaat acggaggatc cgagcgttat ccggatttat tgggtttaaa  60
gggagcgtag gcgggttgtt aagtcagttg tgaaagtttg cggctcaacc gtaaaattgc  120
agttgatact ggcgaccttg agtgcaacag aggtaggcgg aattcgtggt gtagcggtga  180
aatgcttaga tatcacgaag aaccccgatt gcgaaggcag cttgc                  225

SEQ ID NO: 260          moltype = DNA  length = 225
FEATURE                Location/Qualifiers
source                 1..225
                       mol_type = genomic DNA
                       organism = Bacteroides stercoris
SEQUENCE: 260
gtgtcagccg ccgcggtaat acggaggatc cgagcgttat ccggatttat tgggtttaaa  60
gggagcgtag gcgggttgtt aagtcagttg tgaaagtttg cggctcaacc gtaaaattgc  120
agttgatact ggcgaccttg agtgcaacag aggtaggcgg aattcgtggt gtagcggtga  180
aatgcttaga tatcacgaag aactccgatt gcgaaggcag cttac                  225

SEQ ID NO: 261          moltype = DNA  length = 225
FEATURE                Location/Qualifiers
source                 1..225
                       mol_type = genomic DNA
                       organism = Bacteroides stercoris
SEQUENCE: 261
gtgtcagcag ccgcggtaat acggaggatc cgagcgttat ccggatttat tgggtttaaa  60
gggagcgtag gcgggttgtt aagtcagttg tgaaagtttg cggctcaacc gtaaaattgc  120
agttgatact ggcgaccttg agtgcaacag aggtaggcgg aattcgtggt gtagcggtga  180
aatgcttaga tatcacgaag aactccgatt gcgaaggcag cacac                  225

SEQ ID NO: 262          moltype = DNA  length = 90
FEATURE                Location/Qualifiers
source                 1..90
                       mol_type = genomic DNA
                       organism = Catenibacterium mitsuokai
SEQUENCE: 262
tacgtaggtg gcgagcgtta tccggaatca ttgggcgtaa agagggagca ggcggccgca  60
agggtctgtg gtgaaagacc gaagctaaac                                   90

SEQ ID NO: 263          moltype = DNA  length = 225
FEATURE                Location/Qualifiers
source                 1..225
                       mol_type = genomic DNA
                       organism = Catenibacterium mitsuokai
SEQUENCE: 263
gtgtcagccg ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat attgggagga acaccagtgg cgaaggcgcc tttct                  225

SEQ ID NO: 264          moltype = DNA  length = 225
FEATURE                Location/Qualifiers
source                 1..225
```

```
                        mol_type = genomic DNA
                        organism = Catenibacterium mitsuokai
SEQUENCE: 264
gtgccagccg ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat attaggagga acaccagtgg cgaaagcggc tttct                 225

SEQ ID NO: 265          moltype = DNA  length = 225
FEATURE                 Location/Qualifiers
source                  1..225
                        mol_type = genomic DNA
                        organism = Catenibacterium mitsuokai
SEQUENCE: 265
gtgtcagcag ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcagctaga gtgcggaaga ggatcgtgga attccatgtg tagcggtgaa  180
atgcgtagat atatggagga acaccagtgg cgaaagcggc tttct                 225

SEQ ID NO: 266          moltype = DNA  length = 225
FEATURE                 Location/Qualifiers
source                  1..225
                        mol_type = genomic DNA
                        organism = Catenibacterium mitsuokai
SEQUENCE: 266
gtgcagccgc cgcggtaata cgtaggtggc gagcgttatc cggaatcatt gggcgtaaag  60
agggagcagg cggccgcaag ggtctgtggt gaaagaccga agctaaactt cggtaagcca  120
tggaaaccgg gcagctagag tgcggaagag gatcgtggaa ttccatgtgt agcggtgaaa  180
tgcgtagata tatggaggaa caccagtggc gaaggcgacg gtctg                 225

SEQ ID NO: 267          moltype = DNA  length = 225
FEATURE                 Location/Qualifiers
source                  1..225
                        mol_type = genomic DNA
                        organism = Catenibacterium mitsuokai
SEQUENCE: 267
gtgtcagcag ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat attaggagga acaccagtgg cgaaggcggc ttact                 225

SEQ ID NO: 268          moltype = DNA  length = 225
FEATURE                 Location/Qualifiers
source                  1..225
                        mol_type = genomic DNA
                        organism = Catenibacterium mitsuokai
SEQUENCE: 268
gtgccagcag ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcagctaga gtgcggaaga ggatcgtgga attccatgtg tagcggtgaa  180
atgcgtagat atatggagga acaccagtgg cgaaggcgac ggtct                 225

SEQ ID NO: 269          moltype = DNA  length = 225
FEATURE                 Location/Qualifiers
source                  1..225
                        mol_type = genomic DNA
                        organism = Catenibacterium mitsuokai
SEQUENCE: 269
gtgtcagccg ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat atatggagga acaccagtgg cgaaggcgac ggtct                 225

SEQ ID NO: 270          moltype = DNA  length = 225
FEATURE                 Location/Qualifiers
source                  1..225
                        mol_type = genomic DNA
                        organism = Catenibacterium mitsuokai
SEQUENCE: 270
gttcagcagc cgcggtaata cgtaggtggc gagcgttatc cggaatcatt gggcgtaaag  60
agggagcagg cggccgcaag ggtctgtggt gaaagaccga agctaaactt cggtaagcca  120
tggaaaccgg gcggctagag tgcggaagag gatcgtggaa ttccatgtgt agcggtgaaa  180
tgcgtagata tatggaggaa caccagtggc gaaggcgacg gtctg                 225

SEQ ID NO: 271          moltype = DNA  length = 225
FEATURE                 Location/Qualifiers
source                  1..225
                        mol_type = genomic DNA
                        organism = Catenibacterium mitsuokai
```

-continued

```
SEQUENCE: 271
gtgtcagcag ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat attgggaaga acaccagtgg cgaaggcggc tttct                 225

SEQ ID NO: 272         moltype = DNA  length = 225
FEATURE                Location/Qualifiers
source                 1..225
                       mol_type = genomic DNA
                       organism = Catenibacterium mitsuokai
SEQUENCE: 272
gtgccagcag ccgcggtaat acgtaggtgg cgagcgttat ccggaatcat tgggcgtaaa  60
gagggagcag gcggccgcaa gggtctgtgg tgaaagaccg aagctaaact tcggtaagcc  120
atggaaaccg ggcggctaga gtgcggaaga ggatcgtgga attccatgtg tagcggtgaa  180
atgcgtagat atatggagga acaccagtgg cgaaggcggc tttct                 225

SEQ ID NO: 273         moltype = DNA  length = 90
FEATURE                Location/Qualifiers
source                 1..90
                       mol_type = genomic DNA
                       organism = Streptosporangium album
SEQUENCE: 273
tacgtagggc gcaagcgttg tccggaatta ttgggcgtaa agagctcgta ggtggcttgt  60
cacgtcgggt gtgaaagctt ggggcttaac                                   90

SEQ ID NO: 274         moltype = DNA  length = 90
FEATURE                Location/Qualifiers
source                 1..90
                       mol_type = genomic DNA
                       organism = Clostridium cocleatum
SEQUENCE: 274
tacgtaggtg gcaagcgtta tccggaatta ttgggcgtaa agagggagca ggcggcagca  60
aaggtctgtg gtgaaagact gaagcttaac                                   90

SEQ ID NO: 275         moltype = DNA  length = 90
FEATURE                Location/Qualifiers
source                 1..90
                       mol_type = genomic DNA
                       organism = Eubacerium callanderi
SEQUENCE: 275
tacggagggg acaagcgttg tccggaatga ctgggcgtaa agggcgcgta ggcggtctat  60
taagtctgat gtgaaaggta ccggctcaac                                   90

SEQ ID NO: 276         moltype = DNA  length = 90
FEATURE                Location/Qualifiers
source                 1..90
                       mol_type = genomic DNA
                       organism = Terrisporobacter glycolicus
SEQUENCE: 276
tacggagggg gctagcgtta tccggattta ctgggcgtaa agggtgcgta ggtggtttct  60
taagtcagga gtgaaaggct acggctcaac                                   90

SEQ ID NO: 277         moltype = DNA  length = 90
FEATURE                Location/Qualifiers
source                 1..90
                       mol_type = genomic DNA
                       organism = Bifidobacterium animalis
SEQUENCE: 277
tacgtagggt gcgagcgtta tccggattta ttgggcgtaa agggctcgta ggcggttcgt  60
cgcgtccggt gtgaaagtcc atcgcctaac                                   90

SEQ ID NO: 278         moltype = DNA  length = 90
FEATURE                Location/Qualifiers
source                 1..90
                       mol_type = genomic DNA
                       organism = Clostridium papyrosolvens
SEQUENCE: 278
tacgtaggtg gcaagcgttg tccggaatta ctgggtgtaa agggagcgta ggcgggaagg  60
caagtcagat gtgaaatcca caggcttaac                                   90

SEQ ID NO: 279         moltype = DNA  length = 90
FEATURE                Location/Qualifiers
source                 1..90
                       mol_type = genomic DNA
                       organism = Glautia glucerasea
SEQUENCE: 279
tacgtagggg gcaagcgtta tccggattta ctgggtgtaa agggagcgta gacggagcag  60
caagtctgat gtgaaaggca ggggctcaac                                   90
```

```
SEQ ID NO: 280          moltype = DNA  length = 225
FEATURE                 Location/Qualifiers
source                  1..225
                        mol_type = genomic DNA
                        organism = Glautia glucerasea
SEQUENCE: 280
gtgcagcagc cgcggtaata cgtagggggc aagcgttatc cggatttact gggtgtaaag  60
ggagcgtaga cggagcagca agtctgatgt gaaaggcagg ggctcaaccc ctggactgca  120
ttggaaactg ttgatcttga gtaccggagg ggtaagcgga attcctagtg tagcggtgaa  180
atgcgtagat attaggagga acaccagtgg cgaaggcggc ttact                  225

SEQ ID NO: 281          moltype = DNA  length = 225
FEATURE                 Location/Qualifiers
source                  1..225
                        mol_type = genomic DNA
                        organism = Glautia glucerasea
SEQUENCE: 281
gtgccagcag ccgcggtaat acgtaggggg caagcgttat ccggatttac tgggtgtaaa  60
gggagcgtag acggagcagc aagtctgatg tgaaaggcag gggctcaacc cctggactgc  120
attggaaact gttgatcttg agtaccggag gggtaagcgg aattcctagt gtagcggtga  180
aatgcgtaga tattaggagg aacaccagtg gcgaaggcgc ctttc                  225

SEQ ID NO: 282          moltype = DNA  length = 225
FEATURE                 Location/Qualifiers
source                  1..225
                        mol_type = genomic DNA
                        organism = Glautia glucerasea
SEQUENCE: 282
gtgtcagccg ccgcggtaat acgtaggggg caagcgttat ccggatttac tgggtgtaaa  60
gggagcgtag acggagcagc aagtctgatg tgaaaggcag gggctcaacc cctggactgc  120
attggaaact gttgatcttg agtaccggag gggtaagcgg aattcctagt gtagcggtga  180
aatgcgtaga tattgggaag aacaccagtg gcgaaggcgg ctttc                  225

SEQ ID NO: 283          moltype = DNA  length = 225
FEATURE                 Location/Qualifiers
source                  1..225
                        mol_type = genomic DNA
                        organism = Glautia glucerasea
SEQUENCE: 283
gtgtcagccg ccgcggtaat acgtaggggg caagcgttat ccggatttac tgggtgtaaa  60
gggagcgtag acggagcagc aagtctgatg tgaaaggcag gggctcaacc cctggactgc  120
attggaaact gttgatcttg agtaccggag gggtaagcgg aattcctagt gtagcggtga  180
aatgcgtaga tattaggagg aacaccagtg gcgaaggcgg cttac                  225

SEQ ID NO: 284          moltype = DNA  length = 225
FEATURE                 Location/Qualifiers
source                  1..225
                        mol_type = genomic DNA
                        organism = Glautia glucerasea
SEQUENCE: 284
gtgccagcag ccgcggtaat acgtaggggg caagcgttat ccggatttac tgggtgtaaa  60
gggagcgtag acggagcagc aagtctgatg tgaaaggcag gggctcaacc cctggactgc  120
attggaaact gttgatcttg agtaccggag aggtaagcgg aattcctagt gtagcggtga  180
aatgcgtaga tattaggagg aacaccagtg gcgaaggcgg cttac                  225

SEQ ID NO: 285          moltype = DNA  length = 225
FEATURE                 Location/Qualifiers
source                  1..225
                        mol_type = genomic DNA
                        organism = Glautia glucerasea
SEQUENCE: 285
gtgccagccg ccgcggtaat acgtaggggg caagcgttat ccggatttac tgggtgtaaa  60
gggagcgtag acggagcagc aagtctgatg tgaaaggcag gggctcaacc cctggactgc  120
attggaaact gttgatcttg agtaccggag gggtaagcgg aattcctagt gtagcggtga  180
aatgcgtaga tattaggagg aacaccagtg gcgaaagcgg ctttc                  225

SEQ ID NO: 286          moltype = DNA  length = 90
FEATURE                 Location/Qualifiers
source                  1..90
                        mol_type = genomic DNA
                        organism = Holdemanella biformis
SEQUENCE: 286
tacgtaggtg gcgagcgtta tccggaatga ttgggcgtaa agggtgcgta ggtggcagat  60
caagtctgga gtaaaaggta tggctcaac                                   90

SEQ ID NO: 287          moltype = DNA  length = 90
FEATURE                 Location/Qualifiers
source                  1..90
```

```
                         mol_type = genomic DNA
                         organism = Prevotella saccharolytica
SEQUENCE: 287
tacggaaggt ccaggcgtta tccggattta ttgggtttaa agggagcgca ggcggactct  60
taagtcagtt gtgaaatacg gcggctcaac                                   90

SEQ ID NO: 288           moltype = DNA  length = 225
FEATURE                  Location/Qualifiers
source                   1..225
                         mol_type = genomic DNA
                         organism = Prevotella saccharolytica
SEQUENCE: 288
gtgccagccg cggtaatacg gaaggtccag gcgttatccg gatttattgg gtttaaaggg  60
agcgcaggcg gactcttaag tcagttgtga aatacggcgg ctcaaccgtc ggactgcagt  120
tgatactggg agtcttgagt gcacacaggg atgctggaat tcatggtgta gcggtgaaat  180
gctcagatat catgaagaac tccgatcgcg aaggcaggta tccgg                  225

SEQ ID NO: 289           moltype = DNA  length = 225
FEATURE                  Location/Qualifiers
source                   1..225
                         mol_type = genomic DNA
                         organism = Prevotella saccharolytica
SEQUENCE: 289
gtgtcagccg ccgcggtaat acggaaggtc caggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcgtggt gtagcggtga  180
aatgcttaga tatcacgaag aactccgatt gcgaaggcag ctcac                  225

SEQ ID NO: 290           moltype = DNA  length = 225
FEATURE                  Location/Qualifiers
source                   1..225
                         mol_type = genomic DNA
                         organism = Prevotella saccharolytica
SEQUENCE: 290
gtgccagcag ccgcggtaat acggaaggtc caggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcatggt gtagcggtga  180
aatgctcaga tatcatgaag aactccgatc gcgaaggcag cttgc                  225

SEQ ID NO: 291           moltype = DNA  length = 225
FEATURE                  Location/Qualifiers
source                   1..225
                         mol_type = genomic DNA
                         organism = Prevotella saccharolytica
SEQUENCE: 291
gtgtcagccg ccgcggtaat acggaaggtc caggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcatggt gtagcggtga  180
aatgctcaga tatcatgaag aactccgatc gcgaaggcag gtatc                  225

SEQ ID NO: 292           moltype = DNA  length = 225
FEATURE                  Location/Qualifiers
source                   1..225
                         mol_type = genomic DNA
                         organism = Prevotella saccharolytica
SEQUENCE: 292
gtgccagccg ccgcggtaat acggaaggtc caggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcatggt gtagcggtga  180
aatgctcaga tatcacgaag aactccgatt gcgaaggcag ctcac                  225

SEQ ID NO: 293           moltype = DNA  length = 225
FEATURE                  Location/Qualifiers
source                   1..225
                         mol_type = genomic DNA
                         organism = Prevotella saccharolytica
SEQUENCE: 293
gtgcagccgc cgcggtaata cggaaggtcc aggcgttatc cggatttatt gggtttaaag  60
ggagcgcagg cggactctta agtcagttgt gaaatacggc ggctcaaccg tcggactgca  120
gttgatactg ggagtcttga gtgcacacag ggatgctgga attcatggtg tagcggtgaa  180
atgctcagat atcatgaaga actccgatcg cgaaggcagg tatcc                  225

SEQ ID NO: 294           moltype = DNA  length = 90
FEATURE                  Location/Qualifiers
source                   1..90
                         mol_type = genomic DNA
                         organism = Blautia stercoris
SEQUENCE: 294
tacgtagggg gcaagcgtta tccggattta ctgggtgtaa agggagcgta gacggaagag  60
```

```
caagtctgat gtgaaaggct ggggcttaac                                90

SEQ ID NO: 295         moltype = DNA  length = 225
FEATURE                Location/Qualifiers
source                 1..225
                       mol_type = genomic DNA
                       organism = Blautia stercoris
SEQUENCE: 295
gtgccagcag ccgcggtaat acgtaggggg caagcgttat ccggatttac tgggtgtaaa  60
gggagcgtag acggaagagc aagtctgatg tgaaaggctg gggcttaacc ccaggactgc  120
attggaaact gtttttctag agtgccggag aggtaagcgg aattcctagt gtagcggtga  180
aatgcgtaga tattaggagg aacaccagtg gcgaaggcga cttgc                 225

SEQ ID NO: 296         moltype = DNA  length = 225
FEATURE                Location/Qualifiers
source                 1..225
                       mol_type = genomic DNA
                       organism = Blautia stercoris
SEQUENCE: 296
gttcagcagc cgcggtaata cgtagggggc aagcgttatc cggatttact gggtgtaaag  60
ggagcgtaga cggaagagca agtctgatgt gaaaggctgg ggcttaaccc caggactgca  120
ttggaaactg tttttctaga gtgccggaga ggtaagcgga attcctagtg tagcggtgaa  180
atgcgtagat attaggagga acaccagtgg cgaaggcggc ttact                 225

SEQ ID NO: 297         moltype = DNA  length = 225
FEATURE                Location/Qualifiers
source                 1..225
                       mol_type = genomic DNA
                       organism = Blautia stercoris
SEQUENCE: 297
gtgtcagccg ccgcggtaat acgtaggggg caagcgttat ccggatttac tgggtgtaaa  60
gggagcgtag acggaagagc aagtctgatg tgaaaggctg gggcttaacc ccgggactgc  120
attggaaact gtccatcctg agtgccggag aggtaagcgg aattcctagt gtagcggtga  180
aatgcgtaga tgttaggagg aacaccagtg gcgaaggcgg ctttc                 225

SEQ ID NO: 298         moltype = DNA  length = 225
FEATURE                Location/Qualifiers
source                 1..225
                       mol_type = genomic DNA
                       organism = Blautia stercoris
SEQUENCE: 298
gtgccagccg ccgcggtaat acgtaggggg caagcgttat ccggatttac tgggtgtaaa  60
gggagcgtag acggaagagc aagtctgatg tgaaaggctg gggcttaacc ccaggactgc  120
attggaaact gtttttctag agtgccggag aggtaagcgg aatccctagt gtagcggtga  180
aatgcgtaga tattaggagg aacaccagtg gcgaaagcgg ctttc                 225

SEQ ID NO: 299         moltype = DNA  length = 225
FEATURE                Location/Qualifiers
source                 1..225
                       mol_type = genomic DNA
                       organism = Blautia stercoris
SEQUENCE: 299
gtgtcagcag ccgcggtaat acgtaggggg caagcgttat ccggatttac tgggtgtaaa  60
gggagcgtag acggaagagc aagtctgatg tgaaaggctg gggcttaacc ccaggactgc  120
attggaaact gtttttctag agtgccggag aggtaagcgg aattcctagt gtagcggtga  180
aatgcgtaga tattaggagg aacaccagtg gcgaaagcgg ctttc                 225

SEQ ID NO: 300         moltype = DNA  length = 225
FEATURE                Location/Qualifiers
source                 1..225
                       mol_type = genomic DNA
                       organism = Blautia stercoris
SEQUENCE: 300
gtgtcagccg ccgcggtaat acgtaggggg caagcgttat ccggatttac tgggtgtaaa  60
gggagcgtag acggaagagc aagtctgatg tgaaaggctg gggcttaacc ccaggactgc  120
attggaaact gtttttctag agtgccggag aggtaagcgg aattcctagt gtagcggtga  180
aatgcgtaga tattaggagg aacaccagtg gcgaaggcgg cttac                 225

SEQ ID NO: 301         moltype = DNA  length = 225
FEATURE                Location/Qualifiers
source                 1..225
                       mol_type = genomic DNA
                       organism = Blautia stercoris
SEQUENCE: 301
gtgccagcag ccgcggtaat acgtaggggg caagcgttat ccggatttac tgggtgtaaa  60
gggagcgtag acggaagagc aagtctgatg tgaaaggctg gggcttaacc ccaggactgc  120
attggaaact gtttttctag agtgccggag aggtaagcgg aattcctagt gtagcggtga  180
aatgcgtaga tattgggagg aacaccagtg gcgaaggcgc ctttc                 225
```

```
SEQ ID NO: 302          moltype = DNA  length = 225
FEATURE                 Location/Qualifiers
source                  1..225
                        mol_type = genomic DNA
                        organism = Blautia stercoris
SEQUENCE: 302
gtgtcagccg ccgcggtaat acgtaggggg caagcgttat ccggatttac tgggtgtaaa  60
gggagcgtag acggaagagc aagtctgatg tgaaaggctg ggcttaacc ccaggactgc  120
attggaaact gtttttctag agtgccggag aggtaagcgg aattcctagt gtagcggtga  180
aatgcgtaga tattgggaag aacaccagtg gcgaaggcgg ctttc                 225

SEQ ID NO: 303          moltype = DNA  length = 90
FEATURE                 Location/Qualifiers
source                  1..90
                        mol_type = genomic DNA
                        organism = Ruminococcus gnavus
SEQUENCE: 303
tacgtagggg gcaagcgtta tccggattta ctgggtgtaa agggagcgta gacggcatgg  60
caagccagat gtgaaagccc ggggctcaac                                   90

SEQ ID NO: 304          moltype = DNA  length = 225
FEATURE                 Location/Qualifiers
source                  1..225
                        mol_type = genomic DNA
                        organism = Ruminococcus gnavus
SEQUENCE: 304
gtgtcagcag ccgcggtaat acgtaggggg caagcgttat ccggatttac tgggtgtaaa  60
gggagcgtag acggcatggc aagccagatg tgaaagcccg gggctcaacc ccgggactgc  120
atttggaact gtcaggctag agtgtcggag aggaaagcgg aattcctagt gtagcggtga  180
aatgcgtaga tattgggagg aacaccagtg gcgaaggcgc ctttc                 225

SEQ ID NO: 305          moltype = DNA  length = 225
FEATURE                 Location/Qualifiers
source                  1..225
                        mol_type = genomic DNA
                        organism = Ruminococcus gnavus
SEQUENCE: 305
gttcagcagc cgcggtaata cgtagggggc aagcgttatc cggatttact gggtgtaaag  60
ggagcgtaga cggcatggca agccagatgt gaaagcccgg ggctcaaccc cgggactgca  120
tttggaactg tcaggctaga gtgtcggaga ggaaagcgga attcctagtg tagcggtgaa  180
atgcgtagat attaggagga acaccagtgg cgaaggcggc tttct                 225

SEQ ID NO: 306          moltype = DNA  length = 225
FEATURE                 Location/Qualifiers
source                  1..225
                        mol_type = genomic DNA
                        organism = Ruminococcus gnavus
SEQUENCE: 306
gtgtcagccg ccgcggtaat acgtaggggg caagcgttat ccggatttac tgggtgtaaa  60
gggagcgtag acggcatggc aagccagatg tgaaagcccg gggctcaacc ccgggactgc  120
atttggaact gtcaggctag agtgtcggag aggtaagcgg aattcctagt gtagcggtga  180
aatgcgtaga tattaggagg aacaccagtg gcgaaggcgg cctac                 225

SEQ ID NO: 307          moltype = DNA  length = 225
FEATURE                 Location/Qualifiers
source                  1..225
                        mol_type = genomic DNA
                        organism = Ruminococcus gnavus
SEQUENCE: 307
gtgtcagcag ccgcggtaat acgtaggggg caagcgttat ccggatttac tgggtgtaaa  60
gggagcgtag acggcatggc aagccagatg tgaaagcccg gggctcaacc ccgggactgc  120
atttggaact gtcaggctag agtgtcggag aggaaagcgg aattcccagt gtagcggtga  180
aatgcgtaga tattgggaag aacaccagtg gcgaaggcgg ctttc                 225

SEQ ID NO: 308          moltype = DNA  length = 225
FEATURE                 Location/Qualifiers
source                  1..225
                        mol_type = genomic DNA
                        organism = Ruminococcus gnavus
SEQUENCE: 308
gtgccagcag ccgcggtaat acgtaggggg caagcgttat ccggatttac tgggtgtaaa  60
gggagcgtag acggcatggc aagccagatg tgaaagcccg gggctcaacc ccgggactgc  120
atttggaact gtcaggctag agtgtcggag aggtaagcgg aattcctagt gtagcggtga  180
aatgcgtaga tattaggagg aacaccagtg gcgaaggcgg cttac                 225

SEQ ID NO: 309          moltype = DNA  length = 225
FEATURE                 Location/Qualifiers
source                  1..225
                        mol_type = genomic DNA
```

```
                         organism = Ruminococcus gnavus
SEQUENCE: 309
gtgtcagccg ccgcggtaat acgtaggggg caagcgttat ccggatttac tgggtgtaaa  60
gggagcgtag acggcatggc aagccagatg tgaaagcccg ggctcaaccc ccgggactgc  120
atttggaact gtcaggctag agtgtcggag aggaaagcgg aattcctagt gtagcggtga  180
aatgcgtaga tattaggagg aacaccagtg gcgaaggcgg ctttc                 225

SEQ ID NO: 310           moltype = DNA  length = 225
FEATURE                  Location/Qualifiers
source                   1..225
                         mol_type = genomic DNA
                         organism = Ruminococcus gnavus
SEQUENCE: 310
gtgccagccg ccgcggtaat acgtaggggg caagcgttat ccggatttac tgggtgtaaa  60
gggagcgtag acggcatggc aagccagatg tgaaagcccg ggctcaaccc ccgggactgc  120
atttggaact gtcaggctag agtgtcggag aggaaagcgg aattcctagt gtagcggtga  180
aatgcgtaga tattgggaag aacaccagtg gcgaaggcgg ctttc                 225

SEQ ID NO: 311           moltype = DNA  length = 225
FEATURE                  Location/Qualifiers
source                   1..225
                         mol_type = genomic DNA
                         organism = Ruminococcus gnavus
SEQUENCE: 311
gtgccagcag ccgcggtaat acgtaggggg caagcgttat ccggatttac tgggtgtaaa  60
gggagcgtag acggcatggc aagccagatg tgaaagcccg ggctcaaccc ccgggactgc  120
atttggaact gtcaggctag agtgtcggag aggaaagcgg aattcctagt gtagcggtga  180
aatgcgtaga tattaggagg aacaccagtg gcgaaagcgg ctttc                 225

SEQ ID NO: 312           moltype = DNA  length = 90
FEATURE                  Location/Qualifiers
source                   1..90
                         mol_type = genomic DNA
                         organism = Murimonas intestini
SEQUENCE: 312
tacgtagggg gcaagcgtta tccggattta ctgggtgtaa agggagcgta gacggacggg  60
caagtctgaa gtgaaaggca ggggctcaac                                   90

SEQ ID NO: 313           moltype = DNA  length = 225
FEATURE                  Location/Qualifiers
source                   1..225
                         mol_type = genomic DNA
                         organism = Murimonas intestini
SEQUENCE: 313
gtgtcagcag ccgcggtaat acgtaggggg caagcgttat ccggatttac tgggtgtaaa  60
gggagcgtag acggacgggc aagtctgaag tgaaaggcag gggctcaact cctggactgc  120
tttggaaact gtccatctag agtgccggag aggtaagcgg aattcctagt gtagcggtga  180
aatgcgtaga tattgggaag aacaccagtg gcgaaggcgg ctttc                 225

SEQ ID NO: 314           moltype = DNA  length = 225
FEATURE                  Location/Qualifiers
source                   1..225
                         mol_type = genomic DNA
                         organism = Murimonas intestini
SEQUENCE: 314
gtccagccgc cgcggtaata cgtagggggc aagcgttatc cggatttact gggtgtaaag  60
ggagcgtaga cggacgggca agtctgaagt gaaaggcagg ggctcaaccc ctggactgct  120
ttggaaactg tccatctaga gtgccggaga ggtaagcgga attcctagtg tagcggtgaa  180
atgcgtagat attaggagga acaccagtgg cgaaggcggc ttact                 225

SEQ ID NO: 315           moltype = DNA  length = 225
FEATURE                  Location/Qualifiers
source                   1..225
                         mol_type = genomic DNA
                         organism = Murimonas intestini
SEQUENCE: 315
gtgccagccg ccgcggtaat acgtaggggg caagcgttat ccggatttac tgggtgtaaa  60
gggagcgtag acggacgggc aagtctgaag tgaaaggcag gggctcaact cctggactgc  120
tttggaaact gtccatctag agtgccggag aggtaagcgg aattcctagt gtagcggtga  180
aatgcgtaga tattaggagg aacaccagtg gcgaaagcgg ctttc                 225

SEQ ID NO: 316           moltype = DNA  length = 225
FEATURE                  Location/Qualifiers
source                   1..225
                         mol_type = genomic DNA
                         organism = Murimonas intestini
SEQUENCE: 316
gtgtcagcag ccgcggtaat acgtaggggg caagcgttat ccggatttac tgggtgtaaa  60
gggagcgtag acggacgggc aagtctgaag tgaaaggcag gggctcaacc cctggactgc  120
```

```
tttggaaact gtccatctag agtgccggag aggtaagcgg aattcctagt gtagcggtga  180
aatgcgtaga tattaggagg aacaccagtg gcgaaggcga cggtc                  225

SEQ ID NO: 317         moltype = DNA  length = 225
FEATURE                Location/Qualifiers
source                 1..225
                       mol_type = genomic DNA
                       organism = Murimonas intestini
SEQUENCE: 317
gtgtcagcag ccgcggtaat acgtaggggg caagcgttat ccggatttac tgggtgtaaa  60
gggagcgtag acggacgggc aagtctgaag tgaaaggcag ggctcaaccc cctggactgc  120
tttggaaact gtccatctag agtgccggag aggtaagcgg aattcctagt gtagcggtga  180
aatgcgtaga tattaggagg aacaccagtg gcgaaggcga cttgc                  225

SEQ ID NO: 318         moltype = DNA  length = 225
FEATURE                Location/Qualifiers
source                 1..225
                       mol_type = genomic DNA
                       organism = Murimonas intestini
SEQUENCE: 318
gtgccagcag ccgcggtaat acgtaggggg caagcgttat ccggatttac tgggtgtaaa  60
gggagcgtag acggacgggc aagtctgaag tgaaaggcag ggctcaactc cctggactgc  120
tttggaaact gtccatctag agtgccggag aggtaagcgg aattcctagt gtagcggtga  180
aatgcgtaga tattaggagg aacaccagtg gcgaaggcgg cttac                  225

SEQ ID NO: 319         moltype = DNA  length = 225
FEATURE                Location/Qualifiers
source                 1..225
                       mol_type = genomic DNA
                       organism = Murimonas intestini
SEQUENCE: 319
gtgtcagccg ccgcggtaat acgtaggggg caagcgttat ccggatttac tgggtgtaaa  60
gggagcgtag acggacgggc aagtctgaag tgaaaggcag ggctcaaccc cctggactgc  120
tttggaaact gtccatctag agtgccggag aggtaagcgg aattcctagt gtagcggtga  180
aatgcgtaga tattaggagg aacaccagtg gcgaaggcgg cttac                  225

SEQ ID NO: 320         moltype = DNA  length = 225
FEATURE                Location/Qualifiers
source                 1..225
                       mol_type = genomic DNA
                       organism = Murimonas intestini
SEQUENCE: 320
gtgtcagcag ccgcggtaat acgtaggggg caagcgttat ccggatttac tgggtgtaaa  60
gggagcgtag acggacgggc aagtctgaag tgaaaggcag ggctcaaccc cctggactgc  120
tttggaaact gtccatctag agtgccggag aggtaagcgg aattcctagt gtagcggtga  180
aatgcgtaga tattaggagg aacaccagtg gcgaaagcgg ctttc                  225

SEQ ID NO: 321         moltype = DNA  length = 225
FEATURE                Location/Qualifiers
source                 1..225
                       mol_type = genomic DNA
                       organism = Murimonas intestini
SEQUENCE: 321
gtgccagccg ccgcggtaat acgtaggggg caagcgttat ccggatttac tgggtgtaaa  60
gggagcgtag acggacgggc aagtctgaag tgaaaggcag ggctcaaccc cctggactgc  120
tttggaaact gtccatctag agtgccggag aggtaagcgg aattcctagt gtagcggtga  180
aatgcgtaga tattgggaag aacaccagtg gcgaaggcgg ctttc                  225

SEQ ID NO: 322         moltype = DNA  length = 225
FEATURE                Location/Qualifiers
source                 1..225
                       mol_type = genomic DNA
                       organism = Murimonas intestini
SEQUENCE: 322
gtgtcagcag ccgcggtaat acgtaggggg caagcgttat ccggatttac tgggtgtaaa  60
gggagcgtag acggacgggc aagtctgaag tgaaaggcag ggctcaaccc cctggactgc  120
tttggaaact gtccatctag agtgccggag aggtaagcgg aattcctagt gtagcggtga  180
aatgcgtaga tattgggagg aacaccagtg gcgaaggcgc ctttc                  225

SEQ ID NO: 323         moltype = DNA  length = 90
FEATURE                Location/Qualifiers
source                 1..90
                       mol_type = genomic DNA
                       organism = Pediococcus acidilactici
SEQUENCE: 323
tacgtaggtg gcaagcgttg tccggattta ttgggcgtaa agcgagcgca ggcggtcttt  60
taagtctaat gtgaaagcct tcggctcaac                                   90

SEQ ID NO: 324         moltype = DNA  length = 90
```

```
FEATURE                 Location/Qualifiers
source                  1..90
                        mol_type = genomic DNA
                        organism = Collinsella intestinalis
SEQUENCE: 324
tacgtagggg gcgagcgtta tccggattca ttgggcgtaa agcgcgcgta ggcggcccgg  60
caggcagggg gtcaaatggc ggggctcaac                                   90

SEQ ID NO: 325          moltype = DNA  length = 90
FEATURE                 Location/Qualifiers
source                  1..90
                        mol_type = genomic DNA
                        organism = Megasphaera indica
SEQUENCE: 325
tacgtaggtg gcaagcgttg tccggaatta ttgggcgtaa agggcgcgca ggcggcgtcg  60
taagtcggtc ttaaaagtgc ggggcttaac                                   90

SEQ ID NO: 326          moltype = DNA  length = 225
FEATURE                 Location/Qualifiers
source                  1..225
                        mol_type = genomic DNA
                        organism = Enterococcus sp.
SEQUENCE: 326
gtgtcagccg ccgcggtaat acgtaggtgg caagcgttgt ccggatttat tgggcgtaaa  60
gcgagcgcag gcggtttctt aagtctgatg tgaaagcccc cggctcaacc ggggagggtc  120
attggaaact gggagacttg agtgcagaag aggagagtgg aattccatgt gtagcggtga  180
aatgcgtaga tatatggagg aacaccagtg gcgaaggcgg ctctc                  225

SEQ ID NO: 327          moltype = DNA  length = 225
FEATURE                 Location/Qualifiers
source                  1..225
                        mol_type = genomic DNA
                        organism = Clostridium sp.
SEQUENCE: 327
gtgtcagcag ccgcggtaat acgtaggtgg cgagcgttgt ccggatttac tgggcgtaaa  60
gggagcgtag gcggattttt aagtgggatg tgaaataccc gggctcaacc tgggtgctgc  120
attccaaact gggaatctag agtgcaggag gggagagtgg aattcctagt gtagcggtga  180
aatgcgtaga gattaggaag aacaccagtg gcgaaggcga ctctc                  225

SEQ ID NO: 328          moltype = DNA  length = 225
FEATURE                 Location/Qualifiers
source                  1..225
                        mol_type = genomic DNA
                        organism = Bacteroides sp.
SEQUENCE: 328
gtgtcagccg ccgcggtaat acgtaggggg caagcgttat ccggatttac tgggtgtaaa  60
gggagcgtag acggttctgc aagtctggag tgaaagcccg gggctcaacc ccgggactgc  120
tttggaaact gtggaactag agtgcaggag aggtaagtgg aattcctagt gtagcggtga  180
aatgcgtaga tattaggagg aacaccagtg gcgaaggcgg cttac                  225

SEQ ID NO: 329          moltype = DNA  length = 225
FEATURE                 Location/Qualifiers
source                  1..225
                        mol_type = genomic DNA
                        organism = Fusobacterium sp.
SEQUENCE: 329
gtgtcagcag ccgcggtaat acgtatgtcg caagcgttat ccggatttat tgggcgtaaa  60
gcgcgtctag gtggtttggt aagtctgatg tgaaaatgcg gggctcaact ccgtattgcg  120
ttggaaactg cctaactaga gtatcggaga ggtgggcgga actacaagtg tagaggtgaa  180
attcgtagat atttgtagga atgccgatag agaagtcagc tcact                  225

SEQ ID NO: 330          moltype = DNA  length = 225
FEATURE                 Location/Qualifiers
source                  1..225
                        mol_type = genomic DNA
                        organism = Collinsella sp.
SEQUENCE: 330
gtgtcagcag ccgcggtaat acgtaggggg cgagcgttat ccggattcat tgggcgtaaa  60
gcgcgcgtag gcggcccggc aggcaggggg tcaaatggcg gggctcaacc ccgtcccgcc  120
ccctgaaccg ccgggctcgg gtccggtagg ggagggtgga acacccggtg tagcggtgga  180
atgcgcagat atcgggtgga acaccggtgg cgaaggcggc cctct                  225

SEQ ID NO: 331          moltype = DNA  length = 225
FEATURE                 Location/Qualifiers
source                  1..225
                        mol_type = genomic DNA
                        organism = Fusobacterium sp.
SEQUENCE: 331
gtgtcagcag ccgcggtaat acgtatgtcg caagcgttat ccggatttat tgggcgtaaa  60
```

-continued

```
gcgcgtctag gcggtttggt aagtctgatg tgaaaatgcg gggctcaact ccgtattgcg  120
ttggaaactg ccaaactaga gtactggaga ggtaggcgga actacaagtg tagaggtgaa  180
attcgtagat atttgtagga atgccgatgg ggaagccagc ctact                  225

SEQ ID NO: 332          moltype = DNA  length = 225
FEATURE                 Location/Qualifiers
source                  1..225
                        mol_type = genomic DNA
                        organism = Prevotella bryantii
SEQUENCE: 332
gtgccagcag ccgcggtaat acggaaggtc cgggcgttat ccggatttat tgggtttaaa  60
gggagcgcag gcggactctt aagtcagttg tgaaatacgg cggctcaacc gtcggactgc  120
agttgatact gggagtcttg agtgcacaca gggatgctgg aattcatggt gtagcggtga  180
aatgctcaga tatcatgaag aactccgatc gcgaaggcag gtatc                  225

SEQ ID NO: 333          moltype = DNA  length = 225
FEATURE                 Location/Qualifiers
source                  1..225
                        mol_type = genomic DNA
                        organism = Holdemanella biformis
SEQUENCE: 333
gtgtcagccg ccgcggtaat acgtaggtgg cgagcgttat ccggaatgat tgggcgtaaa  60
gggtgcgtag gtggcagatc aagtctggag taaaaggtat gggctcaacc cgtacttgct  120
ctggaaactg atcagctaga gaacagaaga ggacggcgga actccatgtg tagcggtaaa  180
atgcgtagat atatggaaga acaccggtgg cgaaggcggc cgtct                  225
```